(12) United States Patent
Mohamed et al.

(10) Patent No.: US 11,524,964 B2
(45) Date of Patent: *Dec. 13, 2022

(54) PROCESSES FOR THE PREPARATION OF (3S,4R)-3-ETHYL-4-(3H-IMIDAZO[1,2-A] PYRROLO[2,3-E]-PYRAZIN-8-YL)-N-(2,2,2-TRIFLUOROETHYL)PYRROLIDINE-1-CARBOXAMIDE AND SOLID STATE FORMS THEREOF

(71) Applicant: AbbVie Inc., North Chicago, IL (US)

(72) Inventors: Mohamed-Eslam F. Mohamed, Gurnee, IL (US); Ahmed A. Othman, Libertyville, IL (US); Ben Klünder, Ludwigshafen (DE); Aileen L. Pangan, La Grange, IL (US); In-Ho Song, Vernon Hills, IL (US)

(73) Assignee: Abbvie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/717,486

(22) Filed: Apr. 11, 2022

(65) Prior Publication Data

US 2022/0251101 A1 Aug. 11, 2022

Related U.S. Application Data

(63) Continuation-in-part of application No. 17/184,194, filed on Feb. 24, 2021, which is a continuation of application No. 16/656,237, filed on Oct. 17, 2019, now abandoned, which is a continuation of application No. 15/891,012, filed on Feb. 7, 2018, now abandoned, which is a continuation of application No. 15/295,561, filed on Oct. 17, 2016, now abandoned, application No. 17/717,486, which is a continuation-in-part of application No. 17/039,470, filed on Sep. 30, 2020.

(60) Provisional application No. 62/242,797, filed on Oct. 16, 2015, provisional application No. 62/267,672, filed on Dec. 15, 2015, provisional application No. 62/301,537, filed on Feb. 29, 2016, provisional application No. 62/352,380, filed on Jun. 20, 2016, provisional application No. 62/032,042, filed on May 29, 2020, provisional application No. 62/968,849, filed on Jan. 31, 2020, provisional application No. 62/927,548, filed on Oct. 29, 2019, provisional application No. 62/908,163, filed on Sep. 30, 2019, provisional application No. 63/253,109, filed on Oct. 6, 2021.

(51) Int. Cl.
| | | |
|---|---|---|
| A61K 31/4985 | (2006.01) |
| C07D 487/14 | (2006.01) |
| A61K 9/00 | (2006.01) |
| A61K 47/12 | (2006.01) |
| A61K 47/38 | (2006.01) |

(52) U.S. Cl.
CPC .......... *C07D 487/14* (2013.01); *A61K 9/0053* (2013.01); *A61K 31/4985* (2013.01); *A61K 47/12* (2013.01); *A61K 47/38* (2013.01); *C07B 2200/13* (2013.01)

(58) Field of Classification Search
CPC ........................ C07D 487/14; A61K 31/4985
See application file for complete search history.

(56) References Cited

U.S. PATENT DOCUMENTS

| | | | |
|---|---|---|---|
| 3,663,559 A | 5/1972 | Antoon et al. |
| 3,929,992 A | 12/1975 | Sehgal et al. |
| 4,053,474 A | 10/1977 | Treuner et al. |
| 5,212,310 A | 5/1993 | Thurkauf et al. |
| 5,266,698 A | 11/1993 | Shaw et al. |
| 5,521,173 A | 5/1996 | Venkatesan et al. |
| 5,605,690 A | 2/1997 | Jacobs et al. |
| 5,693,801 A | 12/1997 | Shaw et al. |
| 5,703,244 A | 12/1997 | Li et al. |
| 5,733,905 A | 3/1998 | Albright et al. |
| 5,736,540 A | 4/1998 | Albright et al. |
| 5,753,648 A | 5/1998 | Albright et al. |
| 5,763,137 A | 6/1998 | Deprez et al. |
| 5,840,888 A | 11/1998 | Shaw et al. |
| 5,990,109 A | 11/1999 | Chen et al. |
| 6,090,382 A | 7/2000 | Salfeld et al. |
| 6,120,778 A | 9/2000 | Simonnet et al. |
| 6,245,801 B1 | 6/2001 | Bryans et al. |
| 6,262,241 B1 | 7/2001 | Cook et al. |
| 6,653,471 B2 | 11/2003 | Yohannes et al. |

(Continued)

FOREIGN PATENT DOCUMENTS

| | | |
|---|---|---|
| CA | 2675288 A1 | 7/2008 |
| CN | 1762333 A | 4/2006 |

(Continued)

OTHER PUBLICATIONS

U.S. Appl. No. 17/507,885.
U.S. Appl. No. 17/039,470.
U.S. Appl. No. 17/205,066.
U.S. Appl. No. 17/508,451.
U.S. Appl. No. 17/508,576.
Adamczyk, M., et al., "Synthesis of 3,7-dihydroimidazo[1,2a]pyrazine-3-ones and their Chemiluminescent Properties," Tetrahedron 59(41):8129-8142, Elsevier, England (2003).

(Continued)

*Primary Examiner* — Rei Tsang Shiao
(74) *Attorney, Agent, or Firm* — Womble Bond Dickinson (US) LLP; Danielle L. Herritt; Scott R. Breining

(57) ABSTRACT

The present disclosure relates to processes for preparing (3S,4R)-3-ethyl-4-(3H-imidazo[1,2-a]pyrrolo[2,3-e] pyrazin-8-yl)-N-(2,2,2-trifluoroethyl)pyrrolidine-1-carboxamide, solid state forms thereof, and corresponding pharmaceutical compositions, methods of treatment (including treatment of rheumatoid arthritis and various spondyloarthritic conditions, including types of axial spondyloarthritis (axSpA)), kits, methods of synthesis, and products-by-process. In various aspects, provided are methods for treating active non-radiographic axSpA (nr-axSpA) and methods for treating active ankylosing spondylitis (AS).

10 Claims, 49 Drawing Sheets

(56) References Cited

U.S. PATENT DOCUMENTS

| | | |
|---|---|---|
| 6,949,562 B2 | 9/2005 | Yohannes et al. |
| 7,169,926 B1 | 1/2007 | Burgess et al. |
| 7,452,981 B2 | 11/2008 | Wijdenes et al. |
| 7,593,820 B2 | 9/2009 | Wilks et al. |
| 7,772,231 B2 | 8/2010 | Sheppard et al. |
| 7,902,197 B2 | 3/2011 | Elworthy et al. |
| 8,039,009 B2 | 10/2011 | Rastogi et al. |
| 8,168,624 B2 | 5/2012 | Agarwal et al. |
| 8,361,962 B2 | 1/2013 | Billedeau |
| 8,426,411 B2 | 4/2013 | Wishart et al. |
| 8,637,529 B2 | 1/2014 | Woller et al. |
| 8,785,639 B2 | 7/2014 | Wishart et al. |
| 8,962,629 B2 | 2/2015 | Wishart et al. |
| 9,011,912 B2 | 4/2015 | Zu et al. |
| 9,365,579 B2 | 6/2016 | Wishart et al. |
| 9,879,018 B2 | 1/2018 | Mulhern et al. |
| 9,879,019 B2 | 1/2018 | Nordstroem et al. |
| 9,951,080 B2 | 4/2018 | Allian et al. |
| 9,963,459 B1 | 5/2018 | Jayanth et al. |
| 10,017,517 B2 | 7/2018 | Borchardt et al. |
| RE47,221 E | 2/2019 | Wishart et al. |
| 10,202,393 B2 | 2/2019 | Jayanth et al. |
| 10,202,394 B2 | 2/2019 | Jayanth et al. |
| 10,344,036 B2 | 7/2019 | Jayanth et al. |
| 10,519,164 B2 | 12/2019 | Jayanth et al. |
| 10,550,126 B2 | 2/2020 | Pangan et al. |
| 10,597,400 B2 | 3/2020 | Othman et al. |
| 10,730,883 B2 * | 8/2020 | Allian .................... A61P 37/02 |
| 10,981,923 B2 | 4/2021 | Allian et al. |
| 10,981,924 B2 * | 4/2021 | Jayanth ................. A61P 35/00 |
| 11,186,584 B2 | 10/2021 | Allian et al. |
| 11,198,697 B1 * | 12/2021 | Allian ...................... A61P 1/04 |
| 2003/0078277 A1 | 4/2003 | Hidi et al. |
| 2004/0023992 A1 | 2/2004 | Das et al. |
| 2005/0176796 A1 | 8/2005 | D'Alessio et al. |
| 2006/0160806 A1 | 7/2006 | Haviv et al. |
| 2006/0183758 A1 | 8/2006 | Beard et al. |
| 2006/0183779 A1 | 8/2006 | Brauns et al. |
| 2007/0232653 A1 | 10/2007 | Bachmann et al. |
| 2008/0070914 A1 | 3/2008 | Freyne et al. |
| 2009/0215724 A1 | 8/2009 | Dubois et al. |
| 2009/0215750 A1 | 8/2009 | Bamberg et al. |
| 2009/0215788 A1 | 8/2009 | Elworthy et al. |
| 2009/0264399 A1 | 10/2009 | Inoue et al. |
| 2009/0312338 A1 | 12/2009 | Wishart et al. |
| 2011/0021425 A1 | 1/2011 | Billedeau et al. |
| 2011/0190489 A1 | 8/2011 | Wishart et al. |
| 2011/0311474 A1 | 12/2011 | Wishart et al. |
| 2012/0015963 A1 | 1/2012 | Woller et al. |
| 2012/0034250 A1 | 2/2012 | Shirakami et al. |
| 2012/0330012 A1 | 12/2012 | Frank et al. |
| 2013/0072470 A1 | 3/2013 | Wishart et al. |
| 2013/0216497 A1 | 8/2013 | Wishart et al. |
| 2013/0295189 A1 | 11/2013 | Maier et al. |
| 2014/0140944 A1 | 5/2014 | Duccini et al. |
| 2014/0271842 A1 | 9/2014 | Herbig et al. |
| 2015/0118229 A1 | 4/2015 | Voss et al. |
| 2015/0210708 A1 | 7/2015 | Wishart et al. |
| 2016/0222020 A1 | 8/2016 | Wishart et al. |
| 2016/0326181 A1 | 11/2016 | Wishart et al. |
| 2017/0129902 A1 | 5/2017 | Allian et al. |
| 2017/0266289 A1 | 9/2017 | Lipari et al. |
| 2018/0057502 A1 | 3/2018 | Allian et al. |
| 2018/0162865 A1 | 6/2018 | Borchardt et al. |
| 2018/0186805 A1 | 7/2018 | Jayanth et al. |
| 2018/0291029 A1 | 10/2018 | Wishart et al. |
| 2018/0298016 A1 | 10/2018 | Pangan et al. |
| 2019/0023714 A1 | 1/2019 | Ayman et al. |
| 2019/0046527 A1 | 2/2019 | Thakkar et al. |
| 2020/0291040 A1 | 9/2020 | Allian et al. |
| 2021/0061813 A1 | 3/2021 | Wishart et al. |
| 2021/0363149 A1 | 11/2021 | Allian et al. |
| 2022/0073530 A1 | 3/2022 | Allian et al. |

FOREIGN PATENT DOCUMENTS

| | | |
|---|---|---|
| EA | 007415 B1 | 10/2006 |
| EP | 0423805 A2 | 4/1991 |
| EP | 0423805 B1 | 8/2000 |
| EP | 1097709 A2 | 5/2001 |
| EP | 1112253 B1 | 10/2004 |
| EP | 2123651 A1 | 11/2009 |
| EP | 2438909 A1 | 4/2012 |
| GB | 716327 A | 10/1954 |
| RU | 2158127 C2 | 10/2000 |
| RU | 2250904 C2 | 4/2005 |
| WO | WO-9110671 A1 | 7/1991 |
| WO | WO-9216553 A1 | 10/1992 |
| WO | WO-9222552 A1 | 12/1992 |
| WO | WO-9322314 A1 | 11/1993 |
| WO | WO-9405665 A1 | 3/1994 |
| WO | WO-9411026 A2 | 5/1994 |
| WO | WO-9419351 A1 | 9/1994 |
| WO | WO-9519970 A1 | 7/1995 |
| WO | WO-9609304 A1 | 3/1996 |
| WO | WO-9822437 A1 | 5/1998 |
| WO | WO-9833782 A1 | 8/1998 |
| WO | WO-9945009 A1 | 9/1999 |
| WO | WO-0015231 A1 | 3/2000 |
| WO | WO-0015611 A1 | 3/2000 |
| WO | WO-0031606 A2 | 6/2000 |
| WO | WO-03000695 A1 | 1/2003 |
| WO | WO-03031606 A2 | 4/2003 |
| WO | WO-2004032874 A2 | 4/2004 |
| WO | WO-2004065378 A1 | 8/2004 |
| WO | WO-2004092126 A2 | 10/2004 |
| WO | WO-2004106293 A2 | 12/2004 |
| WO | WO-2005035524 A1 | 4/2005 |
| WO | WO-2005110410 A2 | 11/2005 |
| WO | WO-2006002051 A1 | 1/2006 |
| WO | WO-2006010567 A1 | 2/2006 |
| WO | WO-2006015124 A2 | 2/2006 |
| WO | WO-2006058120 A1 | 6/2006 |
| WO | WO-2006069363 A2 | 6/2006 |
| WO | WO-2006074984 A1 | 7/2006 |
| WO | WO-2006074985 A1 | 7/2006 |
| WO | WO-2006107771 A2 | 10/2006 |
| WO | WO-2006122137 A | 11/2006 |
| WO | WO-2007007919 A2 | 1/2007 |
| WO | WO-2007022268 A2 | 2/2007 |
| WO | WO-2007035935 A1 | 3/2007 |
| WO | WO-2007061764 A2 | 5/2007 |
| WO | WO-2007077949 A1 | 7/2007 |
| WO | WO-2007079164 A2 | 7/2007 |
| WO | WO-2007143434 A2 | 12/2007 |
| WO | WO-2008019996 A2 | 2/2008 |
| WO | WO-2008021369 A2 | 2/2008 |
| WO | WO-2008063287 A2 | 5/2008 |
| WO | WO-2008084861 A1 | 7/2008 |
| WO | WO-2008094602 A2 | 8/2008 |
| WO | WO-2008112695 A2 | 9/2008 |
| WO | WO-2008121748 A2 | 10/2008 |
| WO | WO-2008124850 A1 | 10/2008 |
| WO | WO-2008135090 A1 | 11/2008 |
| WO | WO-2008139293 A1 | 11/2008 |
| WO | WO-2009005675 A1 | 1/2009 |
| WO | WO-2009011705 A1 | 1/2009 |
| WO | WO-2009106443 A1 | 9/2009 |
| WO | WO-2009108827 A1 | 9/2009 |
| WO | WO-2009152133 A1 | 12/2009 |
| WO | WO-2010003133 A2 | 1/2010 |
| WO | WO-2010099039 A1 | 9/2010 |
| WO | WO-2010117796 A2 | 10/2010 |
| WO | WO-201113082 A1 | 2/2011 |
| WO | WO-2011012540 A1 | 2/2011 |
| WO | WO-2011068881 A1 | 6/2011 |
| WO | WO-2011068899 A1 | 6/2011 |
| WO | WO-2011141791 A2 | 11/2011 |
| WO | WO-2011156543 A2 | 12/2011 |
| WO | WO-2012041814 A1 | 4/2012 |
| WO | WO-2013043826 A1 | 3/2013 |
| WO | WO-2013178752 A1 | 12/2013 |
| WO | WO-2014004863 A2 | 1/2014 |

(56) References Cited

FOREIGN PATENT DOCUMENTS

| | | |
|---|---|---|
| WO | WO-2014150289 A1 | 9/2014 |
| WO | WO-2015061665 A1 | 4/2015 |
| WO | WO-2016033308 A1 | 3/2016 |
| WO | WO-2016198983 A1 | 12/2016 |
| WO | WO-2017025849 A1 | 2/2017 |
| WO | WO-2017033093 A1 | 3/2017 |
| WO | WO-2017066775 A1 | 4/2017 |
| WO | WO-2017093857 A1 | 6/2017 |
| WO | WO-2017126488 A1 | 7/2017 |
| WO | WO-2017143014 A1 | 8/2017 |
| WO | WO-2018009566 A1 | 1/2018 |
| WO | WO-2018165581 A1 | 9/2018 |

OTHER PUBLICATIONS

Aletaha, D., et al., "2010 Rheumatoid Arthritis Classification Criteria: an American College of Rheumatology/european League Against Rheumatism Collaborative Initiative," Arthritis & Rheumatism 62(9):2569-2581, Wiley-Blackwell, United States (2010).

Allen., et al., Editors, "Ansel's Pharmaceutical Dosage Forms and Drug Delivery Systems," 9th Edition, Lippincott Williams & Wilkins, 2005 (8 pages, Table of Contents).

Anderson, J., et al., "Rheumatoid Arthritis Disease Activity Measures: American College of Rheumatology Recommendations for Use in Clinical Practice," Arthritis Care & Research 64(5):640-647, American College of Rheumatology, United States (2012).

Arnett, F.C., et al., "The American Rheumatism Association 1987 Revised Criteria for the Classification of Rheumatoid Arthritis," Arthritis and Rheumatism 31 (3):315-324, Wiley-Blackwell, United States (1988).

Banerjee, S., et al., "JAK-STAT Signaling as a Target for Inflammatory and Autoimmune Diseases: Current and Future Prospects," Drugs 77(5):521-546, Springer International, Switzerland (Mar. 2017).

Banker, G.S. and Rhodes, C.T., "Prodrugs," in Modern Pharmaceutics, Third edition, p. 596, Marcel Dekker, Inc., United States (1996).

Baslund, B., et al., "Targeting Interleukin-15 in Patients With Rheumatoid Arthritis, A Proof-of-Concept Study," Arthritis & Rheumatism 52(9):2686-2692, American College of Rheumatology, United States (2005).

Bathon, J.M., et al., "A Comparison of Etanercept and Methotrexate in Patients with Early Rheumatoid Arthritis," The New England Journal of Medicine 343(22):1586-1593, Massachusetts Medical Society, United States (2000).

Bunnage, M.E., et al., "Asymmetric Synthesis of the cis- and trans-stereoisomers of 4-arninopyrrolidine-3-Carboxylic Acid and 4-arninotetrahydrofuran-3-carboxylic Acid," Organic & Biomolecular Chemistry 2(19):2763-2776, Royal Society of Chemistry, England (2004).

Burmester, G.R., et al., "Tofacitinib (CP-690,550) in Combination with Methotrexate in Patients with Active Rheumatoid Arthritis with an Inadequate Response to Tumour Necrosis Factor Inhibitors: A Randomised Phase 3 Trial.," Lancet 381(9865):451-460, Elsevier, England (2013).

Burmester et al., "Safety and efficacy of upadacitinib in patients with rheumatoid arthritis and inadequate response to conventional synthetic disease-modifying anti-rheumatic drugs (SELECT-NEXT): a randomised, double-blind, placebo-controlled phase 3 trial," Lancet, 391(10139): 2503-2512 (2018).

Chaudhari, K., et al., "Rheumatoid Arthritis: Current and Future Trends," Nature Reviews. Drug Discovery 15(5):305-306, Macmillan Publishers Limited, England (May 2016).

Croasdell, G., "American College of Rheumatology/Association of Rheumatology Health Professionals—2015 Annual Meeting," Drugs of the Future 40(12):857-862, Prous Science S.A.U., United States (2015).

Dupre, et al., "An Improved Synthesis of Ethyl N-(methoxycarbonyl)-2,5-dihydro-IH-pyrrole-3-carboxylate," Journal of Organic Chemistry 56(9):3197-3198, (1991).

Dutta, S. and Reed, R.C., "Functional Half-Life is a Meaningful Descriptor of Steady-State Pharmacokinetics of an Extended-Release Formulation of a Rapidly Cleared Drug," Clinical Drug Investigation 26(12):681-690, Springer International, New Zealand (2006).

El-Nabi, H.A.A., et al., "1-Aryl-2-chloro-5-methoxy-1-H-3-pyrrolecarbaldehyde as synthons for fused heterocycles: synthesis of pyrazolo[3,4-d]pyrrolo[2,3-b]pyridine derivatives," Journal of Chemical Research 5:325-327, Science Reviews Ltd., England (2004).

Farnia, et al., "Stille Reaction," Organic Reactions, L. Paquette et al., Editors, John Wiley & Sons, vol. 50, 1997 5 pages, 1997 (Table of Contents).

FDA, "Clinical Pharmacology and Biopharmaceutics Review(s)—Tofacitinib," Application No. 203214Origls000, Center for Drug Evaluation and Research, 181 pages (2011).

FDA, "Guidance for Industry Toxicity Grading Scale for Healthy Adult and Adolescent Volunteers Emolled in Preventive Vaccine Clinical Trials," Department of Health and Human Services, FDA, Center for Biologies Evaluation and Research, 10 pages (2007).

FDA, "Medical Review; Addendum to Primary Clinical Review—Tofacitinib," Application No. 203214Origls000, Center for Drug Evaluation and Research, 303 pages (2012).

Fleischmann, R.M., et al., "A Randomized, Double-blind, Placebo-controlled, Twelve-week, Dose-ranging Study of Decemotinib, an Oral Selective JAK-3 Inhibitor, as Monotherapy in Patients With Active Rheumatoid Arthritis," Arthritis and Rheumatology 67(2):334-343, Wiley, United States (2015).

Gennaro, A., Editor "Remington's Pharmaceutical Sciences", 18th Edition, Mack Publishing Co., 5 pages, 1990 (Table of Contents).

Genovese, M.C., et al., "Safety and Efficacy of ABT-494, a Novel Selective JAK1 Inhibitor, in Patients with Active Rheumatoid Arthritis with an Inadequate Response to Methotrexate," Annals of the Rheumatic Diseases 75(2):141-142, Abstract OP0223, BMJ Publishing Group, England (Jun. 2016).

Genovese, M.C., et al., "Efficacy and Safety of ABT-494, a Selective JAK-1 Inhibitor, in a Phase IIb Study in Patients With Rheumatoid Arthritis and an Inadequate Response to Methotrexate," Arthritis & Rheumatology 68(12):2857-2866, Wiley, United States (Dec. 2016).

Genovese, M.C., et al., "OP0029 Baricitinib, An Oral Janus Kinase (JAK)1/JAK2 Inhibitor, in Patients with Active Rheumatoid Arthritis (RA) and an Inadequate Response to TNF Inhibitors: Results of the Phase 3 RA-Beacon Study:," Annals of the Rheumatic Diseases 74(2):75.3-76, H.K. Lewis, England (2015).

Genovese, M.C., et al., "VX-509 (Decemotinib), an Oral Selective JAK-3 Inhibitor, in Combination with Methotrexate in Patients with Rheumatoid Arthritis," Arthritis & Rheumatology 68(1):46-55, Wiley, United States (2016).

Gilworth, G., et al., "Development of a Work Instability Scale for Rheumatoid Arthritis," Arthritis and Rheumatism 49(3):349-354, Wiley-Blackwell, United States (2003).

Graff, C., et al., "Characterization of ABT-494, a Second Generation JAK1 Selective Inhibitor," 2014 ACR/ARHP Annual Meeting, Abstract No. 1499, 3 pages.

Graul, A.I., et al., "The Year's New Drugs and Biologies 2015—Part II: Trends and highlights that Marked a Complicated Year," Drugs of Today 52(2):131-163, Prous Science S.A.U., United States (Feb. 2016).

Greene, et al., Editors, "Protective Groups in Organic Synthesis," 3rd Ed., John Wiley & Sons, NY, 52 pages, 1999 (Table of Contents, Abbreviations).

Hauser, M., et al., "Pyrazolono(3,4-d)pyrimidines. II. 6-Methylpyrazolono(3,4-d)pyrimidines and some reactions of pyrazolono(3,4-d)pyrimidines," The Journal of Organic Chemistry 26(2):451-455, American Chemical Society, United States (1960).

Hirahara, K., et al., "Targeting Cytokine Signaling in Autoimmunity: Back to the Future and Beyond," Current Opinion in Immunology 43:89-97, Elsevier Ltd., England (Dec. 2016).

Iwata, S. and Tanaka, Y., "Progress in Understanding the Safety and Efficacy of Janus Kinase Inhibitors for Treatment of Rheumatoid Arthritis," Expert Review of Clinical Immunology 12(10):1047-1057, Informa UK Limited, England (Jun. 2016).

(56) References Cited

OTHER PUBLICATIONS

Jacobson, K.A., "Comprehensive Organic Transformations: A Guide to Functional Group Preparations," 2nd ed. Richard C. Larock. Wiley New York, 1999, pp. 2583.

Jain, S., et al., "A Novel Synthesis of DI(1-Methlazacycloalkeno)[2,3-b:2',3'-d]Pyridines Through Annulation on Lactam Acetals," Tetrahedron Letters 31(1):131-134, Pergamon Press PLC, Great Britain (1990).

Jenkins, et al., Editors, "Introduction to X-Ray Powder Diffractometry," John Wiley & Sons, 13 pages, 1996 (Table of Contents).

Jordan, V.C., "Tamoxifen: a most unlikely pioneering medicine," Nat Rev Drug Discov. 2(3):205-213, Nature Publishing Group, England (2003).

Kempson, J., et al., "Synthesis, initial SAR and biological evaluation of 1,6-dihydroimidazo[4,5-d]pyrrolo[2,3-b]pyridin-4-amine derived inhibitors of IkB kinase," Bioorg Med Chem Lett. <https://www.ncbi.nlm.nih.gov/pubmed?term=%22Bioorganic+%26+medicinal+chemistry+letters%22%5BJour%5D+AND+19%5Bvolume%5D+AND+2646%5Bpage%5D&cmd=detailssearch> 19(10):2646-2649, Elsevier Ltd., England (2009).

Kettle, J.G., et al., "Inhibitors of JAK-family Kinases: An Update on the Patent Literature 2013-2015, part 1," Expert Opinion on Therapeutic Patents 27(2):127-143, Informa UK Limited, England (Feb. 2017).

Keystone, E.C., et al., "Safety and Efficacy of Baricitinib at 24 Weeks in Patients with Rheumatoid Arthritis Who Have Had an Inadequate Response to Methotrexate," Annals of the Rheumatic Diseases 74(2):333-340, H.K. Lewis, England (2015).

Keystone, E.C., et al., "Certolizumab Pegol Plus Methotrexate Is Significantly More Effective Than Placebo Plus Methotrexate in Active Rheumatoid Arthritis: Findings of a Fifty-two-week, Phase III, Multicenter, Randomized, Double-blind, Placebo-controlled, Parallel-group Study," Arthritis & Rheumatology 58(11):3319-3329, Wiley, United States (2008).

Keystone, E.C., et al., "Radiographic, Clinical, and Functional Outcomes of Treatment With Adalimumab (a Human Anti-tumor Necrosis Factor Monoclonal Antibody) in Patients With Active Rheumatoid Arthritis Receiving Concomitant Methotrexate Therapy: a Randomized, Placebo-controlled, 52-week Trial," Arthritis and Rheumatism 50(5):1400-1411, Wiley-Blackwell, United States (2004).

Ko, et al., "N-Protecting Group Dependent Aromatization of 3-Pyrroline Systems to Pyrroles," Bulletin of the Korean Chemical Society 11(1):83-84, (1990).

Kremer, J.M., et al., "A Phase IIb Study of ABT-494, a Selective JAK-1 Inhibitor, in Patients with Rheumatoid Arthritis and an Inadequate Response to Anti-Tumor Necrosis Factor Therapy," Arthritis & Rheumatology 68(12):2867-2877, Wiley, United States (Nov. 2016).

Kremer, J.M., et al., "Safety and Efficacy of ABT-494, a Novel Selective JAK1 Inhibitor, in Patients with Active Rheumatoid Arthritis and Inadequate Response or Intolerance to Anti-TNF Biologic Therapy," 2015 ACR/ARHP Annual Meeting, Abstract 14L, 4 pages.

Lam, S., "Jak Inhibitors: A Broadening Approach in Rheumatoid Arthritis," Drugs of Today 52(8):467-469, Prous Science S.A.U., United States (Aug. 2016).

Larock, R.C., Editor, "Comprehensive Organic Transformations, A Guide to Functional Group Preparations," 2nd edition, Wiley-VCH, 22 pages, 1999 (Table of Contents).

Larson, G.L., et al., "Ionic and Organometallic-Catalyzed Organosilane Reductions," Organic Reactions 71:1-737, (2008).

Ma, M.H., et al., "A Systematic Comparison of Combination DMARD Therapy and Tumour Necrosis Inhibitor Therapy With Methotrexate in Patients With Early Rheumatoid Arthritis," Rheumatology 49(1):91-98, Mercury International, England (2010).

Mangoni, A.A. and Jackson, S.H., "Age-related Changes in Pharmacokinetics and Pharmacodynamics: Basic Principles and Practical Applications," British Journal of Clinical Pharmacology 57(1):42900, Wiley-Blackwell, England (2004).

MedDRA, Medical Dictionary for Regulatory Activities (MedDRA, version 17.1), http://www.meddra.ond (2014).

Menet, C.J., et al., "Progress Toward JAK1-selective Inhibitors," Future Medicinal Chemistry 7(2):203-235, Future Science Ltd., England (2015).

Mikhaleva, M.A. and Mamaev, V.P., "XXXV. 6-Hydroxypyrazolo[3,4-d]Pyrimidines," Khimiya Geterotsiklicheskikh Soedinenii, No. 12, pp. 1696-1699, Latvian Institute of Organic Synthesis, Latvia (1972).

Mohamed, M-E., et al., "Assessment of the Effect of CYP3A Inhibition, CYP Induction, OATP1B Inhibition and Administration of High-Fat Meal on the Pharmacokinetics of the Potent and Selective JAK1 Inhibitor ABT-494," 2015 ACR/ARHP Annual Meeting, Abstract 2751, 2 pages.

Mohamed, M-E., et al., "Pharmacokinetics of ABT-494 with the Once-Daily Extended-Release Tablet Formulation Being Utilized in the Ongoing Rheumatoid Arthritis Phase 3 Trials," 2016 ACR/ARHP Annual Meeting, Abstract No. 1629, 2 pages.

Mohamed, M-E., et al., "Pharmacokinetics, Safety and Tolerability of the Selective JAK1 Inhibitor, ABT-494, in Healthy Volunteers and Subjects with Rheumatoid Arthritis," Annals of the Rheumatic Diseases 74(2):258, Abstract THU0176, BMJ Publishing Group Ltd., (2015).

Mohamed, M-E., et al., "Preferential Inhibition of IL-6 Relative to IL-7 Signaling Pathways by ABT-494: Exposure-Response Analysis of Ex-Vivo Data from Two Phase 1 Clinical Trials and Comparison to Tofacitinib," Annals of the Rheumatic Diseases 75(2):256, Abstract THU0195, BMJ Publishing Group Ltd., England (Jun. 2016).

Mohamed, M-E.F., et al., "Population Pharmacokinetics of ABT-494 in Healthy Subjects and in Subjects With Rheumatoid Arthritis: Combined Analysis of Phase I and II Trials," Clinical Pharmacology & Therapeutics 101(1):S79, Abstract PII-098, John Wiley & Sons, Inc., United States (Feb. 2017).

Mohamed-Eslam, F., et al., "Pharmacokinetics, Safety and Tolerability of ABT-494, a Novel Selective JAK 1 Inhibitor, in Healthy Volunteers and Subjects with Rheumatoid Arthritis," Clinical Pharmacokinetics 55(12):1547-1558, Springer International, Switzerland (Jun. 2016).

Nakayamada, S., et al., "Chemical JAK Inhibitors for the Treatment of Rheumatoid Arthritis," Expert Opinion on Pharmacotherapy 17(16):2215-2225, Informa UK Limited, England (Oct. 2016).

Nakayamada, S., et al., "Recent Progress in JAK Inhibitors for the Treatment of Rheumatoid Arthritis," BioDrugs 30(5):407-419, Springer International, Switzerland (Aug. 2016).

Namour, F., "Pharmacokinetics and Pharmacokinetic/Pharmacodynamic Modeling of Filgotinib (GLPG0634), a Selective JAK1 Inhibitor, in Support of Phase IIb Dose Selection," Clinical pharmacokinetics 54(8):859-874, Springer Science+Business Media, Switzerland (2015).

Nayana, M.R.S., et al., "CoMFA and Docking Studies on Triazolopyridine Oxazole Derivatives as p38 MAP Kinase Inhibitors," European Journal of Medicinal Chemistry 43(6):1261-1269, Elsevier Masson SAS, France (2008).

Noble, M.E.M., et al., "Protein Kinase Inhibitors: Insights Into Drug Design From Structure," Science 303(5665):1800-1805, American Association for the Advancement of Science, United States (2004).

Norman, P., "Selective JAK Inhibitors in Development for Rheumatoid Arthritis," Expert Opinion on Investigational Drugs 23(8):1067-1077, Informa UK, Ltd., England (2014).

Olivera, P., et al., "Next Generation of Small Molecules in Inflammatory Bowel Disease," Gut 66(2):199-209, British Medical Assn, England (Feb. 2017).

Paulus, E.F. and Rivo, E., "1-Phenyl-3-carbethoxy-4-hydroxypyrroline," Acta Crystallographica C44:1242-1244, (1988).

Rochais, C., et al., "Synthesis of new dipyrrolo- and furopyrrolopyrazinones related to tripentones and their biological evaluation as potential kinases (CDKs1-5, GSK-3) inhibitors," Eur J Med Chem. 44(2):708-716, Elsevier Masson SAS, France (2009).

Rowe, et al., Editors, "Handbook of Pharmaceutical Excipients," 7th Ed., Pharmaceutical Press, 7 pages 2012 (Table of Contents).

Rowe, R.C., et al., "Handbook of Pharmaceutical Excipients—7th Edition," Pharmaceutical Development and Technology, 18(2):544, Informa Healthcare USA, Inc., United States (2013).

(56) References Cited

OTHER PUBLICATIONS

Sahin, S. and Benet, L.Z., "The Operational Multiple Dosing Half-life: A Key to Defining Drug Accumulation in Patients and to Designing Extended Release Dosage Forms," Pharmaceutical Research 25(12):2869-2877, Kluwer Academic/Plenum Publishers, United States (2008).
Sandborn, W.J., "The Present and Future of Inflammatory Bowel Disease Treatment," Gastroenterology & Hepatology 12(7):438-441, Gastro-Hep Communications, United States (Jul. 2016).
Schram, K.H., et al., "Tricyclic nucleosides I. Synthesis of the new tricyclic ring system tetrazolo[1,5-c]pyrrolo[2,3-d]pyrimidine and certain tetrazolo[],5-c] pyrrolo[2,3-d] pyrimidine ribonucleosides," Journal of Heterocyclic Chemistry 12:1021-1023, Journal of Heterocyclic Chemistry, United States (1975).
Schwartz, D.M., et al., "Type I/II Cytokines, JAKs, and New Strategies for Treating Autoimmune Diseases," Nature Reviews. Rheumatology 12(1):25-36, Macmillan Publishers Limited, United States (Jan. 2016).
Scott, I.C and Scott, D., "Joint Counts in Inflammatory Arthritis," Clinical and Experimental Rheumatology 32(85):S7-S12, (2014).
Semerano, L., et al., "Developments with Investigational Janus Kinase Inhibitors for Rheumatoid Arthritis," Expert Opinion on Investigational Drugs 25(12):1355-1359, Informa UK Limited, England (Oct. 2016).
Semerano, L., et al., "Novel Immunotherapeutic Avenues for Rheumatoid Arthritis," Trends in Molecular Medicine 22(3):214-229, Elsevier Science Ltd., England (Mar. 2016).
Singh, J.A., et al., "2012 Update of the 2008 American College of Rheumatology Recommendations for the Use of Disease-Modifying Antirheumatic Drugs and Biologic Agents in the Treatment of Rheumatoid Arthritis," Arthritis Care & Research 64(5):625-639, John Wiley & Sons, United States (2012).
Sivaraman, P. and Cohen, S.B., "Malignancy and Janus Kinase Inhibition," Rheumatic Diseases Clinics of North America 43(1):79-93, Elsevier Inc., United States (Feb. 2017).
Smolen, J., et al., "EULAR recommendation for the management of rheumatoid arthritis with synthetic and biological disease-modifying antirheumatic drugs," Annals of the Rheumatic Diseases 69(6):964-975, BMJ, England (2010).
Smolen, J.S., et al., "Eular Reconnnendations for the Management of Rheumatoid Arthritis With Synthetic and Biological Disease-modifying Antirheumatic Drugs: 2013 Update," Annals of the Rheumatic Diseases 73(3):492-509, H.K. Lewis, England (2014).
Solomon, D.H. and Bucala, R.J., "The Enduring Value of Reporting Randomized Controlled Clinical Trials in *Arthritis & Rheumatology*: 2016 and Beyond," Arthritis & Rheumatology 68(12):2831-2833, American College of Rheumatology, United States (Aug. 2016).
Stahl, et al., Editors "IUPAC Handbook of Pharmaceutical Salts: Properties, Selection, and Use," Wiley-VCH, Weinheim, Geffilany, 5 pages (2002) (Table of Contents).
Stella, V.J., et al., "A Case for Prodrugs," in Prodrugs: Challenges and Rewards Part 1, p. 24, American Association of Pharmaceutical Sciences, United States (2007).
Strand, V., et al., "Sustained Benefit in Rheumatoid Arthritis Following One Course of Rituximab: Improvements in Physical Function Over 2 Years," Rheumatology 45(12):1505-1513, Mercury International, England (2006).
Trost, B.M., et al., "Palladium-catalyzed DYKAT of Vinyl Epoxides: Enantioselective Total Synthesis and Assignment of the Configuration of (+)-Broussonetine G," Angewandte Chemie 42(48):5987-5990, Wiley-VCH, Germany (2003).
Van Epps, S., et al., "Design and synthesis of tricyclic cores for kinase inhibition," Bioorg Med Chem Lett. 23(3):693-698, Elsevier Ltd., England (2013).
Van Vollenhoven, R.F., et al., "THU0178 Relationship Between NK Cell Count and Important Safety Events in Rheumatoid Arthritis Patients Treated with Tofacitinib," Annals of the Rheumatic Diseases 74(2):258-259, H.K. Lewis, England (2015).
Wang, G.T., et al., "Design, Synthesis, and Structural Analysis of Influenza Neuraminidase Inhibitors Containing Pyrrolidine Cores," Journal of Medicinal Chemistry 44(8):1192-1201, American Chemical Society, United States (2001).
Winthrop, K.L., "The Emerging Safety Profile of JAK Inhibitors in Rheumatic Disease," Nature Reviews. Rheumatology 13(4):234-243, Macmillan Publishers Limited, United States (Apr. 2017).
Wolff, M.E., "Some Considerations for Prodrug Design," in Burger's Medicinal Chemistry and Drug Discovery, Fifth Edition, vol. 1: Principles and Practices, pp. 975-977, John Wiley and Sons, United States (1995).
Woodworth, T., et al., "Standardizing Assessment and Reporting of Adverse Effects in Rheumatology Clinical Trials II: The Rheumatology Common Toxicity Criteria V.2.0.," The Journal of Rheumatology 34(6):1401-1414, Journal of Rheumatology Publishing Co, Canada (2007).
Wormser, H. C., "Synthesis of Azabiotin Analogs as Potential Cofactors for Biotin-dependent Enzymes," Journal of Pharmaceutical Sciences 59(12):1732-1737, Elsevier, United States (1970).
International Search Report and Written Opinion for International Application No. PCT/US2016/057372, European Patent office, Netherlands, dated Feb. 13, 2017, 13 pages.
Stahl, P.H., et al., Chapters 7, 8, and 10 in Handbook of Pharmaceutical Salts, Stahl, P.H., et al., eds., pp. 161-189, 191-220, 237-247, 330-350, Verlag Helvetica Chimica Acta, Switzerland (2002).
AbbVie Announces Positive Phase 2 Study Results for Upadacitinib (ABT-494), an Investigational JAK1-Selective Inhibitor, in Crohn's Disease (May 9, 2017), accessed at https://news.abbvie.com/news/press-releases/abbvie-announces-positive-phase-2-study-results-for-upadacitinib-abt-494-an-investigational-jak1-selective-inhibitor-in-crohns-disease.htm, accessed on Dec. 18, 2017, 3 pages.
AbbVie's Upadacitinib (ABT-494) Meets All Primary and Ranked Secondary Endpoint in Phase 3 Study in Rheumatoid Arthritis (Jun. 7, 2017), accessed at https://news.abbvie.com/news/abbvies-upadacitinib-abt-494-meets-all-primary-and-ranked-secondary-endpoints-in-phase-3-study-in-rheumatoid-arthritis.htm, accessed on Dec. 18, 2017, 4 pages.
AbbVie's Upadacitinib (ABT-494) Meets All Primary and Ranked Secondary Endpoint in Second Phase 3 Study in Rheumatoid Arthritis (Sep. 11, 2017), accessed at https://news.abbvie.com/alert-topics/immunology/abbvies-upadacitinib-abt-494-meets-all-primary-and-ranked-secondary-endpoints-in-second-phase-3-study-in-rheumatoid-arthritis.htm, accessed on Dec. 18, 2017, 4 pages.
AbbVie's Upadacitinib Granted Breakthrough Therapy Designation from the U.S. Food and Drug Administration for Atopic Dermatitis (Jan. 8, 2018), accessed at https://news.abbvie.com/news/abbvies-upadacitinib-granted-breakthrough-therpy-designation-from-food-and-drug-administration-for-atopic-dermatitis.htm, accessed on Aug. 1, 2018, 2 pages.
Amended Pleadings on Behalf of the Opponent in Opposition to Israel Patent Application 248466, mailed on Mar. 26, 2018, 12 pages.
Annex A—Relative IC50 Values for Compounds of Formula I(c), submitted in European Application No. EP10835061.2-1462, dated Nov. 7, 2014, cited as Document TM3 in Opposition to European Patent EP2506 716, mailed on Feb. 16, 2018, 10 pages.
Product Label: "SEPINEO P 600", XP002744402, accessed at http://gyermedhu/pdf/3664_Leaftet_Sepineo_P600_gb.pdf, accessed on Apr. 2008, pp. 1-2.
International Search Report and Written Opinion for International Application No. PCT/US2014/047152, International Search Authority, United States, dated Dec. 19, 2014, 7 pages.
Bannister, M.J. and Freeman, S., "Adult-onset Atopic Dermatitis," Australasian Journal of Dermatology 41(4):225-228 (Nov. 2000).
Burmester, G.R., et al., "A Phase 3 Randomized, Placebo-Controlled, Double-Blind Study of Upadacitinib (ABT-494), a Selective JAK-1 Inhibitor, in Patients with Active Rheumatoid Arthritis with Inadequate Response to Conventional Synthetic Dmards," 2017 ACR/ARHP Annual Meeting, Abstract No. 1904, United States, 5 pages (2017).

(56) References Cited

OTHER PUBLICATIONS

Chamlin, S.L., et al., "The Price of Pruritus: Sleep Disturbance and Cosleeping in Atopic Dermatitis," Archives of Pediatrics & Adolescent Medicine 159(8):745-750, American Medical Association, United States (Aug. 2005).
Cotter, D.G., et al., "Emerging Therapies for Atopic Dermatitis: JAK Inhibitors," Journal of the American Academy of Dermatology 78(3S1):S53-S62, Mosby, United States (Mar. 2018).
Ellis, C.N., et al., "Understanding and Managing Atopic Dermatitis in Adult Patients," Seminars in Cutaneous Medicine and Surgery 31(3 Suppl):S18-S22, Frontline Medical Communications, United States (Sep. 2012).
Fraser, K.A., American Academy of Dermatology Annual Meeting: San Diego, CA, USA, Feb. 16-20, 2018, American Journal of Clinical Dermatology, vol. 19 (2), pp. 287-290 (Apr. 2018).
Genovese, M.C., "Long-Term Safety and Efficacy of Upadacitinib (ABT-494), an Oral JAK-1 Inhibitor in Patients with Rheumatoid Arthritis in an Open Label Extension Study," 2017 ACR/ARHP Annual Meeting, Abstract No. 509, 4 pages.
Goedken, E.R, et al., "Minimum Significant Ratio of Selectivity Ratios (MSRSR) and Confidence in Ratio of Selectivity Ratios (CRSR): Quantitative Measures for Selectivity Ratios Obtained by Screening Assays," Journal of Biomolecular Screening 17(7):857-867, Sage Publications, United States (Apr. 2012).
Grebien, F., et al., "Stat5 Activation Enables Erythropoiesis in the Absence of EpoR and Jak2," Blood 111(9):4511-4522, American Society of Hematology, United States (May 2008).
Guschin, D., et al., "A Major Role for the Protein Tyrosine Kinase JAL1 in the JAK/STAT Signal Transduction Pathway in Response to lnterleukin-6," The EMBO Journal 14(7):1421-1429, Wiley Blackwell, England (Apr. 1995).
Hanifin, J.M. and Rajka, G., "Diagnostic Features of Atopic Dermatitis," Acta Dermatovener 60(92):44-47 (1980).
Hanifin, J.M., et al., "A Population-based Survey of Eczema Prevalence in the United States," Dermatitis 18(2):82-91, Lippincott Williams & Wilkins, United States (Jun. 2007).
Klunder, B., et al., "Exposure-Response Analyses of the Effect of Upadacitinib on ACR Responses in th Phase 2b Rheumatoid Arthritis Trials in Patients with Inadequate Response to Methotrxate or to Anti-Tumor Necrosis Factor Therapy," 2017 ACR/ ARHP Annual Meeting, Abstract No. 505, 4 pages (2017).
Merriam-Webster: Metabolite, accessed at https://www.merriam-webster.com/dictionary/metabolite, accessed on Dec. 2013.
Mohamed, M.E.F., et al., "ABT-494 Pharmacokinetics Following Administration of the Once-Daily Extended-Release Tablet Formulation Being Utilized in the Ongoing Rheumatoid Arthritis Phase 3 Trials," Annals of the Rheumatic Diseases, Abstract No. THU0177, 2 pages (Jun. 2017).
Mohamed, M.F., et al., "Assessment of Effect of CYP3A Inhibition, CYP Induction, OATP1B Inhibition, and High-fat Meal on Pharmacokinetics of the JAK1 Inhibitor Upadacitinib," British Journal of Clinical Pharmacology 83(10):2242-2248, Wiley-Blackwell, England (Oct. 2017).
Mohamed, M.E.F., et al., "ABT-494 Has no Effect on the QT Interval at the Doses Being Evaluated in Rheumatoid Arthritis Phase 3 Trials," Annals of the Rheumatic Diseases, Abstract No. AB0432, 1 page (Jun. 2017).
Mohamed, M.E.F., "Exposure-Response Analysis to Assess the Effect of ABT-494 on QT Interval and Utilization of a Non-Pharmacological Approach to Demonstrate ECG Assay Sensitivity," Clinical Pharmacology & Therapeutics 101(S1):S39, Abstract PI-076, John Wiley & Sons, Inc., United States (Feb. 2017).
Mohamed, M.E.F., et al., "Use of Early Clinical Trial Data to Support Thorough QT Study Waiver for Upadacitinib and Utility of Food Effect to Demonstrate ECG Assay Sensitivity," Clinical Pharmacology & Therapeutics, 7 pages, John Wiley & Sons, Inc., United States (Jul. 2017).
Mohamed, M.E.F., et al., "The Selective JAK1 Inhibitor Upadacitinib has no Effect on Pharmacokinetics of the Hormonal Contraceptives Levonorgesrel and Ethinylestradiol," 2017 ACR/ARHP Annual Meeting, Abstract No. 506, 4 pages (Sep. 2017).
Neubauer, H., et al., "JAK2 Deficiency Defines an Essential Developmental Checkpoint in Definitive Hematopoiesis," Cell 93(3):397-409, Cell Press, United States (May 1998).
International Search Report and Written Opinion for International Application No. PCT/US2014/062145, European Patent Office, Netherlands, dated Jan. 22, 2015, 13 pages.
Notice of Opposition for European Patent Application No. EP2506716, mailed on Feb. 16, 2018, 5 pages.
Nygaard, U., et al., "Emerging Treatment Options in Atopic Dermatitis: Systemic Therapies," Dermatology 233(5):344-357, Karger, Switzerland (2017).
Opposition Brief for European Patent Application No. EP2506716, mailed on Feb. 16, 2018, 16 pages.
Ortmann, R.A., et al., "Janus Kinases and Signal Transducers and Activators of Transcription: Their Roles in Cytokine Signaling, Development and Immunoregulation," Arthritis Research 2(1):16-32, BioMed Central Ltd, England (Dec. 1999).
AbbVie's Upadacitinib Meets All Primary and Ranked Secondary Endpoint including Superiority versus Adalimumab in Phase 3 Study in Rheumatoid Arthritis (Apr. 9, 2018), accessed at https://news.abbvie.com/article_print.cfm?article_id=11629, accessed on Aug. 1, 2018, 5 pages.
Response to Communication pursuant to Art. 94(3) EPC dated Jul. 12, 2016, submitted in European Application No. EP10835061.2-1462, cited as Document TM4 in Opposition to European Patent EP2506716, mailed on Feb. 16, 2018, 3 pages.
"Rituximab," in The Merck Index. 14th Ed., John Wiley & Sons, 2006; p. 1422.
Schwartz, D.M., et al., "JAK Inhibition as a Therapeutic Strategy for Immune and Inflammatory Diseases," Nature Reviews. Drug discovery 16(12):843-862, Nature Pub. Group, England (Dec. 2017).
SEPPIC: "How to use Sepineo P600 in a formulation", XP054976186, accessed at https://www.youtube.com/watch?v=SHiwvwnx1tA, access on Aug. 30, 2012, 1 page.
Silverberg, J.I. and Simpson, E.L., "Association Between Severe Eczema in Children and Multiple Comorbid Conditions and Increased Healthcare Utilization," Pediatric Allergy and Immunology 24(5):476-486, Blackwell Publishing, England (Aug. 2013).
Statement of Case in Opposition for Israel Patent Application 248466, mailed on Nov. 23, 2017, 4 pages.
Strand, V., et al., "Changes in Hemoglobin levels upon Treatment with ABT-494, a Selective JAK-1 Inhibitor and relation to baseline levels of C-Reactive Protein," THU0210, p. 283 (Jun. 2017).
Strand, V., et al., "Early Patient-Reported Outcomes and Clinical Outcomes with ABT-494 in Patients with Active Rheumatoid Arthritis who are Inadequate Responses to Methotrexate or Tumor Necrosis Factor Inhibitors: Post-Hoc Analysis of Phase 2 Randomized Controlled Trials," Annals of the Rheumatic Diseases, Abstract No. SAT0217, Jun. 2017, 1 page.
Strand, V., et al., "Economic Burden of Non-Responders to Biologic DMARD Treatments in Rheumatoid Arthritis," 2016 ACR/ARHP Annual Meeting, Abstract No. 2617, 2 pages (2016).
Strand, V., et al., "Patient-Reported Outcomes of Long-Term Upadacitinib Use in Patients with Rheumatoid Arthritis: Interim Analysis Results of a Phase 2, Open-Label Extension Study," 2017 ACR/ARHP Annual Meeting, Abstract No. 501, 3 pages (2017).
Torres, T., "Atopic Dermatitis: The New Therapeutic Revolution in Dermatology," Acta medica portuguesa 30(10):669-670, Lisboa, Portugal (Oct. 2017).
Voss, J., et al., "THU0127 Pharmacodynamics of a Novel JAK1 Selective Inhibitor in Rat Arthritis and Anemia Models and in Healthy Human Subjects," 2013 ACR/ARHP Annual Meeting, Abstract No. 2374, 4 pages.
Weiss, G. and Goodnough, L.T., "Anemia of Chronic Disease," The New England Journal of Medicine 352:1011-1023, Massachusetts Medical Society, United States (Mar. 2005).
Wermuth, C., et al., "Molecular Variations D Based on Isoteric Replacements," in The Practice of Medicinal Chemistry, Chapter 13, pp. 203-237, Academic Press, London (1996).
Williams, H.C. and Wuthrich, B., The Natural History of Atopic Dermatitis, Supplied by the British Library, pp. 41-59 (Apr. 2018).

(56) References Cited

OTHER PUBLICATIONS

Williams, H.C., "Atopic Dermatitis," The New England Journal of Medicine 352(22):2314-2324, Massachusetts Medical Society, United States (Jun. 2005).
International Search Report and Written Opinion for International Application No. PCT/US2018/021800, European Patent Office, Netherlands, dated May 23, 2018, 23 pages.
International Search Report and Written Opinion for International Application No. PCT/US2009/046714, European Patent Office, Netherlands, dated Aug. 13, 2009, 10 pages.
International Search Report and Written Opinion for International Application No. PCT/US2010/058572, European Patent office, Netherlands, dated Feb. 2, 2011, 10 pages.
Inami, M., "Small molecule drug development beyond biologies: Kinase inhibitors as an approach to autoimmune disease treatment," Folia Pharmacologica Japonica (2013) 142:63-67. With English certified language translation dated Jun. 17, 2019, 13 pages.
Kranz, H. et al., "Development of a single unit extended release formulation for ZK 811 752, a weakly basic drug," European Journal of Pharmaceutical Sciences 26 (2005) 47-53.
Search results of Upadacitinib in File Registry Database of STN® Search from Chemical Abstracts Service (CAS) conducted on May 4, 2020.
Caira, M.R., "Crystalline Polymorhism of Organic Compounds", Topics in Current Chemistry, v. 198, Chapter 3.1, p. 188, paragraph 2 (1998).
AbbVie's Upadacitinib (ABT-494) meets Primary Endpoint in Phase 2b Study in Atopic Dermatitis (Sep.7, 2017), accessed at https://news.abbvie.com/news/abbvies-upadacitinib-abt-494-meets-primary-endpoint-in-phase-2b-study-in-atopic-dermatitis.htm, accessed on Dec. 18, 2017, 3 pages.
Alamanos et al. "Epidemiology of psoriatic arthritis in northwest Greece, 1982-2001," J Rheumatol, 30(12): 2641-2644 (2003).
Alten et al., "Examining patient preferences in the treatment of rheumatoid arthritis using a discrete-choice approach," Patient Prefer Adherence, 10: 2217-2228 (2016).
Aviel et al., "Juvenile Psoriatic Arthritis (JPsA): juvenile arthritis with psoriasis?" Pediatric Rheumatology, 11:11 (2013). https://doi.mg/10.-1186/1546-0096-•17-11.
Bozek et al., "The reliability of three psoriasis assessment tools: Psoriasis area and severity index, body surface area and physician global assessment," Advances in Clinical and Experimental Medicine, 26:851-856 (2017).
Coates et al., "Group for Research and Assessment of Psoriasis and Psoriatic Arthritis 2015 Treatment Recommendations for Psoriatic Arthritis," Arthritis & Rheumatology, 68(5): 1060-1071 (2016). https://doi.org/10.1002/art.39573.
Cohen et al., "THU0167 Safety Profile of Upadacitinib in Rheumatoid Arthritis: Integrated Analysis from the Select Phase 3 Clinical Program," Annals of the Rheumatic Diseases, 78: 357 (2019).
Cortese et al., "Secukinumab may be a valid treatment option in patients with CNS demyelination and concurrent ankylosing spondylitis: Report of two clinical cases," Multiple Sclerosis and Related Disorders, 35: 193-195 (2019).
Deodhar et al., "The Concept of Axial Spondyloarthritis," Arthritis & Rheumatology, 66(10): 2649-2656 (2014).
Deodhar et al., "Three Multicenter, Randomized, Double-Blind, Placebo-Controlled Studies Evaluating the Efficacy and Safety of Ustekinumab in Axial Spondyloarthritis," Arthritis and Rheumatology, 71(2): 258-270 (2019).
Deodhar et al., "Efficacy and Safety of Ixekizumab in the Treatment of Radiographic Axial Spondyloarthritis: Sixteen-Week Results From a Phase III Randomized, Double-Blind, Placebo-Controlled Trial in Patients With Prior Inadequate Response to or Intolerance of Tumor Necrosis Factor Inhibitors," Arthritis & Rheumatology, 71(4): 599-611.
Feld et al., "Axial disease in psoriatic arthritis and ankylosing spondylitis: a critical comparison," Nature Reviews, Rheumatology, 14(6): 363-371 (2018). doi: 10.1038/s41584-018-0006-8.
Feldman et al., "The Self-Administered Psoriasis Area and Severity Index Is Valid and Reliable," J; Investigative Dermatology, 106(1): 183-186 (1996).
Fleischmann et al., "Upadacitinib versus placebo or adalimumab in patients with rheumatoid arthritis and an inadequate response to methotrexate: results of a phase III, double-blind, randomized controlled trial," Arthritis & Rheumatology,71(11): 1788-1800 (2019). [Epub ahead of print, 13 pages] doi: 10.1002/art.41032.
Fragoulis et al., "Inflammatory bowel diseases and spondyloarthropathies: From pathogenesis to treatment," World Journal of Gastroenterology, 25(18): 2162-2176 (2019).
Furst et al., "Targeting inflammatory pathways in axial spondyloarthritis," Arthritis Research and Therapy, 21: 135 (2019). https://doi.org/10.1186/s13075-019-1885-z.
Genovese et al., "Safety and efficacy of upadacitinib in patients with active rheumatoid arthritis refractory to biologic disease-modifying anti-rheumatic drugs (SELECT-BEYOND): a double-blind, randomised controlled phase 3 trial," Lancet, 391(10139): 2513-2524 (2018).
Ghoreschi et al., "Janus Kinases in immune cell signaling," Immunological Reviews, Special Issue: Kinases & Phosphatases of the Immune System, 228(1): 273-287 (2009).
Gladman et al., "Tofacitinib for Psoriatic Arthritis in Patients with an Inadequate Response to TNF Inhibitors," New England Journal of Medicine, 377(16): 1525-1536 (2017).
Glintborg et al., "Clinical response, drug survival and predictors thereof in 432 ankylosing spondylitis patients after switching tumour necrosis factor a inhibitor therapy: results from the Danish nationwide DANBIO registry," Annals of Rheumatic Diseases, 72(7): 1149-1155 (2013).
Gossec et al., "European League Against Rheumatism (EULAR) recommendations for the management of psoriatic arthritis with pharmacological therapies: 2015 update," Annals of Rheumatic Diseases, 75(3): 499-510 (2016).
Gracey et al., "IL-7 primes IL-17 in mucosal-associated invariant T (Mait) cells, which contribute to the Th1 7-axis in ankylosing spondylitis," Annals of Rheumatic Diseases, 75(12): 2124-2132 (2016);.
Ismail et al., "Exposure-Response Analysis for Upadacitinib Efficacy and Safety in Ankylosing Spondylitis—Analyses of the SELECT-AXIS I Study," ACR Meeting Abstract No. 1492. Arthritis Rheumatology, 71(10) (2019).
Landewe et al., "Efficacy of certolizumab pegol on signs and symptoms of axial spondyloarthritis including ankylosing spondylitis: 24-week results of a double-blind randomised placebo-controlled Phase 3 study," Annals of Rheumatic Diseases, 73(1): 39-47 (2014).
Lauter, J., "Book Review of Hochberg et al., Multiple comparison procedures, John Wiley & Sons, Inc., 1987," in Biomedical Journal, 31, 1, 122 (1989).
Lie et al., "Effectiveness of switching between TNF inhibitors in ankylosing spondylitis: data from the NOR-DMARD register," Annals of Rheumatic Diseases, 70(1): 157-163 (2011).
Machado et al., "Ankylosing Spondylitis Disease Activity Score (ASDAS): 2018 update of the nomenclature for disease activity states," Annals of Rheumatic Diseases, 77(10): 1539-1540 (2018).
Maksymowych et al., "Spondyloarthritis research consortium of canada magnetic resonance imaging index for assessment of spinal inflammation in ankylosing spondylitis," Arthritis & Rheumatism (Arthritis Care & Research), 53(4): 502-509 (2005).
Mease et al. "Tofacitinib or Adalimumab versus Placebo for Psoriatic Arthritis," New England Journal of Medicine, 377(16): 1537-1550 (2017).
Mease et al. "Ixekizumab, an interleukin-17A specific monoclonal antibody, for the treatment of biologic-naive patients with active psoriatic arthritis: results from the 24-week randomised, double-blind, placebo-controlled and active (adalimumab)-controlled period of the phase III trial SPIRIT-PI," Annals of Rheumatic Diseases, 76(1):79-87 (2017).
Mease, P.J., "Inhibition of interleukin-17, interleukin-23 and the TH1 7 cell pathway in the treatment of psoriatic arthritis and psoriasis," Current Opinion in Rheumatology, 27(2): 127-133 (2015).
Nash et al., "Ixekizumab for the treatment of patients with active psoriatic arthritis and an inadequate response to tumour necrosis factor inhibitors: results from the 24-week randomised, double-

(56) References Cited

OTHER PUBLICATIONS blind, placebo-controlled period of the SPIRIT-P2 phase 3 trial," Lancet, 389(10086): 2317-2327 (2017).
Nestle et al., "Mechanisms of Disease, Psoriasis," New England Journal of Medicine, 361:496-509 (2009).
Perrotta et al., "Minimal Disease Activity and Remission in Psoriatic Arthritis Patients Treated with Anti-TNF-a Drugs," J Rheumatology, 43(2): 350-355 (2016).
Petty et al., "International League of Associations for Rheumatology classification of juvenile idiopathic arthritis: second revision, Edmonton, 2001," Journal of Rheumatology, 31(2): 390-392 (2004).
Poddubnyy et al., "Similarities and differences between nonradiographic and radiographic axial spondyloarthritis: a clinical, epidemiological and therapeutic assessment," Current Opinion in Rheumatology, 26(4): 377-383 (2014).
Poddubnyy et al., "Comparison of a high sensitivity and standard C reactive protein measurement in patients with ankylosing spondylitis and non-radiographic axial spondyloarthritis," Annals of Rheumatic Diseases, 69(7): 1338-1341 (2010).
RINVOQ1m (upadacitinib) Meets Primary and All Ranked Secondary Endpoints in Phase 3 Study in Psoriatic Arthritis, AbbVie News Release, dated Oct. 31, 2019, retrieved from hitps:/inews.abbvie.com/article_print.cfm?article_id=1874.
Rudwaleit et al., "The development of Assessment of SpondyloArthritis international Society classification criteria for axial spondyloarthritis (part II): validation and final selection," Annals of Rheumatic Diseases, 68: 777-783 (2009).
Rudwaleit et al., "Effectiveness and safety of adalimumab in patients with ankylosing spondylitis or psoriatic arthritis and history of anti-tumor necrosis factor therapy," Arthritis Research & Therapy, 12: R117 (2010).
Saber et al., "Remission in psoriatic arthritis: is it possible and how can it be predicted?," Arthritis Research & Therapy, 12: R94 (2010).
Sandborn W.J., "State-of-the-Art: Immunosuppression and Biologic Therapy," Digestive Diseases, 28(3): 536-542 (2010).
Savolainen et al., J Rheumatol, "Total incidence and distribution of inflammatory joint diseases in a defined population: results from the Kuopio 2000 arthritis survey," 30(11): 2460-2468 (2003).
Sieper et al., "Axial spondyloarthritis," Lancet, 390(10089): 73-84 (2017).
Sieper et al., "The Assessment of SpondyloArthritis international Society (ASAS) handbook: a guide to assess spondyloarthritis," Annals of Rheumatic Diseases, 68 Suppl 2:iil-44 (2009). doi: 10.1136/ard.2008.104018.
Sieper et al., "Secukinumab efficacy in anti-TNF-naive and anti-TNF-experienced subjects with active ankylosing spondylitis: results from the MEASURE 2 Study," Annals of Rheumatic Diseases, 76(3): 571- 592 (2017).
Sieper et al., "Assessment of short-term symptomatic efficacy of tocilizumab in ankylosing spondylitis: results of randomised, placebo-controlled trials," Annals of Rheumatic Diseases, 73(1): 95-100 (2014).
Sieper et al., "Sarilumab for the treatment of ankylosing spondylitis: results of a Phase II, randomised, double-blind, placebo-controlled study (ALIGN)," Annals of Rheumatic Diseases, 74(6): 1051-1057 (2015).
Smolen et al., "Treating axial spondyloarthritis and peripheral spondyloarthritis, especially psoriatic arthritis, to target: 2017 update of recommendations by an international task force," Annals of Rheumatic Diseases, 77(1): 3-17 (2018).
Song et al., "Treatment of active ankylosing spondylitis with abatacept: an open-label, 24-week pilot study," Annals of Rheumatic Diseases, 70(6): 1108-1110 (2011).

Sornasse et al., "THU0181 Treatment with Upadacitinib Results in the Normalization of Key Pathobiologic Pathways in Patients with Rheumatoid Arthritis: Biomarker Results from the Phase 3 Select-Next and Select-Beyond Studies," Annals of Rheumatic Diseases, 78(Supp2): 365-366 (2019).
Stahl et al., Editors, Handbook of Pharmaceutical Salts: Properties, Selection, and Use (Wiley-VCR, Weinheim, Germany, 2002) (Table of Contents only).
Taylor et al., "Classification criteria for psoriatic arthritis: Development of new criteria from a large international study," Arthritis & Rheumatology, 54(8): 2665-2673 (2006).
Torgutalp et al., "Emerging treatment options for spondyloarthritis," Best Practice & Research Clinical Rheumatology, 32(3): 472-484 (2018).
Van Der Heijde et al., "Limited radiographic progression and sustained reductions in MRI inflammation in patients with axial spondyloarthritis: 4-year imaging outcomes from the RAPID-axSpA phase III randomized trial," Annals of Rheumatic Diseases, 0: 1-8 (2018) doi:10.1136/annrheumdis-2017-212377.
Van Der Heijde et al., "Efficacy and Safety of Upadacitinib in a Randomized Double-Blind, Placebo-Controlled, Multicenter Phase 2/3 Clinical Study of Patients with Active Ankylosing Spondylitis," ACR Meeting Abstract No. 2728. Arthritis Rheumatol., 71(10) (2019).
Van Der Heijde et al., "2016 update of the ASAS-EULAR management recommendations for axial spondyloarthritis," Annals of Rheumatic Diseases, 76(6): 978-991 (2017).
Van Der Heijde et al., "Efficacy and safety of filgotinib, a selective Janus kinase 1 inhibitor, in patients with active ankylosing spondylitis (TORTUGA): results from a randomised, placebo-controlled, phase 2 trial," Lancet, 392(10162): 2378-2387 (2018).
Van Der Heijde et al., "Ixekizumab, an interleukin-17A antagonist in the treatment of ankylosing spondylitis or radiographic axial spondyloarthritis in patients previously untreated with biological disease-modifying anti-rheumatic drugs (COAST-V): 16 week results of a phase 3 randomised, double-blind, active-controlled and placebo-controlled trial," Lancet 392(10163): 2441-2451 (2018).
Van Der Heijde et al., "Proposal of a linear definition of the Bath Ankylosing Spondylitis Metrology Index (BASMI) and comparison with the 2-step and 10-step definitions," Annals of Rheumatic Diseases, 67(4): 489-493 (2008).
Van Der Heijde et al., "Tofacitinib in patients with ankylosing spondylitis: a phase II, 16-week, randomised, placebo-controlled, dose-ranging study," Annals of Rheumatic Diseases, 76(8): 1340-1347 (2017).
Van Der Heijde et al., "Comparison of three methods for calculating the Bath Ankylosing Spondylitis Metrology Index in a randomized placebo-controlled study," Arthritis Care & Research, 64(12): 1919-1922 (2012).
Van Der Linden et al., "Evaluation of diagnostic criteria for ankylosing spondylitis," Arthritis and Rheumatism, 27(4): 361-368 (1984).
Veale et al., "The rationale for Janus kinase inhibitors for the treatment of spondyloarthritis," Rheumatology, 58(2): 197-205 (2019).
Ward et al., "American College of Rheumatology/Spondylitis Association of America/Spondyloarthritis Research and Treatment Network 2015 Recommendations for the Treatment of Ankylosing Spondylitis and Nomadiographic Axial Spondyloarthritis," Arthritis Rheumatol, 68(2): 282-298 (2016).
Zisman et al., "The juvenile psoriatic arthritis cohort in the CARRA registry: clinical characteristics, classification, and outcomes," Journal of Rheumatology, 44(3): 342-351 (2017).

* cited by examiner

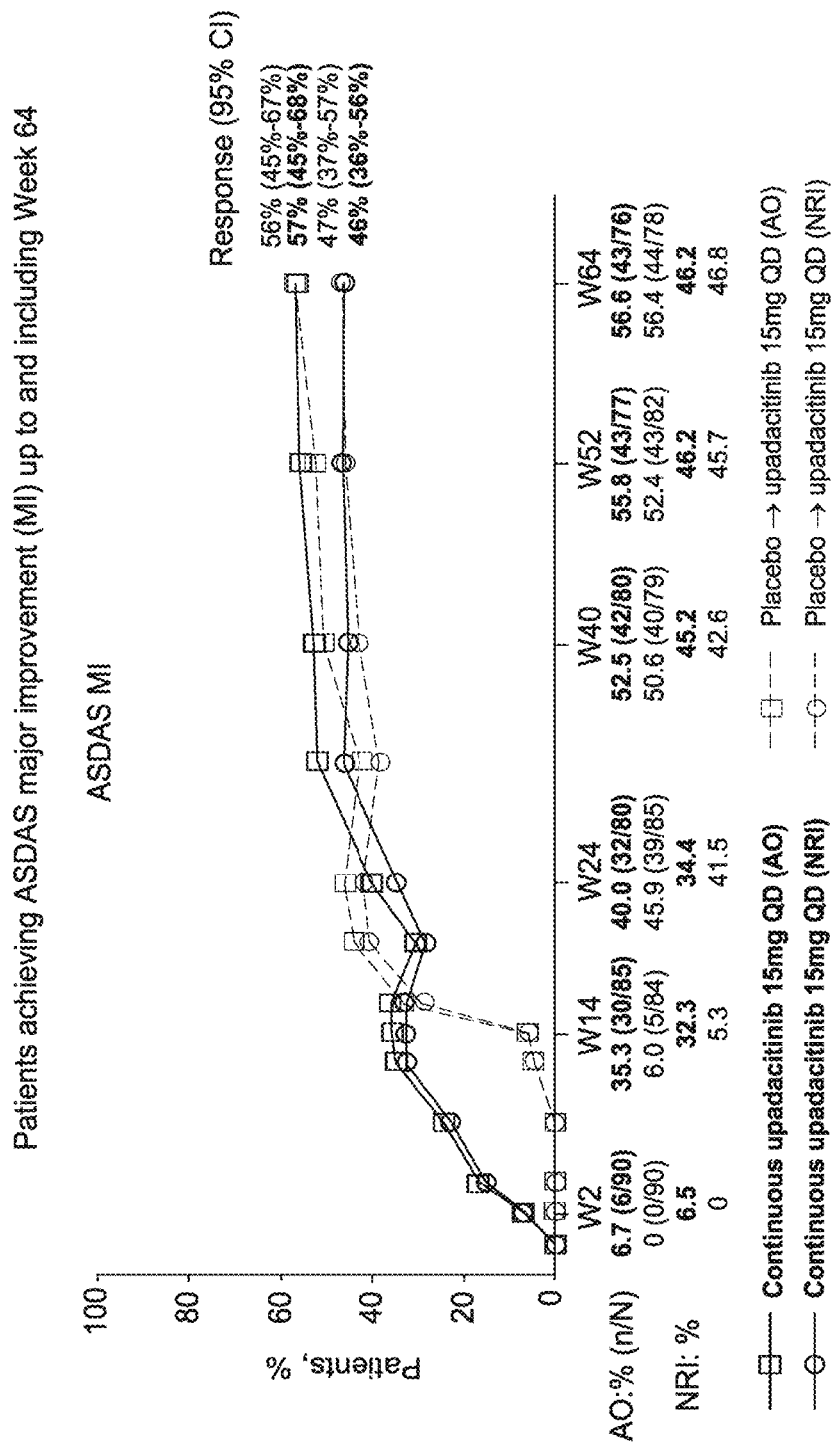

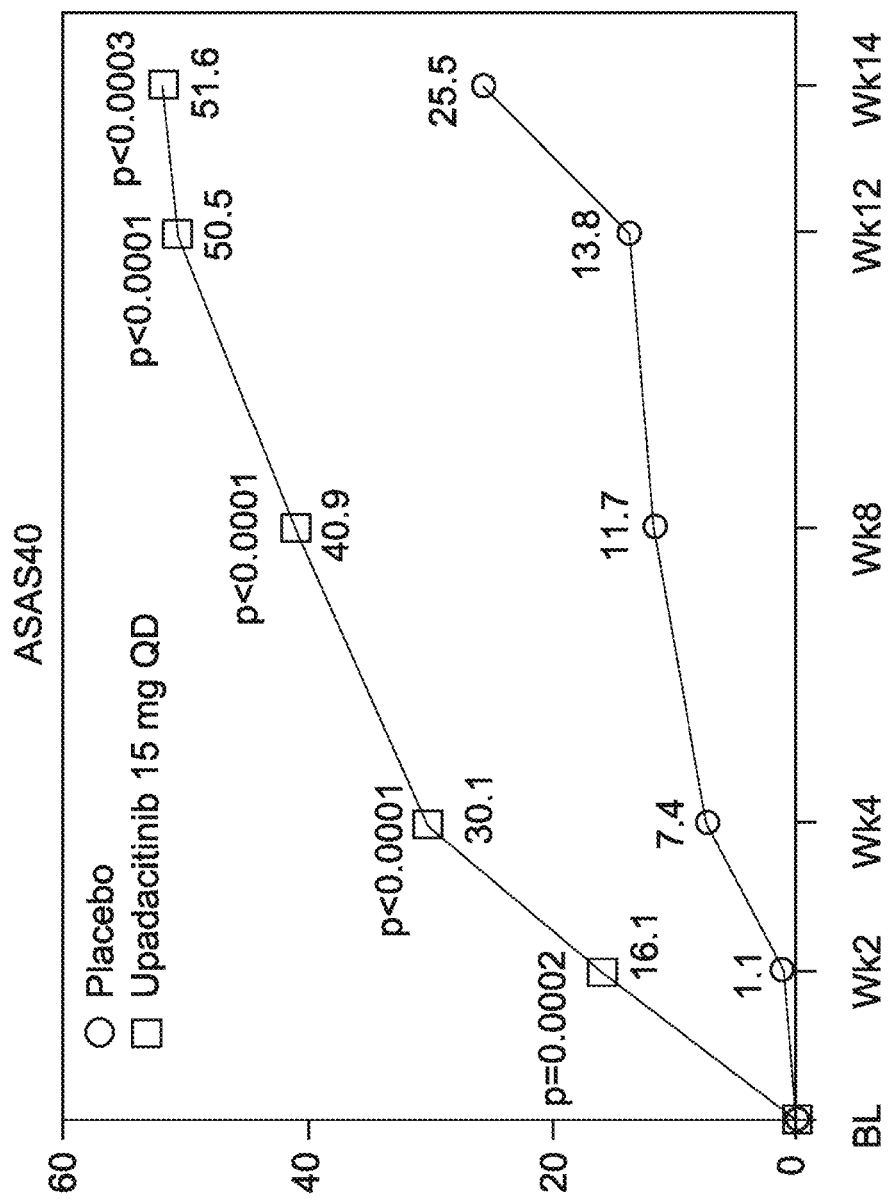

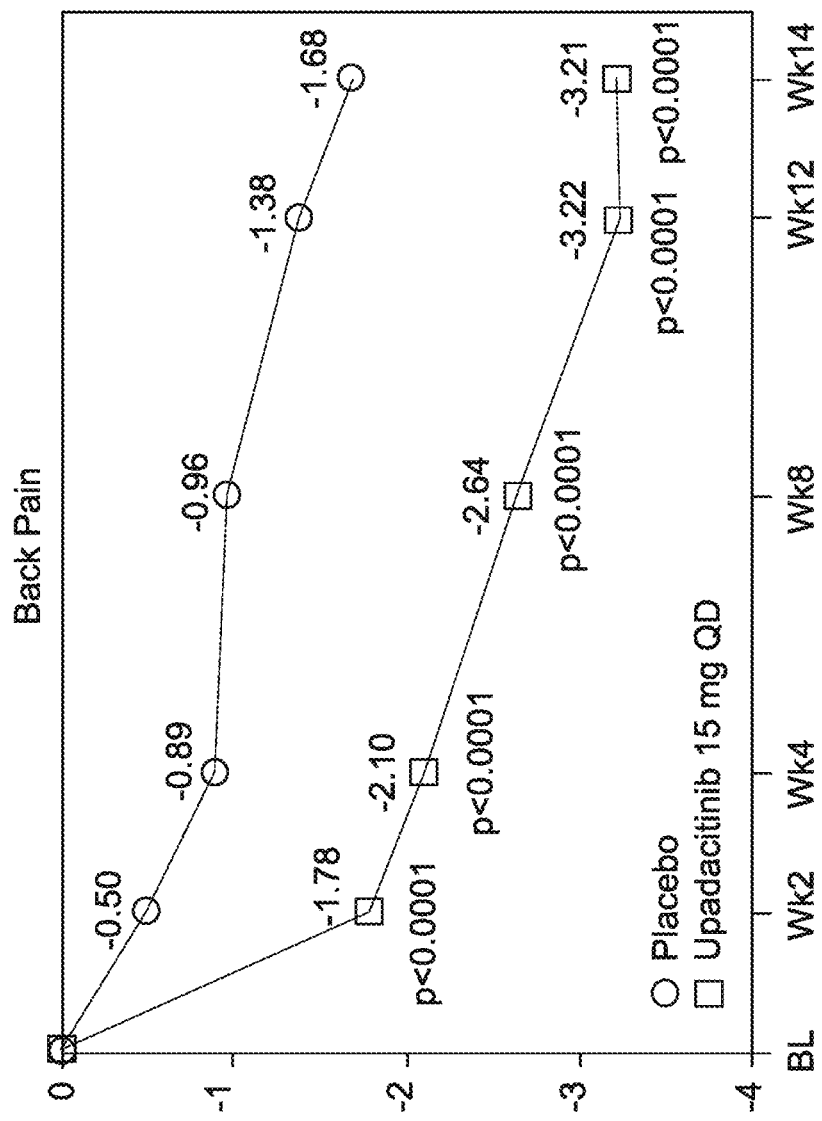

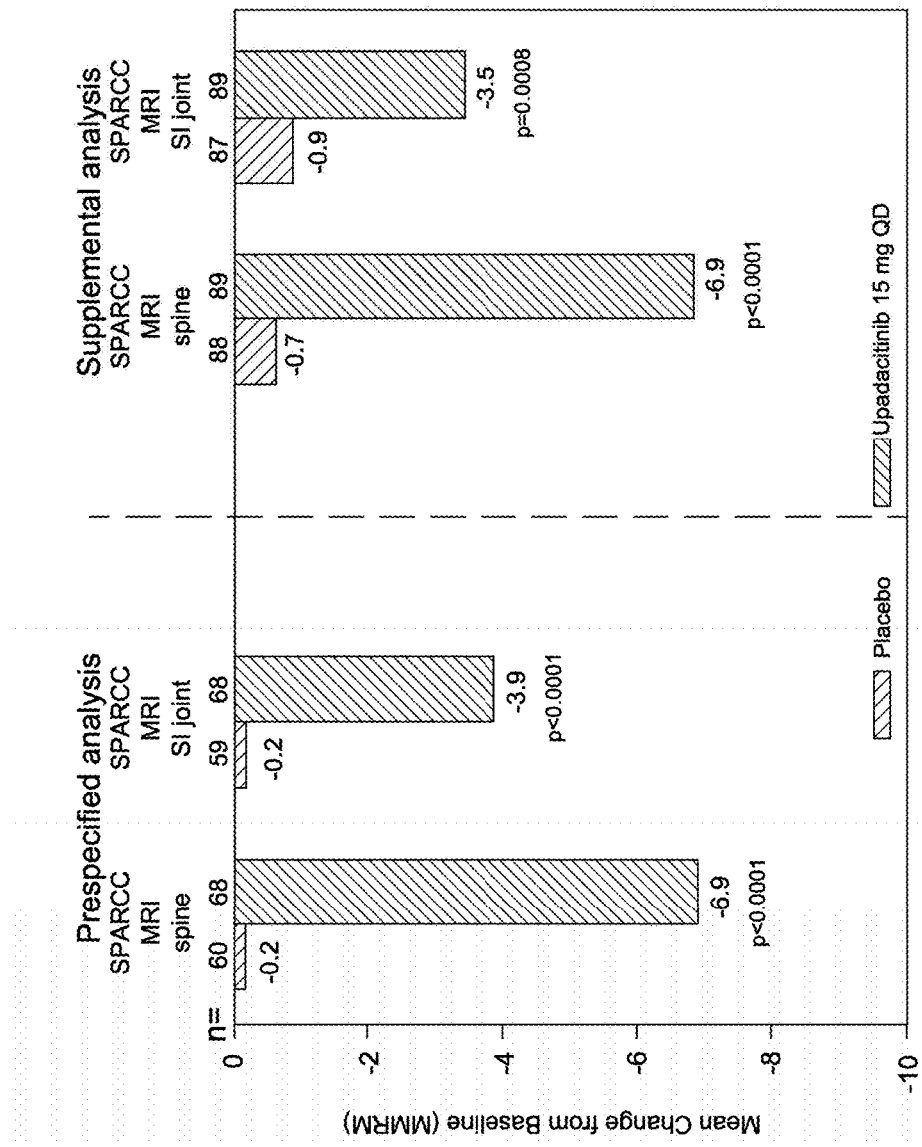

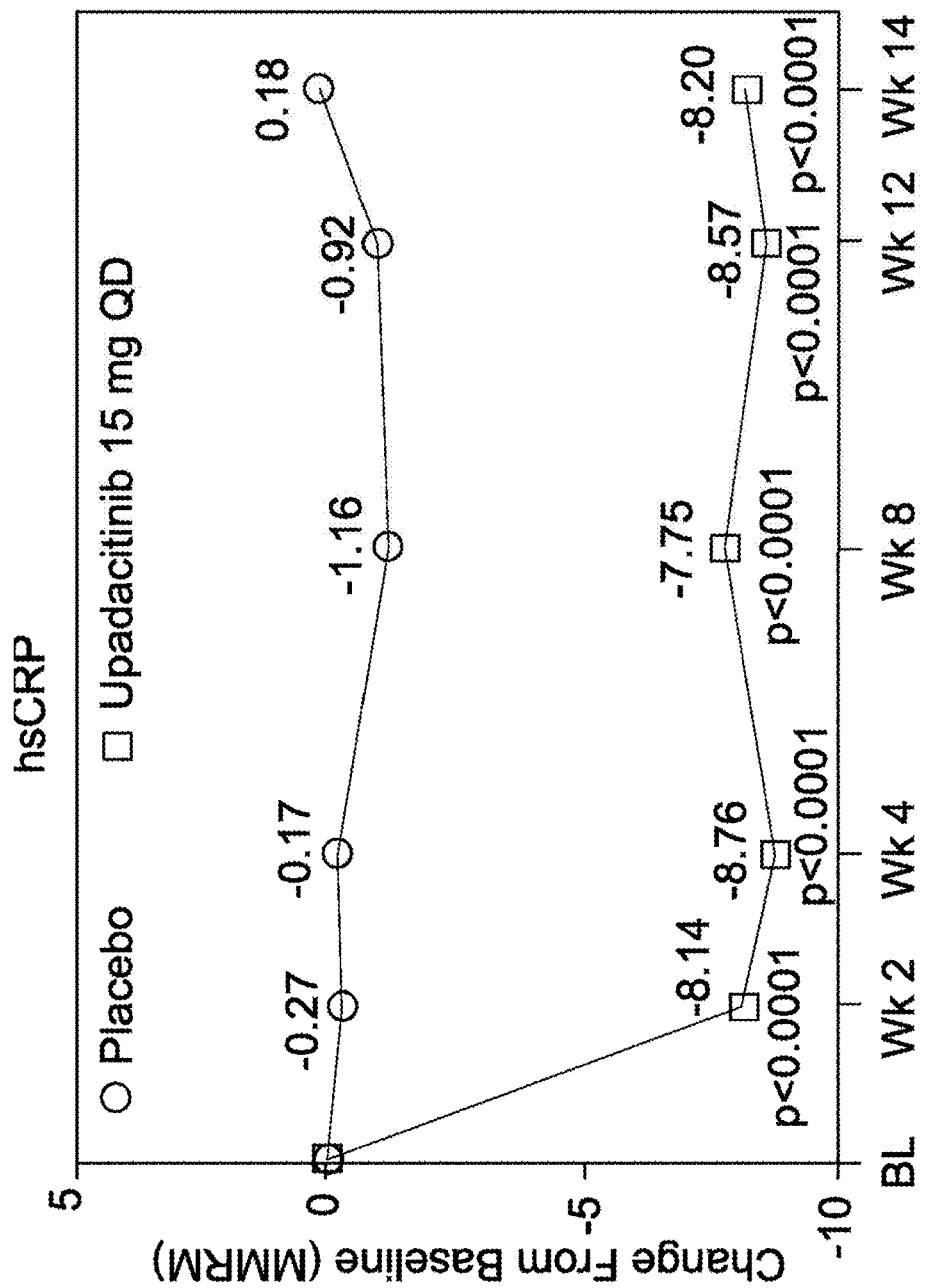

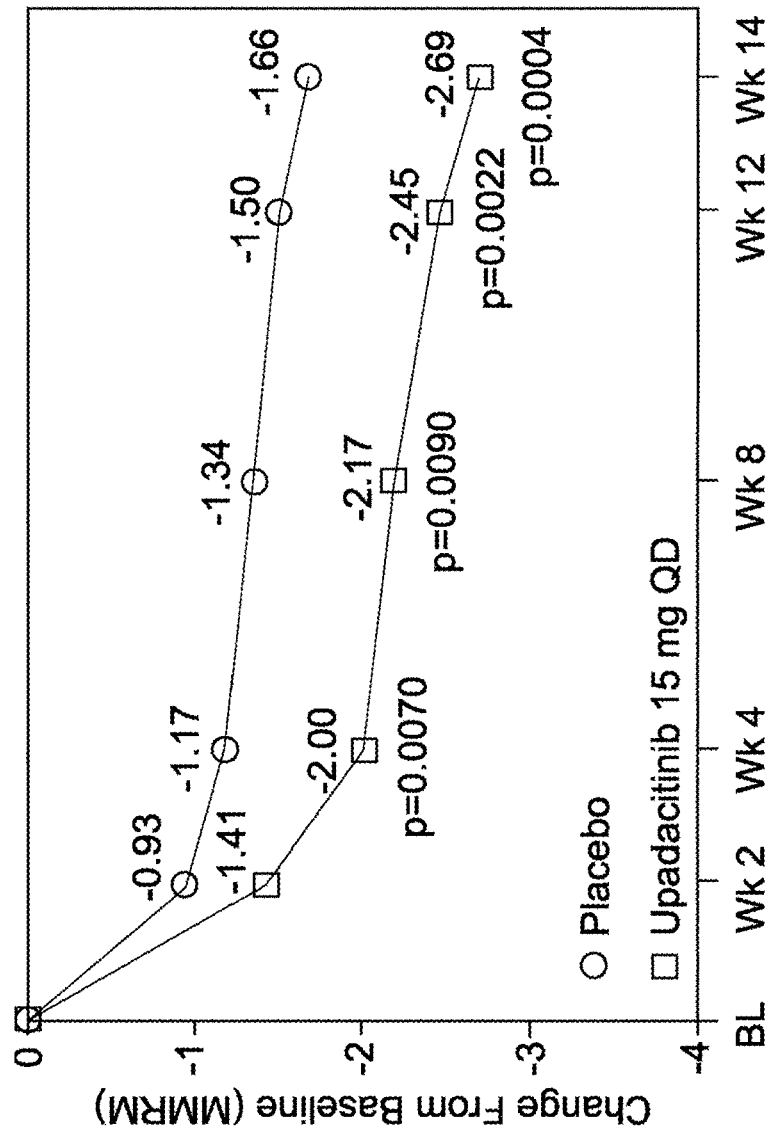

Note: Nominal p-value ≤ 0.05 starting from Week 2.

PROCESSES FOR THE PREPARATION OF (3S,4R)-3-ETHYL-4-(3H-IMIDAZO[1,2-A]PYRROLO[2,3-E]-PYRAZIN-8-YL)-N-(2,2,2-TRIFLUOROETHYL)PYRROLIDINE-1-CARBOXAMIDE AND SOLID STATE FORMS THEREOF

CROSS-REFERENCE TO RELATED APPLICATIONS

This application is a continuation-in-part of U.S. patent application Ser. No. 17/184,194, filed Feb. 24, 2021, which is a continuation of U.S. patent application Ser. No. 16/656,237, filed Oct. 17, 2019, which is a continuation of U.S. patent application Ser. No. 15/891,012, filed Feb. 7, 2018, which is a continuation of U.S. patent application Ser. No. 15/295,561, filed Oct. 17, 2016, and which claims the benefit of U.S. Provisional Application No. 62/242,797, filed Oct. 16, 2015; and claims the benefit of U.S. Provisional Application No. 62/267,672, filed Dec. 15, 2015; and claims the benefit of U.S. Provisional Application No. 62/301,537, filed Feb. 29, 2016; and claims the benefit of U.S. Provisional Application No. 62/352,380, filed Jun. 20, 2016; all of which are herein incorporated by reference in their entirety. This application is also a continuation-in-part of U.S. patent application Ser. No. 17/039,470, filed Sep. 30, 2020, which claims priority to U.S. Provisional Patent Application No. 63/032,042, filed on May 29, 2020; U.S. Provisional Patent Application No. 62/968,849, filed Jan. 31, 2020; U.S. Provisional Patent Application No. 62/927,548, filed Oct. 29, 2019; and U.S. Provisional Patent Application No. 62/908,163, filed Sep. 30, 2019, all of which are herein incorporated by reference in their entirety. This application also claims the benefit of U.S. Provisional Application No. 63/253,109, filed Oct. 6, 2021, which is herein incorporated by reference in its entirety.

FIELD OF THE INVENTION

The present disclosure relates to: (a) processes for the preparation of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (referred to herein as "Compound 1"), (b) intermediates used in the preparation of Compound 1 and processes for preparing the intermediates; (c) solid state forms of Compound 1, (d) pharmaceutical compositions comprising one or more solid state forms of Compound 1, and, optionally, one or more additional therapeutic agents; (e) methods of treating Janus kinase-associated conditions (including rheumatoid arthritis) by administering one or more solid state forms of Compound 1 to a subject in need thereof; (f) kits comprising a first pharmaceutical composition comprising a solid state form of Compound 1, and, optionally, a second pharmaceutical composition comprising one or more additional therapeutic agents; (g) methods for the preparation of solid state forms of Compound 1; and (h) solid state forms of Compound 1 prepared in accordance with such methods.

BACKGROUND OF THE INVENTION (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide ("Compound 1") was first disclosed in International Application WO2011/068881A1, which is herein incorporated by reference in its entirety. The compound has activity as a Janus kinase ("JAK") inhibitor, particularly as a JAK-1 inhibitor. Clinical trials are ongoing to evaluate the use of the compound to treat rheumatoid arthritis.

The isolation and commercial-scale preparation of a solid state form of Compound 1 and corresponding pharmaceutical formulations having acceptable solid state properties (including chemical stability, thermal stability, solubility, hygroscopicity, and/or particle size), compound manufacturability (including yield, impurity rejection during crystallization, filtration properties, drying properties, and milling properties), and formulation feasibility (including stability with respect to pressure or compression forces during tableting) present a number of challenges that are discussed in greater detail below. Accordingly, there is a current need for one or more solid state forms of Compound 1 that have an acceptable balance of these properties and can be used in the preparation of pharmaceutically acceptable solid dosage forms.

Additionally, currently known processes for the preparation of Compound 1 involve the use of particularly hazardous reagents, such as trimethylsilyldiazomethane or diazomethane, and do not produce a crystalline product. There is thus also a need for a process for preparing Compound 1, and pharmaceutically acceptable salts thereof, that avoids the use of particularly hazardous reagents, and can produce a crystalline product and crystalline intermediates.

Additionally, sustained peak plasma concentrations can theoretically be achieved by means of sustained release matrix systems. However, when such systems are made of hydrophilic polymers, such as HPMC, they seldom provide pH independent drug release of pH-dependent soluble drugs, and they are normally incapable of attaining zero-order release except for practically insoluble drugs. Unexpectedly, is has been discovered that when tartaric acid is used as a pH-modifier in such a system, it allows Compound 1 to be released at a steady rate regardless of the pH of the environment. In an unexpected finding, it was discovered that as a tablet containing the hydrophilic polymer matrix system erodes, Compound 1 reacts with the HPMC, creating a thicker gel layer which slows the release of Compound 1 from the tablet. The resulting gel layer provided an environment suitable for Compound 1 to dissolve.

Axial spondyloarthritis (axSpA) encompasses a spectrum of inflammatory involvement of the axial skeleton. Based on the Assessment of SpondyloArthritis International Society (ASAS) axSpA criteria, the disease can be further divided into 2 categories by radiographic findings: ankylosing spondylitis (AS), and an "early" form of axial SpA, referred to as non-radiographic axial spondyloarthritis (nr-axSpA). Patients with nr-axSpA and AS share common epidemiological, genetic, and clinical disease characteristics, including with regard to disease activity, and similar response to treatment. See, e.g., Poddubnyy and Sieper, *Curr Opin Rheumatol.* (2014) 26:377-383.

Per international treatment recommendations, nonsteroidal anti-inflammatory drugs (NSAIDs) are the first-line therapy in axSpA. See, e.g., van der Heijde D et al., *Ann Rheum Dis.* (2017) 76:978-991; Ward et al., *Arthritis Rheumatol.* (2016) 68:282-298. After failure of two NSAIDs given over a maximum of four weeks, biologic disease-modifying anti-rheumatic drugs (bDMARDs) are the next recommended treatment option. In axSpA, conventional synthetic disease-modifying anti-rheumatic drugs (csDMARDs) and long-term corticosteroids are not efficacious and therefore not recommended for treatment of axial symptoms. See, e.g., van der Heijde D et al., *Ann Rheum Dis.* (2017) 76:978-991. Furthermore, only approximately 45% to 50% of patients show an Assessment of SpondyloArthritis International Society 40 (ASAS40) response and only approximately 15% to 20% achieve a state of remission in biologic-naïve patients, and response rates are even less in axSpA patients who had an inadequate response to bDMARDs. See, e.g., Sieper and Poddubnyy, *Lancet* (2017) 390:73-84; Sieper et al., *Ann Rheum Dis.* (2017) 76:571-592; Rudwaleit et al., *Arthritis Res Ther.* (2010) 12:R117; Deodhar et al., *Arthritis Rheumatol.* (2019) 71:599-611. To date, other than NSAIDs, there have been no oral targeted therapies approved for the treatment of ankylosing spondylitis (AS) or non-radiographic axSpA.

Psoriatic Arthritis (PsA) is a chronic systemic inflammatory disease classified as a sub-type of spondyloarthritis (SpA) and characterized by the association of arthritis and psoriasis. The course of PsA is usually characterized by flares and remissions. Left untreated, patients with PsA can have persistent inflammation, progressive joint damage, disability, and a reduced life expectancy. Initial treatment of the musculoskeletal symptoms is composed of nonsteroidal anti-inflammatory drugs (NSAIDs) and local corticosteroid injections, while topical therapies are used for the initial treatment of psoriasis. For subjects who experience lack of efficacy or toxicity with these measures, systemic therapy with non-biologic disease modifying anti-rheumatic drugs (non-biologic DMARDs) (e.g., methotrexate [MTX], leflunomide [LEF], sulfasalazine [SSZ]) and ciclosporin A, followed by anti-tumor necrosis factor (TNF) therapy in subjects who do not respond adequately, is recommended. Other biologic therapies (e.g., IL-12/23 or IL-17 inhibitors) are also recommended as alternatives to anti-TNF inhibitors in selected PsA subjects. See, e.g., Gossec et al., *Ann Rheum Dis.* (2016) 75:499-510; Coates et al., *Arthritis Rheumatol.* (2016) 68:1060-71. However, despite the beneficial results achieved with currently available biologic agents, approximately 40% of patients do not have at least 20% improvement in American College of Rheumatology (ACR) scores and only 58% to 61% of patients with PsA who receive them are able to achieve clinical remission after 1 year of treatment, with only approximately 43% achieving sustained remission for at least 1 year. See, e.g., Gossec et al., *Ann Rheum Dis.* (2016) 75:499-510; Alamanos et al., *J Rheumatol.* (2003) 30:2641-2644; Savolainen et al., *J Rheumatol.* (2003) 30:2460-8; Sandborn, *Dig Dis.* (2010) 28:536-42; Saber et al., *Arthritis Res Therapy* (2010) 12: R94; Perrotta et al., *J Rheumatol.* (2016) 43:350-5.

Thus, there continues to remain a clear medical need for additional therapeutic options for the treatment of non-radiographic axial spondyloarthritis (nr-axSpA), ankylosing spondylitis (AS), psoriatic arthritis (PsA), and psoriasis (PsO), including PsO as a skin manifestation of PsA.

SUMMARY OF THE INVENTION

In one aspect, the present disclosure relates to pharmaceutical compositions comprising one or more solid state forms of Compound 1, and, optionally, one or more additional therapeutic agents.

In another aspect, the present disclosure relates to methods for the preparation of a solid state form of Compound 1.

In another aspect, the present disclosure relates to solid state forms of Compound 1 prepared in accordance with such methods.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 7.5 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 15 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 30 mg of Compound 1 freebase equivalent. In this or another particular aspect, the hydrate may be a hemihydrate. In this or another aspect, the hemihydrate may be Freebase Hydrate Form C.

In another aspect, the present disclosure relates to a pharmaceutical composition comprising a crystalline hydrate of Compound 1 and a pharmaceutically acceptable carrier, wherein the composition comprises the crystalline hydrate in an amount sufficient to deliver about 45 mg of Compound 1 freebase equivalent. In this or another particular aspect, the hydrate may be a hemihydrate. In this or another aspect, the hemihydrate may be Freebase Hydrate Form C.

In another aspect, the present disclosure is directed to an extended release formulation for oral administration comprising Compound 1 or a pharmaceutically acceptable salt thereof, a hydrophilic polymer, and a pH modifier, wherein the hydrophilic polymer, in contact with water, forms a gel layer that provides an environment suitable for Compound 1 and the pH modifier to dissolve.

In another aspect, the present disclosure relates to methods of treating a JAK-associated condition (such as rheumatoid arthritis) in a human subject suffering from or susceptible to such a condition comprising administering to the subject a therapeutically effective amount of a solid state form of Compound 1. In another aspect, the disclosure relates to a pharmaceutical composition comprising a therapeutically effective amount of a solid state form of Compound 1 as described in the present disclosure, for use in treatment of a JAK-associated condition (such as rheumatoid arthritis) in a subject, particularly in a human subject suffering from or susceptible to the condition.

In another aspect, the present disclosure relates to methods of treating rheumatoid arthritis, wherein the term "rheumatoid arthritis" includes juvenile rheumatoid arthritis, juvenile idiopathic arthritis, ankylosing spondylitis disease, Sjogren's syndrome, psoriatic arthritis.

In another aspect, the present disclosure relates to methods of treating inflammatory bowel disease, wherein the term "inflammatory bowel disease" includes Crohn's disease, pediatric Crohn's disease and ulcerative colitis.

In another aspect, the present disclosure relates to a method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis and systemic lupus erythematosus in a human subject suffering from or susceptible to such a condition, the method comprising administering to the subject a therapeutically effective amount a solid state form of Compound 1. In another aspect, the disclosure relates to a pharmaceutical composition comprising a therapeutically effective amount of a solid state form of Compound 1 as described in the present disclosure, for use in treatment of a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, particularly in a human subject suffering from or susceptible to the condition.

In another aspect, the present disclosure relates to methods of treating a JAK-associated condition (such as rheumatoid arthritis) in a human subject suffering from or susceptible to such a condition comprising administering to the subject a solid state form of Compound 1, in combination with one or more additional therapeutic agents (e.g., a therapeutic agent for treating rheumatoid arthritis that is not a JAK inhibitor). In another aspect, the disclosure relates to a pharmaceutical composition comprising a solid state form of Compound 1, as described in the present disclosure, in combination with one or more additional therapeutic agents (e.g., a therapeutic agent for treating rheumatoid arthritis that is not a JAK inhibitor), for use in treatment of a JAK-associated condition (such as rheumatoid arthritis) in a subject, particularly in a human subject suffering from or susceptible to the condition.

In another aspect, the present disclosure relates to a method of treating active non-radiographic axial spondyloarthritis in a subject in need thereof, the method comprising orally administering to the subject once a day for at least 14 weeks a dose of upadacitinib freebase, or a pharmaceutically acceptable salt thereof, in an amount sufficient to deliver 15 mg of upadacitinib freebase equivalent, wherein the subject achieves an ASAS40 response within 14 weeks of administration of the first dose. In some embodiments, the subject fulfills at baseline the 2009 ASAS classification criteria for axial spondyloarthritis, but does not meet the radiologic criteria of the 1984 modified New York criteria for ankylosing spondylitis. In some embodiments, the subject meets the following criteria at screening and baseline: a) Bath Ankylosing Spondylitis Disease Activity Index (BASDAI) score of ≥4; b) a Patient's Assessment of Total Back Pain (Total Back Pain score) of ≥4 based on a 0-10 numerical rating scale; and c) an objective sign of inflammatory activity selected from the group consisting of: i. an objective sign of active inflammation on MRI of sacroiliac (SI) joints, and ii. high-sensitivity C reactive protein>upper limit of normal (ULN). In some embodiments, the subject is bDMARD naïve at baseline. In some embodiments, the subject has had an inadequate response or intolerance to a bDMARD at baseline. In some embodiments, prior to administration of the first dose, the subject has been administered one bDMARD, and discontinued use of the bDMARD due to intolerance or lack of efficacy at baseline. In some embodiments, the bDMARD is a tumor necrosis factor (TNF) inhibitor or an interleukin (IL)-17 inhibitor. In some embodiments, the subject has had an inadequate response or intolerance to at least 2 NSAIDs, has an intolerance to NSAIDS, and/or has a contraindication for NSAIDs at baseline. In some embodiments, the subject achieves within 14 weeks of administration of the first dose at least one additional result selected from the group consisting of: improvement from baseline in Ankylosing Spondylitis Disease Activity Score (ASDAS); improvement from baseline in magnetic resonance imaging (MRI) Spondyloarthritis Research Consortium of Canada (SPARCC) score for SI joints (MRI-SI joints SPARCC); BASDAI 50 response; ASDAS (CRP) Inactive Disease (ID); Improvement from baseline in Total Back Pain; Improvement from baseline in Nocturnal Back Pain; ASDAS (CRP) Low Disease Activity; ASAS partial remission (PR); improvement from baseline in Bath Ankylosing Spondylitis Functional Index (BASFI); improvement from baseline in Ankylosing Spondylitis Quality of Life (ASQoL); improvement from baseline in ASAS Health Index (HI); ASAS20 response; improvement from baseline in Maastricht Ankylosing Spondylitis Enthesitis Score (MASES); and improvement from baseline in Linear Bath Ankylosing Spondylitis Metrology Index (BASMI$_{lin}$).

In another aspect, the present disclosure relates to a method of treating active ankylosing spondylitis in a subject in need thereof, the method comprising orally administering to the subject once a day for at least 14 weeks a dose of upadacitinib freebase, or a pharmaceutically acceptable salt thereof, in an amount sufficient to deliver 15 mg of upadacitinib freebase equivalent, wherein the subject achieves an Assessment of SpondyloArthritis International Society 40 (ASAS40) response within 14 weeks of administration of the first dose, and wherein the subject has had an inadequate response or intolerance to a biologic disease-modifying anti-rheumatic drug (bDMARD) at baseline. In some embodiments, the method is used to treat a population of subjects, at least 10% of the subjects in the treated population achieve an ASAS40 response within 14 weeks of administration of the first dose, wherein the subjects in the treated population have had an inadequate response or intolerance to a biologic disease-modifying anti-rheumatic drug (bDMARD) at baseline. In some embodiments, the subject or subjects in the treated population further achieve within 14 weeks of administration of the first dose at least one result selected from the group consisting of: improvement from baseline in Ankylosing Spondylitis Disease Activity Score (ASDAS) (CRP); improvement from baseline in magnetic resonance imaging (MRI) Spondyloarthritis Research Consortium of Canada (SPARCC) score for spine (MRI-Spine SPARCC); Bath Ankylosing Spondylitis Disease Activity Index 50 (BASDAI50) response; ASAS20 response; ASDAS inactive disease (ID); Improvement from baseline in Patient's Assessment of Total Back Pain (Total Back Pain score); Improvement from baseline in Patient's Assessment of Nocturnal Back Pain (Nocturnal Back Pain); ASDAS (CRP) Low Diseases Activity (LDA); Improvement from baseline in Bath Ankylosing Spondylitis Functional Index (BASFI) (Function); ASAS partial remission (PR); Improvement from baseline in Ankylosing Spondylitis Quality of Life (ASQoL); Improvement from baseline in ASAS Health Index (HI); Improvement from baseline in Linear Bath Ankylosing Spondylitis Metrology Index (BASMIlin) (Mobility); and improvement from baseline in Maastricht Ankylosing Spondylitis Enthesitis Score (MASES) (Enthesitis). In some embodiments, the subject or subjects in the treated population further achieve within 14 weeks of administration of the first dose each result. In some embodiments, the subject or subjects in the treated population fulfill the 1984 modified New York Criteria for ankylosing spondylitis at baseline. In some embodiments, the subject or subjects in the treated population meet the following criteria: a Bath Ankylosing Spondylitis Disease Activity Index (BASDAI) score ≥4; and a Patient's Assessment of Total Back Pain (Total Back Pain score) of ≥4 based on a 0-10 numerical rating scale. In some embodiments, the subject or subjects in the treated population have had an inadequate response or intolerance to a biologic disease-modifying anti-rheumatic drug (bDMARD) at baseline. In some embodiments, prior to administration of the first dose, the subject or subjects in the treated population have been administered one bDMARD, and discontinued use of the bDMARD due to intolerance or lack of efficacy at baseline. In some embodiments, the bDMARD is a tumor necrosis factor (TNF) inhibitor or an interleukin (IL)-17 inhibitor. In some embodiments, the subject or subjects in the treated population have had an inadequate response or intolerance to at least two NSAIDs, intolerance to NSAIDS, and/or contraindication for NSAIDs at baseline.

In another aspect, the present disclosure relates to kits comprising one or more pharmaceutical compositions comprising a solid state form of Compound 1. The kit optionally can comprise another pharmaceutical composition comprising one or more additional therapeutic agents and/or instructions, for example, instructions for using the kit.

The below recited Embodiments 1-25 set forth certain aspects of the methods as described herein.

Embodiment 1: In certain aspects, provided is a method of treating active ankylosing spondylitis (AS) in a subject in need thereof, the method comprising orally administering to the subject once a day for at least 14 weeks a dose of upadacitinib freebase, or a pharmaceutically acceptable salt thereof, in an amount sufficient to deliver 15 mg of upadacitinib freebase equivalent, wherein the subject achieves an Assessment of SpondyloArthritis International Society 40 (ASAS40) response within 14 weeks of administration of the first dose.

Embodiment 2: The method of Embodiment 1, wherein when the method is used to treat a population of subjects, at least 10%, at least 15%, at least 20%, at least 25%, at least 30%, at least 35%, at least 40%, at least 44%, or at least 45% of the subjects in the treated population achieve an ASAS40 response within 14 weeks of administration of the first dose. In certain embodiments of the method of Embodiment 1, wherein when the method is used to treat a population of subjects, a statistically significant population of the subjects in the treated population achieves an ASAS40 response within 14 weeks of administration of the first dose.

Embodiment 3: The method of Embodiment 1 or 2, wherein the subject or subjects in the treated population suffering from active AS at baseline further achieve within 14 weeks of administration of the first dose at least one result selected from the group consisting of:
a. improvement from baseline in Ankylosing Spondylitis Disease Activity Score (ASDAS) (CRP);
b. improvement from baseline in magnetic resonance imaging (MRI) Spondyloarthritis Research Consortium of Canada (SPARCC) score for spine (MRI-Spine SPARCC);
c. Bath Ankylosing Spondylitis Disease Activity Index 50 (BASDAI50) response;
d. ASAS20 response;
e. ASDAS (CRP) Inactive Disease (ASDAS score <1.3);
f. Improvement from baseline in Patient's Assessment of Total Back Pain (Total Back Pain score);
g. Improvement from baseline in Patient's Assessment of Nocturnal Back Pain (Nocturnal Back Pain);
h. ASDAS low disease activity (LDA);
i. improvement from baseline in Bath Ankylosing Spondylitis Functional Index (BASFI);
j. ASAS partial remission (PR);
k. Improvement from baseline in Ankylosing Spondylitis Quality of Life (ASQoL);
l. improvement from baseline in ASAS Health Indes (HI);
m. improvement from baseline in Linear Bath Ankylosing Spondylitis Metrology Index (BASMI$_{lin}$); and
n. Improvement from baseline in Maastricht Ankylosing Spondylitis Enthesitis Score (MASES) (Enthesitis).

In certain embodiments of the method of Embodiment 1 or 2, when the method is used to treat a population of subjects, at least 10%, at least 15%, at least 20%, at least 25%, at least 30%, at least 35%, at least 40%, at least 44%, or at least 45% of the subjects in the treated population achieve at least one of these results within 14 weeks of administration of the first dose. In other embodiments of the method of Embodiment 1 or 2, when the method is used to treat a population of subjects, a statistically significant population of subjects in the treated population achieves at least one result within 14 weeks of administration of the first dose.

Embodiment 4: The method of Embodiment 3, wherein the subject or subjects in the treated population suffering from active AS at baseline further achieve within 14 weeks of administration of the first dose each result.

Embodiment 5: The method of any one of Embodiments 1-4, wherein the subject or subjects in the treated population fulfill the 1984 modified New York Criteria for ankylosing spondylitis at baseline.

Embodiment 6: The method of any one of Embodiments 1-5, wherein the subject or subjects in the treated population meet the following criteria at screening and baseline:
a. a Bath Ankylosing Spondylitis Disease Activity Index (BASDAI) score ≥4; and
b. a Patient's Assessment of Total Back Pain (Total Back Pain score) of ≥4 based on a 0-10 numerical rating scale.

Embodiment 7: The method of any one of Embodiments 1-6, wherein the subject or subjects in the treated population have had an inadequate response or intolerance to a biologic disease-modifying anti-rheumatic drug (bDMARD) at baseline.

Embodiment 8: The method of Embodiment 7, wherein prior to administration of the first dose, the subject or subjects in the treated population have been administered one bDMARD, and discontinued use of the bDMARD due to intolerance or lack of efficacy.

Embodiment 9: The method of Embodiment 8, wherein the bDMARD is a tumor necrosis factor (TNF) inhibitor or an interleukin (IL)-17 inhibitor.

Embodiment 10: The method of any one of Embodiments 1-9, wherein the subject or subjects in the treated population have had an inadequate response or intolerance to at least two NSAIDs, intolerance to NSAIDS, and/or contraindication for NSAIDs at baseline.

Embodiment 11: In other aspects, provided is a method of treating active non-radiographic axial spondyloarthritis in a subject in need thereof, the method comprising orally administering to the subject once a day for at least 14 weeks a dose of upadacitinib freebase, or a pharmaceutically acceptable salt thereof, in an amount sufficient to deliver 15 mg of upadacitinib freebase equivalent, wherein the subject achieves an ASAS40 response within 14 weeks of administration of the first dose. In certain embodiments, when the method is used to treat a population of subjects, at least 10%, at least 15%, at least 20%, at least 25%, at least 30%, at least 35%, at least 40%, at least 44%, or at least 45% of the subjects in the treated population achieve an ASAS40 response within 14 weeks of administration of the first dose. In certain embodiments, a statistically significant population of subjects in the treated population achieve an ASAS40 response within 14 weeks of administration of the first dose.

Embodiment 12: The method of Embodiment 11, wherein the subject or subjects in the treated population fulfill at baseline the 2009 ASAS classification criteria for axial spondyloarthritis, but does not meet the radiologic criteria of the 1984 modified New York criteria for ankylosing spondylitis.

Embodiment 13: The method of Embodiment 11, wherein the subject or subjects in the treated population meet the following criteria at screening and baseline:
a. Bath Ankylosing Spondylitis Disease Activity Index (BASDAI) score of ≥4;
b. a Patient's Assessment of Total Back Pain (Total Back Pain score) of ≥4 based on a 0-10 numerical rating scale; and
c. an objective sign of inflammatory activity selected from the group consisting of:
  i. an objective sign of active inflammation on MRI of sacroiliac (SI) joints, and
  ii. high-sensitivity C reactive protein>upper limit of normal (ULN).

Embodiment 14: The method of any one of Embodiments 11-13, wherein the subject or subjects in the treated population are bDMARD naïve at baseline.

Embodiment 15: The method of any one of Embodiments 11-13, wherein the subject or subjects in the treated population have had an inadequate response or intolerance to a bDMARD at baseline.

Embodiment 16: The method of Embodiment 15, wherein prior to administration of the first dose, the subject or subjects in the treated population have been administered one bDMARD, and discontinued use of the bDMARD due to intolerance or lack of efficacy.

Embodiment 17: The method of Embodiment 16, wherein the bDMARD is a tumor necrosis factor (TNF) inhibitor or an interleukin (IL)-17 inhibitor.

Embodiment 18: The method of any one of Embodiments 11-17, wherein the subject or subjects in the treated population have had an inadequate response or intolerance to at least 2 NSAIDs, has an intolerance to NSAIDS, and/or has a contraindication for NSAIDs at baseline.

Embodiment 19: The method of any one of Embodiments 11-18, wherein the subject or subjects in the treated population achieve within 14 weeks of administration of the first dose at least one additional result selected from the group consisting of:
a. improvement from baseline in Ankylosing Spondylitis Disease Activity Score (ASDAS) (CRP);
b. improvement from baseline in magnetic resonance imaging (MRI) Spondyloarthritis Research Consortium of Canada (SPARCC) score for SI joints (MRI-SI joints SPARCC);
c. Bath Ankylosing Spondylitis Disease Activity Index (BASDAI) 50 response;
d. ASDAS (CRP) Inactive Disease (ASDAS score <1.3);
e. improvement from baseline in Total Back Pain;
f. improvement from baseline in Nocturnal Back Pain;
g. ASDAS Low Disease (ASDAS score <2.1);
h. ASAS partial remission (PR);
i. improvement from baseline in Bath Ankylosing Spondylitis Functional Index (BASFI);
j. improvement from baseline in Ankylosing Spondylitis Quality of Life (ASQoL);
k. improvement from baseline in ASAS Health Index (HI);
l. ASAS20 response;
m. improvement from baseline in Linear Bath Ankylosing Spondylitis Metrology Index ($BASMI_{lin}$) and
n. improvement from baseline in Maastricht Ankylosing Spondylitis Enthesitis Score (MASES).

In certain embodiments of the method of any one of Embodiments 11-18, wherein when the method is used to treat a population of subjects, at least 10%, at least 15%, at least 20%, at least 25%, at least 30%, at least 35%, at least 40%, at least 44%, or at least 45% of the subjects in the treated population achieve at least one result within 14 weeks of administration of the first dose. In certain embodiments of the method of any one of Embodiments 11-18, wherein when the method is used to treat a population of subjects, a statistically significant population of subjects in the treated population achieves at least one result within 14 weeks of administration of the first dose.

Embodiment 20: The method of any one of Embodiments 1-19, wherein the subject is an adult subject, or the subjects in the treated population are adult subjects.

Embodiment 21: The method of any one of Embodiments 1-19, wherein the ASAS40 response is maintained or improved after Week 14 by continuing to administer the daily dose. In one aspect, the ASAS40 response is maintained or improved up to and including Week 104 or up to and including Week 152.

Embodiment 22: The method of any one of Embodiments 1-10, wherein the subject or subjects in the treated population further achieve ASAS40 within 4 weeks of administration of the first dose.

Embodiment 23: The method of any one of Embodiments 1-10, wherein the subject or subjects in the treated population further achieved ASAS40 within 4 weeks of administration of the first dose, and wherein the ASAS40 is maintained or improved after Week 14 by continuing to administer the daily dose.

Embodiment 24: The method of any one of Embodiments 11-19, wherein the subject or subjects in the treated population further achieve ASAS40 within 2 weeks of administration of the first dose.

Embodiment 25: The method of any one of Embodiments 11-19, wherein the subject or subjects in the treated population further achieved ASAS40 within 2 weeks of administration of the first dose, and wherein the ASAS40 is maintained or improved after Week 14 by continuing to administer the daily dose.

Embodiment 26: In another aspect, provided is a method of treating active ankylosing spondylitis in a subject in need thereof, the method comprising orally administering to the subject once a day for at least 14 weeks a dose of upadacitinib freebase, or a pharmaceutically acceptable salt thereof, in an amount sufficient to deliver 15 mg of upadacitinib freebase equivalent, wherein the subject achieves ASAS partial remission (PR), ASDAS low disease activity (LDA), ASDAS inactive disease (ID), ASDAS major improvement (MI), and/or ASDAS clinically important improvement (CII) within 14 weeks of administration of the first dose.

Embodiment 27: The method of Embodiment 26, wherein when the method is used to treat a population of subjects, a portion of the subjects in the treated population achieve ASAS partial remission (PR), ASDAS low disease activity (LDA), ASDAS inactive disease (ID), ASDAS major improvement (MI), and/or ASDAS clinically important improvement (CII) within 14 weeks of administration of the first dose. In certain embodiments of Embodiment 50, at least 10%, at least 15%, at least 20%, at least 25%, at least 30%, at least 35%, at least 40%, or at least 45% of the subjects in the treated population achieve ASAS partial remission (PR), ASDAS low disease activity (LDA), ASDAS inactive disease (ID), ASDAS major improvement (MI), and/or ASDAS clinically important improvement (CII) within 14 weeks of administration of the first dose. In certain embodiments of Embodiment 50, a statistically significant population of subjects in the treated population achieves ASAS partial remission (PR), ASDAS low disease activity (LDA), ASDAS inactive disease (ID), ASDAS major improvement (MI), and/or ASDAS clinically important improvement (CII) within 14 weeks of administration of the first dose.

Embodiment 28: The method of Embodiment 26 or 27, wherein the subject or subjects in the treated population further achieve within 14 weeks of administration of the first dose each result.

Embodiment 29: The method of any one of Embodiments 26-28, wherein the subject or subjects in the treated population fulfill the 1984 modified New York Criteria for ankylosing spondylitis at baseline.

Embodiment 30: The method of any one of Embodiments 26-28, wherein the subject or subjects in the treated population fulfill the 2009 ASAS classification criteria at baseline.

Embodiment 31: The method of any one of Embodiments 26-30, wherein the subject or subjects in the treated population meet at least one criteria at baseline selected from the group consisting of:
 a. a Bath Ankylosing Spondylitis Disease Activity Index (BASDAI) score ≥4;
 b. an Ankylosing Spondylitis Disease Activity Score (ASDAS) of ≥2.1; and
 c. a Patient's Assessment of Total Back Pain (Total Back Pain score) of ≥4 based on a 0-10 numerical rating scale.

Embodiment 32: The method of any one of Embodiments 26-31, wherein the subject or subjects in the treated population are biologic disease-modifying anti-rheumatic drug (bDMARD) naïve at baseline.

Embodiment 33: The method of any one of Embodiments 26-32, wherein the subject or subjects in the treated population have had an inadequate response or intolerance to a biologic disease-modifying anti-rheumatic drug (bDMARD) at baseline.

Embodiment 34: The method of Embodiments 33, wherein prior to administration of the first dose, the subject or subjects in the population have been administered one bDMARD, and discontinued use of the bDMARD due to intolerance or lack of efficacy.

Embodiment 35: The method of Embodiments 34, wherein the bDMARD is a tumor necrosis factor (TNF) inhibitor or an interleukin (IL)-17 inhibitor.

Embodiment 36: The method of any one of Embodiments 26-32, wherein the subject or subjects in the population have had an inadequate response or intolerance to at least two NSAIDs, intolerance to NSAIDS, and/or contraindication for NSAIDs at baseline.

Embodiment 37: The method of any one of Embodiments 26-36, wherein the ASAS partial remission (PR), ASDAS low disease activity (LDA), ASDAS inactive disease (ID), ASDAS major improvement (MI), and/or ASDAS clinically important improvement (CII) is maintained or improved after Week 14 by continuing to administer the daily dose.

Embodiment 38: The method of any one of Embodiments 26-37, wherein the subject or subjects in the treated population further achieve ASAS partial remission (PR), ASDAS low disease activity (LDA), ASDAS inactive disease (ID), ASDAS major improvement (MI), and/or ASDAS clinically important improvement (CII) within 2 weeks of administration of the first dose. In certain embodiments of Embodiment 61, a statistically significant population of subjects in the treated population achieve ASAS partial remission (PR), ASDAS low disease activity (LDA), ASDAS inactive disease (ID), ASDAS major improvement (MI), and/or ASDAS clinically important improvement (CII) within 2 weeks of administration of the first dose. In certain embodiments of Embodiment 61, at least 10%, at least 15%, at least 20%, at least 25%, at least 30%, at least 35%, at least 40%, or at least 45% of the subjects in the treated population achieve ASAS partial remission (PR), ASDAS low disease activity (LDA), ASDAS inactive disease (ID), ASDAS major improvement (MI), and/or ASDAS clinically important improvement (CII) within 2 weeks of administration of the first dose.

BRIEF DESCRIPTION OF THE DRAWINGS

FIGS. 3A-3C and FIGS. 3D-3N, respectively depict the Week 14 results of the Phase 2/3 Ankylosing Spondylitis (SELECT-AXIS 1) clinical trial for key clinical efficacy endpoints, and time course of key endpoints up to and including Week 64. FIG. 3A depicts the ASAS20, ASAS40, ASAS PR, and BASDAI50 Responses at Week 14; FIG. 3B depicts the change from Baseline in SPARCC MRI Spine and SI Joint Scores at Week 14; and FIG. 3C depicts other Multiplicity-Controlled Key Secondary Efficacy Endpoints at Week 14. The results demonstrate the study met its primary endpoint, with statistically significantly more patients treated with upadacitinib freebase versus placebo achieving ASAS40 response at Week 14 (48/93 [51.6%] vs 24/94 [25.5%]; p=0.0003) with a treatment difference (95% CI) of 26.1% (12.6-39.5%). All endpoints were multiplicity controlled, except for ASAS20 and SPARCC MRI SI joint. The multiplicity-controlled secondary endpoints were tested in a sequential manner: ASDAS, SPARCC MRI Spine, group of endpoints tested by Hochberg procedure (BASDAI50, ASQoL, ASAS PR, BASFI, BASMI, MASES, and WPAI), and ASAS HI. For FIGS. 12L-12N, Asterisk (*) indicates P<0.001, Asterisk () P<0.01; and Asterisk (*) P<0.05. For other Figures, Asterisk (*) indicates statistically significant in multiplicity-controlled analysis, otherwise nominal p values are shown. Accounting for multiplicity adjustment, change from baseline to Week 14 in ASDAS (FIG. 12C), SPARCC MRI spine (FIG. 3B), and BASFI (FIG. 3C) and proportion of patients who achieved BASDAI50 (FIG. 3A) and ASAS PR (FIG. 12A) were statistically significant for upadacitinib freebase versus placebo. FIGS. 3D-3K depict the time course of the ASAS40 (FIG. 12D), ASAS20 (FIG. 3E), ASAS partial remission (PR) (FIG. 3F), BASDAI50 Responses (FIG. 3G), ASDAS inactive disease (ID) (FIG. 3H), ASDAS low disease activity (LDA) (FIG. 3I), ASDAS major improvement (MI) (FIG. 3J), and ASDAS clinically important improvement (CII) (FIG. 3K) up to and including Week 64. At week 14, the placebo group was rescued and administered 15 mg upadacitinib free base (Placebo→Upadacitinib 15 mg QD). Patients who switched from placebo to upadacitinib at week 14 showed a similar efficacy response compared with those who received continuous upadacitinib free base from Day 0. The data suggests upadacitinib 15 mg QD, showing achievement of efficacy at Week 14, and sustaining or even improving upon this efficacy up to and including Week 64, will help to address an unmet need for patients with AS (as well as in patients with non-radiographic axial spondyloarthritis (nr-axSpA)), especially in those patients who have active disease and have inadequately responded to NSAIDs. A significantly higher proportion of patients receiving upadacitinib versus placebo achieved ≥30% (FIG. 3L) and ≥50% reduction (FIG. 3M) in Patient's Global Assessment of pain (PtPain) as early as week 2, and ≥70% reduction (FIG. 3N) as early as week 4, and efficacy achieved was sustained thereafter. Patients who switched from placebo to open-label upadacitinib at week 14 generally reached the same level of pain reduction after week 14 as those initially randomized to upadacitinib. MASES assessment includes patients with baseline enthesitis; WPAI assessment includes patients currently employed; SPARCC MRI assessment population as pre-specified in the statistical analysis plan (baseline included MRI data ≤3 days after first dose of study drug, and Week 14 included MRI data up to first dose of Period 2 study drug). ASAS20=Assessment of SpondyloArthritis international Society 20 response. ASAS40=Assessment of SpondyloArthritis international Society 40 response. ASQoL=Ankylosing Spondylitis Quality of Life score. ASDAS=Ankylosing Spondylitis Disease Activity Score. BASDAI50=50% improvement from baseline in Bath Ankylosing Spondylitis Disease Activity Index. BASFI=Bath Ankylosing Spondylitis Functional Index. BASMI=Bath Ankylosing Spondylitis Metrology Index. HI=Health Index. MASES=Maastricht Ankylosing Spondylitis Enthesitis Score. MRI=magnetic resonance imaging. MMRM=mixed model for repeated measures. NRI=non-responder imputation. AO=As Observed. PR=partial remission. QD=once daily. SI, sacroiliac. SPARCC=Spondyloarthritis Research Consortium of Canada. WPAI=Work Productivity and Activity Impairment.

FIGS. 4A-4E depict data for ASAS domains (ASAS40, PtGA, Back Pain, BASFI, and Inflammation) measured at Weeks 2, 4, 8, 12, and 14 in the Phase 2/3 Ankylosing Spondylitis (SELECT-AXIS 1) clinical trial. A significant difference for upadacitinib freebase versus placebo in ASAS40 (FIG. 4A) and the mean change for each of its four individual domains (FIGS. 4B-4E) was observed as early as the first post-baseline visit (Week 2), and this difference was maintained consistently through Week 14, with Week 14 achieving a statistically significant difference in multiplicity-controlled analysis. Back pain defined on a numerical rating scale (0-10) based on the following question, "What is the amount of back pain that you experienced at any time during the last week? Inflammation is defined as mean of Questions 5 and 6 of the BASDAI. BASDAI=Bath Ankylosing Spondylitis Disease Activity Index. BASFI=Bath Ankylosing Spondylitis Functional Index. BL=baseline. LSM=least squares mean. MMRM=mixed model for repeated measures. NRI=non-responder imputation. PtGA=Patient Global Assessment of disease activity. QD=once daily.

FIG. 5 depicts the pre-specified and supplemental SPARCC MRI Analysis of the Phase 2/3 Ankylosing Spondylitis (SELECT-AXIS 1) clinical trial. The SPARCC MRI assessment population was pre-specified in the statistical analysis plan (baseline included MRI data ≤3 days after first dose of study drug, and Week 14 included MRI data up to first dose of period 2 study drug). The supplemental SPARCC MRI analysis included all MRI data collected at nominal visits at baseline and Week 14, and confirmed the results of the primary SPARCC MRI analysis for both the spine and SI joints. MMRM=mixed model for repeated measures. MRI=magnetic resonance imaging. QD=once daily. SI=sacroiliac. SPARCC=Spondyloarthritis Research Consortium of Canada.

FIGS. 8A-8D depict the least squares mean (LSM) change from baseline in individual ASDAS components over time in the Phase 2/3 Ankylosing Spondylitis (SELECT-AXIS 1) clinical trial. Improvement in the mean ASDAS (FIG. 8B) and the individual ASDAS components (FIGS. 8A-17D) was seen as early as Week 2 with continued improvement up to Week 14 with upadacitinib freebase.

Spinal pain=BASDAI Question 2. Peripheral pain/swelling=BASDAI Question 3. Duration of morning stiffness=BASDAI Question 6. ASDAS=Ankylosing Spondylitis Disease Activity Score. BASDAI=Bath Ankylosing Spondylitis Disease Activity Index. BL=baseline. hsCRP=high-sensitivity C-reactive protein. MMRM=mixed model for repeated measures. PtGA=Patient Global Assessment of disease activity. QD=once daily.

Figure 9:
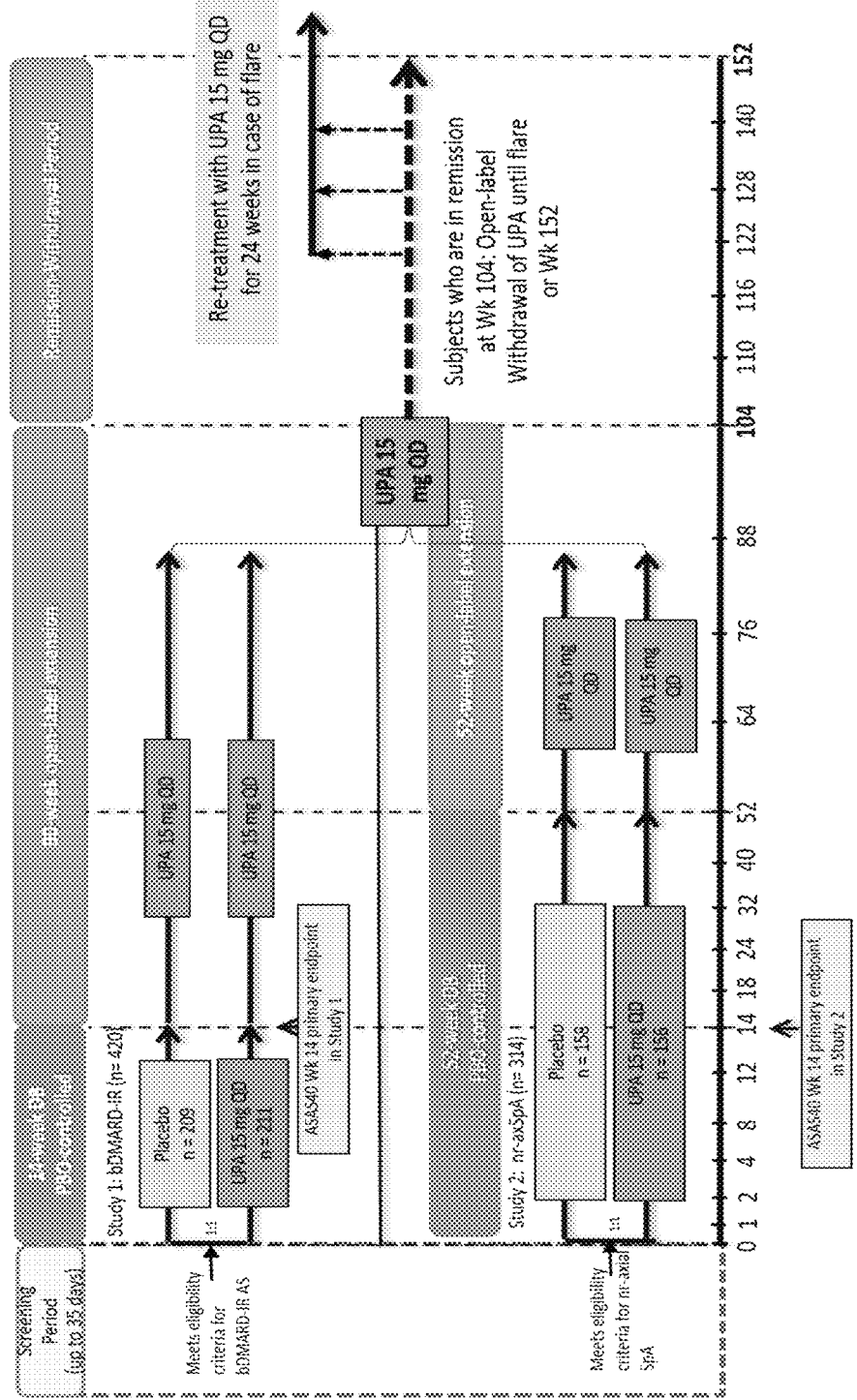

FIG. 9 depicts the Phase 3 study design for the treatment of AS and nr-AxSpA subjects. AS=ankylosing spondylitis; ASAS=Assessment of SpondyloArthritis International Society; bDMARD-IR=biologic disease-modifying anti-rheumatic drug inadequate responder; nr-axSpA=non-radiographic axial spondyloarthritis; DB=double blind; PBO=placebo; QD=once daily; UPA=upadacitinib freebase.

Figure 10A:
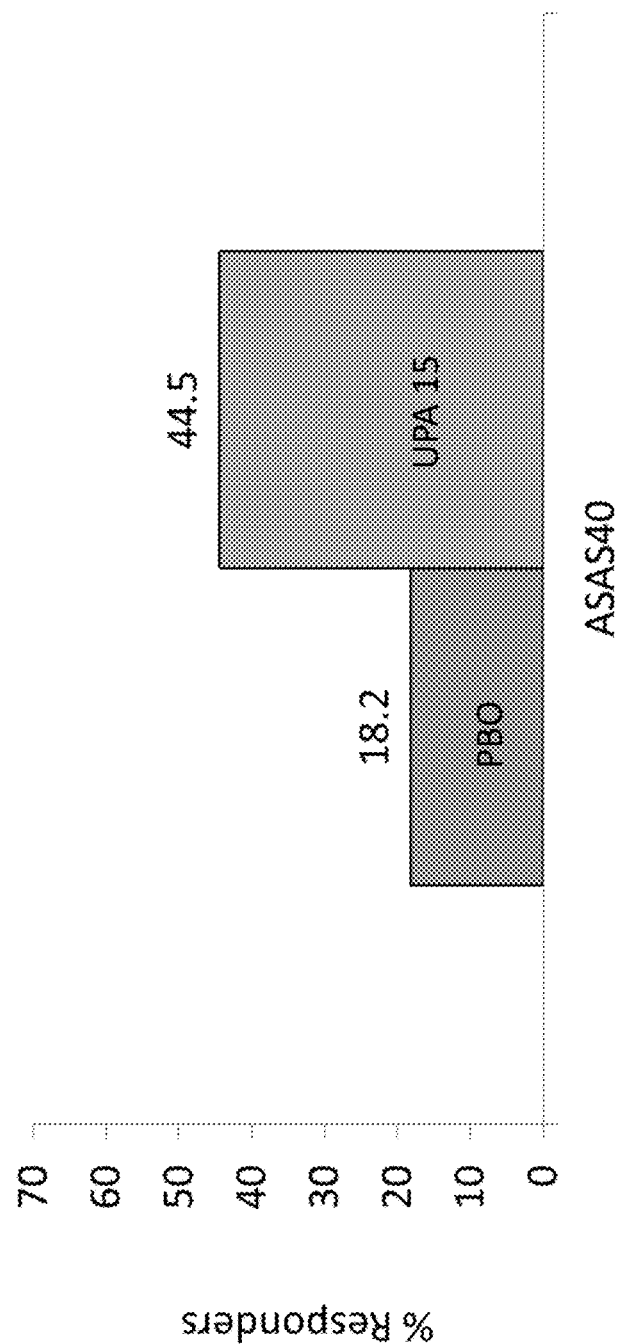
Figure 10B:
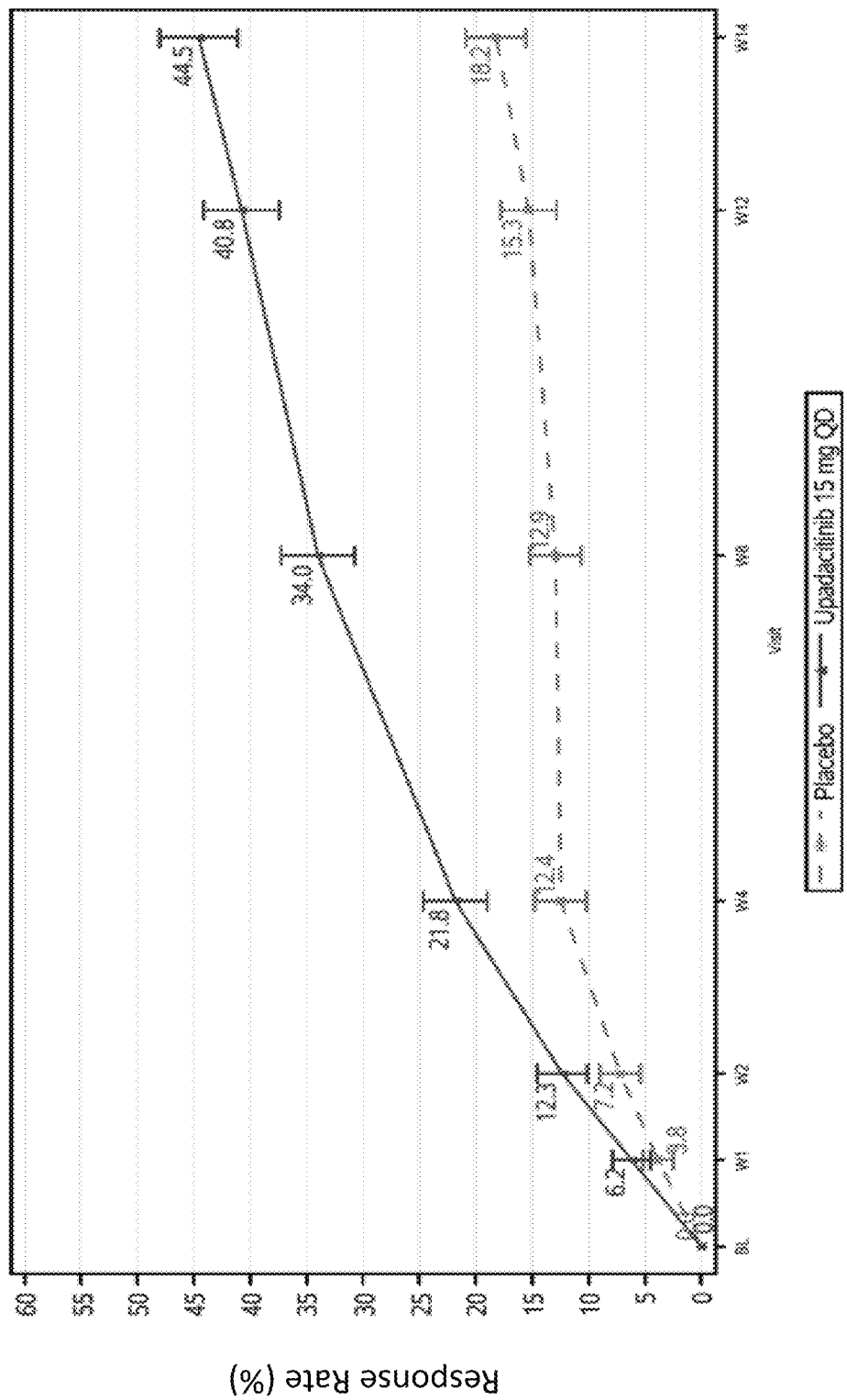

FIGS. 10A-10B depict the Week 14 results of the Phase 3 Ankylosing Spondylitis (SELECT AXIS-2) clinical trial for the primary endpoint ASAS40 response in bDMARD-IR subjects. FIG. 2A depicts ASAS40 response for placebo vs. upadacitinib freebase 15 mg QD at Week 14; FIG. 2B depicts the ASAS40 response rate for placebo vs. upadacitinib freebase 15 mg QD over time (Baseline to Week 14). The results demonstrate the study met the primary endpoint. Upadacitinib showed onset of effect in ASAS40 as early as Week 4. ASAS40=Assessment of SpondyloArthritis International Society 40 Response; QD=once daily; PBO=placebo; UPA=upadacitinib freebase; *=significant after multiplicity adjustment.

Figure 11A:
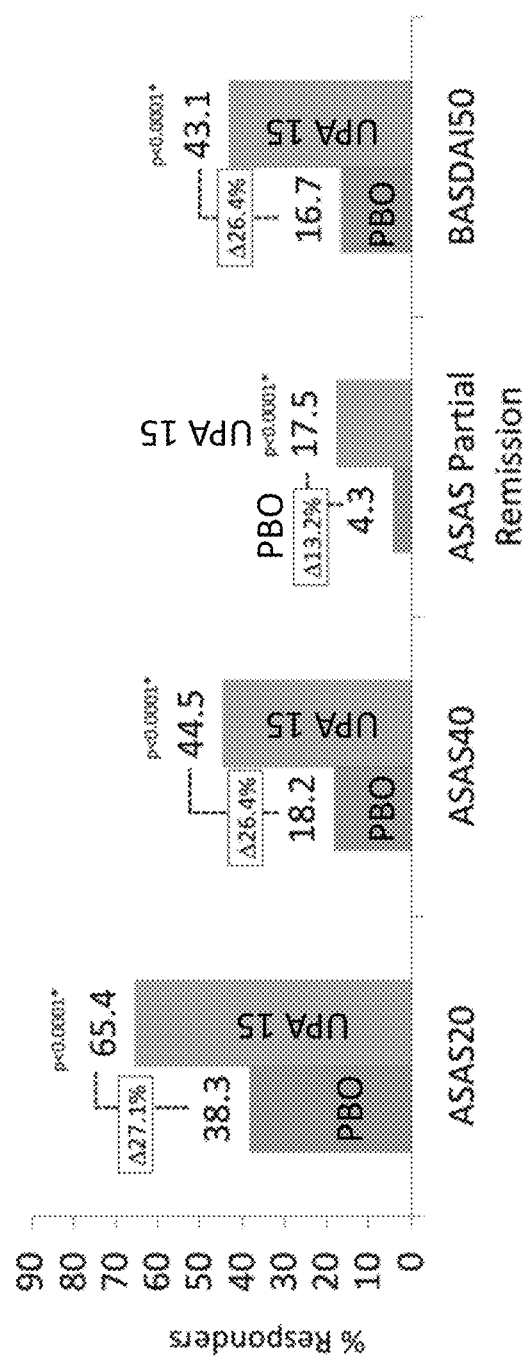
Figure 11B:
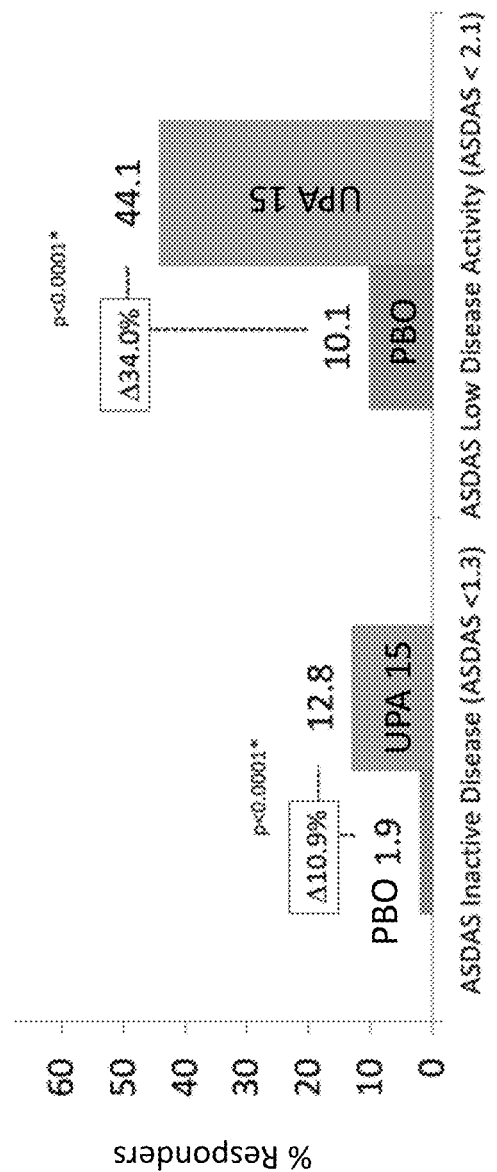
Figure 11C:
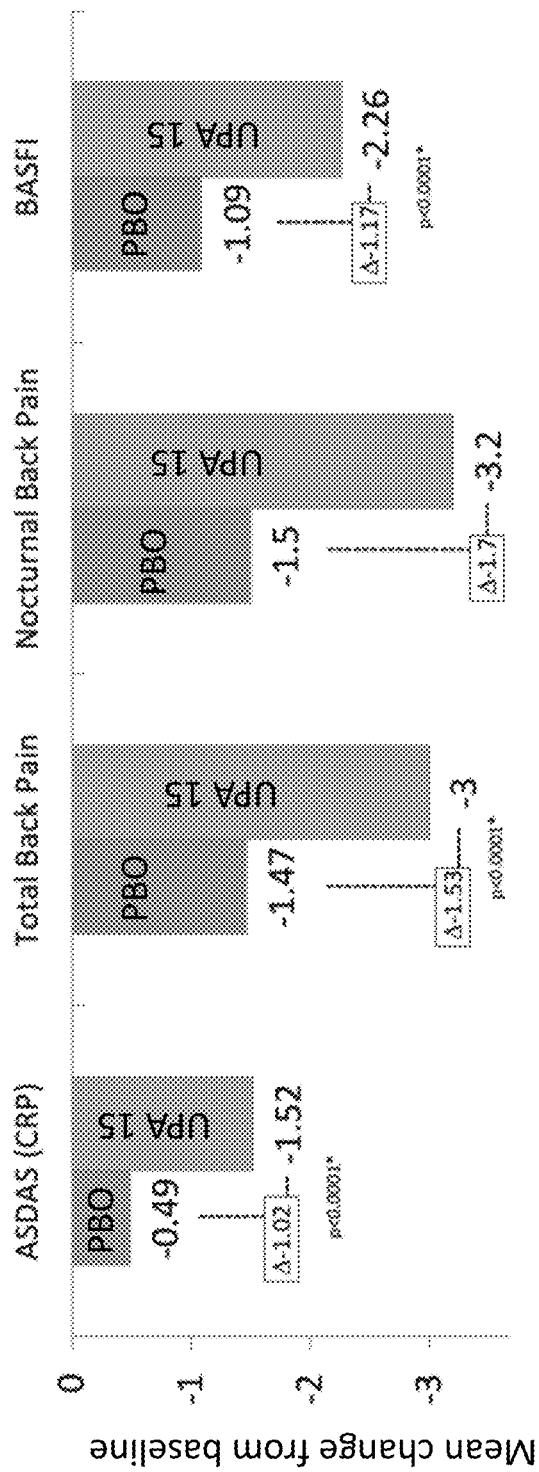
Figure 11D:
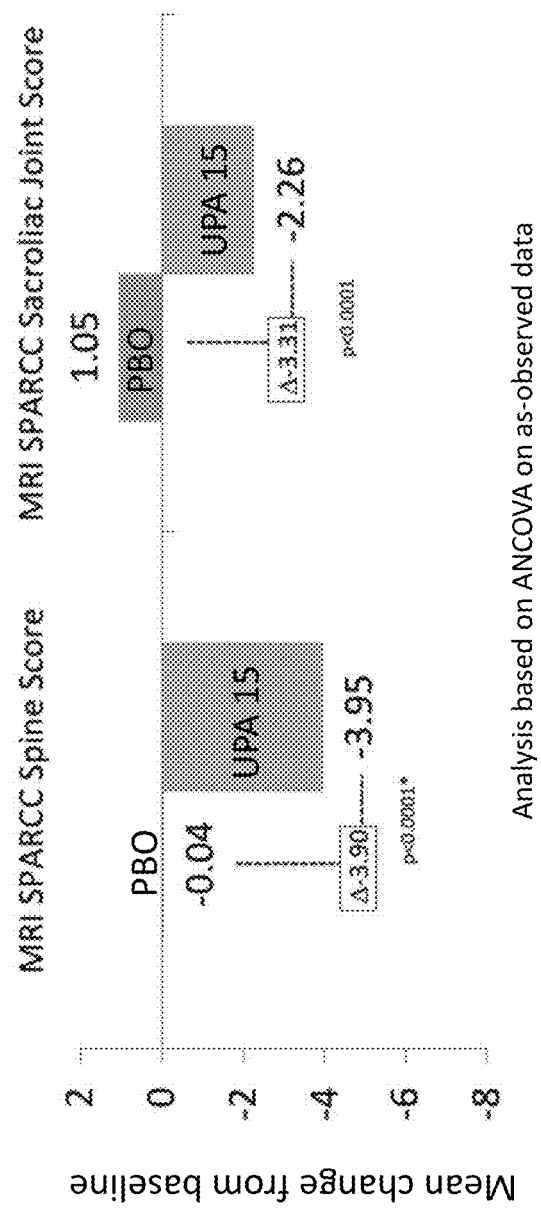
Figure 11E:
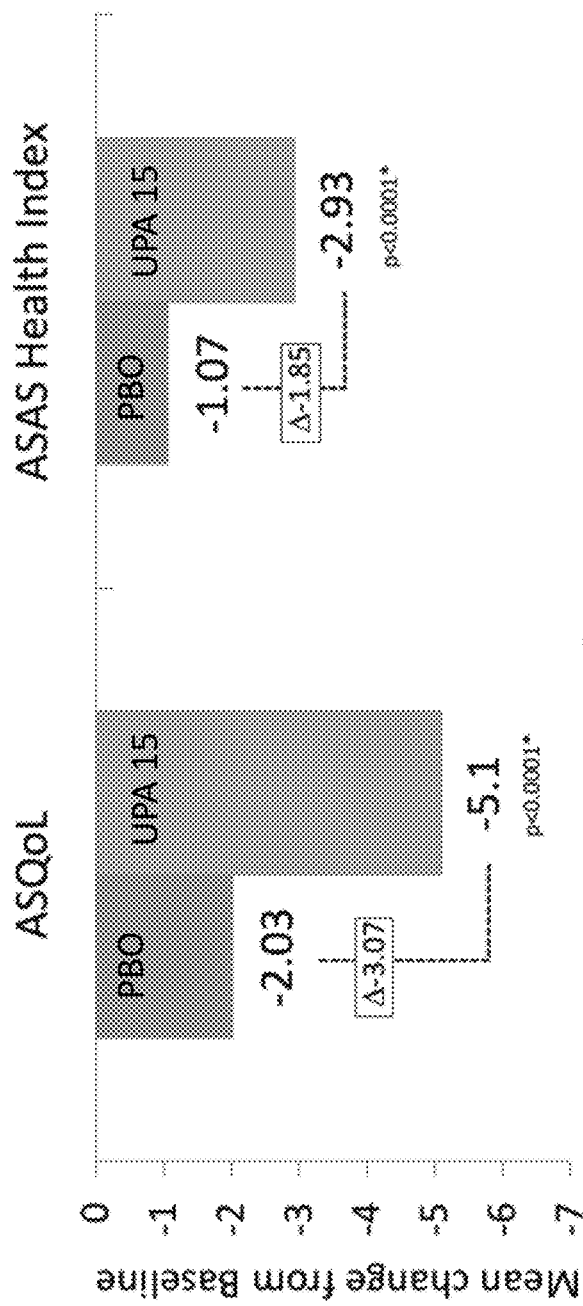
Figure 11F:
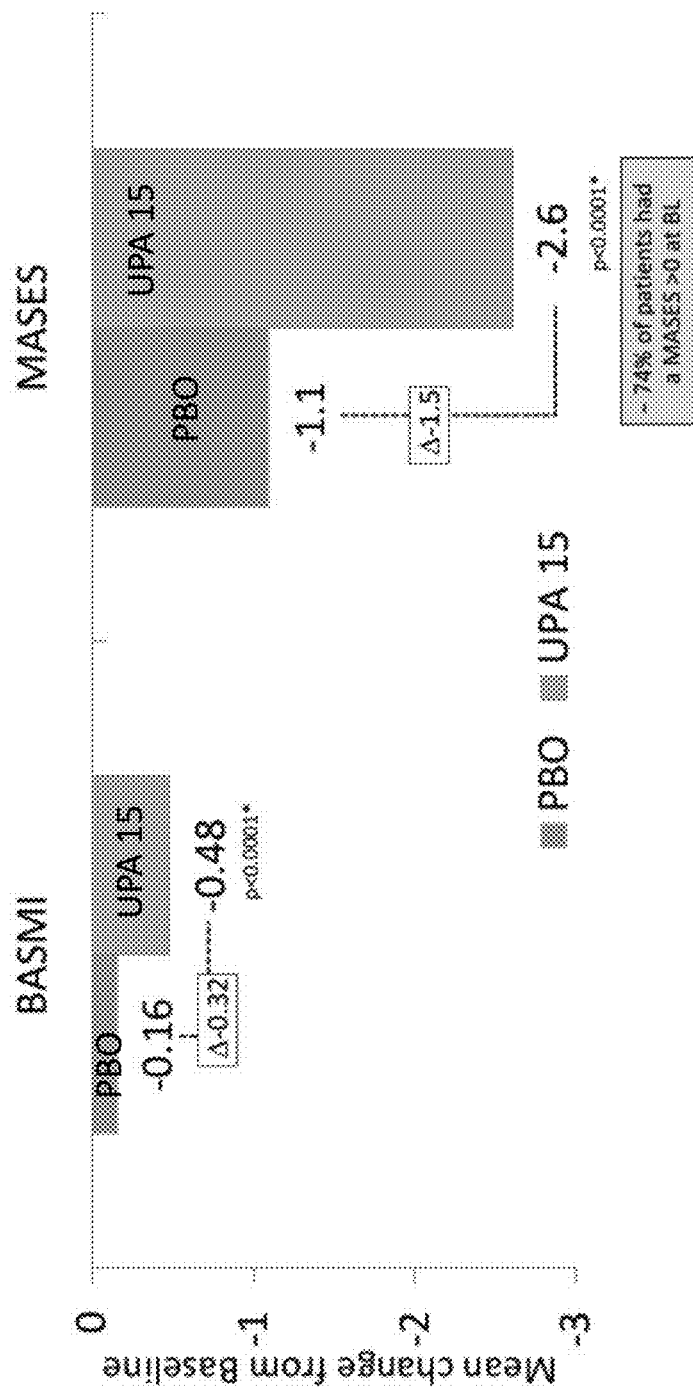

FIGS. 11A-11F depict the Week 14 results of the Phase 3 Ankylosing Spondylitis (SELECT AXIS-2) clinical trial for key clinical efficacy endpoints for placebo vs 15 mg upadacitinib freebase once daily. FIG. 11A depicts the ASAS20, ASAS40, ASAS PR, and BASDAI50 responses at Week 14; FIG. 11B depicts the ASDAS Inactive Disease and ASDAS Low Disease Activity responses at Week 14; FIG. 11C depicts the ASDAS (CRP), Total Back Pain, Nocturnal Back Pain, and BASFI responses at Week 14; FIG. 11D depicts the MRI SPARCC Spine score and the MRI SPARCC Sacroliac Joint Score at Week 14; FIG. 11E depicts the ASQoL and ASAS Health Index scores at Week 14; and FIG. 11F depicts the BASMI and MASES scores at Week 14. PBO=placebo; UPA=upadacitinib freebase; ASDAS=Ankylosing Spondylitis Disease Activity Score; BASDAI50=50% improvement from baseline in Bath Ankylosing Spondylitis Disease Activity Index; BASFI=Bath Ankylosing Spondylitis Functional Index; MRI=magnetic resonance imaging; SPARCC=Spondyloarthritis Research Consortium of Canada; ASQoL=Ankylosing Spondylitis Quality of Life score; ASAS=Assessment of SpondyloArthritis International Society; BASMI=Bath Ankylosing Spondylitis Metrology Index; MASES=Maastricht Ankylosing Spondylitis Enthesitis Score; BL=Baseline; *=significant after multiplicity-adjustment.

Figure 12:
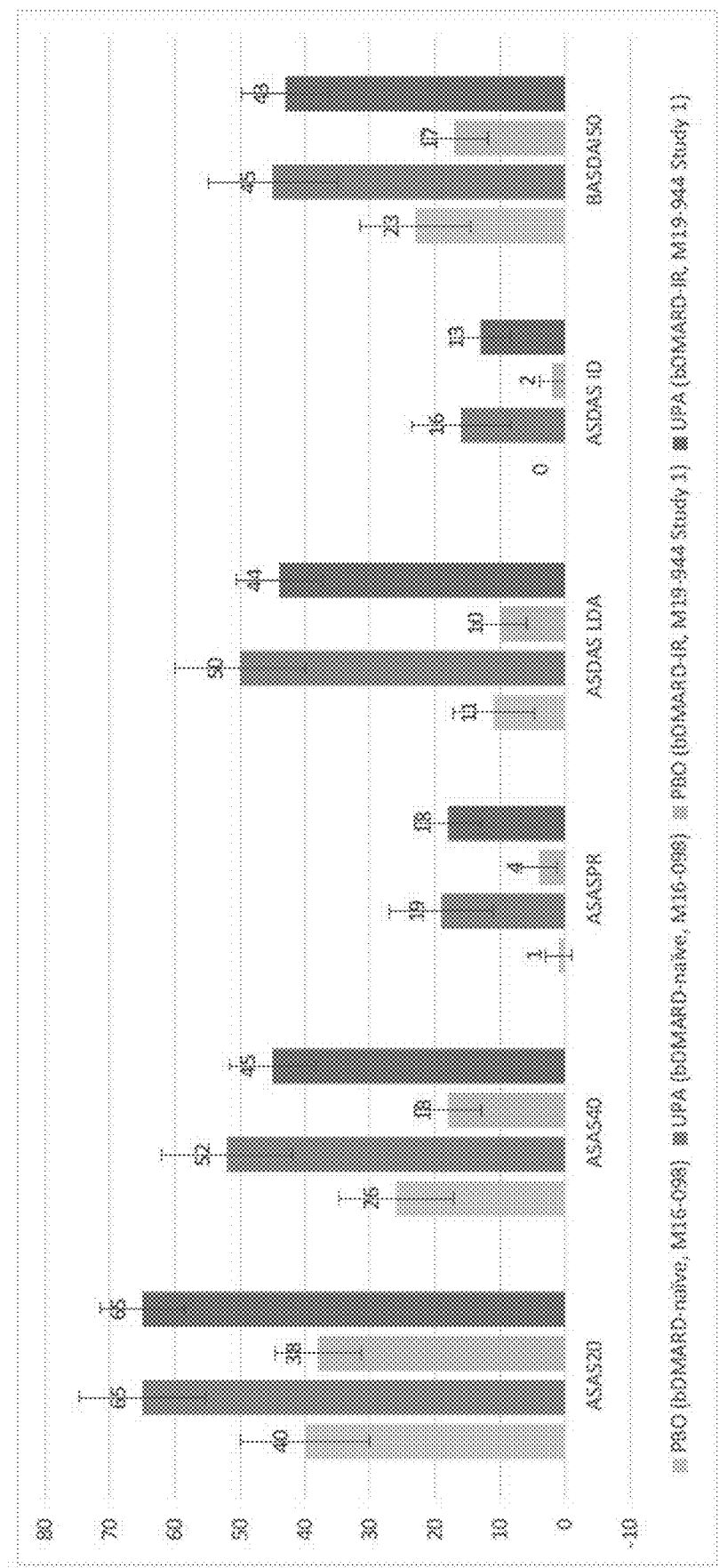

FIG. 12 depicts the response rate for placebo and upadacitinib freebase in bDMARD-naïve (SELECT AXIS-1; US Pat App No. 2021/0228575) and bDMARD-IR (SELECT AXIS-2, Study 1) studies at Week 14 for ASAS20, ASAS40, ASASPR; ASDAS LDA; ASDAS ID; and BASDAI50. PBO=placebo; UPA=upadacitinib; ASAS=Assessment of SpondyloArthritis International Society; ASASPR=Assessment of SpondyloArthritis International Society Partial Remission; ASDAS=Ankylosing Spondylitis Disease Activity Score; LDA=Low Disease Activity; ID=Inactive Disease; BASDAI50=50% improvement from baseline in Bath Ankylosing Spondylitis Disease Activity Index.

Figure 13A:
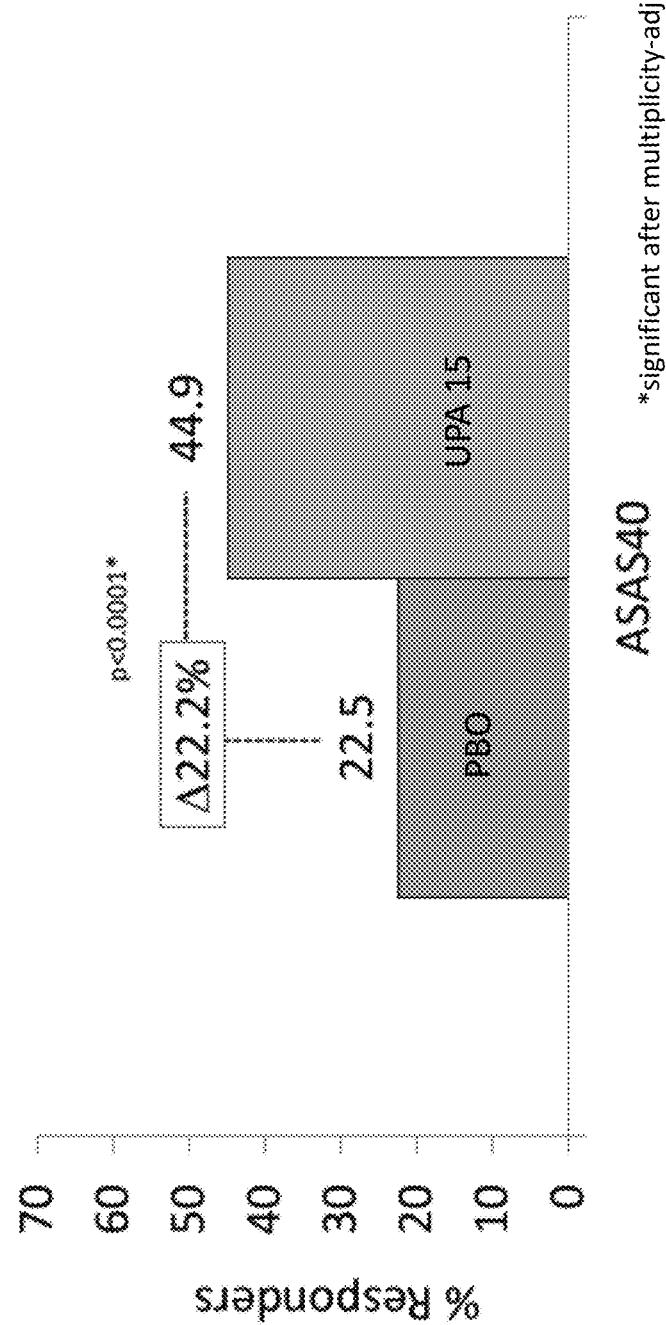
Figure 13B:
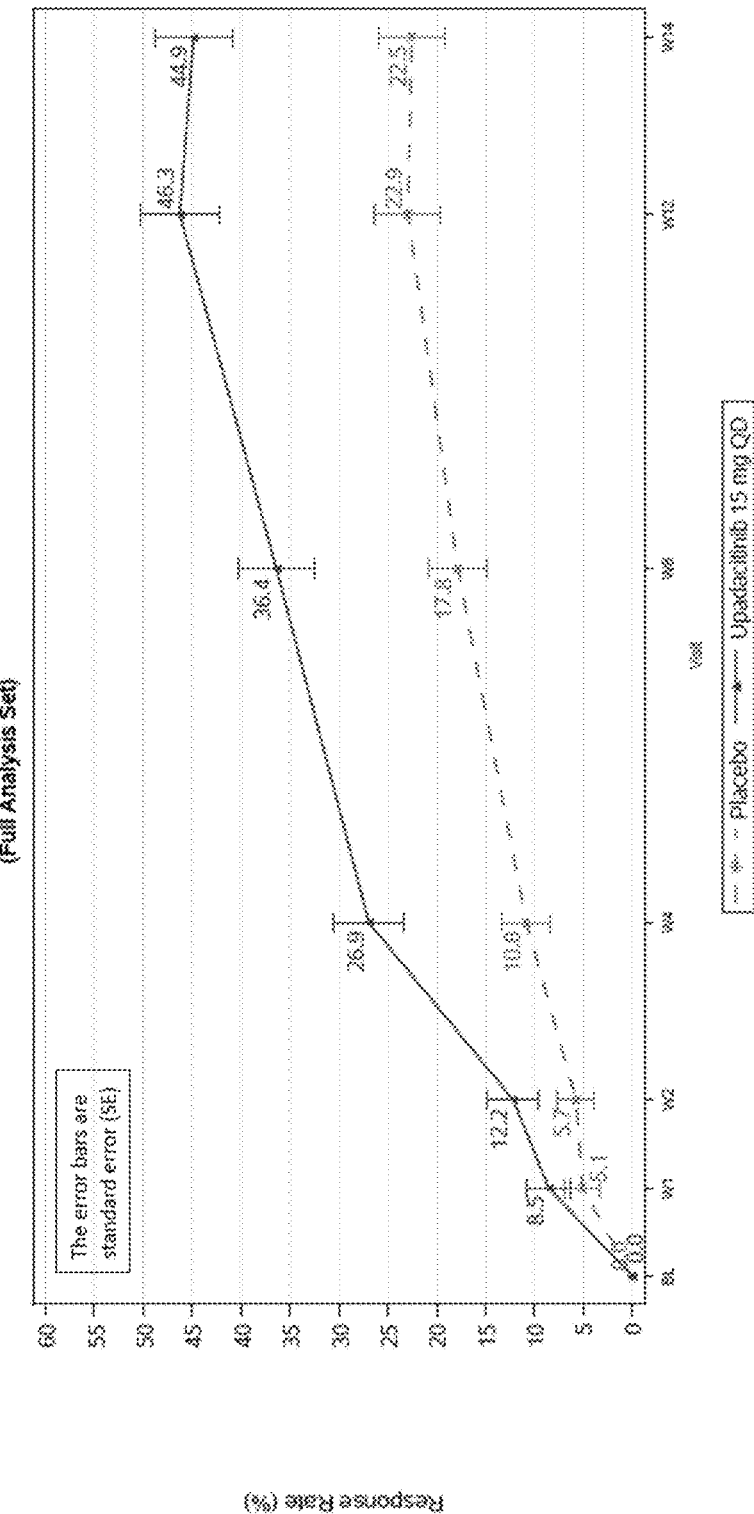

FIGS. 13A and 13B depict the Week 14 results of the Phase 3 non-radiographic axial spondyloarthritis (nr-axSpA) (SELECT AXIS-2) clinical trial for the primary endpoint ASAS40 response. FIG. 13A depicts ASAS40 response for placebo vs. upadacitinib freebase 15 mg QD at Week 14; FIG. 13B depicts the ASAS40 response rate for placebo vs. upadacitinib freebase 15 mg QD over time (Baseline to Week 14). The results demonstrate the study met the primary endpoint. Upadacitinib showed onset of effect in ASAS40 as early as Week 2. ASAS40=Assessment of SpondyloArthritis International Society 40 Response; QD=once daily; PBO=placebo; UPA=upadacitinib freebase; *=significant after multiplicity adjustment.

Figure 14A:
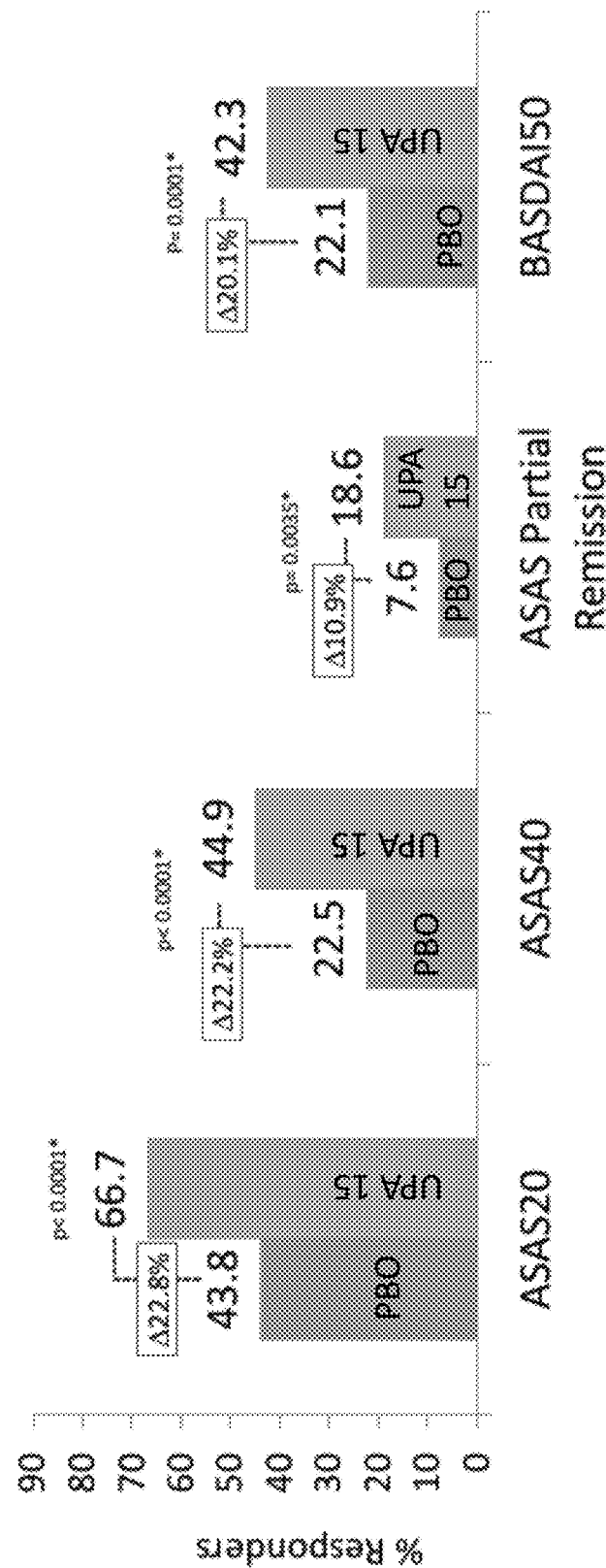
Figure 14B:
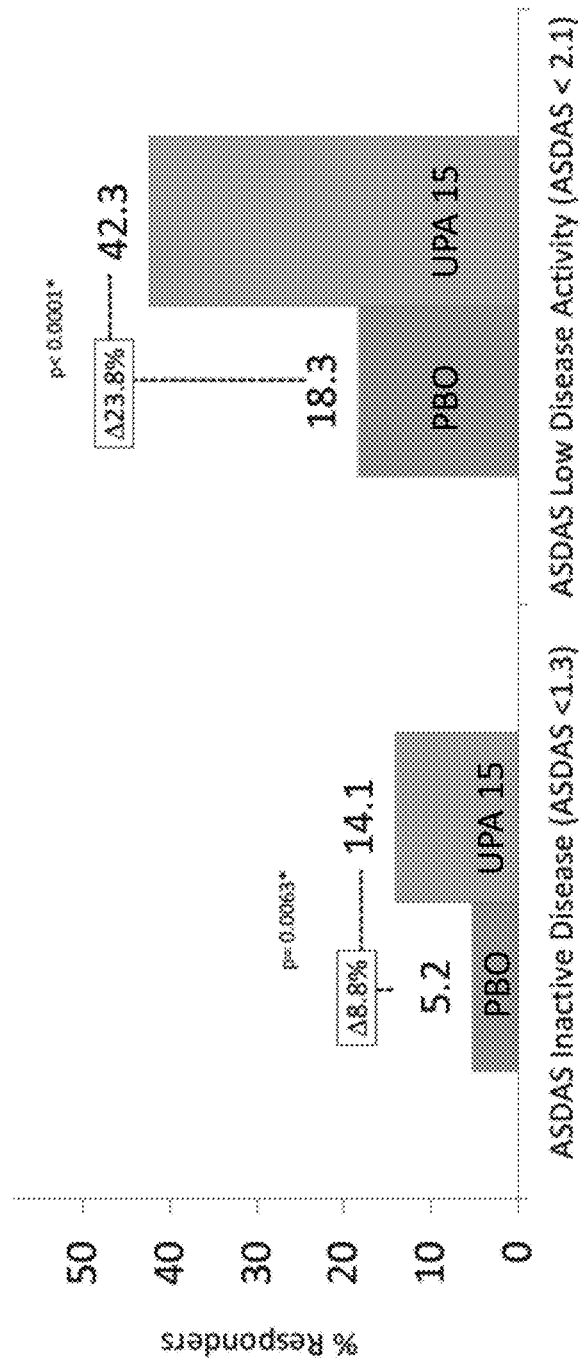
Figure 14C:
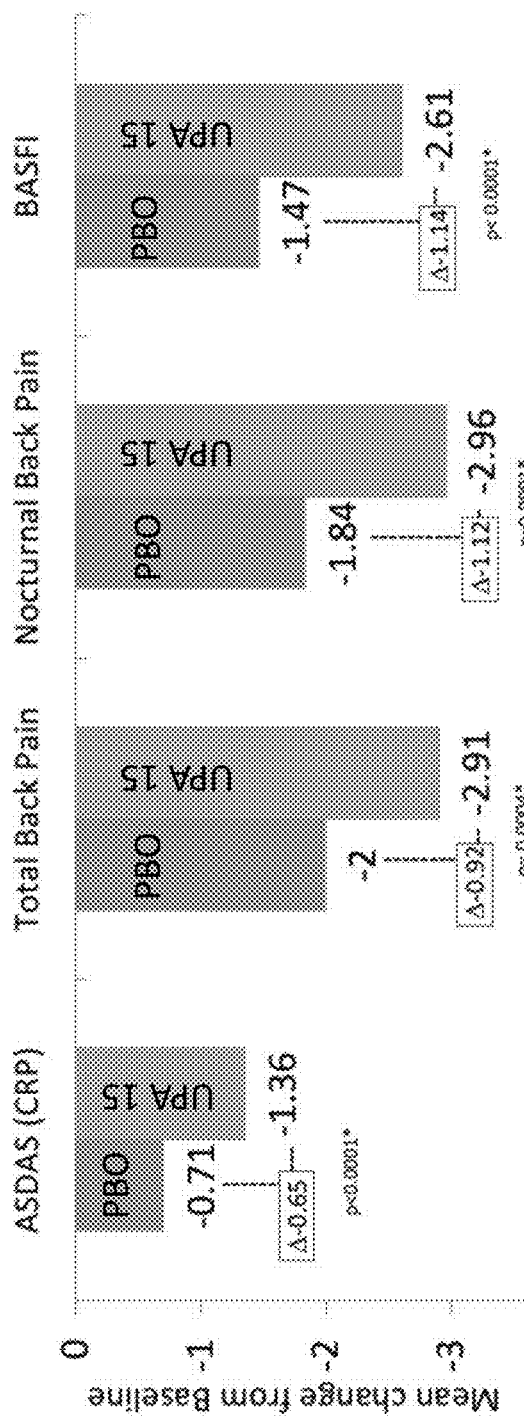
Figure 14D:
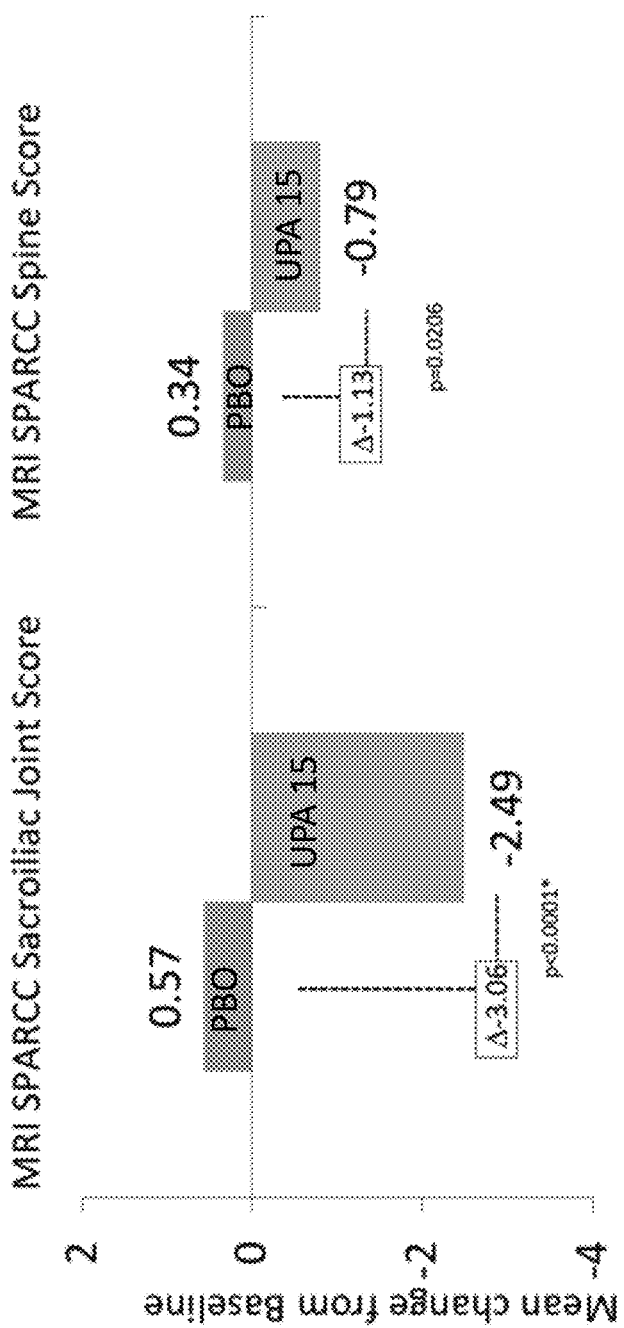
Figure 14E:
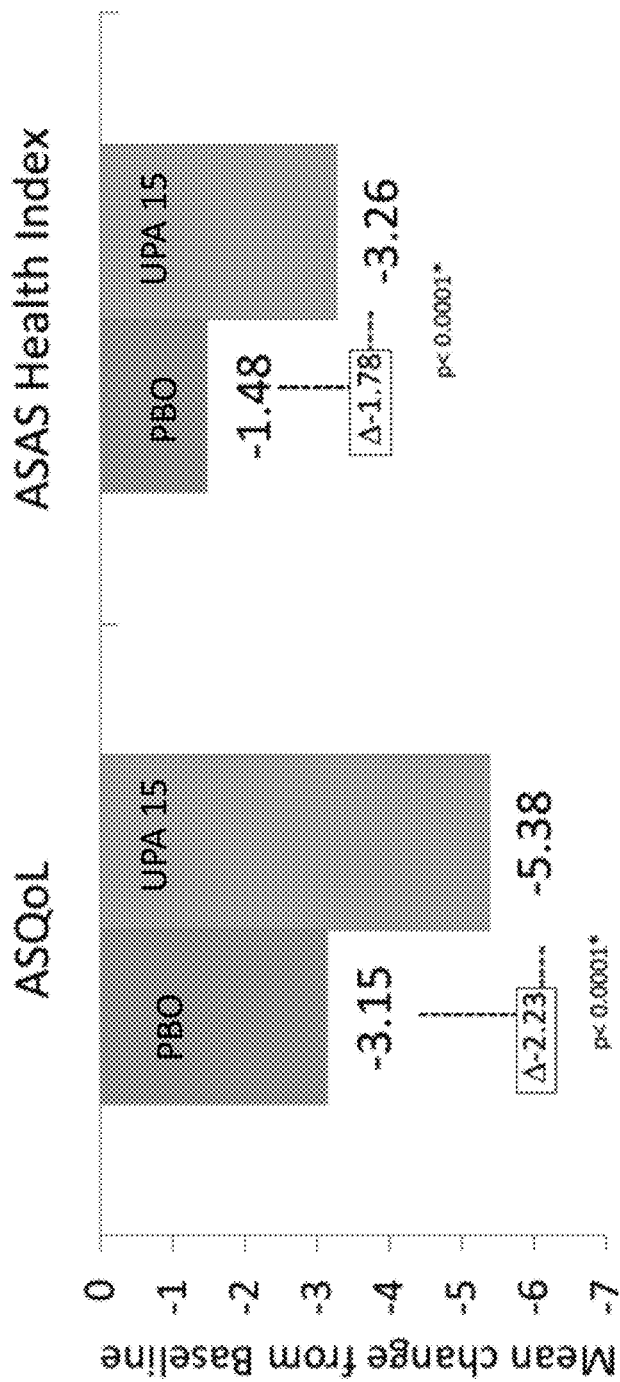
Figure 14F:
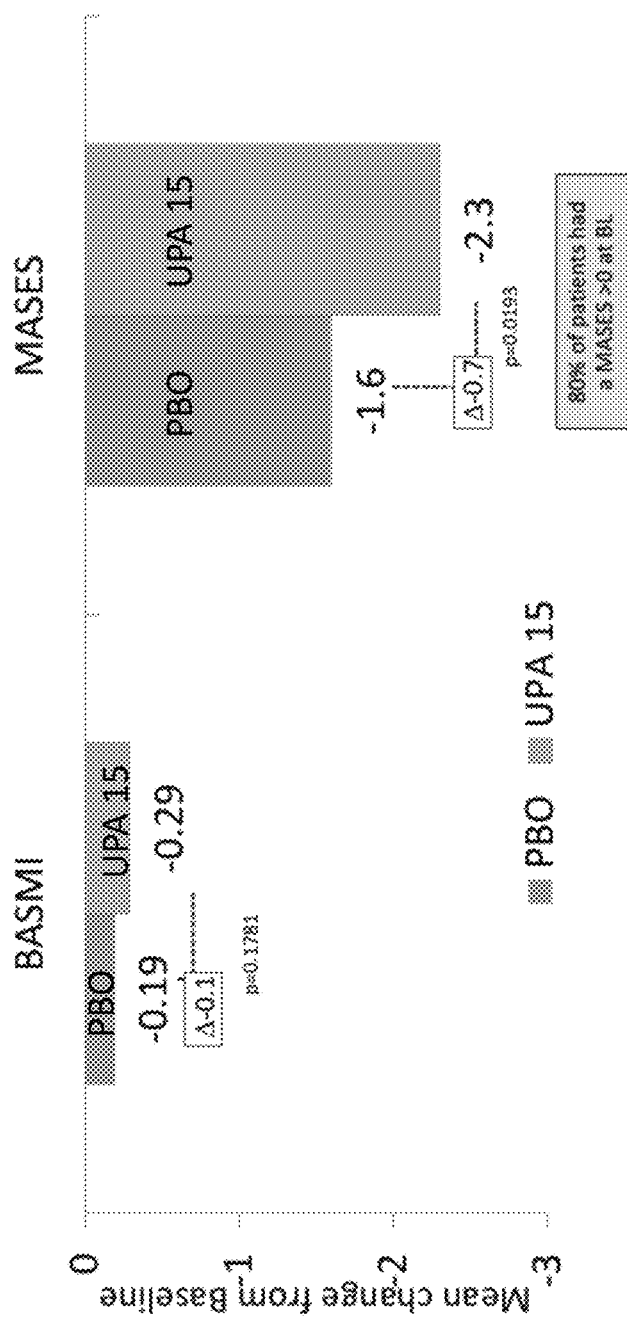

FIGS. 14A-14F depict the Week 14 results of the Phase 3 non-radiographic axial spondyloarthritis (nr-axSpA) (SELECT AXIS-2) clinical trial for key clinical efficacy endpoints for placebo vs 15 mg upadacitinib freebase once daily. FIG. 14A depicts the ASAS20, ASAS40, ASAS Partial Remission, and BASDAI50 responses at Week 14; FIG. 14B depicts the ASDAS Inactive Disease and ASDAS Low Disease Activity responses at Week 14; FIG. 14C depicts the ASDAS (CRP), Total Back Pain, Nocturnal Back Pain, and BASFI responses at Week 14; FIG. 14D depicts the MRI SPARCC Spine score and the MRI SPARCC Sacroliac Joint Score at Week 14; FIG. 14E depicts the ASQoL and ASAS Health Index scores at Week 14; and FIG. 14F depicts the BASMI and MASES scores at Week 14. PBO=placebo; UPA=upadacitinib freebase; ASDAS=Ankylosing Spondylitis Disease Activity Score; BASDAI50=50% improvement from baseline in Bath Ankylosing Spondylitis Disease Activity Index; BASFI=Bath Ankylosing Spondylitis Functional Index; MRI=magnetic resonance imaging; SPARCC=Spondyloarthritis Research Consortium of Canada; ASQoL=Ankylosing Spondylitis Quality of Life score; ASAS=Assessment of SpondyloArthritis International Society; BASMI=Bath Ankylosing Spondylitis Metrology Index; MASES=Maastricht Ankylosing Spondylitis Enthesitis Score; BL=Baseline; *=significant after multiplicity-adjustment.

DETAILED DESCRIPTION OF THE INVENTION

This written description uses examples to disclose the invention and also to enable any person skilled in the art to practice the invention, including making and using any of the disclosed solid state forms or compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements.

I. Definitions

Section headings as used in this section and the entirety of the disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "about" generally refers to a range of numbers that one of skill in the art would consider equivalent to the recited value (i.e., having the same function or result). In many instances, the term "about" may include numbers that are rounded to the nearest significant figure.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The term "subject" refers to a human subject.

The terms "treating" and "treatment" refer to ameliorating, suppressing, eradicating, reducing the severity of, decreasing the frequency of incidence of, preventing, reducing the risk of, slowing the progression of damage caused by or delaying the onset of the condition or improving the quality of life of a patient suffering from the condition.

The abbreviation "% CV" refers to the coefficient of variation, expressed as a percent. % CV is calculated according to the following equation: % CV=(SD/x)*100, wherein x is the mean value and SD is the standard deviation.

As used herein, the term "entry into a use environment" means contact of a formulation of the disclosure with the gastric fluids of the subject to whom it is administered, or with a fluid intended to simulate gastric fluid.

The abbreviation "MTX" refers to methotrexate.

Clinical Endpoint Definitions

Assessment of SpondyloArthritis International Society (ASAS), ASAS20, ASAS40, ASAS-PR, and ASAS 5/6 Responses.

Domains used for the ASAS responses are as follows:
a. Patient's Global Assessment—Represented by the PtGA-disease activity (NRS score 0-10)
b. Pain—Represented by the Patient's Assessment of Total Back Pain (Total Back Pain, NRS score 0-10)
c. Function—Represented by the BASFI (NRS score 0-10)
d. Inflammation—Represented by the mean of the 2 morning stiffness-related BASDAI (mean of Questions 5 and 6 of the BASDAI NRS score 0-10)

ASAS20 Response: Improvement of ≥20% and absolute improvement of ≥1 unit (on a scale of 0 to 10; 0=no pain and 10=worst possible pain) from Baseline in ≥3 of the above 4 domains above, with no deterioration (defined as a worsening of ≥20% and a net worsening of ≥1 unit) in the potential remaining domain.

ASAS40 Response: Improvement of ≥40% and absolute improvement of ≥2 units (on a scale of 0 to 10; 0=no pain and 10=worst possible pain) from Baseline in ≥3 of the above 4 domains above, with no deterioration (defined as a net worsening of >0 units) in the potential remaining domain.

ASAS partial remission (PR): an absolute score of <2 units (on a scale of 0 to 10; 0=no pain and 10=worst possible pain) from Baseline for each of the 4 domains above.

ASAS 5/6 Response: Improvement of ≥20% from Baseline in 5 out of the following 6 domains: BASFI, Patient's Assessment of Total Back Pain, PtGA-disease activity, inflammation (mean of Questions 5 and 6 of the BASDAI]), lateral lumbar flexion from BASMI, and hs-CRP.

ASAS Health Index (HI)

The ASAS HI is a linear composite measure with a dichotomous response option: "I agree" and "I do not agree" to a listing of 17 Questions. Each statement on the ASAS HI is given a score of "1"="I agree" or "0"="I do not agree." The total sum of the ASAS HI ranges from 0-17, with a lower score indicating a better health status. Questions 7 and 8 are not applicable to all patients. For those patients who ticked the response "not applicable," the sum score is analyzed based on n=16 or n=15 respectively. A total score can be analyzed if no more than 20% of the data (i.e., 3 Questions) are missing. The total score is calculated as follows for respondents with up to a maximum of three missing responses: Sum.score=x/(17−m)*17, where x is the Question summation score and m is the number of missing Questions and m≤3. Cases with more than three missing responses (m>3) cannot be allocated a total score and the total score will be set as missing. The 17 ASAS Health Index Questions are as follows:

1. Pain sometimes disrupts my normal activities.
2. I find it hard to stand for long.
3. I have problems running
4. I have problems using toilet facilities.
5. I am often exhausted.
6. I am less motivated to do anything that requires physical effort.
7. I have lost interest in sex.
8. I have difficulty operating the pedals in my car.
9. I am finding it hard to make contact with people.
10. I am not able to walk outdoors on flat ground.
11. I find it hard to concentrate.
12. I am restricted in traveling because of my mobility.
13. I often get frustrated.
14. I find it difficult to wash my hair.
15. I have experienced financial changes because of my rheumatic disease.
16. I sleep badly at night.
17. I cannot overcome my difficulties.

Ankylosing Spondylitis Disease Activity Score (ASDAS)

Parameters used for the calculation of ASDAS:
1. Patient's Assessment of Total Back Pain (BASDAI Question 2 NRS score 0-10),
2. Duration of morning stiffness (BASDAI Question 6 NRS score 0-10),
3. Patient global assessment of disease activity (PtGA NRS score 0-10),
4. Peripheral pain/swelling (BASDAI Question 3 NRS score 0-10), and
5. high-sensitivity C reactive protein (hsCRP) (in mg/mL) or erythrocyte sedimentation rate (ESR).

Calculation of ASDAS:

$$ASDAS_{hs\text{-}CRP} = 0.121 \times \text{total back pain} + 0.110 \times \text{PtGA} + 0.073 \times \text{peripheral pain/swelling} + 0.058 \times \text{duration of morning stiffness} + 0.579 \times Ln(hs\text{-}CRP+1).$$

$$ASDAS_{ESR} = 0.113 \times \text{patient global} + 0.293 \times \sqrt{ESR} + 0.086 \times \text{peripheral pain/swelling} + 0.069 \times \text{duration of morning stiffness} + 0.079 \times \text{total back pain}.$$

To calculate observed ASDAS scores, the observed component value will be calculated first. Then the components will be included in the calculation per the ASDAS formula. If any observed component is missing in a window, then the observed ASDAS score will be missing.

When the conventional CRP is below the limit of detection or when the high sensitivity CRP is <2 mg/L, the constant value of 2 mg/L should be used to calculate ASDAS-CRP.

ASDAS score is categorized by the following ASDAS Disease Activity States:
ASDAS Inactive Disease (ID): ASDAS<1.3
ASDAS Moderate Disease: 1.3≤ASDAS<2.1
ASDAS Low Disease Activity (LDA): ASDAS<2.1
ASDAS High Disease: 2.1≤ASDAS≤3.5

ASDAS Very High Disease: ASDAS>3.5

ASDAS Response categories are defined as follows:

ASDAS Major Improvement (MI) (a change from baseline ≤−2.0; ≥2-point decrease from baseline)

ASDAS Clinically Important Improvement (CII) (a change from baseline ≤−1.1; (≥1.1-point decrease from baseline)

Ankylosing Spondylitis Quality of Life Questionnaire (ASQoL)

Each of the 18 statements on the ASQoL (provided below) is given a score of "1" (yes) or "0" (no). Concepts measured include activities of daily life, emotional functioning, pain, fatigue, and sleep problems. A score of "1" is given where the Question is affirmed (with a "yes" answer), indicating adverse QoL. All Question scores are summed to give a total score or index. Scores can range from 0 (good QoL) to 18 (poor QoL), with higher scores equaling worsening functioning. Cases with more than three missing responses (i.e., more than 20%) cannot be allocated a total score. For cases with between one and three missing responses, the total score is calculated as follows: T=18x/18−m where: T is the total score, x is the total score for the Questions affirmed and m is the number of missing Questions.

1. My condition limits the places I can go
2. I sometimes feel like crying
3. I have difficulty dressing
4. I struggle to do jobs around the house
5. It's impossible to sleep
6. I am unable to join in activities with my friends/family
7. I am tired all the time
8. I have to keep stopping what I am doing to rest
9. I have unbearable pain
10. It takes a long time to get going in the morning
11. I am unable to do jobs around the house
12. I get tired easily
13. I often get frustrated
14. The pain is always there
15. I feel I miss out on a lot
16. I find it difficult to wash my hair
17. My condition gets me down
18. I worry about letting people down Bath Ankylosing Spondylitis Disease Activity Index (BASDAI), BASDAI 50 Response, and the Morning Stiffness Score The BASDAI consists of a 1 through 10 scale (1 being no problem and 10 being the worst problem) and is used to answer 6 questions pertaining to the 5 symptoms: Fatigue, Spinal pain, Joint pain/swelling, Areas of localized tenderness (also called enthesitis, or inflammation of tendons and ligaments), Morning stiffness duration, and Morning stiffness severity. A lower score indicates less disease activity.

The six BASDAI Questions (Components) are as follows:

Q1. How would you describe the overall level of fatigue/tiredness you have experienced?

Q2. How would you describe the overall level of AS neck, back or hip pain you have had?

Q3. How would you describe the overall level of pain/swelling in joints, other than neck, back or hips you have had?

Q4. How would you describe the overall level of discomfort you have had from any areas tender to touch or pressure?

Q5. How would you describe the overall level of morning stiffness you have had from the time you wake up?

Q6. How long does your morning stiffness last from the time you wake up?

Questions 1 through 5 have responses that can range from 0 (none) to 10 (very severe); Question 6 have response range from 0 (0 hr) to 10 (2 or more hrs), with 5 representing 1 hr.

Scoring of the BASDAI: BASDAI will be reported 0 to 10. The score has a maximum value of 10 and is calculated as follows:

$$BASDAI\ Score=0.2(Q1+Q2+Q3+Q4+Q5/2+Q6/2)$$

If one of the 5 Questions (Questions 1-Question 4, inflammation) is missing, then the score is the mean of the 4 non-missing Questions (total of 4 non-missing Questions divided by 4). If more than 1 of the 5 Questions is missing, then the BASDAI score is missing. Question 5 and Question 6 jointly constitute Question 5 (inflammation). If both Questions 5 and 6 are missing, and questions 1 through 4 are non-missing, then only one Question will be considered missing. The BASDAI score can still be calculated as the mean of Questions 1-4. However, if, for example, both Question 6 and Question 1 are missing, then 2 Questions will be considered missing, as the inflammation calculation would be incomplete. The BASDAI score would then be considered missing in this case.

A BASDAI 50 response is a categorical response based on BASDAI that represents an at least 50% improvement from baseline in BASDAI.

The Morning Stiffness Score is the average of BASDAI Questions 5 and 6, and it ranges from 0-10.

A "change from baseline in BASDAI and BASDAI Questions (Components), including change from baseline in mean of Question 5 and 6 of the BASDAI" means (1) a change from baseline from the BASDAI Score, (2) a change from baseline in all of the BASDAI Questions, and (3) a change from baseline of the mean of Questions 5 and 6 (which represent inflammation).

Bath Ankylosing Spondylitis Functional Index (BASFI)

The BASFI consists of the following 10 questions, assessing ability to perform activities such as dressing, bending, reaching, turning, and climbing steps, each with a response ranging from 0 (easy) to 10 (impossible):

1. Putting on your socks or tights without help or aids (e.g., sock-aid).
2. Bending forward from the waist to pick up a pen from the floor without an aid.
3. Reaching up to a high shelf without help or aids (e.g., helping hand).
4. Getting up out of an armless dining room chair without using your hands or any other help.
5. Getting up off the floor without help from lying on your back.
6. Standing unsupported for 10 minutes without discomfort.
7. Climbing 12 to 15 steps without using a handrail or walking aid. One foot on each step.
8. Looking over your shoulder without turning your body.
9. Doing physically demanding activities (e.g., physiotherapy, exercises, gardening, or sports).
10. Doing a full day's activities whether at home or at work.

See, e.g., Sieper et al., *Ann Rheum Dis* (2009) 68 (Suppl II): ii1-ii44. doi:10.1136/ard.2008.104018.

Scoring of BASFI. The BASFI score will be derived based on the average of Questions 1 through 10. If up to 2 Questions are missing, corresponding scores will be replaced with the mean of the remaining non-missing Questions. If 3 or more Questions are missing, BASFI will be considered missing.

Bath Ankylosing Spondylitis Metrology Linear Index (BASMI$_{lin}$)

The Linear BASMI (BASMI$_{lin}$) composite score will be calculated using the BASMI components. The table below presents the components of BASMI$_{lin}$ and assessment ranges for score.

TABLE 1

| Components of BASMI$_{lin}$ | 0 | Between 0 and 10 | 10 |
|---|---|---|---|
| Lateral Lumbar flexion (cm) | A ≥ 21.1 | (21.1 − A)/2.1 | A ≤ 0.1 |
| Tragus to wall distance (cm) | A ≤ 8 | (A − 8)/3 | A ≥ 38 |
| Lumbar flexion (modified Schober) (cm) | A ≥ 7.4 | (7.4 − A)/0.7 | A ≤ 0.4 |
| Intermalleolar | A ≥ 124.5 | (124.5 − A)/10 | A ≤ 24.5 |

TABLE 1-continued

| Components of BASMI$_{lin}$ | 0 | Between 0 and 10 | 10 |
|---|---|---|---|
| distance (cm) | | | |
| Cervical rotation (°) | A ≥ 89.3 | (89.3 − A)/8.5 | A ≤ 4.3 |

BASMI$_{lin}$ = Assessment measurements for tragus to wall, cervical rotation and lateral lumbar flexion are the means of the left and right measurement;
A = assessment measurement Scores for each assessment range from 0 to 10, and the BASMI$_{lin}$ total score will be the average of the 5 assessment scores. If 1 Question is missing, the BASMI$_{lin}$ will be calculated as the mean of remaining 4 Questions. Hence, the range of the BASMI$_{lin}$ total score should be between 0 and 10. If 2 or more Questions are missing, then the BASMI$_{lin}$ score will be considered missing. See e.g., van der Heijde et al., *Arth. Care & Res.* (2012) 64:1919-1922 and van der Heijde et al., *Ann Rheum Dis* (2008) 67:489-93.

Enthesitis Scoring: Spondyloarthritis Research Consortium of Canada (SPARCC) Enthesitis Index, Leeds Enthesitis Index (LEI), Total Enthesitis Count, and Maastricht Ankylosing Spondylitis Enthesitis Score (MASES)

For the Spondyloarthritis Research Consortium of Canada (SPARCC) Enthesitis Index, 16 sites are evaluated as indicated in rows 1-8 in the table below. Tenderness on examination is recorded as either present (coded as 1), absent (coded as 0), or not assessed (NA) for each site. The SPARCC enthesitis index is calculated by taking the sum of the scores from the 16 sites. The SPARCC score ranges from 0 to 16.

The Leeds Enthesitis Index evaluates enthesitis at the 6 entheseal sites indicated in rows 2, 7 and 9 in the table below. Tenderness on examination is recorded as either present (coded as 1), absent (coded as 0), or not assessed (NA) for each of the 6 sites. The LEI is calculated by taking the sum of the scores from the 6 sites. The LEI ranges from 0 to 6.

The Total Enthesitis Count is calculated by taking the sum of the tenderness scores from all 18 sites in the table below.

The proportion of subjects with resolution of enthesitis sites included in the LEI is defined as the proportion of subjects with LEI=0; the proportion with resolution of the SPARCC Enthesitis Index and of the total enthesitis count are similarly defined (score=0).

TABLE 2

| | | Tenderness in Left | | | Tenderness in Right | | |
|---|---|---|---|---|---|---|---|
| | | Present | Absent | NA | Present | Absent | NA |
| 1 | Medial epicondyle | | | | | | |
| 2 | Lateral epicondyle | | | | | | |
| 3 | Supraspinatus insertion into the greater tuberosity of humerus | | | | | | |
| 4 | Greater trochanter | | | | | | |
| 5 | Quadriceps insertion into superior border of patella | | | | | | |
| 6 | Patellar ligament insertion into inferior pole of patella or tibial tubercle | | | | | | |
| 7 | Achilles tendon insertion into calcaneum | | | | | | |
| 8 | Plantar fascia insertion into calcaneum | | | | | | |
| 9 | Medial femoral condyle | | | | | | |

Present = 1;
Absent = 0;
NA = Not assessed

The Maastricht Ankylosing Spondylitis Enthesitis Score (MASES) will be measured to assess the presence (1) or absence (0) of enthesitis at 13 different sites (first costochondral joint left/right, seventh costochondral joint left/right, posterior superior iliac spine left/right, anterior superior iliac spine left/right, iliac crest left/right, fifth lumbar spinous process, and proximal insertion of Achilles tendon left/right), noting the subjects' responses, yielding a total score ranging 0-13. If one or more locations are missing, the score will be calculated using available data. If all locations are missing, then MASES is set to be missing.

EuroQoL-5D (EQ-5D-5L)

The EQ-5D-5L questionnaire is one of the most commonly used questionnaires to measure health-related quality of life. It consists of a questionnaire and a visual analogue scale (VAS). The self-assessment questionnaire measures 5 dimensions of health status (mobility, self-care, usual activities, pain/discomfort, and anxiety/depression). The AS subject is asked to grade their own current level of function in each dimension into 1 of 3 degrees of disability (severe, moderate, or none). The PsA subject is asked to grade their own current level of function in each dimension into 5 levels per dimension (no problems, slight problems, moderate problems, severe problems, and extreme problems corresponding to Level 1 to Level 5 respectively) and includes the EQ Visual Analogue Scale (EQ VAS). The 5 dimensions of health status are converted into a single index value. Using the VAS, subjects record perceptions of current perceived health status with a grade ranging from 0 (the worst possible health status) to 100 (the best possible health status).

High-Sensitivity C Reactive Protein (hs-CRP)

C-reactive protein (CRP), which is measured in blood plasma, is an acute phase protein that appears in blood circulation in response to inflammation, and serves as a biomarker for systemic inflammation. However, routine methods of CRP detection (turbidimetric, nephelometric) demonstrated poor sensitivity in detecting concentrations of CRP below 6-10 mg/litre. See, e.g., Poddubnyy et al., Ann. Rheum. Dis. (2010) 69:1338-1341.

The high-sensitivity C-reactive protein (hs-CRP) assay is a more precise measurement than routine CRP. Several different tests may be used to measure the hs-CRP normal range versus abnormal value for the subject to be treated; thus the upper limit of normal (ULN) will be determined by the laboratory for the hs-CRP test used and may differ from laboratory to laboratory.

Joint Count Assessment: SJC and TJC

Swollen Joint Count Assessment (SJC or SJC66): An assessment of 66 joints will be done by physical examination. The joints to be examined for swelling are the same as those examined for tenderness, except the hip joints are excluded. Joint swelling will be classified as present ("1"), absent ("0"), replaced ("9"), or no assessment ("NA"). Joints injected with corticosteroid will be considered non-evaluable for 90 days from the time of the injection. The range for SJC66 will be 0 to 66.

Tender Joint Count Assessment (TJC or TJC68): An assessment of 68 joints will be done for tenderness by pressure manipulation on physical examination. Joint pain/tenderness will be classified as: present ("1"), absent ("0"), replaced ("9"), or no assessment ("NA"). Joints injected with corticosteroid will be considered non-evaluable for 90 days from the time of the injection. The range for TJC68 will be 0 to 68.

Anatomical joints are evaluated for swelling and tenderness at every study visit. The 34 anatomical joints in the below table are assessed in this study for both the left and right side of the body.

TABLE 3

Anatomical Joints Assessed for Calculation of Tender and Swollen Joint Counts (TJC68 and SJC66)

| | | | |
|---|---|---|---|
| Temporomandibular | Sternoclavicular | Acromio-clavicular | Shoulder |
| Elbow | Wrist | Metacarpophalangeal I | Metacarpophalangeal II |
| Metacarpophalangeal III | Metacarpophalangeal IV | Metacarpophalangeal V | Thumb Interphalangeal |
| Proximal Interphalangeal II | Proximal Interphalangeal III | Proximal Interphalangeal IV | Proximal Interphalangeal V |
| Distal Interphalangeal II | Distal Interphalangeal III | Distal Interphalangeal IV | Distal Interphalangeal V |
| Hip[a] | Knee | Ankle | Tarsus |
| Metatarsophalangeal I | Metatarsophalangeal II | Metatarsophalangeal III | Metatarsophalangeal IV |
| Metatarsophalangeal V Interphalangeal IV | Great Toe/Hallux Interphalangeal V | Interphalangeal II | Interphalangeal III |

[a]Hip joints are not assessed for swelling.

Modified Stoke Ankylosing Spondylitis Spine Score (mSASSS)

The mSASSS is a scoring method that measure radiographic progression in the spine of patients with ankylosing spondylitis. The mSASSS has a range of 0 to 72, which is derived from scoring the anterior site of the lumbar spine from the lower border of T12 to the upper border of S1 and the anterior site of the cervical spine from the lower border of C2 to the upper border of T1 as either 0 (normal), 1 (erosion, sclerosis, or squaring), 2 (syndesmophyte), 3 (bridging syndesmophyte), or NA vertebral body not evaluable. X-ray of spinal films will be analyzed for radiographic progression (from Baseline to the follow-up timepoint).

SpondyloArthritis Research Consortium of Canada (SPARCC) Assessment for Spine (MRI SPARCC—Spine or MRI-Spine SPARCC) and Sacroiliac (SI) Joints (MRI SPARCC—Joints or MRI-SI Joints SPARCC)

SPARCC scores for spine and sacroiliac (SI) joints are calculated by adding up the dichotomous outcomes from evaluations of the presence, depth and intensity of bone marrow edema lesions of the spine and SI joints, respectively.

In the MRI SPARCC score of Spine, the entire spine is evaluated for active inflammation (bone marrow edema) using the Short-TI Inversion Recovery (STIR) image sequence. 23 discovertebral units (DVUs) are assessed, and the six most severely affected DVUs are selected and used to calculate the MRI Spine SPARCC score. For each of the six DVUs, 3 consecutive sagittal slices are assessed in four quadrants in order to evaluate the extent of inflammation in all three dimensions:

1. Each quadrant is scored for presence of increased signal on STIR (1=increased signal; 0=normal signal)
2. Presence, on each of the sagittal slices, of a lesion exhibiting high signal intensity (comparable to cerebrospinal fluid) in any disco-vertebral unit is given an additional score of 1.
3. Slices that included a lesion demonstrating continuous increased signal of depth ≥1 cm extending from the endplate are to be scored as +1 per slice.

The maximum possible score for any individual slice is 6, with a maximum score for all 6 discovertebral units being 108.

The MRI SPARCC score of SI joints is conducted on 6 consecutive slices of the STIR image sequence. All lesions within the iliac bone and within the sacrum up to the sacral foramina are to be scored. The SI joint is divided into 4 quadrants: upper iliac, lower iliac, upper sacral and lower sacral. Each consecutive slice is scored separately for the right and left joint in all four quadrants as follows:

1. Each quadrant is scored for presence of increased signal on STIR (1=increased signal; 0=normal signal)
2. Joints that include a lesion exhibiting intense signal on the STIR sequence are scored as +1 per slice.

3. Joints that included a lesion demonstrating continuous increased signal of depth ≥1 cm from the articular surface are be scored as +1 per slice.

The maximum possible score for any individual slice is 12, with a maximum score for all 6 slices being 72.

36-Item Short Form Health Survey (Form SF-36)

The 36-Item Short Form, Version 2 (SF-36v2) (Quality Metric) health survey consists of 36 general health questions. It has 2 components: physical and mental. For each component, a transformed summary score is calculated using 8 sub domains: physical functioning, role-physical, bodily pain, general health, vitality, social functioning, role-emotional, and mental health. The range is from 0 to 100, with higher scores indicating better outcomes. The coding and scoring for the SF-36 will use the software provided by the vendor.

Additional Definitions

A "subject" means a human. The terms "patient" and "subject" are used interchangeably herein.

An "adult subject" means a subject 18 years or older.

A "juvenile" or "pediatric" subject means a subject 1 to <18 years old. Juvenile subjects to be treated are subjects diagnosed with juvenile AS (JAS), juvenile PsA (JPsA), and/or juvenile PsO (JPsO) and in need of treatment as determined by a physician ("active juvenile AS" and "active juvenile PsA", "active juvenile PsO", respectively). Juvenile AS may be classified per International League of Associations for Rheumatology (ILAR) (defining 7 discrete categories of arthritis starting before the age of 18 years: systemic arthritis, oligoarthritis, polyarthritis (rheumatoid factor [RF]-negative), polyarthritis (RF-positive), PsA, enthesitis-related JIA (or juvenile enthesitis-related arthritis [ERA]), and undifferentiated arthritis). See, e.g., Petty et al., *J Rheumatol.* (2004) 31:390-2. Juvenile PsA may be classified per pediatric International League of Associations for Rheumatology (ILAR) and/or adult criteria [Classification criteria for Psoriatic Arthritis (CASPAR)]. See e.g., Aviel et al., *Pediatric Rheumatology* (2013) 11:11; Zisman et al., *J. Rheum.* (2017) 44:342-351.

The "2009 ASAS classification criteria" for the classification of a subject with axial spondyloarthritis (axial SpA, or axSpA) is described in Rudwaleit et al., *Ann. Rheum. Dis.* (2009) 68:777-783. The criteria require chronic back pain (≥3 months) in the subject and age at onset <45 years, with the subject also having the following conditions (1) the presence of sacroiliitis by radiography or by magnetic resonance imaging (MRI) plus at least one SpA feature ("imaging arm") or (2) the presence of human leukocyte antigen (HLA) B27 plus at least two SpA features ("clinical arm"). Sacroiliitis on imaging refers to active (acute) inflammation on MRI highly suggestive of sacroiliitis associated with SpA, or definite radiographic sacroiliitis. SpA features are selected from the group consisting of inflammatory back pain, arthritis, enthesitis (heel), uveitis, dactylitis, psoriasis, Crohn's disease or ulcerative colitis, good response to NSAISs (24-48 hours after a full dose of an NSAID the back pain is not present any more or is much better), family history for SpA, positive HLA-B27, and elevated C-reactive protein (above the upper normal limit in the presence of back pain, and after exclusion of other reasons for elevation). See also Deodhar et al., *Arth. & Rheum.* (2014) 66:2649-2656.

The "1984 modified New York criteria" for the classification of a subject with ankylosing spondylitis (AS), is described in van der Linden et al., *Arthritis and Rheumatism* (1984) 27:361-368, and has two components: diagnosis and grading; the diagnosis component further has two criteria: clinical and radiologic. The clinical criteria require: (i) low back pain and stiffness for more than 3 months which improves with exercise, but is not relieved by rest; (ii) limitation of motion of the lumbar spine in both the sagittal and frontal planes, and (iii) limitation of chest expansion relative to normal values corrected for age and sex. The radiologic criterion requires sacroiliitis grade ≥2 bilaterally or sacroiliitis grade 3-4 unilaterally. The grading component requires: (i) definite ankylosing spondylitis if the radiologic criterion is associated with at least 1 clinical criterion; and (ii) probable ankylosing spondylitis if 3 clinical criteria are present, and the radiologic criterion is present without any signs or symptoms satisfying the clinical criteria. See also Deodhar et al., *Arth. & Rheum.* (2014) 66:2649-2656.

The term "axial Spondyloarthritis" (axial SpA or axSpA) encompasses both "ankylosing spondylitis" (AS) and "non-radiographic axial spondyloarthritis" (nr-axial SpA, or nr-axSpA). A subject with "active axial Spondyloarthritis" (active axSpA) means a subject with a clinical diagnosis of active AS or active nr-axial SpA, and in need of treatment as determined by a physician.

A subject with "active ankylosing spondylitis" (active AS) means a subject with a clinical diagnosis of AS and in need of treatment as determined by a physician. In certain embodiments, the subject diagnosed as suffering from AS is further classified (e.g., in the United States) as fulfilling the 1984 modified New York Criteria for AS and/or as fulfilling the 2009 ASAS classification criteria. In certain embodiments, the subject with a high disease activity of AS has a Bath Ankylosing Spondylitis Disease Activity Index score ≥4 and/or ASDAS ≥2.1 and/or a Patient's Assessment of Total Back Pain (Total Back Pain score) ≥4 based on a 0-10 numerical rating scale at baseline. See, e.g., van der Heijde et al., Ann Rheum Dis. (2017)76:978-991; Sieper and Poddubnyy, Lancet (2017) 73-84.

A subject with "active non-radiographic axial spondyloarthritis" (active nr-axial SpA or active nr-axSpA) means a subject with a clinical diagnosis of nr-axial SpA and in need of treatment as determined by a physician. In certain embodiments, the subject diagnosed as suffering from nr-axial SpA is further classified (e.g., in the United States) as fulfilling the 2009 ASAS classification criteria for axSpA but not meeting the radiologic criterion of the 1984 modified New York criteria for AS. In certain embodiments, the subject with high disease activity of nr-axial SpA has a Bath Ankylosing Spondylitis Disease Activity Index score ≥4 and/or an ASDAS ≥2.1 and/or a Patient's Assessment of Total Back Pain Score (Total Back Pain score) ≥4 based on a 0-10 numerical rating scale at baseline; and an objective sign of inflammatory activity selected from the group consisting of (i) an objective sign of active inflammation on MRI of SI joints or (ii) hsCRP>upper limit of normal (ULN) at baseline. See, e.g., van der Heijde et al., Ann Rheum Dis. (2017) 76:978-991 Sieper et al. Ann. Rheum. Dis. (2009) 68 Suppl 2:ii1-44. doi: 10.1136/ard.2008.104018; Van der Heijde et al. Ann Rheum Dis. (2017) 76:978-991; Sieper and Poddubnyy, Lancet (2017) 73-84.

The abbreviation "AS" refers to ankylosing spondylitis.

A result being achieved "within X weeks" of administration of the first dose of the JAK1 inhibitor wherein X is a integer greater than 0 (e.g., 1, 2, 4, 6, 8, 10, 12, 14, 16, 18, 20, 22, 24, 52, 64 weeks, etc.) means the result occurs within the time frame beginning at the time of the administration of the first dose (Week 0) of the JAK1 inhibitor, and ending on and including the last day of the given specified week. A measurement or score used to determine if a result is achieved "at week X" (e.g., at week 1, 2, 4, 6, 8, 10, 12, 14, 16, 18, 20, 22, 24, 52, 64 weeks, etc.) may be taken at any point during, as well as on and including the first and last day, of given week X for the subject.

The abbreviation "axSpA" refers to axial spondyloarthritis.

The abbreviations "bDMARDs" and "biologic DMARDs" refer to biologic Disease Modifying Anti-Rheumatic Drugs. Examples of bDMARDs include, but are not limited to, biologic tumor necrosis factor inhibitors (e.g., adalimumab, etanercept) and interleukin (IL)-17 inhibitors (e.g., secukinumab, ixekizumab).

The term "bDMARD-IR" refers to a subject who is a bDMARD inadequate responder. bDMARD-IR subjects include those who have had an inadequate response to treatment with at least one bDMARD, or who have an intolerance to or contraindication for bDMARDs. Subjects who are bDMARD-IR include subjects who have discontinued treatment with at least one bDMARD due to intolerance or lack of efficacy.

The term "bDMARD naïve" refers to a subject who has not had prior exposure to any biologic therapy, including any bDMARD, that may potentially have a therapeutic impact on the disorder or condition that is being treated.

The term "baseline" or "BL" refers to the time immediately before first dosing with the JAK1 inhibitor. Baseline measurements (i.e., on the "Baseline Visit" or on the "Screening Visit") are collected prior to administration of the first dose of the JAK1 inhibitor (i.e., upadacitinib freebase or a pharmaceutically acceptable salt thereof), and may include a measurement taken the day of but prior to first dosing with the JAK1 inhibitor.

The term "change from baseline" for a particular score or measurement means the score or measurement has improved (e.g., demonstrating a positive clinical effect in the subject or population of subjects) as compared to the score or measurement taken at baseline.

The abbreviation "CII" means Clinically Important Improvement.

The phrase "concomitant administration" or "concomitant treatment" when referencing a therapy in addition to administration of the JAK1 inhibitor means the additional therapy is occurring at baseline and/or during treatment with the JAK1 inhibitor.

The abbreviations "DMARDs" and "non-biologic DMARDs" refer to non-biologic Disease Modifying Anti-Rheumatic Drugs. Non-biologic DMARDs include, but are not limited to, methotrexate (MTX), sulfasalazine (SSZ), leflunomide (LEF), apremilast, hydroxychloroquine (HCQ), bucillamine, and iguratimod. "Non-biologic DMARDs" and "conventional-synthetic disease modifying anti-rheumatic drugs" (csDMARDs) are used interchangeably herein.

The term "DMARD-IR" or "non-biologic DMARD-IR" refers a subject who is a non-biologic DMARD inadequate responder. DMARD-IR subjects include those who have had an inadequate response to treatment with at least one non-biologic DMARD, or who have an intolerance to or contraindication for non-biologic DMARDs.

The abbreviation "EMA" means European Medicines Agency.

The abbreviation "FDA" means Food and Drug Administration.

The abbreviation "hsCRP" means high-sensitivity C-reactive protein.

The abbreviation "ID" means Inactive Disease.

The phrase "improving physical function" in a subject with active PsA means an improvement in activities or tasks compared to baseline.

"In need of treatment" or "in need of treatment . . . as determined by a physician" refers to the physician's opinion that, at baseline, the condition is not sufficiently well-controlled, such as by other medical management (e.g., by other therapy or therapies previously administered to treat the condition).

The phrase "inhibiting the progression of structural damage" or "preventing structural progression" in a subject with active PsA means demonstrating prevention of bony changes on x-ray compared to baseline.

"JAK1 inhibitor" refers to the compound upadacitinib ((3S,4R)-3-ethyl-4-(3H-imidazo[1,2-a]pyrrolo[2,3-e]pyrazin-8-yl)-N-(2,2,2-trifluoroethyl)pyrrolidine-1-carboxamide) freebase or a pharmaceutically acceptable salt thereof. Solid state forms of the JAK1 inhibitor are further described herein.

The abbreviation "LDA" means low disease activity.

The abbreviation "MI" means major improvement.

The abbreviation "MRI" means magnetic resonance imaging.

A result is considered "non-inferior" (NI) as compared to adalimumab if administration of the JAK1 inhibitor preserves at least 50% of the placebo-subtracted adalimumab effect.

The abbreviation "nr-axSpA" refers to non-radiographic axial spondyloarthritis.

The abbreviation "NRI" means non-responder imputation.

The abbreviation "NSAIDs" refers to non-steroidal anti-inflammatory drugs. Examples NSAIDs include, but are not limited to, traditional NSAIDs (e.g., ibuprofen) and salicylates (e.g., aspirin).

The term "pharmaceutically acceptable" (such as in the recitation of a "pharmaceutically acceptable salt" or a "pharmaceutically acceptable diluent") refers to a material that is compatible with administration to a human subject, e.g., the material does not cause an undesirable biological effect. Examples of pharmaceutically acceptable salts are described in "Handbook of Pharmaceutical Salts: Properties, Selection, and Use" by Stahl and Wermuth (Wiley-VCH, Weinheim, Germany, 2002). Examples of pharmaceutically acceptable excipients are described in the "Handbook of Pharmaceutical Excipients," Rowe et al., Ed. (Pharmaceutical Press, 7th Ed., 2012).

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methane sulfonic acid, ethane sulfonic acid, p-toluene sulfonic acid, citric acid, fumaric acid, maleic acid, succinic acid, benzoic acid, salicylic acid, lactic acid, mono-malic acid, mono oxalic acid, tartaric acid such as mono tartaric acid (e.g., (+) or (−)-tartaric acid or mixtures thereof), amino acids (e.g., (+) or (−)-amino acids or mixtures thereof), and the like. These salts can be prepared by methods known to those skilled in the art.

A "population of subjects" refers to the group of subjects participating in a clinical trial, with all subjects suffering from the same disease or symptom to be treated, wherein the clinical trial comprises a treatment arm (a subgroup of the subjects treated with the JAK1 inhibitor), and a placebo arm (a subgroup of the subjects not treated with the JAK1 inhibitor). When used in connection with the treatment of a population of subjects, the phrase "at least X % of the subjects in the treated population achieve" a particular response refers to the placebo corrected X % response (subjects treated—subjects not treated).

The abbreviation "PR" means partial remission.

The abbreviation "PsA" refers to psoriatic arthritis.

The abbreviation "PsO" refers to psoriasis. Psoriasis includes psoriasis as a skin manifestation of PsA.

The abbreviation "QD" means once daily.

The phrase "reducing signs and symptoms" means an improvement in disease activity, function, and/or quality of life compared to baseline.

The abbreviation "SI" means sacroiliac.

"Statistically significant" means when observed p value<alpha for a given hypothesis testing. The pre-specified significance level, alpha, is the probability of rejecting the null hypothesis given that it is true. Alpha is also called type I error or false positive rate. It is usually set at or below 0.05. The observed p value is the probability, under the null hypothesis, of observing an effect of the same magnitude or more extreme. When observed p value<alpha, the null hypothesis is rejected, and statistical significance is claimed. In a multiplicity-controlled analysis, when the adjusted p value<alpha, the result is statistically significant. In the fixed sequence of a multiplicity-controlled analysis, statistical significance can be claimed for a lower ranked endpoint only if the previous endpoint in the sequence meets the requirements of statistical significance.

A result is considered "superior" as compared to adalimumab if the multiplicity adjusted p value for the null hypothesis testing of the treatment difference between the JAK1 inhibitor and adalimumab is less than pre-specified significance level.

"Total spinal ankylosis" refers to bridging syndesmophytes (fusion) in a total sum of ≥5 segments of the C2-T1 or T12-S1 spine (e.g., 2 segments fused in the cervical and 3 segments fused in the lumbar spine would be considered positive for total spinal ankylosis).

The terms "treating", "treatment", and "therapy" and the like, as used herein, are meant to include but not limited to alleviation or relief of one or more symptoms of the condition from which the subject is suffering (i.e., axial spondyloarthritis (axSpA) (e.g., non-radiographic axSpA (nr-axSpA), ankylosing spondylitis (AS)), psoriatic arthritis (PsA), psoriasis (PsO)), including the slowing or cessation of the progression of the condition, such as slowing or cessation of the progression of structural damage associated with the condition, the structural progression of the condition, and/or improving the physical function of a subject suffering from the condition.

The term "upadacitinib freebase" refers to freebase (non-salt, neutral) forms of upadacitinib. Examples of upadacitinib freebase solid state forms include amorphous upadacitinib freebase and crystalline freebases of upadacitinib, such as crystalline freebase solvates, crystalline freebase hydrates, crystalline freebase hemihydrates, and crystalline freebase anhydrates of upadacitinib. Specific examples of upadacitinib freebase solid state forms include but are not limited to Amorphous Upadacitinib Freebase, Upadacitinib Freebase Solvate Form A, Upadacitinib Freebase Hydrate Form B, Upadacitinib Freebase Hydrate Form C (which is a hemihydrate), and Upadacitinib Freebase Anhydrate Form D, each as described in WO 2017/066775 and WO 2018/165581.

The term "upadacitinib freebase equivalent" refers to the amount of the neutral upadacitinib freebase (active ingredient) administered, and not including any coformer (e.g., solvent or water molecule(s)) of a solvate or hydrate (including hemihydrate), and not including any pharmaceutically acceptable salt counter anions of a pharmaceutically acceptable salt. For example, 15.4 mg of crystalline upadacitinib freebase hemihydrate (which includes 1/2 of a water conformer molecule per upadacitinib freebase molecule) delivers 15 mg of upadacitinib freebase equivalent, while 30.7 mg of crystalline upadacitinib freebase hemihydrate (which includes 1/2 of a water conformer molecule per upadacitinib freebase molecule) delivers 30 mg of upadacitinib freebase equivalent.

II. Methods of Treatment

The present disclosure also relates to methods of treating a JAK-associated condition in a subject, particularly a human subject suffering from or susceptible to the condition, comprising administering to the subject a therapeutically effective amount of Compound 1 freebase or a pharmaceutically acceptable salt thereof or one or more solid state forms of Compound 1 as described in the present disclosure. Another aspect of the disclosure relates to Compound 1 freebase or a pharmaceutically acceptable salt thereof or one or more solid state forms of Compound 1 as described in the present disclosure for use in treatment of a JAK-associated condition in a subject, particularly in a human subject suffering from or susceptible to the condition, the use comprising administering to the subject a therapeutically effective amount of Compound 1 freebase or a pharmaceutically acceptable salt thereof or one or more solid state forms of Compound 1. In one aspect, the condition is a JAK-1-associated condition. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of immunomodulation, inflammation, and proliferative disorders (such as cancer) in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of immunomodulation, inflammation, and proliferative disorders (such as cancer) in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Anhydrate Form D. In another aspect, the solid state form is the Freebase Hydrate Form B. In another aspect, the solid state form is the Freebase Hydrate Form C. In another aspect, the solid state form is the Tartrate Hydrate.

In one embodiment, the present disclosure relates to methods of treating a condition selected from the group consisting of rheumatoid arthritis, multiple sclerosis, experimental allergic encephalomyelitis, systemic lupus erythematosus, Crohn's disease, atopic dermatitis, vasculitis, cardiomyopathy, psoriasis, Reiter's syndrome, glomerulonephritis, ulcerative colitis, allergic asthma, insulin-dependent diabetes, peripheral neuropathy, uveitis, fibrosing alveolitis, type I diabetes, juvenile diabetes, juvenile arthritis, Castleman disease, neutropenia, endometriosis, autoimmune thyroid disease, sperm and testicular autoimmunity, scleroderma, axonal and neuronal neuropathies, allergic rhinitis, Sjogren's syndrome, hemolytic anemia, Graves' disease, Hashimoto's thyroiditis, IgA nephropathy, amyloidosis, ankylosing spondylitis, Behcet's disease, sarcoidosis, vesiculobullous dermatosis, myositis, primary biliary cirrhosis, polymyalgia rheumatica, autoimmune immunodeficiency, Chagas disease, Kawasaki syndrome, psoriatic arthritis, celiac sprue, myasthenia gravis, autoimmune myocarditis, POEMS syndrome, and chronic fatigue syndrome in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of rheumatoid arthritis, multiple sclerosis, experimental allergic encephalomyelitis, systemic lupus erythematosus, Crohn's disease, atopic dermatitis, vasculitis, cardiomyopathy, psoriasis, Reiter's syndrome, glomerulonephritis, ulcerative colitis, allergic asthma, insulin-dependent diabetes, peripheral neuropathy, uveitis, fibrosing alveolitis, type I diabetes, juvenile diabetes, juvenile arthritis, Castleman disease, neutropenia, endometriosis, autoimmune thyroid disease, sperm and testicular autoimmunity, scleroderma, axonal and neuronal neuropathies, allergic rhinitis, Sjogren's syndrome, hemolytic anemia, Graves' disease, Hashimoto's thyroiditis, IgA nephropathy, amyloidosis, ankylosing spondylitis, Behcet's disease, sarcoidosis, vesiculobullous dermatosis, myositis, primary biliary cirrhosis, polymyalgia rheumatica, autoimmune immunodeficiency, Chagas disease, Kawasaki syndrome, psoriatic arthritis, celiac sprue, myasthenia gravis, autoimmune myocarditis, POEMS syndrome, and chronic fatigue syndrome in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of rheumatoid arthritis (including moderate to severe rheumatoid arthritis), systemic lupus erythematosus, multiple sclerosis, Crohn's disease (including moderate to severe Crohn's disease), psoriasis (including moderate to severe chronic plaque psoriasis), ulcerative colitis (including moderate to severe ulcerative colitis), ankylosing spondylitis, psoriatic arthritis, juvenile idiopathic arthritis (including moderate to severe polyarticular juvenile idiopathic arthritis), diabetic nephropathy, dry eye syndrome, Sjogren's syndrome, alopecia areata, vitiligo, and atopic dermatitis in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1.

In another aspect, the present disclosure relates to Compound 1 freebase or a pharmaceutically acceptable salt thereof or a solid state form of Compound 1 for use in treatment of a condition selected from the group consisting of rheumatoid arthritis (including moderate to severe rheumatoid arthritis), systemic lupus erythematosus, multiple sclerosis, Crohn's disease (including moderate to severe Crohn's disease), psoriasis (including moderate to severe chronic plaque psoriasis), ulcerative colitis (including moderate to severe ulcerative colitis), ankylosing spondylitis, psoriatic arthritis, juvenile idiopathic arthritis (including moderate to severe polyarticular juvenile idiopathic arthritis), diabetic nephropathy, dry eye syndrome, Sjogren's syndrome, alopecia areata, vitiligo, and atopic dermatitis in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of an ocular condition, systemic inflammatory response syndrome, juvenile rheumatoid arthritis, systemic onset juvenile rheumatoid arthritis, type III hypersensitivity reactions, type W hypersensitivity, inflammation of the aorta, iridocyclitis/uveitis/optic neuritis, juvenile spinal muscular atrophy, diabetic retinopathy or microangiopathy, chronic inflammation, ulcerative colitis, inflammatory bowel disease, allergic diseases, dermatitis scleroderma, acute or chronic immune disease associated with organ transplantation, psoriatic arthropathy, ulcerative colitic arthropathy, autoimmune bullous disease, autoimmune hemolytic anemia, rheumatoid arthritis associated interstitial lung disease, systemic lupus erythematosus associated lung disease, dermatomyositis/polymyositis associated lung disease, Sjogren's syndrome/disease associated lung disease, ankylosing spondylitis and ankylosing spondylitis-associated lung disease, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, psoriasis type 1, psoriasis type 2, plaque psoriasis, moderate to severe chronic plaque psoriasis, autoimmune neutropenia, sperm autoimmunity, multiple sclerosis (all subtypes), acute rheumatic fever, rheumatoid spondylitis, Sjogren's syndrome, and autoimmune thrombocytopenia in a subject, wherein the method comprises administering to the subject, particularly a human subject suffering from or susceptible to the condition, a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of an ocular condition, systemic inflammatory response syndrome, juvenile rheumatoid arthritis, systemic onset juvenile rheumatoid arthritis, type III hypersensitivity reactions, type W hypersensitivity, inflammation of the aorta, iridocyclitis/uveitis/optic neuritis, juvenile spinal muscular atrophy, diabetic retinopathy or microangiopathy, chronic inflammation, ulcerative colitis, inflammatory bowel disease, allergic diseases, dermatitis scleroderma, acute or chronic immune disease associated with organ transplantation, psoriatic arthropathy, ulcerative colitic arthropathy, autoimmune bullous disease, autoimmune hemolytic anemia, rheumatoid arthritis associated interstitial lung disease, systemic lupus erythematosus associated lung disease, dermatomyositis/polymyositis associated lung disease, Sjogren's syndrome/disease associated lung disease, ankylosing spondylitis and ankylosing spondylitis-associated lung disease, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, psoriasis type 1, psoriasis type 2, plaque psoriasis, moderate to severe chronic plaque psoriasis, autoimmune neutropenia, sperm autoimmunity, multiple sclerosis (all subtypes), acute rheumatic fever, rheumatoid spondylitis, Sjogren's syndrome, and autoimmune thrombocytopenia in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus in a subject, particularly in a human subject suffering from or susceptible to the condition, the use comprising administering to the subject a therapeutically effective amount of Compound 1 freebase or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating a condition selected from the group consisting of rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, and atopic dermatitis in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a condition selected from the group consisting of rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, and atopic dermatitis in a subject, particularly in a human subject suffering from or susceptible to the condition, the use comprising administering to the subject a therapeutically effective amount of Compound 1 freebase or a pharmaceutically acceptable salt thereof or a solid state form of Compound 1. In one aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D.

In one embodiment, the present disclosure relates to methods of treating arthritis in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of arthritis in a subject, particularly in a human subject suffering from or susceptible to arthritis, the use comprising administering to the subject a therapeutically effective amount of Compound 1 freebase or a pharmaceutically acceptable salt thereof or a solid state form of Compound 1. In one aspect, the arthritis is selected from the group consisting of rheumatoid arthritis, juvenile idiopathic arthritis, and psoriatic arthritis. In another aspect, the arthritis is rheumatoid arthritis. In another aspect, the arthritis is juvenile idiopathic arthritis. In another aspect, the arthritis is psoriatic arthritis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

In one embodiment, the present disclosure relates to methods of treating a spondyloarthropathy in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of spondyloarthropathy, particularly in a human subject suffering from or susceptible to spondyloarthropathy, the use comprising administering to the subject a therapeutically effective amount of Compound 1 freebase or a pharmaceutically acceptable salt thereof or a solid state form of Compound 1. In one aspect, the spondyloarthropathy is ankylosing spondylitis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

In one embodiment, the present disclosure relates to methods of treating a gastrointestinal condition in a subject, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a gastrointestinal condition, particularly in a human subject suffering from or susceptible to a gastrointestinal condition, the use comprising administering to the subject a therapeutically effective amount of Compound 1 freebase or a pharmaceutically acceptable salt thereof or a solid state form of Compound 1. In one aspect, the gastrointestinal condition is selected from the group consisting of Crohn's disease and ulcerative colitis. In another aspect, the gastrointestinal condition is Crohn's disease. In another aspect, the gastrointestinal condition is ulcerative colitis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

In one embodiment, the present disclosure relates to methods of treating a skin condition, wherein the method comprises administering to the subject a therapeutically effective amount of Compound 1 freebase or a pharmaceutically acceptable salt thereof or a solid state form of Compound 1. In another aspect, the present disclosure relates to Compound 1 freebase or a pharmaceutically acceptable salt thereof or a solid state form of Compound 1 for use in treatment of a skin condition, particularly in a human subject suffering from or susceptible to a skin condition, the use comprising administering to the subject a therapeutically effective amount of Compound 1 freebase or a pharmaceutically acceptable salt thereof or a solid state form of Compound 1. In one aspect, the skin condition is selected from the group consisting of psoriasis, plaque psoriasis, nail psoriasis, and hidradenitis suppurativa. In another aspect, the skin condition is psoriasis. In another aspect, the skin condition is plaque psoriasis. In another aspect, the skin condition is nail psoriasis. In another aspect, the skin condition is hidradenitis suppurativa. In another aspect, the skin condition is atopic dermatitis. In another aspect, the solid state form is the Amorphous Freebase. In another aspect, the solid state form is the Freebase Hydrate Form B. In another aspect, the solid state form is the Freebase Hydrate Form C. In another aspect, the solid state form is the Tartrate Hydrate. In another aspect, the solid state form is the Freebase Anhydrate Form D. In another aspect, the solid state form is the Freebase Solvate Form A. In another aspect, the solid state form is the Hydrochloride Solvate form AA. In another aspect, the solid state form is the Hydrochloride Solvate Form BB. In another aspect, the solid state form is the Hydrochloride Solvate Form CC. In another aspect, the solid state form is the L-Maleate Form AAA. In another aspect, the solid state form is the L-Maleate Form BBB.

The therapeutically effective dose level for any particular subject will depend upon the specific situation and can depend upon a variety of factors including the type, age, weight, sex, diet, and condition of the subject being treated; the severity of the pathological condition; activity of the specific compound employed; the specific composition employed; the age, body weight, general health, sex and diet of the subject; the route of administration; the duration of the treatment; pharmacological considerations, such as the activity, efficacy, pharmacokinetic, and toxicology profiles of the particular compound or salt used; whether a drug delivery system is utilized; drugs used in combination or coincidental with the specific compound employed; and like factors well-known in the medical arts. An ordinarily skilled physician provided with the disclosure of the present application will be able to determine appropriate dosages and regimens for administration of the therapeutic agent to the subject, and to adjust such dosages and regimens as necessary during the course of treatment, in accordance with methods well-known in the therapeutic arts. It is well within the skill of the art to start doses of the compound at levels lower than required to achieve the desired therapeutic effect and to gradually increase the dosage until the desired effect is achieved. Thus, the dosage regimen actually employed can vary widely, and therefore, can derive from the preferred dosage regimen set forth below.

The total daily dose of the solid state form (administered in single or divided doses) typically is from about 0.001 to about 100 mg/kg, or from about 0.001 to about 30 mg/kg, or from about 0.001 to about 15 mg/kg. In another embodiment, the total daily dose is from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

In one embodiment, the daily dose of the solid state form administered to the subject is from about 0.01 mg to about 3000 mg. In one aspect, the daily dose is from about 0.1 mg to about 1000 mg. In another aspect, the daily dose is from is from about 1 mg to about 500 mg. In another aspect, the daily dose is from about 1 mg to about 250 mg. In another aspect, the daily dose is from about 1 mg to about 100 mg. In another aspect, the daily dose is from about 1 mg to about 50 mg. In another aspect, the daily dose is from about 1 mg to about 45 mg. In another aspect, the daily dose is from about 1 mg to about 30 mg. In another aspect, the daily dose is from about 1 mg to about 25 mg. In another aspect, the daily dose is from about 1 mg to about 24 mg. In another aspect, the daily dose is from about 1 mg to about 15 mg. In another aspect, the daily dose is from about 1 mg to about 7.5 mg. In another aspect, the daily dose is from about 25 mg to about 50 mg. In another aspect, the daily dose is from about 1 mg to about 10 mg. In another aspect, the daily dose is from about 10 mg to about 20 mg. In another aspect, the daily dose is from about 20 mg to about 30 mg. In another aspect, the daily dose is from about 30 mg to about 40 mg. In another aspect, the daily dose is from about 7.5 mg to about 45 mg. In another aspect, the daily dose is from about 15 mg to about 30 mg. In another aspect, the daily dose is about 3 mg. In another aspect, the daily dose is about 6 mg. In another aspect, the daily dose is about 7.5 mg. In another aspect, the daily dose is about 12 mg. In another aspect, the daily dose is about 15 mg. In another aspect, the daily dose is about 18 mg. In another aspect, the daily dose is about 24 mg. In another aspect, the daily dose is about 30 mg. In another aspect, the daily dose is about 36 mg. In another aspect, the daily dose is about 45 mg.

In one embodiment, a dose of about 3 mg, about 6 mg, about 12 mg, or about 24 mg per unit dosage form (e.g., per tablet or capsule) of a solid state form of Compound 1 is administered orally BID (twice daily) in equal amounts (e.g., twice a day, about 3 mg each time) to a human subject.

In another embodiment, the methods or uses comprise administering orally QD (once daily) to a human subject a dose of about 7.5 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 7.5 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 7.5 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 15 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 15 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 15 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 24 mg of Compound 1 freebase or a pharmaceutically acceptable salt thereof. The 24 mg QD dose of Compound 1 freebase or a pharmaceutically acceptable salt thereof may be administered as either a single dosage form comprising about 24 mg per unit dosage form (e.g., per tablet or capsule) of Compound 1 freebase or a pharmaceutically acceptable salt thereof, or two dosage forms comprising about 12 mg per unit dosage form (e.g., per tablet or capsule) of Compound 1 freebase or a pharmaceutically acceptable salt thereof administered simultaneously.

In another embodiment, the methods or uses comprise administering orally QD (once daily) to a human subject a dose of about 24 mg of a solid state form of Compound 1. In one embodiment, the methods or uses comprise administering orally QD (once daily) to a human subject a solid state form of Compound 1 in an amount sufficient to deliver 24 mg of Compound 1 freebase equivalent to the subject. The 24 mg QD dose of the solid state form of Compound 1 may be administered as either a single dosage form comprising about 24 mg per unit dosage form (e.g., per tablet or capsule) of the solid state form of Compound 1, or two dosage forms comprising about 12 mg per unit dosage form (e.g., per tablet or capsule) of the solid state form of Compound 1 administered simultaneously. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 30 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 30 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 30 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 36 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 36 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 36 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

In another embodiment, the methods or uses comprise administering orally QD (once daily) to a human subject a dose of about 45 mg per unit dosage form (e.g., per tablet or capsule) of Compound 1 freebase or a pharmaceutically acceptable salt thereof.

In another embodiment, the methods or uses comprise administering orally QD (once daily) to a human subject a dose of about 45 mg per unit dosage form (e.g., per tablet or capsule) of a solid state form of Compound 1. In one embodiment, the methods or uses comprise administering orally QD (once daily) to a human subject a solid state form of Compound 1 in an amount sufficient to deliver 45 mg per unit dosage form (e.g., per tablet or capsule) of Compound 1 freebase equivalent to the subject. In one embodiment, the solid state form is the Amorphous Freebase. In one embodiment, the solid state form is the Freebase Hydrate Form B. In one embodiment, the solid state form is the Freebase Hydrate Form C. In one embodiment, the solid state form is the Tartrate Hydrate. In another aspect, the solid state form is the Freebase Anhydrate Form D.

Compound 1 freebase or a pharmaceutically acceptable salt thereof or solid state forms thereof may be used alone, or in combination with methotrexate or other non-biologic disease-modifying anti-rheumatic drugs (DMARDs), and/or in combination with anti-TNFα biological agents, such as TNF antagonists like chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept).

In certain embodiments, Compound 1 freebase or a pharmaceutically acceptable salt thereof or solid state forms thereof halt disease progression, and/or relieves at least a symptom of the disease, which may be detected or monitored by X-ray results, including radiographic progression of joint damage.

In certain embodiments, structural joint damage can be assessed radiographically and expressed as change in Total Sharp Score (TSS) and its components, the erosion score and Joint Space Narrowing (JSN) score, for example, at week 12 compared to baseline, or at week 24 as compared to baseline.

In another embodiment, the adult subject is a subject who has had an inadequate response or intolerance to one or more disease-modifying antirheumatic drugs (DMARDs). In one embodiment, the DMARD is a conventional synthetic DMARD (csDMARD). In another embodiment, the DMARD is a biologic DMARD (bDMARD). Examples of csDMARDs include, but are not limited to, methotrexate (MTX), sulfasalazine, hydroxychloroquine, chloroquine, leflunomide, and azathioprine. Examples of bDMARDs include, but are not limited to, tocilizumab such as ACTEMRA™, etanercept such as p75TNFR1gG (ENBREL™ brand etanercept), adalimumab (such as HUMIRA™ brand adalimumab), and golimumab such as SIMPONI™ (golimumab). In one embodiment, the csDMARD is MTX. In one embodiment, the bDMARD is an anti-TNF biologic. An inadequate response or intolerance to one or more DMARDs can be measured using any of the indices described herein (e.g., failure to achieve an ACR20 response). In one embodiment, a subject having an inadequate response to a DMARD is a subject who does not achieve reduced disease activity, does not achieve an improvement in physical function, exhibits no evidence of stopping disease progression, or who experiences disease relapse after treatment with the DMARD. In one embodiment, a subject having an inadequate response to a DMARD is a subject who does not achieve an ACR20 response after treatment with the DMARD. In one embodiment, a subject having an inadequate tolerance (intolerance) to a DMARD is a subject who experiences toxicity or complicating co-morbidities after treatment with the DMARD.

In one embodiment, the adult subject is a subject who has had an inadequate response to stable methotrexate therapy. In one embodiment, the adult subject received methotrexate therapy for at least three months prior to treatment. In another embodiment, the adult subject received a stable dose of methotrexate of about 7.5 to about 25 mg per week for at least four weeks prior to treatment. In another embodiment, the adult subject is administered a stable dose of methotrexate (e.g., from about 7.5 to about 25 mg per week) during treatment with Compound 1. In another embodiment, the adult subject received a supplement of folic acid for at least four weeks prior to treatment. In another embodiment, the adult subject is administered a supplement of folic acid during treatment.

In one embodiment, the adult subject is a subject who has had an inadequate response or intolerance to at least one anti-TNF therapy. Anti-TNF biologic agents are described elsewhere herein, and include TNF antagonists such as chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept). In one embodiment, the adult subject received methotrexate therapy for at least three months prior to treatment. In another embodiment, the adult subject received a stable dose of methotrexate of about 7.5 to about 25 mg per week for at least four weeks prior to treatment. In another embodiment, the adult subject is administered a stable dose of methotrexate (e.g., from about 7.5 to about 25 mg per week) during treatment with Compound 1. In another embodiment, the adult subject has been treated with at least one anti-TNF biologic agent for at least three months prior to treatment with Compound 1. In another embodiment, the adult subject received a supplement of folic acid for at least four weeks prior to treatment. In another embodiment, the adult subject is administered a supplement of folic acid during treatment In certain embodiments, the adult subject, who has had an inadequate response or tolerance to one or more DMARDS (including methotrexate and/or an anti-TNF biologic agent), achieves an ACR20 response, an ACR50 response, an ACR70 response, and/or a decrease in DAS28(CRP) as compared to baseline following treatment for at least twelve weeks (e.g., at week 12 of treating), and/or following treatment for at least 8 weeks (e.g., at week 8 of treating), and/or following treatment for at least 6 weeks (e.g., at week 6 of treating), and/or following treatment for at least 4 weeks (e.g., at week 4 of treating), and/or following treatment for at least 2 weeks (e.g., at week 2 of treating).

In another embodiment, the Compound 1 freebase or a pharmaceutically acceptable salt thereof and/or solid state forms of Compound 1 used in any of the methods set forth herein may be administered to the subject in a once daily extended release solid oral dosage form. In particular, in one embodiment, the methods comprise once daily administration to the subject of an extended release (e.g., modified release) solid oral dosage form comprising the Compound 1 freebase or a pharmaceutically acceptable salt thereof or the solid state form of Compound 1, and a pharmaceutically acceptable polymeric carrier substantially contributing to the modification of the release of the Compound 1 freebase or a pharmaceutically acceptable salt thereof or the solid state form of Compound 1. In one aspect, the dosage form sustains release of the Compound 1 freebase or a pharmaceutically acceptable salt thereof or the solid state form of Compound 1 for from about 4 hours to about 24 hours following entry of the dosage form into a use environment. In one embodiment, the dosage form has a release rate of not more than about 60% after passage of about 4 hours following entry of the dosage form into a use environment. The term "entry into a use environment" refers to contact of the dosage form with gastric fluids of the subject to whom it is administered. As used herein, the term "release rate" refers to the percentage of the active ingredient (e.g., Compound 1 or a solid state form of Compound 1) in the dosage form that is released in the given time period, and under the specified conditions. In one embodiment, the dosage form comprises about 7.5 mg or about 15 mg or about 30 mg or about 45 mg, per unit dosage form (e.g., per tablet or capsule), of Compound 1 (freebase), or a pharmaceutically acceptable salt thereof or a solid state form of Compound 1 in an amount sufficient to deliver to the subject about 7.5 mg or about 15 mg or about 30 mg or about 45 mg, per unit dosage form (e.g., per tablet or capsule), per day of Compound 1 freebase equivalent. In one embodiment, the dosage form comprises about 7.5 mg or about 15 mg or about 30 mg or about 45 mg, per unit dosage form (e.g., per tablet or capsule), per day of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the pharmaceutically acceptable polymeric carrier is a release control polymer, as set forth herein.

Thus, in one aspect, the dosage form sustains release of the Compound 1 freebase or a pharmaceutically acceptable salt thereof or the solid state form of Compound 1 for from about 4 hours to about 24 hours. In one embodiment, the dosage form releases the active ingredient (i.e., Compound 1 or a solid state form of Compound 1), at a release rate of not more than about 25%, or from about 10% to about 25%, or from about 15% to about 20%, or about 20% after passage of about 1 hour following entry into the use environment. In one embodiment, the dosage form releases the active ingredient at a release rate of not more than about 40%, or from about 20% to about 40%, or from about 25% to about 35% after passage of about 2 hours following entry into the use environment. In one embodiment, the dosage form releases the active ingredient at a release rate of not more than about 60%, or from about 30% to about 60%, or from about 40% to about 60%, or from about 45% to about 55% after passage of about 4 hours following entry into the use environment. In one embodiment, the dosage form releases the active ingredient at a release rate of not more than about 70% or from about 40% to about 70%, or from about 55% to about 70% after passage of about 6 hours following entry into the use environment. In one embodiment, the dosage form releases the active ingredient at a release rate of not more than about 80% or from about 55% to about 80%, or from about 60% to about 80% after passage of about 6 hours following entry into the use environment. In one embodiment, the dosage form releases the active ingredient at a release rate of not more than about 80%, or not less than about 50%, or not less than about 60%, or not less than about 70%, or not less than about 75%, or from about 50% to about 80%, or from about 60% to about 80%, or from about 65% to about 80% after passage of about 8 hours following entry into the use environment. In one embodiment, the dosage form releases the active ingredient at a release rate of not less than about 55%, or not less than about 60% or not less than about 70%, or not less than about 80%, or not less than about 85%, or from about 55% to about 90%, or from about 70% to about 90% after passage of about 10 hours following entry into the use environment. In one embodiment, the dosage form releases the active ingredient at a release rate of not less than about 65%, or not less than about 70%, or not less than about 80%, or not less than about 90%, or from about 65% to about 99%, or from about 80% to about 99%, or from about 90% to about 99% after passage of about 16 hours following entry into the use environment. In one embodiment, the dosage form releases the active ingredient at a release rate of not less than about 70%, or not less than about 80%, or not less than about 90%, or from about 70% to 100%, or from about 80% to 100% after passage of about 20 hours following entry into the use environment. In one aspect, the dosage form has a release rate of not more than about 60% after passage of about 4 hours following entry of the dosage form into a use environment, from about 50% to about 80% after passage of about 8 hours following entry of the dosage form into a use environment, from about 55% to about 90% after passage of about 10 hours following entry of the dosage form into a use environment, and from about 70% to 100% after passage of about 20 hours following entry of the dosage form into a use environment.

In one embodiment, the present disclosure is directed to a method of treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the method comprising once daily administration to a subject suffering from or susceptible to the condition, of an extended release solid oral dosage form comprising about 7.5 mg or about 15 mg or about 30 mg or about 45 mg, per unit dosage form (e.g., per tablet or capsule), of Compound 1 freebase or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In another aspect, the disclosure is directed to an extended release solid oral dosage form comprising Compound 1 freebase or a pharmaceutically acceptable salt thereof or a solid state form of Compound 1 for use in treating a condition selected from the group consisting of rheumatoid arthritis, juvenile idiopathic arthritis, Crohn's disease, ulcerative colitis, psoriasis, plaque psoriasis, nail psoriasis, psoriatic arthritis, ankylosing spondylitis, alopecia areata, hidradenitis suppurativa, atopic dermatitis, and systemic lupus erythematosus, the use comprising once daily administration to a subject suffering from or susceptible to the condition, of the extended release solid oral dosage form, wherein the solid dosage form comprises about 7.5 mg or about 15 mg or about 30 mg or about 45 mg, per unit dosage form (e.g., per tablet or capsule) of Compound 1 freebase, or a pharmaceutically acceptable salt thereof or a solid state form of Compound 1 in an amount sufficient to deliver to the subject about 7.5 mg, or about 15 mg, or about 30 mg, or about 45 mg, per unit dosage form (e.g., per tablet or capsule), of Compound 1 freebase equivalent, and a pharmaceutically acceptable polymeric carrier substantially contributing to the modification of the release of the Compound 1 freebase or a pharmaceutically acceptable salt thereof or the solid state form of Compound 1, wherein the dosage form sustains release of the Compound 1 freebase or a pharmaceutically acceptable salt thereof or the solid state form of Compound 1 for from about 4 to about 24 hours following entry of the dosage form into a use environment, wherein the dosage form has a release rate of not more than about 60% after passage of about 4 hours following said entry into said use environment. In one embodiment, the dosage form comprises about 7.5 mg or about 15 mg or about 30 mg or about 45 mg, per unit dosage form (e.g., per tablet or capsule), of a solid state form of Compound 1. In one embodiment, the solid state form is Freebase Hydrate Form B. In one embodiment, the solid state form is Freebase Hydrate Form C. In one embodiment, the solid state form is Freebase Anhydrate Form D. In one embodiment, the solid state form is Tartrate Hydrate. In one embodiment, the dosage form further has a release rate of from about 50% to about 80% after passage of about 8 hours following entry of the dosage form into a use environment, from about 55% to about 90% after passage of about 10 hours following entry of the dosage form into a use environment, and/or from about 70% to 100% after passage of about 20 hours following entry of the dosage form into a use environment.

In the foregoing methods, in one embodiment, the pharmaceutically acceptable polymeric carrier comprises a release control polymer. In one embodiment, the release control polymer is hydroxypropylmethyl cellulose. In one embodiment, the dosage form comprises a pH modifier. In one embodiment, the pH modifier is tartaric acid. In one embodiment, the dosage form comprises from about 10 w/w % to about 35 w/w % tartaric acid. In one embodiment, the dosage form comprises about 10 w/w % tartaric acid. In one embodiment, the dosage form comprises about 20 w/w % tartaric acid. In one embodiment, the dosage form comprises about 30 w/w % tartaric acid.

In another embodiment the methods of the present disclosure further comprise administering Compound 1 or a solid state form thereof for at least 8 weeks. In another embodiment, the methods of the present disclosure comprise administering Compound 1 or a solid state form thereof for at least 12 weeks.

In another embodiment, the present disclosure relates to the use of a solid state form of Compound 1 for treating a condition as described in the various embodiments of the present disclosure.

In another embodiment, the present disclosure relates to a solid state form of Compound 1 for use in treatment of a condition as described in the various embodiments of the present disclosure.

III. Combination Therapy and Fixed-Dose Combinations

The present disclosure further relates to (i) methods of treatment and uses as previously described that further comprise the administration of one or more additional therapeutic agents (i.e., combination therapies), and (ii) pharmaceutical compositions as previously described that further comprise one or more additional therapeutic agents (i.e., fixed-dose combinations). When administered to a subject in combination with one or more additional therapeutic agents, the solid state form of Compound 1 and the additional therapeutic agent(s) can be administered as separate dosage forms or as a single dosage form comprising the solid state form of Compound 1 and the additional therapeutic agent(s). If administered as a separate dosage form, the additional therapeutic agent may be administered either simultaneously with, or sequentially with, the dosage form comprising the solid state form of Compound 1.

For example, the solid state forms of the present disclosure may be administered in a pharmaceutically acceptable form either alone or in combination with one or more additional agents that modulate a mammalian immune system or with anti-inflammatory agents. These agents may include but are not limited to cyclosporin A (e.g., SAND-IMMUNE® or NEORAL®), rapamycin, FK-506 (tacrolimus), leflunomide, deoxyspergualin, mycophenolate (e.g., CELLCEPT®), azathioprine (e.g., IMURAN®), daclizumab (e.g., ZENAPAX®), OKT3 (e.g., ORTHOCLONE®), AtGam, aspirin, acetaminophen, aminosalicylate, ciprofloxacin, corticosteroid, metronidazole, probiotic, tacrolimus, ibuprofen, naproxen, piroxicam, and anti-inflammatory steroids (e.g., prednisolone or dexamethasone). In certain embodiments, the one or more additional agents are selected from the group consisting of aspirin, acetaminophen, aminosalicylate, ciprofloxacin, corticosteroid, cyclosporine, metronidazole, probiotic, tacrolimus, ibuprofen, naproxen, piroxicam, prednisolone, dexamethasone, anti-inflammatory steroid, methotrexate, chloroquine, azathioprine, hydroxychloroquine, penicillamine, sulfasalazine, leflunomide, tocilizumab, anakinra, abatacept, certolizumab pegol, golimumab, vedolizumab, natalizumab, ustekinumab, rituximab, efalizumab, belimumab, etanercept, infliximab, adalimumab, and immune modulator (e.g., activator) for CD4+CD25+ Treg cells.

Non-limiting examples of therapeutic agents for rheumatoid arthritis with which a compound of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L). Combinations of therapeutic agents may interfere at different points in the autoimmune and subsequent inflammatory cascade. Such examples may include TNF antagonists like chimeric, humanized or human TNF antibodies, adalimumab (such as HUMIRA™ brand adalimumab), infliximab such as CA2 (REMICADE™ brand infliximab), golimumab such as SIMPONI™ (golimumab), certolizumab pegol such as CIMZIA™, tocilizumab such as ACTEMRA™, CDP 571, and soluble p55 or p75 TNF receptors, derivatives, thereof, etanercept such as p75TNFR1gG (ENBREL™ brand etanercept) or p55TNFR1gG (lenercept), and also TNFα converting enzyme (TACE) inhibitors; similarly IL-1 inhibitors (Interleukin-1-converting enzyme inhibitors, IL-1RA etc.) may be effective for the same reason. Other combinations include Interleukin 11.

The solid state form may also be combined with nonbiologic DMARDS or other agents, such as methotrexate, 6-mercaptopurine, azathioprine sulphasalazine, mesalamine, olsalazine chloroquinine/hydroxychloroquine, penicillamine aurothiomalate (intramuscular and oral), azathioprine, colchicine, corticosteroids (oral, inhaled and local injection), beta-2 adrenoreceptor agonists (salbutamol, terbutaline, salmeterol), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, and 6-mercaptopurines. The solid state form may also be combined with methotrexate.

Non-limiting examples of therapeutic agents for inflammatory bowel disease (IBD) with which the solid state form can be combined may include (but are not limited to) the following: budesonide; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signaling by proinflammatory cytokines such as TNFα or IL-1 (e.g., NIK, IKK, or MAP kinase inhibitors); IL-1β converting enzyme inhibitors; TNFα converting enzyme inhibitors; T-cell signaling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and anti-inflammatory cytokines (e.g., IL-4, IL-10, IL-11, IL-13 and TGFβ). The solid state form may also be combined with methotrexate.

Examples of therapeutic agents for Crohn's disease with which the solid state form can be combined include the following: TNF antagonists, for example, anti-TNF antibodies, adalimumab (such as HUMIRA™ brand adalimumab), infliximab such as CA2 (REMICADE™ brand infliximab), certolizumab pegol such as CIMZIA™, golimumab such as SIMPONI™ (golimumab), CDP 571, TNFR-Ig constructs, etanercept such as p75TNFRIgG (ENBREL™ brand etanercept) and lenercept such as p55TNFRIgG (Lenercept™) inhibitors and PDE4 inhibitors.

The solid state form can be combined with corticosteroids, for example, budesonide and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis (MS) with which the solid state form can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of the invention can be combined with antibodies to cell surface molecules such as CD2, CD3, CD4, CD8, CD19, CD20, CD25, CD28, CD30, CD40, CD45, CD69, CD80, CD86, CD90 or their ligands. The solid state form may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenosineagonists, antithrombotic agents, complement inhibitors, adrenergic agents, agents which interfere with signaling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and anti-inflammatory cytokines (e.g. IL-4, IL-10, IL-13 and TGFβ). Examples of therapeutic agents for multiple sclerosis in which a compound of the invention can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

The solid state form may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis (AS) with which the solid state form can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, adalimumab (such as HUMIRA™ brand adalimumab), infliximab such as CA2 (REMICADE™ brand infliximab), CDP 571, TNFR-Ig constructs, etanercept such as p75TNFRIgG (ENBREL™ brand etanercept) and lenercept such as p55TNFRIgG (LENERCEPT™).

Non-limiting examples of therapeutic agents for psoriasis (Ps, such as moderate to severe plaque psoriasis) with which the solid state form can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874, ustekinumab, and adalimumab (such as HUMIRA™ brand adalimumab).

Non-limiting examples of therapeutic agents for psoriatic arthritis (PsA) with which the solid state form can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, adalimumab (such as HUMIRA™ brand adalimumab), and efalizumab.

Examples of therapeutic agents for SLE (Lupus) with which the solid state form can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budesonide, dexamethasone; cytotoxics, for example, azathioprine, cyclophosphamide, mycophenolate mofetil, methotrexate; inhibitors of PDE4 or purine synthesis inhibitor, for example CELLCEPT®. The solid state form may also be combined with agents such as sulfasalazine, 5-aminosalicylic acid, olsalazine, IMURAN® and agents which interfere with synthesis, production or action of proinflammatory cytokines such as IL-1, for example, caspase inhibitors like IL-1β converting enzyme inhibitors and IL-1ra. The solid state form may also be used with T cell signaling inhibitors, for example, tyrosine kinase inhibitors; or molecules that target T cell activation molecules, for example, CTLA-4-IgG or anti-B7 family antibodies, anti-PD-1 family antibodies. The solid state form can be combined with IL-11 or anti-cytokine antibodies, for example, fontolizumab (anti-IFNg antibody), or anti-receptor receptor antibodies, for example, anti-IL-6 receptor antibody and antibodies to B-cell surface molecules. The solid state form may also be used with UP 394 (abetimus), agents that deplete or inactivate B-cells, for example, Rituximab (anti-CD20 antibody), lymphostat-B (anti-BlyS antibody), TNF antagonists, for example, anti-TNF antibodies, adalimumab (such as HUMIRA™ brand adalimumab), infliximab such as CA2 (REMICADE™ brand infliximab), CDP 571, TNFR-Ig constructs, etanercept such as p75TNFRIgG (ENBREL™ brand etanercept) and lenercept such as p55TNFRIgG (LENERCEPT™).

The solid state form may also be combined with an immune modulator for CD4+CD25+ Treg cells. Treg cells are essential for maintaining normal immune homeostasis. In patients with autoimmune diseases, reduced numbers or functional impairment of Treg cells has been observed, leading to loss of this finely-tuned mechanism. A humanized agonistic monoclonal antibody, BT-061, binds to a unique epitope of human CD4, and induces Treg-specific signaling events that lead to their functional activation. Pre-clinical data using isolated Treg cells and rheumatoid arthritis synovial fluid indicate that BT-061 leads to suppression of CD4+ and CD8+T effector cell proliferation, reduction of the expression of pro-inflammatory cytokines, and increase in the production of the anti-inflammatory cytokine TGFβ. Thus similar immune modulators for CD4+CD25+ Treg cells can also be co-administered with a compound of the invention for treating any of the inflammatory disease/disorder, or an autoimmune disease/disorder described herein, including but not limited to rheumatoid arthritis, Crohn's disease, ankylosing spondylitis, psoriatic arthritis, psoriasis, ulcerative colitis, systemic lupus erythematosus, lupus nephritis, diabetic nephropathy, dry eye syndrome, Sjogren's syndrome, alopecia areata, vitiligo, or atopic dermatitis. In certain embodiments, the combination treats rheumatoid arthritis, Crohn's disease, psoriasis, or psoriatic arthritis, including moderately to severely active rheumatoid arthritis, Crohn's disease, psoriasis, or psoriatic arthritis. In certain embodiments, the rheumatoid arthritis, Crohn's disease, psoriasis, or psoriatic arthritis patient being treated has inadequately responded to or has discontinued therapy due to loss of response to or intolerance to a first line therapy (such as a DMARD, including methotrexate) or an anti-TNFα therapy.

In certain embodiments, the immune modulator has one or more (or all) of the following properties: (1) activates a subset of CD4+ T cells comprising CD4+CD25+ regulatory T cells (Treg), or CD4+CD25+ Treg cells; (2) binds only to a special epitope of the human CD4 antigen (such as the IgG-like C2 type 1 domain of CD4), which said epitope of human CD4 may be bound by a mouse IgG1 anti-CD4 monoclonal antibody B-F5 or a humanized version thereof, such as the BT-061 hB-F5 antibody tregalizumab as described in U.S. Pat. No. 7,452,981 (incorporated herein by reference, including all sequences of the VH and VL chains disclosed therein); (3) provides an activation signal to naturally occurring Treg cells but does not activate conventional T cells (e.g., CD4+ T cells that are not activated in (1), CD8+ cytotoxic T cells, etc.); and (4) is not a depleting anti-CD4 antibody that depletes CD4+ T cells, and/or does not appreciably trigger ADCC or CDC.

IV. Pharmaceutical Compositions

The present disclosure further relates, in part, to compositions comprising Compound 1 or a pharmaceutically acceptable salt thereof, or one or more solid state forms of Compound 1. Although the solid state form may be administered alone or in the form of a pharmaceutical composition, administration generally will be in the form of a pharmaceutical composition. In some embodiments, the composition comprises Compound 1 or a pharmaceutically acceptable salt thereof or a solid state form of Compound 1 in association with a pharmaceutically acceptable carrier. The preferred composition depends on the method of administration, and typically comprises one or more conventional pharmaceutically acceptable carriers, adjuvants, and/or vehicles (together referred to as "excipients"). Such compositions can be formulated for various routes of systemic or local delivery for example, by oral administration, topical administration, transmucosal administration, rectal administration, intravaginal administration, or administration by subcutaneous, intrathecal, intravenous, intramuscular, intraperitoneal, intranasal, intraocular or intraventricular injection.

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise pH modifiers, such as sodium citrate; magnesium or calcium carbonate or bicarbonate; tartaric acid, fumaric acid, citric acid, succinic acid, malic acid, and phosphoric acid and combinations thereof. Tablets and pills additionally can be prepared with enteric coatings.

In one embodiment, the pharmaceutical composition is a tablet dosage form. In one aspect, the tablet is coated with a pharmaceutically acceptable polymer.

In one embodiment, tablet is a controlled-release formulation, such as an extended release tablet dosage form (also referred to herein as a modified release or sustained release formulation). Such formulations permit the sustained release of the active ingredient over an extended period of time, as compared to immediate release solid dosage forms, which permit the release of most or all of the active ingredient over a short period of time (e.g., typically around 60 minutes or less). In one aspect, the tablet comprises an active ingredient and at least one additive selected from the group consisting of a release control polymer, a filler, a glidant, a lubricant (e.g., for use in compacting the granules), a pH modifier, a surfactant, and combinations thereof. In one aspect, the tablet comprises an active ingredient, a release control polymer, a filler, a glidant, and a lubricant. In one aspect, the tablet comprises an active ingredient, a release control polymer, a filler, a glidant, a lubricant, and a pH modifier.

In certain embodiments, the release control polymer will be a hydrophilic polymer. Examples of suitable release control polymers include, but are not limited to a cellulose derivative with a viscosity of between 1000 and 150,000 mPA-s, hydroxypropylmethyl cellulose (e.g., Hypromellose 2208 or controlled release grades of hydroxypropylmethyl cellulose, including the E, F, and K series), copolymers of acrylic acid crosslinked with a polyalkenyl polyether (e.g., Carbopol® polymers), hydroxypropyl cellulose, hydroxyethyl cellulose, non-ionic homopolymers of ethylene oxide (e.g., Polyox™), water soluble natural gums of polysaccharides (e.g., xanthan gum, alginate, locust bean gum, etc.), crosslinked starch, polyvinyl acetates, polyvinylpyrrolidone, mixtures of polyvinyl acetates and polyvinyl pyrrolidone, and combinations thereof. In one embodiment, the release control polymer is selected from the group consisting of hydroxypropylmethyl cellulose, copolymers of acrylic acid crosslinked with a polyalkenyl polyether (e.g., Carbopol® polymers), and combinations thereof. Examples of suitable fillers ("bulking agents") include, but are not limited to, microcrystalline cellulose (e.g., Avicel® PH 101; Avicel® PH 102), mannitol (e.g., Pearlitol® 100 SD or Pearlitol® 200 SD), lactose, sucrose, sorbitol, and the like. In one embodiment, the filler is selected from the group consisting of microcrystalline cellulose, mannitol, and combinations thereof. Examples of suitable glidants include, but are not limited to, silicone dioxide (e.g., colloidal silicon dioxide), calcium silicate, magnesium silicate, talc, and combinations thereof. In one embodiment, the glidant is colloidal silicone dioxide. Examples of suitable lubricants include, but are not limited to, polyethylene glycol (e.g., having a molecular weight of from 1000 to 6000), magnesium stearate, calcium stearate, sodium stearyl fumarate, talc, and the like. In one embodiment, the lubricant is magnesium stearate. Examples of suitable pH modifiers include, but are not limited to, organic acids, such as tartaric acid, citric acid, succinic acid, fumaric acid; sodium citrate; magnesium or calcium carbonate or bicarbonate; and combinations thereof. In one embodiment, the pH modifier is tartaric acid. Examples of suitable surfactants include sodium lauryl sulfate.

In one embodiment, the pharmaceutical composition comprises from about 10 w/w % to about 35 w/w % of a pH modifier, and in particular, tartaric acid, fumaric acid, citric acid, succinic acid, malic acid, or combinations thereof. In other embodiments, the formulation comprises from about 20 w/w % to about 35 w/w %, or from about 20 w/w % to about 30 w/w %, or from about 20 w/w % to about 25 w/w %, or about 10 w/w %, about 15 w/w %, about 20 w/w %, about 25 w/w % or about 30 w/w % pH modifier. In one embodiment, the pH modifier is tartaric acid.

V. Pharmacokinetic Parameters 15 mg Dosage Formulations

In certain embodiments, the methods of the present disclosure comprise administering to an adult subject (e.g., a human subject) Compound 1 (freebase), or a pharmaceutically acceptable salt thereof, or a crystalline hydrate of Compound 1 in an amount sufficient to deliver to the subject 15 mg of Compound 1 freebase equivalent. In one embodiment, the freebase or the hydrate is in a once daily extended release formulation.

Unless otherwise indicated, the following pharmacokinetic parameters are achieved after administration of a single 15 mg dose the Compound 1 (freebase) or a pharmaceutically acceptable salt thereof or the crystalline hydrate (e.g., Freebase Hydrate Form C) to the adult subject, or after administration of a sufficient number of once-daily 15 mg doses to achieve a steady-state. By a single 15 mg dose, it is meant a single dosage unit containing an amount of freebase or pharmaceutically acceptable salt or crystalline hydrate sufficient to deliver to the subject 15 mg of Compound 1 freebase equivalent. In one embodiment, the single dosage unit is a once daily extended release formulation.

30 mg Dosage Formulations

In certain embodiments, the methods of the present disclosure comprise administering to an adult subject (e.g., a human subject) 30 mg of Compound 1 (freebase), or a pharmaceutically acceptable salt thereof or a crystalline hydrate of Compound 1 in an amount sufficient to deliver to the subject 30 mg of Compound 1 freebase equivalent. In one embodiment, the freebase or the hydrate is in a once daily extended release formulation.

Unless otherwise indicated, the following pharmacokinetic parameters are achieved after administration of a single 30 mg dose the Compound 1 (freebase) or a pharmaceutically acceptable salt thereof or the crystalline hydrate (e.g., Freebase Hydrate Form C) to the adult subject, or after administration of a sufficient number of once-daily 30 mg doses to achieve a steady-state. By a single 30 mg dose, it is meant a single dosage unit containing an amount of freebase or pharmaceutically acceptable salt or crystalline hydrate sufficient to deliver to the subject 30 mg of Compound 1 freebase equivalent. In one embodiment, the single dosage unit is a once daily extended release formulation.

Extended Release Tablets

In one embodiment, the Compound 1 (freebase) or a pharmaceutically acceptable salt thereof or the crystalline hydrate used in the methods of the present disclosure is in a once daily extended release formulation. In one embodiment, the Compound 1 (freebase) or a pharmaceutically acceptable salt thereof or the crystalline hydrate is in a once daily extended release formulation, and the formulation delivers about 7.5 mg or about 15 mg or about 30 mg or about 45 mg per unit dosage form (e.g., per tablet or capsule) of Compound 1 (freebase equivalent) orally QD (once daily). In one particular embodiment, the crystalline hydrate is Freebase Hydrate Form C.

In one embodiment, the Compound 1 (freebase) or a pharmaceutically acceptable salt thereof or the crystalline hydrate is in a once daily extended release formulation, and the formulation delivers 7.5 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 3 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended release formulation, and the formulation delivers 15 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 6 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended release formulation, and the formulation delivers 30 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 12 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

In one embodiment, the Compound 1 (freebase) or a pharmaceutically acceptable salt thereof or the crystalline hydrate is in a once daily extended release formulation, and the formulation delivers 45 mg of Compound 1 (freebase equivalent) orally QD (once daily). In some such embodiments, the once daily extended release formulation will have a relative bioavailability approximately equivalent to that of an immediate release capsule comprising Compound 1 (freebase) or a pharmaceutically acceptable salt thereof or a solid state form thereof that delivers 18 mg of Compound 1 (freebase equivalent) and that is administered two times per day (BID). In one embodiment, the immediate release capsule comprises a crystalline hydrate of Compound 1. In one embodiment, the immediate release capsule comprises Freebase Hydrate Form C. In one embodiment, the immediate release capsule comprises Tartrate Hydrate.

VI. Ankylosing Spondylitis

Ankylosing Spondylitis (AS) is a chronic, inflammatory rheumatic disease primarily affecting the axial skeleton, characterized by chronic back pain (including nocturnal back pain), morning stiffness, enthesitis, peripheral arthritis, and extra-articular manifestations. The "early" form of this disease (non-radiographic axial spondyloarthritis (nr-axSpA)) shares many of AS disease characteristics.

Due to the longstanding debilitating nature of AS, irreversible structural damage often occurs, negatively impacting patients' lives. No cure for AS exists, thus the primary goal of treatment is to maximize patients' quality of life through controlling the signs and symptoms of disease, preventing structural damage, and maintaining physical function, ideally by achieving sustained clinical remission or, at minimum, low disease activity. Nonsteroidal anti-inflammatory drugs (NSAIDs) are the first-line treatment for AS, followed by biologic disease-modifying antirheumatic drugs (bDMARDs), such as tumor necrosis factor (TNF) inhibitors or interleukin-17 (IL-17) inhibitors, in patients who do not sufficiently respond to NSAIDs. TNF inhibitors and IL-17 inhibitors are efficacious in some patients with AS, but there are still patients for whom neither of these approved therapies address individual treatment goals. AS is a difficult disease to treat, as shown based on low efficacy achieved with IL-6 inhibitors tocilizumab and sarilumab, as well as IL-12/23 inhibitor ustekinumab and T cell blockade inhibitor abatacept. See, e.g., Sieper et al., Ann. Rheum. Dis. 2014 73:95-100, Sieper et al., Ann. Rheum. Dis. 2015 74:1051-1057; Deodhar et al., Arthritis and Rheumatology 2019 71:258-270, and Song et al., Ann. Rheum. Dis. 2011 70:1108-1110.

The JAK family is composed of 4 members: JAK1, 2, 3, and tyrosine kinase 2 (Tyk2). These cytoplasmic tyrosine kinases act in tandem to activate the Signal Transducer and Activator of Transcription (STAT) that transduce cytokine-mediated signals and are associated with multiple membrane cytokine receptors such as common gamma-chain (CGC) receptors and the glycoprotein 130 trans-membrane proteins. JAK3 and JAK1 are components of the CGC cytokine receptor complexes that are responsible for the signaling of the inflammatory cytokines IL-2, -4, -7, -9, -15 and –21; whereas IL-12 and IL-23 signal through JAK2 and Tyk2. See Ghoreschi, et al., Immunol Rev. (2009), 228:273-87. Propagation of these signals is important in the amplification of inflammatory responses in axial spondyloarthritis (axSpA). Upadacitinib, a JAK inhibitor engineered for increased selectivity for JAK1 over JAK2, JAK3, and tyrosine kinase 2, has been investigated for the treatment of bDMARD-naïve patients with AS who had an inadequate response to non-steroidal anti-inflammatory drugs (NSAIDs) in the randomized, placebo-controlled phase 2/3 SELECT-AXIS 1 study. See Example 31, herein. A second study (SELECT-AXIS-2) expanded the scope of enrollment to non-radiographic axial spondyloarthritis (nr-axSpA) patients and AS bDMARD-IR patients. See Examples 32 and 33 herein.

The SELECT-AXIS 1 met its primary endpoint of significantly greater achievement of Assessment of SpondyloArthritis International Society (ASAS40) response at Week 14, as well as several disease activity measures (ASDAS, BASDAI, ASAS, and their components), inflammation (based on MRI of spine and sacroiliac joints as well as hsCRP), physical function (BASFI), quality of life (ASQoL, ASAS HI), and other aspects of disease (BASMI, MASES), reflecting significant improvement in outcomes for upadacitinib versus placebo. Furthermore, a review of the placebo corrected data for upadacitinib at Week 14, biologics Ixekizumab and Adalimumab at Week 16, and JAK small molecule inhibitors Tofacitinib and Filgotinib at Week 12 for key primary and secondary endpoints, while not a head to head comparison, suggests that upadacitinib 15 mg QD shows decided promise for the more difficult to achieve endpoints ASAS PR, ASDAS ID, and ASDAS LDA versus the other two JAK small molecule inhibitors, with a remarkable efficacy only comparable to that demonstrated with the biologics. See U.S. Pat. App. No. 2021/0228575 (Example 2), and van der Heijde et al. Lancet (2018) 392: 2441-2451, van der Heijde D, et al. Ann. Rheum. Dis. (2017) 1-8; van der Heijde et al. Lancet (2018) 2378-2387. Furthermore, this efficacy, once achieved at Week 14, was sustained or improved over time, with long term efficacy in these difficult to achieve endpoints (including ASDAS major improvement (MI) and ASDAS clinically important improvement (CII)), sustained or improved up to and including Week 64. In patients who switched from placebo to upadacitinib at Week 14, a similar speed of onset and magnitude of efficacy response was observed up to and including Week 64 compared with those who received continuous upadacitinib starting at Week 0. Based on the results of phase 2/3 study SELECT-AXIS 1 and the consistent safety data from other upadacitinib clinical trials, the benefit-risk profile of upadacitinib in AS (particularly compared to the risk profile of other small molecule JAK inhibitors), and viewed in the context of the benefit-risk of TNF inhibitors and IL-17 inhibitors, presents a promising oral targeted treatment option for patients with AS, especially for those AS (as well as nr-axSpA patients) who have active disease and inadequate response to NSAIDs.

In one embodiment, the JAK1 inhibitor useful in the methods disclosed herein is upadacitinib freebase. Upadacitinib freebase solid state forms include amorphous upadacitinib freebase and crystalline freebases of upadacitinib. Crystalline freebases of upadacitinib include those selected from the group consisting of crystalline freebase solvates of upadacitinib, crystalline freebase hydrates of upadacitinib (e.g., crystalline freebase hemihydrates of upadacitinib), and crystalline freebase anhydrates of upadacitinib. In one embodiment, the crystalline freebase of upadacitinib is a crystalline freebase hemihydrate of upadacitinib. In one embodiment, the crystalline freebase of upadacitinib is Upadacitinib Freebase Hydrate Form C (which is a hemihydrate) as described in WO 2018/165581 and WO 2017/066775. Other specific examples of solid state forms of the JAK1 inhibitor suitable for use in the methods disclosed herein include those selected from the group consisting of Amorphous Upadacitinib Freebase, Upadacitinib Freebase Solvate Form A, Upadacitinib Freebase Hydrate Form B, Upadacitinib Freebase Anhydrate Form D, and Upadacitinib Tartrate Hydrate, each as described in WO 2018/165581 and WO 2017/066775.

VII. Methods of Treating Ankylosing Spondylitis (AS)

Further provided are methods of treating ankylosing spondylitis (AS). For example, in one aspect, provided is a method of treating AS, including active AS, comprising administering orally once a day a dose of the JAK1 inhibitor to a subject in need thereof in certain amounts and/or at certain intervals. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the subject is bDMARD naïve. In one aspect, the subject is bDMARD-IR.

Disease activity/severity for AS may be measured using a variety of indexes, including those set forth herein for the treatment of axSpA. In one particular aspect, provided is a method of treating AS, including active AS, comprising administering a dose of the JAK1 inhibitor to a subject in need thereof in certain amounts and/or at certain intervals as described herein, wherein the subject achieves an Assessment of SpondyloArthritis International Society 40 (ASAS40) response following administration of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the subject is bDMARD naïve. In one aspect, the subject is bDMARD-IR. In one aspect, the subject is an adult.

In one aspect, the subject achieves an ASAS40 response within 14 weeks of administration of the first dose of the JAK1 inhibitor (including at week 14). In one aspect, the subject achieves an ASAS40 response within 14 weeks of administration of the first dose of the JAK1 inhibitor (including at week 14), and the response is maintained or improved after week 14 by continuing to administer a daily dose of the JAK1 inhibitor. In one aspect, the subject achieves an ASAS40 response within 2 weeks of administration of the first dose of the JAK1 inhibitor (including at week 2). In one aspect, the subject achieves an ASAS40 response within 2 weeks of administration of the first dose of the JAK1 inhibitor (including at week 2), and the response is maintained or improved after week 2 by continuing to administer a daily dose of the JAK1 inhibitor. In one aspect, the subject achieves an ASAS40 response within 2 weeks, within 4 weeks, within 8 weeks, within 12 weeks, within 14 weeks, within 16 weeks, within 18 weeks, within 20 weeks, within 24 weeks, within 32 weeks, within 40 weeks, within 52 weeks, within 64 weeks, within 76 weeks, within 88 weeks, within 96 weeks, within 104 weeks, and/or within 152 weeks (including at week 2, week 4, week 8, week 12, week 14, week 16, week 18, week 20, week 24, week 32, week 40, week 52, week 64, week 76, week 88, week 96, week 104, and/or week 152) of administration of the first dose of the JAK1 inhibitor. In one aspect, the subject achieves an ASAS 40 response within 14 weeks of administration of the first dose of the JAK1 inhibitor (including at week 14), and the ASAS40 response is maintained or improved until at least 64 weeks after administration of the first dose (e.g., up to and including week 64). In one embodiment, the subject achieves an ASAS 40 response within 2 weeks of administration of the first dose (including at week 2), and maintains or improves the ASAS40 response until at least 14 weeks after administration of the first dose (e.g., until at least week 14). In one embodiment, the subject achieves an ASAS 40 response within 2 weeks of administration of the first dose of the JAK1 inhibitor (including at week 2), and the ASAS40 response is maintained or improved until at least 64 weeks after administration of the first dose (e.g., up to and including week 64). In one aspect, the subject achieves an ASAS 40 response within 14 weeks of administration of the first dose of the JAK1 inhibitor (including at week 14), and the ASAS40 response is maintained or improved until at least 104 weeks after administration of the first dose (e.g., up to and including week 104). In one aspect, the subject achieves an ASAS 40 response within 14 weeks of administration of the first dose of the JAK1 inhibitor (including at week 14), and the ASAS40 response is maintained or improved until at least 152 weeks after administration of the first dose (e.g., up to and including week 152). In one embodiment, the subject achieves an ASAS 40 response within 4 weeks of administration of the first dose (including at week 4), and maintains or improves the ASAS40 response until at least 14 weeks after administration of the first dose (e.g., until at least week 14). In one embodiment, the subject achieves an ASAS 40 response within 4 weeks of administration of the first dose of the JAK1 inhibitor (including at week 4), and the ASAS40 response is maintained or improved until at least 64 weeks after administration of the first dose (e.g., up to and including week 64). In one embodiment, the subject achieves an ASAS 40 response within 4 weeks of administration of the first dose of the JAK1 inhibitor (including at week 4), and the ASAS40 response is maintained or improved until at least 104 weeks after administration of the first dose (e.g., up to and including week 104). In one embodiment, the subject achieves an ASAS 40 response within 4 weeks of administration of the first dose of the JAK1 inhibitor (including at week 4), and the ASAS40 response is maintained or improved until at least 152 weeks after administration of the first dose (e.g., up to and including week 152).

In one aspect, the subject alternately or additionally achieves within 14 weeks of administration of the first dose of the JAK1 inhibitor (including at week 14) at least one additional result selected from the group consisting of: ASAS partial remission (PR); BASDAI50 response; change (improvement) from baseline in MRI SPARCC score for spine (MRI-Spine SPARCC); change (improvement) from baseline in ASDAS; change (improvement) from baseline in BASFI; ASDAS low disease activity (LDA); ASDAS inactive disease (ID); ASDAS major improvement (MI); and ASDAS clinically important improvement (CII). In one aspect, the subject alternately or additionally achieves within 14 weeks of administration of the first dose of the JAK1 inhibitor (including at week 14) at least one additional result selected from the group consisting of: change (improvement) from baseline in ASDAS (e.g., ASDAS CRP); change (improvement) from baseline in MRI SPARCC score for spine (MRI-Spine SPARCC); BASDAI50 response; ASAS20 response; ASDAS inactive disease (ID); change (improvement) from baseline in Patient's Assessment of Total Back Pain (Total Back Pain score); change (improvement) from baseline in Patient's Assessment of Nocturnal Back Pain (Nocturnal Back Pain score); ASDAS low disease activity (LDA); (change (improvement) from baseline in BASFI; ASAS partial remission (PR); change (improvement) from Baseline in Ankylosing Spondylitis Quality of Life (ASQoL); change (improvement) from baseline in ASAS Health Index (HI); change (improvement) from baseline in Linear Bath Ankylosing Spondylitis Metrology Index (BASMIlin) (Mobility); and change (improvement) from baseline in Maastricht Ankylosing Spondylitis Enthesitis Score (MASES) (Enthesitis). In one aspect, the subject achieves the result within 14 weeks of administration of the first dose of the JAK1 inhibitor (including at week 14), and the result is maintained or improved after week 14 by continuing to administer a daily dose of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 2 weeks, for at least 4 weeks, for at least 8 weeks, for at least 12 weeks, for at least 14 weeks, for at least 16 weeks, for at least 18 weeks, for at least 20 weeks, for at least 24 weeks, for at least 32 weeks, for at least 40 weeks, for at least 52 weeks, for at least 64 weeks, for at least 76 weeks, for at least 88 weeks, for at least 96 weeks, for at least 104 weeks, and/or for at least 152 weeks. In one embodiment, the JAK1 inhibitor is administered orally once a day for at least 14 weeks. In one aspect, provided is a method of treating AS, including active AS, in a population of subjects in need thereof, the method comprising administering a dose of the JAK1 inhibitor to the subjects in certain amounts and/or at certain intervals as described herein, wherein a portion of subjects in the treated population (e.g., a statistically significant population of subjects in the treated population, and/or at least 10%, at least 15%, at least 20%, at least 25%, at least 30%, at least 35%, at least 40%, at least 44%, or at least 45% of the subjects in the treated population) achieve an ASAS40 response following administration of the JAK1 inhibitor. In one aspect, subjects in the treated population achieve an ASAS40 response within 14 weeks of administration of the first dose of the JAK1 inhibitor (including at week 14). In one aspect, subjects in the treated population achieve an ASAS40 response within 14 weeks of administration of the first dose of the JAK1 inhibitor (including at week 14), and the response is maintained or improved after week 14 by continuing to administer a daily dose of the JAK1 inhibitor. In one aspect, subjects in the treated population achieve an ASAS40 response within 4 weeks of administration of the first dose of the JAK1 inhibitor (including at week 4). In one aspect, subjects in the treated population of the subjects achieve an ASAS40 response within 4 weeks of administration of the first dose of the JAK1 inhibitor (including at week 4), and the response is maintained or improved after week 4 by continuing to administer a daily dose of the JAK1 inhibitor. In one aspect, subjects in the treated population achieve an ASAS40 response within 2 weeks, within 4 weeks, within 8 weeks, within 12 weeks, within 14 weeks, within 16 weeks, within 18 weeks, within 20 weeks, within 24 weeks, within 32 weeks, within 40 weeks, within 52 weeks, within 64 weeks, within 76 weeks, within 88 weeks, within 96 weeks, within 104 weeks, and/or within 152 weeks (including at week 2, week 4, week 8, week 12, week 14, week 16, week 18, week 20, week 24, week 32, week 40, week 52, week 64, week 76, week 88, week 96, week 104, and/or week 152) of administration of the first dose of the JAK1 inhibitor. In one embodiment, subjects in the treated population achieve an ASAS 40 response within 14 weeks of administration of the first dose of the JAK1 inhibitor (including at week 14), and the ASAS40 response is maintained or improved until at least 64 weeks, at least 104 weeks, and/or at least 152 weeks after administration of the first dose (e.g., up to and including week 64, week 104, and/or week 152). In one embodiment, subjects in the treated population achieve an ASAS 40 response within 4 weeks of administration of the first dose (including at week 4), and maintains or improves the ASAS40 response until at least 14 weeks after administration of the first dose (e.g., until at least week 14). In one aspect, subjects in the treated population alternately or additionally achieve within 14 weeks of administration of the first dose of the JAK1 inhibitor (including at week 14) at least one additional result selected from the group consisting of: change (improvement) from baseline in ASDAS (e.g., ASDAS CRP); change (improvement) from baseline in MRI SPARCC score for spine (MRI-Spine SPARCC); BASDAI50 response; ASAS20 response; ASDAS inactive disease (ID); change (improvement) from baseline in Patient's Assessment of Total Back Pain (Total Back Pain score); change (improvement) from baseline in Patient's Assessment of Nocturnal Back Pain (Nocturnal Back Pain score); ASDAS low disease activity (LDA); (change (improvement) from baseline in BASFI; ASAS partial remission (PR); change (improvement) from Baseline in Ankylosing Spondylitis Quality of Life (ASQoL); change (improvement) from baseline in ASAS Health Index (HI); change (improvement) from baseline in Linear Bath Ankylosing Spondylitis Metrology Index (BASMIlin) (Mobility); and change (improvement) from baseline in Maastricht Ankylosing Spondylitis Enthesitis Score (MASES) (Enthesitis). In one aspect, subjects in the treated population achieve the result within 14 weeks of administration of the first dose of the JAK1 inhibitor (including at week 14), and the result is maintained or improved after week 14 by continuing to administer a daily dose of the JAK1 inhibitor. In certain embodiments, for any of the aforementioned results achieved, a statistically significant population of the subjects in the treated population, and/or at least 10%, at least 15%, at least 20%, at least 25%, at least 30%, at least 35%, at least 40%, at least 44%, or at least 45% of the subjects in the treated population, achieve the result. In one aspect, the JAK1 inhibitor is upadacitinib freebase. In one aspect, a dose of the JAK1 inhibitor is administered to the population in an amount sufficient to deliver 15 mg of upadacitinib freebase equivalent. In one aspect, the JAK1 inhibitor is administered to the population orally once a day for at least 14 weeks. In one aspect, the subjects in the population are bDMARD-IR.

Further provided are methods of treating AS, including active AS, in a subject in need thereof, comprising administering orally once a day a dose of a JAK1 inhibitor to a subject in need thereof in certain amounts and/or at certain intervals as described herein, wherein the subject achieves ASAS partial remission (PR), ASDAS low disease activity (LDA), ASDAS inactive disease (ID), ASDAS major improvement (MI), and/or ASDAS clinically important improvement (CII) following administration of the JAK1 inhibitor. In one embodiment, the subject achieves ASAS PR, ASDAS LDA, ASDAS ID, ASDAS MI, and/or ASDAS CII within 14 weeks of administration of the first dose of the JAK1 inhibitor (including at week 14). In one embodiment, the subject achieves each result (e.g., ASAS PR, ASDAS LDA, ASDAS ID, ASDAS MI, and ASDAS CII) within 14 weeks of administration of the first dose of the JAK1 inhibitor (including at week 14). In one aspect, the subject achieves ASAS PR, ASDAS LDA, ASDAS ID, ASDAS MI, and/or ASDAS CII within 2 weeks of administration of the first dose of the JAK1 inhibitor (including at week 2). In one aspect, the subject achieves ASAS PR, ASDAS LDA, ASDAS ID, ASDAS MI, and/or ASDAS CII within 2 weeks, within 4 weeks, within 8 weeks, within 12 weeks, within 14 weeks, within 16 weeks, within 18 weeks, within 20 weeks, within 24 weeks, within 32 weeks, within 40 weeks, within 52 weeks, within 64 weeks, within 76 weeks, within 88 weeks, within 96 weeks, and/or within 104 weeks (including at week 2, week 4, week 8, week 12, week 14, week 16, week 18, week 20, week 24, week 32, week 40, week 52, week 64, week 76, week 88, week 96, and/or week 104) of administration of the first dose of the JAK1 inhibitor. In one aspect, the subject achieves ASAS PR, ASDAS LDA, ASDAS ID, ASDAS MI, and/or ASDAS CII within 14 weeks of administration of the first dose of the JAK1 inhibitor (including at week 14), and the response is maintained or improved after week 14 by continuing to administer a daily dose of the JAK1 inhibitor. In one aspect, the subject achieves ASAS PR, ASDAS LDA, ASDAS ID, ASDAS MI, and/or ASDAS CII within 2 weeks of administration of the first dose of the JAK1 inhibitor (including at week 2), and the response is maintained or improved after week 2 by continuing to administer the daily dose of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 2 weeks, for at least 4 weeks, for at least 8 weeks, for at least 12 weeks, for at least 14 weeks, for at least 16 weeks, for at least 18 weeks, for at least 20 weeks, for at least 24 weeks, for at least 32 weeks, for at least 40 weeks, for at least 52 weeks, for at least 64 weeks, for at least 76 weeks, for at least 88 weeks, for at least 96 weeks, and/or for at least 104 weeks. In one embodiment, the JAK1 inhibitor is administered orally once a day for at least 14 weeks. In one aspect, the subject is bDMARD naïve. In one aspect, the subject is bDMARD-IR. In one aspect, the subject is an adult.

Further provided are methods of treating AS, including active AS, in a population of subjects in need thereof, the method comprising administering orally once a day a dose of the JAK1 inhibitor to a subject in need thereof in certain amounts and/or at certain intervals as described herein, wherein a portion of the subjects in the treated population (e.g., a statistically significant population of subjects in the treated population, and/or at least 10%, at least 15%, at least 20%, at least 25%, at least 30%, at least 35%, at least 40%, at least 44% or at least 45% of the subjects in the treated population) achieve change (improvement) from baseline in ASDAS (e.g., ASDAS CRP); change (improvement) from baseline in MRI SPARCC score for spine (MRI-Spine SPARCC); BASDAI50 response; ASAS20 response; ASDAS inactive disease (ID); change (improvement) from baseline in Patient's Assessment of Total Back Pain (Total Back Pain score); change (improvement) from baseline in Patient's Assessment of Nocturnal Back Pain (Nocturnal Back Pain score); ASDAS low disease activity (LDA); (change (improvement) from baseline in BASFI; ASAS partial remission (PR); change (improvement) from Baseline in Ankylosing Spondylitis Quality of Life (ASQoL); change (improvement) from baseline in ASAS Health Index (HI); change (improvement) from baseline in Linear Bath Ankylosing Spondylitis Metrology Index (BASMIlin) (Mobility); and/or change (improvement) from baseline in Maastricht Ankylosing Spondylitis Enthesitis Score (MASES) (Enthesitis) following administration of the JAK1 inhibitor. In one aspect, subjects in the treated population achieve any one or more of the aforementioned results within 14 weeks of administration of the first dose of the JAK1 inhibitor (including at week 14). In one aspect, subjects in the treated population achieve each result within 14 weeks of administration of the first dose of the JAK1 inhibitor (including at week 14). In one aspect, subjects in the treated population achieve any one or more of the aforementioned results within 4 weeks of administration of the first dose of the JAK1 inhibitor (including at week 4). In one aspect, subjects in the treated population achieve any one or more of the aforementioned results within 2 weeks, within 4 weeks, within 8 weeks, within 12 weeks, within 14 weeks, within 16 weeks, within 18 weeks, within 20 weeks, within 24 weeks, within 32 weeks, within 40 weeks, within 52 weeks, within 64 weeks, within 76 weeks, within 88 weeks, within 96 weeks, within 104 weeks, and/or within 152 weeks (including at week 2, week 4, week 8, week 12, week 14, week 16, week 18, week 20, week 24, week 32, week 40, week 52, week 64, week 76, week 88, week 96, week 104, and/or week 152) of administration of the first dose of the JAK1 inhibitor. In one aspect, subjects in the treated population achieve any one or more of the aforementioned results within 14 weeks of administration of the first dose of the JAK1 inhibitor (including at week 14), and the response is maintained or improved after week 14 by continuing to administer the daily dose of the JAK1 inhibitor. In one aspect, subjects in the treated population achieve any one or more of the aforementioned results within 4 weeks of administration of the first dose of the JAK1 inhibitor (including at week 4), and the response is maintained or improved after week 4 by continuing to administer the daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, at least 44%, or at least 45% of the subjects in the treated population, achieve the result. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 2 weeks, for at least 4 weeks, for at least 8 weeks, for at least 12 weeks, for at least 14 weeks, for at least 16 weeks, for at least 18 weeks, for at least 20 weeks, for at least 24 weeks, for at least 32 weeks, for at least 40 weeks, for at least 52 weeks, for at least 64 weeks, for at least 76 weeks, for at least 88 weeks, for at least 96 weeks, for at least 104 weeks, and/or for at least 152 weeks. In one embodiment, the JAK1 inhibitor is administered orally once a day for at least 14 weeks In one aspect, provided is a method of treating AS, including active AS, in a population of subjects in need thereof, the method comprising administering a dose of the JAK1 inhibitor to the subjects in certain amounts and/or at certain intervals as described herein, wherein a portion of subjects in the treated population (e.g., a statistically significant population of subjects in the treated population, and/or at least 10%, at least 15%, at least 20%, at least 25%, at least 30%, at least 35%, at least 40%, or at least 45% of the subjects in the treated population) achieve an ASAS40 response following administration of the JAK1 inhibitor. In one aspect, subjects in the treated population achieve an ASAS40 response within 14 weeks of administration of the first dose of the JAK1 inhibitor (including at week 14). In one aspect, subjects in the treated population achieve an ASAS40 response within 14 weeks of administration of the first dose of the JAK1 inhibitor (including at week 14), and the response is maintained or improved after week 14 by continuing to administer a daily dose of the JAK1 inhibitor. In one aspect, subjects in the treated population achieve an ASAS40 response within 2 weeks of administration of the first dose of the JAK1 inhibitor (including at week 2). In one aspect, subjects in the treated population of the subjects achieve an ASAS40 response within 2 weeks of administration of the first dose of the JAK1 inhibitor (including at week 2), and the response is maintained or improved after week 2 by continuing to administer a daily dose of the JAK1 inhibitor. In one aspect, subjects in the treated population achieve an ASAS40 response within 2 weeks, within 4 weeks, within 8 weeks, within 12 weeks, within 14 weeks, within 16 weeks, within 18 weeks, within 20 weeks, within 24 weeks, within 32 weeks, within 40 weeks, within 52 weeks, within 64 weeks, within 76 weeks, within 88 weeks, within 96 weeks, and/or within 104 weeks (including at week 2, week 4, week 8, week 12, week 14, week 16, week 18, week 20, week 24, week 32, week 40, week 52, week 64, week 76, week 88, week 96, and/or week 104) of administration of the first dose of the JAK1 inhibitor. In one embodiment, subjects in the treated population achieve an ASAS 40 response within 14 weeks of administration of the first dose of the JAK1 inhibitor (including at week 14), and the ASAS40 response is maintained or improved until at least 64 weeks after administration of the first dose (e.g., up to and including week 64). In one embodiment, subjects in the treated population achieve an ASAS 40 response within 2 weeks of administration of the first dose (including at week 2), and maintains or improves the ASAS40 response until at least 14 weeks after administration of the first dose (e.g., until at least week 14). In one aspect, subjects in the treated population alternately or additionally achieve within 14 weeks of administration of the first dose of the JAK1 inhibitor (including at week 14) at least one additional result selected from the group consisting of: ASAS partial remission (PR); BASDAI50 response; change (improvement) from baseline in MRI SPARCC score for spine (MRI-Spine SPARCC); change (improvement) from baseline in ASDAS; change (improvement) from baseline in BASFI; ASDAS low disease activity (LDA); ASDAS inactive disease (ID); ASDAS major improvement (MI); and ASDAS clinically important improvement (CII). In one aspect, subjects in the treated population achieve the result within 14 weeks of administration of the first dose of the JAK1 inhibitor (including at week 14), and the result is maintained or improved after week 14 by continuing to administer a daily dose of the JAK1 inhibitor. In certain embodiments, for any of the aforementioned results achieved, a statistically significant population of the subjects in the treated population, and/or at least 10%, at least 15%, at least 20%, at least 25%, at least 30%, at least 35%, at least 40%, or at least 45% of the subjects in the treated population, achieve the result. In one aspect, the JAK1 inhibitor is upadacitinib freebase. In one aspect, a dose of the JAK1 inhibitor is administered to the population in an amount sufficient to deliver 15 mg of upadacitinib freebase equivalent. In one aspect, the JAK1 inhibitor is administered to the population orally once a day for at least 14 weeks. In one aspect, the subjects in the population are bDMARD naïve. In one aspect, the subjects in the population are bDMARD-IR.

Further provided are methods of treating AS, including active AS, in a population of subjects in need thereof, the method comprising administering orally once a day a dose of the JAK1 inhibitor to a subject in need thereof in certain amounts and/or at certain intervals as described herein, wherein a portion of the subjects in the treated population (e.g., a statistically significant population of subjects in the treated population, and/or at least 10%, at least 15%, at least 20%, at least 25%, at least 30%, at least 35%, at least 40%, or at least 45% of the subjects in the treated population) achieve ASAS partial remission (PR), ASDAS low disease activity (LDA), ASDAS inactive disease (ID), ASDAS major improvement (MI), and/or ASDAS clinically important improvement (CII) following administration of the JAK1 inhibitor. In one aspect, subjects in the treated population achieve ASAS PR, ASDAS LDA, ASDAS ID, ASDAS MI, and/or ASDAS CII within 14 weeks of administration of the first dose of the JAK1 inhibitor (including at week 14). In one aspect, subjects in the treated population achieve each result (e.g., ASAS PR, ASDAS LDA, ASDAS ID, ASDAS MI, and ASDAS CII) within 14 weeks of administration of the first dose of the JAK1 inhibitor (including at week 14). In one aspect, subjects in the treated population achieve ASAS PR, ASDAS LDA, ASDAS ID, ASDAS MI, and/or ASDAS CII within 2 weeks of administration of the first dose of the JAK1 inhibitor (including at week 2). In one aspect, subjects in the treated population achieve ASAS PR, ASDAS LDA, ASDAS ID, ASDAS MI, and/or ASDAS CII within 2 weeks, within 4 weeks, within 8 weeks, within 12 weeks, within 14 weeks, within 16 weeks, within 18 weeks, within 20 weeks, within 24 weeks, within 32 weeks, within 40 weeks, within 52 weeks, within 64 weeks, within 76 weeks, within 88 weeks, within 96 weeks, and/or within 104 weeks (including at week 2, week 4, week 8, week 12, week 14, week 16, week 18, week 20, week 24, week 32, week 40, week 52, week 64, week 76, week 88, week 96, and/or week 104) of administration of the first dose of the JAK1 inhibitor. In one aspect, subjects in the treated population achieve ASAS PR, ASDAS LDA, ASDAS ID, ASDAS MI, and/or ASDAS CII within 14 weeks of administration of the first dose of the JAK1 inhibitor (including at week 14), and the response is maintained or improved after week 14 by continuing to administer the daily dose of the JAK1 inhibitor. In one aspect, subjects in the treated population achieve ASAS PR, ASDAS LDA, ASDAS ID, ASDAS MI, and/or ASDAS CII within 2 weeks of administration of the first dose of the JAK1 inhibitor (including at week 2), and the response is maintained or improved after week 2 by continuing to administer the daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve the result. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 2 weeks, for at least 4 weeks, for at least 8 weeks, for at least 12 weeks, for at least 14 weeks, for at least 16 weeks, for at least 18 weeks, for at least 20 weeks, for at least 24 weeks, for at least 32 weeks, for at least 40 weeks, for at least 52 weeks, for at least 64 weeks, for at least 76 weeks, for at least 88 weeks, for at least 96 weeks, and/or for at least 104 weeks. In one embodiment, the JAK1 inhibitor is administered orally once a day for at least 14 weeks. In one aspect, the subjects in the population are bDMARD naïve. In one aspect, the subjects in the population are bDMARD-IR. In one aspect, the subjects are adults.

Further provided are methods of reducing the signs and symptoms of AS. In one aspect, provided is a method of reducing the signs and symptoms of AS, including active AS, the method comprising administering a dose of the JAK1 inhibitor to a subject in need thereof in certain amounts and/or at certain intervals. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the subject is bDMARD naïve. In one aspect, the subject is bDMARD-IR.

In one aspect of a method of reducing the signs and symptoms of AS, including active AS, wherein the subject achieves within 14 weeks of administration of the first dose of the JAK1 inhibitor (including at week 14), at least one result selected from the group consisting of: an ASAS40 response; a change (improvement) from baseline in ASDAS; a change (improvement) from baseline in MRI-Spine SPARCC; ASAS partial remission (PR); a BASDAI50 response; a change (improvement) from baseline in BASFI; a change (improvement) from baseline in ASQoL; a change (improvement) from baseline in ASAS Health Index (HI); a change (improvement) from baseline in MASES (enthesitis); a change (improvement) from baseline in $BASMI_{lin}$ (mobility); and a change (improvement) from baseline in WPAI-Axial SpA. In certain embodiments, for any of the aforementioned results achieved, a statistically significant population of the subjects in the treated population, and/or at least 10%, at least 15%, at least 20%, at least 25%, at least 30%, at least 35%, at least 40%, or at least 45% of the subjects in the treated population, achieve the result. In certain embodiments, for any of the aforementioned results achieved, the subject (or subjects in the treated population) achieve the result or results within 14 weeks of administration of the first dose of the JAK1 inhibitor (including at week 14), and the result (or results) is maintained or improved after week 14 by continuing to administer a daily dose of the JAK1 inhibitor.

In one aspect of a method of reducing the signs and symptoms of AS, including active AS, wherein the subject achieves within 14 weeks of administration of the first dose of the JAK1 inhibitor (including at week 14), at least one result selected from the group consisting of: an ASAS40 response; change (improvement) from baseline in ASDAS (e.g., ASDAS CRP); change (improvement) from baseline in MRI SPARCC score for spine (MRI-Spine SPARCC); BASDAI50 response; ASAS20 response; ASDAS inactive disease (ID); change (improvement) from baseline in Patient's Assessment of Total Back Pain (Total Back Pain score); change (improvement) from baseline in Patient's Assessment of Nocturnal Back Pain (Nocturnal Back Pain score); ASDAS low disease activity (LDA); (change (improvement) from baseline in BASFI; ASAS partial remission (PR); change (improvement) from Baseline in Ankylosing Spondylitis Quality of Life (ASQoL); change (improvement) from baseline in ASAS Health Index (HI); change (improvement) from baseline in Linear Bath Ankylosing Spondylitis Metrology Index ($BASMI_{lin}$) (Mobility); and/or change (improvement) from baseline in Maastricht Ankylosing Spondylitis Enthesitis Score (MASES) (Enthesitis). In certain embodiments, for any of the aforementioned results achieved, a statistically significant population of the subjects in the treated population, and/or at least 10%, at least 15%, at least 20%, at least 25%, at least 30%, at least 35%, at least 40%, at least 44%, or at least 45% of the subjects in the treated population, achieve the result. In certain embodiments, for any of the aforementioned results achieved, the subject (or subjects in the treated population) achieve the result or results within 14 weeks of administration of the first dose of the JAK1 inhibitor (including at week 14), and the result (or results) is maintained or improved after week 14 by continuing to administer a daily dose of the JAK1 inhibitor.

In one aspect of a method of reducing the signs and symptoms of AS, including active AS, wherein the subject achieves within 14 weeks of administration of the first dose of the JAK1 inhibitor (including at week 14), at least one result selected from the group consisting of: an ASAS40 response; change (improvement) from baseline in ASDAS (e.g., ASDAS CRP); change (improvement) from baseline in MRI SPARCC score for spine (MRI-Spine SPARCC); BASDAI50 response; ASAS20 response; ASDAS inactive disease (ID); change (improvement) from baseline in Patient's Assessment of Total Back Pain (Total Back Pain score); change (improvement) from baseline in Patient's Assessment of Nocturnal Back Pain (Nocturnal Back Pain score); ASDAS low disease activity (LDA); (change (improvement) from baseline in BASFI; ASAS partial remission (PR); change (improvement) from Baseline in Ankylosing Spondylitis Quality of Life (ASQoL); change (improvement) from baseline in ASAS Health Index (HI); change (improvement) from baseline in Linear Bath Ankylosing Spondylitis Metrology Index (BASMIlin) (Mobility); and/or change (improvement) from baseline in Maastricht Ankylosing Spondylitis Enthesitis Score (MASES) (Enthesitis). In certain embodiments, for any of the aforementioned results achieved, a statistically significant population of the subjects in the treated population, and/or at least 10%, at least 15%, at least 20%, at least 25%, at least 30%, at least 35%, at least 40%, at least 44%, or at least 45% of the subjects in the treated population, achieve the result. In certain embodiments, for any of the aforementioned results achieved, the subject (or subjects in the treated population) achieve the result or results within 14 weeks of administration of the first dose of the JAK1 inhibitor (including at week 14), and the result (or results) is maintained or improved after week 14 by continuing to administer a daily dose of the JAK1 inhibitor.

In one aspect of a method of reducing the signs and symptoms of AS, including active AS, wherein the subject achieves within 14 weeks of administration of the first dose of the JAK1 inhibitor (including at week 14), at least one result selected from the group consisting of: an ASAS40 response; change (improvement) from baseline in ASDAS (e.g., ASDAS CRP); change (improvement) from baseline in MRI SPARCC score for spine (MRI-Spine SPARCC); BASDAI50 response; ASAS20 response; ASDAS inactive disease (ID); change (improvement) from baseline in Patient's Assessment of Total Back Pain (Total Back Pain score); change (improvement) from baseline in Patient's Assessment of Nocturnal Back Pain (Nocturnal Back Pain score); ASDAS low disease activity (LDA); (change (improvement) from baseline in BASFI; ASAS partial remission (PR); change (improvement) from Baseline in Ankylosing Spondylitis Quality of Life (ASQoL); change (improvement) from baseline in ASAS Health Index (HI); change (improvement) from baseline in Linear Bath Ankylosing Spondylitis Metrology Index (BASMIlin) (Mobility); and/or change (improvement) from baseline in Maastricht Ankylosing Spondylitis Enthesitis Score (MASES) (Enthesitis). In certain embodiments, for any of the aforementioned results achieved, a statistically significant population of the subjects in the treated population, and/or at least 10%, at least 15%, at least 20%, at least 25%, at least 30%, at least 35%, at least 40%, at least 44%, or at least 45% of the subjects in the treated population, achieve the result. In certain embodiments, for any of the aforementioned results achieved, the subject (or subjects in the treated population) achieve the result or results within 14 weeks of administration of the first dose of the JAK1 inhibitor (including at week 14), and the result (or results) is maintained or improved after week 14 by continuing to administer a daily dose of the JAK1 inhibitor.

Further provided are methods of reducing the signs and symptoms of AS. In one aspect, provided is a method of reducing back pain, inflammation, physical function, mobility, and/or quality of life, the method comprising administering a dose of the JAK1 inhibitor to a subject in need thereof in certain amounts and/or at certain intervals. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the subject is bDMARD naïve. In one aspect, the subject is bDMARD-IR.

Further provided are methods of statistically significant treatment of AS. In one aspect, provided is a method of statistically significant treatment of AS, including active AS, in a subject or a population of subjects, the method comprising administering a dose of the JAK1 inhibitor to a subject in need thereof or to subjects in the population in certain amounts and/or at certain intervals, wherein the treatment results in a statistically significant higher ASAS40 response rate as compared to placebo control within 14 weeks of administration of the first dose of the JAK1 inhibitor (including at week 14). In another aspect, the statistically significant higher ASAS40 response rate has a p value of less than 0.05. In one aspect, the statistically significant higher ASAS40 response rate has a p-value of less than 0.01. In one aspect, the statistically significant higher ASAS40 response rate has a p-value of less than 0.001. In one aspect, the statistically significant higher ASAS40 response rate has a p value of less than 0.0001. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered in an amount sufficient to deliver a 15 mg dose of upadacitinib. In one aspect, the JAK1 inhibitor is administered orally once a day for at least 14 weeks. In one aspect, the subject is bDMARD naïve. In one aspect, the subject is bDMARD-IR. In one aspect, the subject is an adult.

Further provided are methods of reducing the signs and symptoms of AS. In one aspect, provided is a method of reducing back pain, inflammation, physical function, mobility, and/or quality of life, the method comprising administering a dose of the JAK1 inhibitor to a subject in need thereof in certain amounts and/or at certain intervals. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the subject is bDMARD naïve. In one aspect, the subject is bDMARD-IR.

Further provided are methods of statistically significant treatment of AS. In one aspect, provided is a method of statistically significant treatment of AS, including active AS, in a subject or a population of subjects, the method comprising administering a dose of the JAK1 inhibitor to a subject in need thereof or to subjects in the population in certain amounts and/or at certain intervals, wherein the treatment results in a statistically significant higher ASAS40 response rate as compared to placebo control within 14 weeks of administration of the first dose of the JAK1 inhibitor (including at week 14). In another aspect, the statistically significant higher ASAS40 response rate has a p value of less than 0.05. In one aspect, the statistically significant higher ASAS40 response rate has a p-value of less than 0.01. In one aspect, the statistically significant higher ASAS40 response rate has a p-value of less than 0.001. In one aspect, the statistically significant higher ASAS40 response rate has a p value of less than 0.0001. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered in an amount sufficient to deliver a 15 mg dose of upadacitinib. In one aspect, the JAK1 inhibitor is administered orally once a day for at least 14 weeks. In one aspect, the subject is bDMARD naïve. In one aspect, the subject is bDMARD-IR. In one aspect, the subject is an adult.

In another aspect, the subject has (or subjects in the treated population have) active AS at baseline. In one aspect, the subject (or subjects in the treated population) fulfills the 1984 modified New York Criteria for AS at baseline. In another aspect, the subject (or subjects in the treated population) fulfills the 2009 ASAS classification criteria at baseline. In yet another aspect, the subject (or subjects in the treated population) fulfills the 1984 modified New York Criteria for AS and the 2009 ASAS classification criteria at baseline. In one embodiment, the subject (or subjects in the treated population) meets at least one criteria selected from the group consisting of: (i) a BASDAI score ≥4; (ii) an ASDAS of ≥2.1; and (iii) a Patient's Assessment of Total Back Pain (Total Back Pain score) of ≥4 (based on a 0-10 numerical rating scale) at baseline. In one embodiment, the subject (or subjects in the treated population) has both a BASDAI score ≥4 and a Patient's Assessment of Total Back Pain (Total Back Pain score) of ≥4 at baseline. In another embodiment, the subject (or subjects in the treated population) has both a BASDAI score ≥4 and an ASDAS of ≥2.1 at baseline. In certain embodiments, the subject (or subjects in the treated population) has (i) a BASDAI score ≥4; (ii) an ASDAS of ≥2.1; and (iii) a Patient's Assessment of Total Back Pain (Total Back Pain score) of ≥4 (based on a 0-10 numerical rating scale) at baseline. In one aspect, the subject (or subjects in the treated population) does not have total spinal ankylosis at baseline. In one aspect, the subject (or subjects in the treated population) is an adult subject. In another aspect, the subject (or subjects in the treated population) is a juvenile subject.

In another aspect, the subject has (or subjects in the treated population have) active AS at baseline. In one aspect, the subject (or subjects in the treated population) fulfills the 1984 modified New York Criteria for AS at baseline. In one embodiment, the subject (or subjects in the treated population) meets the following criteria at screening and baseline: (i) a BASDAI score ≥4 and (ii) a Patient's Assessment of Total Back Pain (Total Back Pain score) of ≥4 (based on a 0-10 numerical rating scale) at baseline. In one embodiment, the subject (or subjects in the treated population) has both a BASDAI score ≥4 and a Patient's Assessment of Total Back Pain (Total Back Pain score) of ≥4 at baseline. In one aspect, the subject (or subjects in the treated population) does not have total spinal ankylosis at baseline. In one aspect, the subject (or subjects in the treated population) is an adult subject. In another aspect, the subject (or subjects in the treated population) is a juvenile subject.

In one aspect, the subject (or subjects in the treated population) is bDMARD naïve at baseline. Exemplary bDMARDs include, but are not limited to, a biologic tumor necrosis factor inhibitor (e.g., adalimumab, etanercept) and interleukin IL)-17 inhibitors (e.g., secukinumab, ixekizumab).

In one aspect, the subject (or subjects in the treated population) is bDMARD naïve at baseline, and further has had i) an inadequate response or intolerance to at least two NSAIDs (e.g., over at least a four-week period at the maximum recommended or tolerated doses); ii) intolerance to NSAIDs; and/or iii) contraindication for NSAIDs, as determined by a physician. Examples of NSAIDs include, but are not limited to, traditional NSAIDs (e.g., ibuprofen) and salicylates (e.g., aspirin).

In certain aspects, the subject (or subjects in the treated population) to be treated is bDMARD naïve at baseline, has had an inadequate response or intolerance to at least two NSAIDS (as described above), or an intolerance to or contraindication for NSAIDS, and is further receiving at least one additional therapy. Additional therapies include, but are not limited to concomitant administration of non-biologic DMARDs, NSAIDs, corticosteroids, and combinations thereof. Suitable additional therapies for use in combination with the methods described herein include:

1) Concomitant administration of non-biologic DMARDs, including methotrexate (MTX), leflunomide (LEF), sulfasalazine (SSZ), and/or hydroxychloroquine (HCQ). In one embodiment, the subject is on a stable dose of MTX (≤25 mg/week), SSZ (≤3 g/day), hydroxychloroquine (≤400 mg/day), and/or leflunomide (≤20 mg/day) for at least 28 days prior to baseline. In some embodiments, a combination of up to two background non-biologic DMARDs is allowed, except the combination of MTX and leflunomide. In one embodiment, the subject has not received any non-biologic DMARDs (other than MTX, LEF, SSZ, and/or HCQ), thalidomide, or apremilast within 28 days or five half-lives (whichever is longer) prior to baseline.
2) Concomitant administration of oral corticosteroids. In one embodiment, the subject is on a stable dose of prednisone (≤10 mg/day), or oral corticosteroid equivalents, for at least 14 days prior to baseline.
3) Concomitant administration of NSAIDs, tramadol, a combination of acetaminophen and codeine or hydrocodone, and/or non-opioid analgesics. In one embodiment, the subject is on stable dose(s) for at least 14-days prior baseline.

In another aspect, the subject (or subjects in the treated population) is bDMARD-IR at baseline. In one aspect, the subject has had an inadequate response or intolerance to a bDMARD at baseline. Subjects who are bDMARD-IR include those subjects who have had prior exposure to one bDMARD (either 1 tumor necrosis factor (TNF) inhibitor (e.g., adalimumab, etanercept) or 1 interleukin (IL)-17 inhibitor (e.g., secukinumab, ixekizumab)), and have discontinued the bDMARD due to either intolerance or lack of efficacy (e.g., as determined by a physician). In one embodiment, the subject (or subjects in the treated population) has not had prior exposure to a second bDMARD, if the reason for discontinuation was not due to lack of efficacy. In one embodiment, the subject (or subjects in the treated population) has not discontinued both a TNF inhibitor and an IL-17 inhibitor due to lack of efficacy.

In certain embodiments, the subject (or subjects in the treated population) has discontinued the bDMARD prior to receiving the first dose of the JAK1 inhibitor for:
≥4 weeks for etanercept;
≥8 weeks for adalimumab, infliximab, certolizumab, golimumab, abatacept, tocilizumab, and ixekizumab;
≥12 weeks for ustekinumab;
≥16 weeks for secukinumab;
≥1 year for rituximab or ≥6 months if B cells have returned to pre-treatment level or normal reference range (central lab) if pre-treatment levels are not available; or
≥12 weeks or at least 5 times the mean terminal elimination half-life, whichever is longer, for other bDMARDs.

In one aspect, the subject (or subjects in the treated population) is bDMARD-IR a baseline, and further has had i) an inadequate response or intolerance to at least two NSAIDs (e.g., over at least a four week period at the maximum recommended or tolerated doses); ii) intolerance to NSAIDs; and/or iii) contraindication for NSAIDs. In one aspect, the subject (or population of subjects) is bDMARD-IR, and has had an inadequate response to at least two NSAIDS or intolerance to and/or contraindication for NSAIDs. Examples of NSAIDs include, but are not limited to, traditional NSAIDs (e.g., ibuprofen) and salicylates (e.g., aspirin).

In certain aspects, the subject (or subjects in the treated population) to be treated is bDMARD-IR at baseline, has had an inadequate response or intolerance to at least two NSAIDS (as described above), and/or an intolerance to NSAIDs and/or contraindication for NSAIDS, and is further receiving at least one additional therapy. Additional therapies include, but are not limited to concomitant administration of non-biologic DMARDs, NSAIDs, corticosteroids, and combinations thereof. Suitable additional therapies for use in combination with the methods described herein include:

1) Concomitant administration of non-biologic DMARDs, including methotrexate (MTX), leflunomide, sulfasalazine (SSZ), hydroxychloroquine, chloroquine, and/or apremilast. In one embodiment, the subject is on a stable dose of MTX (≤25 mg/week), SSZ (≤3 g/day), hydroxychloroquine (≤400 mg/day), chloroquine (≤400 mg/day); leflunomide (≤20 mg/day), or apremilast (≤60 mg/day)), for at least 28 days prior to baseline. In some embodiments, a combination of up to two background non-biologic DMARDs is allowed, except the combination of MTX and leflunomide.
2) Concomitant administration of oral corticosteroids. In one embodiment, the subject is on a stable dose of prednisone (≤10 mg/day), or oral corticosteroid equivalents, for at least 14 days prior to baseline.
3) Concomitant administration of NSAIDs, tramadol, a combination of acetaminophen/paracetamol and codeine or combination of acetaminophen/paracetamol and hydrocodone, and/or non-opioid analgesics. In one embodiment, the subject is on stable dose(s) for at least 14 days prior to baseline.

In one embodiment, the subject (or subjects in the treated population) is bDMARD-IR at baseline, has not been exposed to any JAK inhibitor, and has not had any of the following treatments/conditions within the specified time frame prior to baseline:

1) Intra-articular joint injections, spinal/paraspinal injection(s), or parenteral administration of corticosteroids within 28 days prior to baseline (not including inhaled or topical corticosteroids);
2) Any other non-biologic DMARDs (other than those mentioned above for concomitant treatment), including thalidomide, within 28 days or 5 half-lives (whichever is longer) of the drug prior to baseline;
3) Opioid analgesics (except for combination of acetaminophen/paracetamol and codeine or combination of acetaminophen/paracetamol and hydrocodone) within 14 days prior to the Baseline Visit:
4) No live vaccine within 28 days (or longer if required locally) prior to the first dose of JAK1 inhibitor, or have expected need of live vaccination during treatment with the JAK1 inhibitor, including at least 30 days (or longer if required locally) after the last dose of the JAK1 inhibitor;
5) No systemic use of known strong cytochrome P450 3A (CYP3A) inhibitors during administration of the JAK1 inhibitor, or strong CYP3A inducers 30 days prior to administration of the JAK1 inhibitor through the end of treatment;
6) Herbal therapies or other traditional medicines with unknown effects on CYP3A during treatment;
7) Investigational drug of chemical or biologic nature within a minimum of 30 days or 5 half-lives of the drug (whichever is longer) prior to the first dose of the JAK1 inhibitor; or
8) History of an allergic reaction or significant sensitivity to constituents of the JAK1 inhibitor (and its excipients) and/or other products in the same class.

In one embodiment, the subject (or subjects in the treated population) is bDMARD naïve or bDMARD-IR, and has not been previously exposed to any JAK inhibitor at baseline.

In one aspect of the methods of treating AS described herein, the subject (or subjects in the treated population) is bDMARD naïve at baseline, and achieves an ASAS40 response within 14 weeks of administration of the first dose (including at week 14). In another embodiment, the subject (or subjects in the treated population) is bDMARD naïve at baseline, and achieves an ASAS40 response within 2 weeks of administration of the first dose (including at week 2). In one embodiment, the subject (or subjects in the treated population) is bDMARD naïve at baseline, and achieves an ASAS40 response within 2 weeks of administration of the first dose (including at week 2) and maintains the ASAS40 response until at least 14 weeks after administration of the first dose (i.e., including until at least week 14). In one aspect, the subject (or subjects in the treated population) further achieves ASAS PR, ASDAS LDA, ASDAS ID, ASDAS MI, and/or ASDAS CII within 2 weeks of administration of the first dose (including at week 2). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve the result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD-IR at baseline, and achieves an ASAS40 response within 14 weeks of administration of the first dose (including at week 14). In another embodiment, the subject is bDMARD-IR at baseline, and achieves an ASAS40 response within 4 weeks of administration of the first dose (including at week 4). In one embodiment, the subject achieves an ASAS40 response within 4 weeks of administration of the first dose (including at week 2) and maintains the ASAS40 response until at least 14 weeks after administration of the first dose (i.e., including until at least week 14). In one aspect, the subject (or population of subjects) further achieves change (improvement) from baseline in ASDAS (e.g., ASDAS CRP; ASDAS ESR); change (improvement) from baseline in MRI SPARCC score for spine (MRI-Spine SPARCC); BASDAI50 response; ASAS20 response; ASDAS inactive disease (ID); change (improvement) from baseline in Patient's Assessment of Total Back Pain (Total Back Pain score); change (improvement) from baseline in Patient's Assessment of Nocturnal Back Pain (Nocturnal Back Pain score); ASDAS low disease activity (LDA); (change (improvement) from baseline in BASFI; ASAS partial remission (PR); change (improvement) from Baseline in Ankylosing Spondylitis Quality of Life (ASQoL); change (improvement) from baseline in ASAS Health Index (HI); change (improvement) from baseline in Linear Bath Ankylosing Spondylitis Metrology Index (BASMIlin) (Mobility); and/or change (improvement) from baseline in Maastricht Ankylosing Spondylitis Enthesitis Score (MASES) (Enthesitis) within 4 weeks of administration of the first dose (including at week 4). In certain embodiments, for any of the aforementioned results achieved, a statistically significant population of subjects in the treated population, and/or at least 10%, at least 15%, at least 20%, at least 25%, at least 30%, at least 35%, at least 40%, at least 44%, or at least 45% of the subjects in the treated population, achieved the result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and achieves within 14 weeks of administration of the first dose (including at week 14) an improvement of ≥40% and absolute improvement of ≥2 units (on a scale of 0 to 10) from baseline in each of the following 4 (ASAS40) domains:

a) Patient Global Assessment of disease activity (PtGA) as assessed on a numeric rating scale (NRS 0-10);

b) Patient's Assessment of Total Back Pain (Total Back Pain score) as assessed on a numeric rating scale (NRS 0-10);

c) Bath Ankylosing Spondylitis Functional Index (BASFI); and d) inflammation, as represented by the mean of Questions 5 and 6 of the Bath Ankylosing Spondylitis Disease Activity Index (BASDAI).

In one embodiment, the above described improvements are achieved within 2 weeks of administration of the first dose (including at week 2). In one embodiment, the improvements are achieved within 14 weeks of administration of the first dose (including at week 14). In certain embodiments, a statistically significant population of subjects in the treated population, and/or at least 10%, at least 15%, at least 20%, at least 25%, at least 30%, at least 35%, at least 40%, or at least 45% of the subjects in the treated population, achieve the result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves within 14 weeks of administration of the first dose (including at week 14) at least one result selected from the group consisting of: a) a change (improvement) from baseline in ASDAS (CRP); b) a change (improvement) from baseline in MRI SPARCC score for spine (MRI-Spine SPARCC); c) ASAS partial remission (PR); d) BASDAI50 response; e) a change (improvement) from baseline in BASFI; f) change from baseline in ASQoL; g) a change (improvement) from baseline in ASAS Health Index (HI); h) a change (improvement) from baseline in MASES (i.e., for subjects with baseline enthesitis); i) a change (improvement) from baseline in BASMIlin (mobility); and j) a change (improvement) from baseline in WPAI-Axial SpA. In one embodiment, the subject achieves the result within 2 weeks of administration of the first dose (including at week 2). In one embodiment, the subject achieves the result within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves within 14 weeks of administration (including at week 14) of the first dose at least one result selected from the group consisting of: a) a change (improvement) from baseline in ASDAS; b) a change (improvement) from baseline in MRI SPARCC score for spine (MRI-Spine SPARCC); c) ASAS partial remission (PR); d) BASDAI50 response; and e) a change (improvement) from baseline in BASFI. In one embodiment, each of the results are achieved within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves within 14 weeks of administration of the first dose (including at week 14) at least one result selected from the group consisting of: k) ASAS 20 response; and l) a change (improvement) from baseline in MRI SPARCC score for sacroiliac (SI) joints (MRI-SI joints SPARCC). In one embodiment, each of the results are achieved within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves at least one result selected from the group consisting of: m) ASAS20 response; n) ASAS40 response; o) ASAS PR; p) ASAS 5/6 response; q) ASDAS Inactive Disease (based on ASDAS (CRP) and ASDAS (ESR)); r) ASDAS Low Disease; s) ASDAS Major Improvement (based on ASDAS (CRP) and ASDAS (ESR)); t) ASDAS Clinically Important Improvement (based on ASDAS (CRP) and ASDAS(ESR); u) change (improvement) from baseline in ASAS HI; v) change (improvement) from baseline in ASDAS(CRP) and ASDAS (ESR); w) change (improvement) from baseline in ASQoL; x) change (improvement) from baseline in BASDAI; y) change (improvement) from baseline in BASFI; z) change (improvement) from baseline in BASMIlin; aa) change (improvement) from baseline in C-reactive protein (CRP); bb) change (improvement) from baseline in FACIT-F; cc) change (improvement) from baseline in ISI; dd) change (improvement) from baseline in MASES (in subjects with baseline MASES >0); ee) change (improvement) from baseline in mASSS (with conventional radiograph); ff) change (improvement) from baseline in MRI SPARCC score of SI joints; gg) change (improvement) from baseline in MRI SPARCC score of spine; hh) change (improvement) from baseline in Patient's Assessment of Total Back Pain score (Total Back Pain score); ii) change (improvement) from baseline in Patient's Assessment of Nocturnal Back Pain (Nocturnal Back Pain); jj) change (improvement) from baseline in Patient's Global Assessment of Pain (Pt Pain); kk) change (improvement) from baseline in Physician's Global Assessment of Disease Activity (PGA-Disease Activity); ll) change (improvement) from baseline in inflammation, as represented by the change (improvement) from baseline in the mean of Questions 5 and 6 of the BASDAI; mm) change (improvement) from baseline in the Patient's Assessment of Total Back Pain, as represented by a change (improvement) from baseline in question 2 of BASDAI; nn) change (improvement) from baseline in peripheral pain/swelling, as represented by a change (improvement) in baseline in question 3 of BASDAI; oo) change (improvement) from baseline in duration of morning stiffness, as represented by a change (improvement) in baseline in question 6 of BASDAI; pp) change (improvement) from baseline in Patient's Global Assessment of Disease Activity (PtGA); qq) change (improvement) from baseline in TJC68 and SJC66; rr) change (improvement) from baseline in WPAI-Axial SpA; ss) resolution (improvement) of dactylitis in subjects with baseline presence of dactylitis; and tt) change (improvement) from baseline in total dactylitis count in subjects with baseline presence of dactylitis. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves within 14 weeks of administration (including at week 14) of the first dose at least one result selected from the group consisting of: q) ASDAS Inactive Disease; r) ASDAS Low Disease; s) ASDAS Major Improvement; and t) ASDAS Clinically Important Improvement. In one embodiment, each of the results are achieved within 14 weeks of administration of the first dose (including at week 14). In certain embodiments, for any of the aforementioned results achieved, a statistically significant population of subjects in the treated population and/or at least 10%, at least 15%, at least 20%, at least 25%, at least 30%, at least 35%, at least 40%, or at least 45% of the subjects in the treated population, achieved at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD naïve at baseline, and alternately or additionally achieves at least one result selected from the group consisting of: ASDAS Inactive Disease, ASDAS Moderate Disease, ASDAS Low Disease Activity (LDA), ASDAS High Disease, ASDAS Very High Disease, ASDAS Major Improvement, and ASDAS Clinically Important Improvement. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD-IR at baseline, and achieves an ASAS40 response within 14 weeks of administration of the first dose (including at week 14). In another embodiment, the subject is bDMARD-IR at baseline, and achieves an ASAS40 response within 2 weeks of administration of the first dose (including at week 2). In one embodiment, the subject achieves an ASAS40 response within 2 weeks of administration of the first dose (including at week 2) and maintains the ASAS40 response until at least 14 weeks after administration of the first dose (i.e., including until at least week 14). In one aspect, the subject (or population of subjects) further achieves ASAS PR, ASDAS LDA, ASDAS ID, ASDAS MI, and/or ASDAS CII within 2 weeks of administration of the first dose (including at week 2). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieved the result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD-IR at baseline, and alternately or additionally achieves within 14 weeks of administration (including at week 14) of the first dose at least one result selected from the group consisting of: a) change (improvement) from baseline in ASDAS; b) change (improvement) from baseline in MRI SPARCC score for spine (MRI-Spine SPARCC); c) ASAS partial remission (PR); d) BASDAI 50 response; e) change (improvement) from baseline in BASFI; f) change (improvement) from baseline in ASQoL; g) change (improvement) from baseline in ASAS Health Index (HI); h) change (improvement) from baseline in MASES (enthesitis); and i) change (improvement) from baseline in BASMIlin (mobility). In one embodiment, the result is achieved within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD-IR at baseline, and alternately or additionally achieves at least one result selected from the group consisting of: j) ASAS 20 response; and k) change (improvement) from baseline in MRI SPARCC score for SI joints (MRI-SI joints SPARCC). In one embodiment, the result is achieved within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

In one aspect of the methods of treating AS described herein, the subject (or subjects in the treated population) is bDMARD-IR at baseline, and alternately or additionally achieves at least one result selected from the group consisting of: l) ASAS20 response; m) ASAS40 response; n) ASAS PR; o) ASDAS Inactive Disease; p) ASDAS Low Disease; q) ASDAS Major Improvement; r) ASDAS Clinically Important Improvement; s) discontinuation of opioids among subjects with opioid use at baseline; t) change (improvement) from baseline in ASAS HI; u) change (improvement) from baseline in ASDAS; v) change (improvement) from baseline in ASQoL; w) change (improvement) from baseline in BASDAI and BASDAI Questions, including change (improvement) from baseline in mean of question 5 and 6 of the BASDAI; x) change (improvement) from baseline in BASFI; y) change (improvement) from baseline in BASMIlin; z) change (improvement) from baseline in high sensitivity C-reactive protein (hsCRP); aa) change (improvement) from baseline in FACIT-F; bb) change (improvement) from baseline in EuroQoL-5D-5L (EQ-5D-5L); cc) change (improvement) from baseline in MASES; dd) change (improvement) from baseline in mSASSS (with conventional radiograph); ee) change (improvement) from baseline in MRI SPARCC score of SI joints; ff) change (improvement) from baseline in MRI SPARCC score of spine; gg) change (improvement) from baseline in Patient's Assessment of Total Back Pain score (Total Back Pain score); hh) change (improvement) from baseline in Patient's Assessment of Nocturnal Back Pain (Nocturnal Back Pain); ii) change (improvement) from baseline in Patient's Global Assessment of Pain (Pt Pain); jj) change (improvement) from baseline in Physician's Global Assessment of Disease Activity (PGA-Disease Activity); kk) change (improvement) from baseline in Patient's Global Assessment of Disease Activity (PtGA); ll) change (improvement) from baseline in SF-36; mm) change (improvement) from baseline in TJC68 and SJC66; nn) change (improvement) from baseline in WPAI-Axial SpA; oo) change (improvement) from baseline in Change of NSAID score; and pp) change (improvement) from baseline in Physical Activity Assessment. In one embodiment, the result is achieved within 14 weeks of administration of the first dose (including at week 14). In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result. In certain embodiments, for any of the aforementioned results achieved, the result (or results) is maintained or improved after achieving the result (or results) by continuing to administer a daily dose of the JAK1 inhibitor.

VIII. Methods of Treating Axial Spondyloarthritis

Provided herein are methods of treating axial spondyloarthritis (axSpA). In a particular aspect, provided are methods of treating active axSpA, which encompasses treating subjects with active ankylosing spondylitis (AS) and active non-radiographic axial spondyloarthritis (nr-axSpA), comprising administering orally once a day a dose of the JAK1 inhibitor, upadacitinib freebase, or a pharmaceutically acceptable salt thereof, to a subject in need thereof in certain amounts and/or at certain intervals. In one aspect, the JAK1 inhibitor is upadacitinib freebase. In one aspect, the JAK1 inhibitor is administered orally once a day in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks.

Disease activity/severity for axSpA may be measured using a variety of indexes, including the Assessment of SpondyloArthritis International Society (ASAS) responses (e.g., ASAS20, ASAS40, ASAS partial remission (PR), ASAS5/6); the Ankylosing Spondylitis Disease Activity Score (ASDAS), ASDAS low disease activity (LDA), ASDAS inactive disease (ID), ASDAS major improvement (MI), ASDAS clinically important improvement (CII), the magnetic resonance imaging (MRI) Spondyloarthritis Research Consortium of Canada (SPARCC) score for spine (MRI-Spine SPARCC); the MRI SPARCC score for sacroiliac (SI) joints (MRI-SI joints SPARCC); the Bath Ankylosing Spondylitis Disease Activity Index (BASDAI); a BASDAI 50 (BASDAI50) response; the Bath Ankylosing Spondylitis Functional Index (BASFI); the Ankylosing Spondylitis Quality of Life Questionnaire (ASQoL); the ASAS Health Index (HI); the Maastricht Ankylosing Spondylitis Enthesitis Score (MASES) (enthesitis); the Linear Bath Ankylosing Spondylitis Metrology Index (BASMIlin) (mobility); the Work Productivity and Activity Impairment Questionnaire—Axial Spondyloarthritis (WPAI-Axial SpA); high-sensitivity C-reactive protein levels (hsCRP); the Functional Assessment of Chronic Illness Therapy-Fatigue (FACIT-F) Questionnaire; the Insomnia Severity Index (ISI); the Modified Stroke Ankylosing Spondylitis Spine Score (mSASSS); the Patient's Assessment of Total Back Pain (Total Back Pain score); the Patient's Assessment of Nocturnal Back Pain (Nocturnal Back Pain); the Patient's Global Assessment of Pain (Pt Pain); the Physician's Global Assessment of Disease Activity (PGA-Disease Activity); Inflammation (mean of Questions 5 and 6 of the BASDAI); Patient's Assessment of Total Back Pain (Question 2 of BASDAI); Peripheral pain/swelling (Question 3 of BASDAI); duration of morning stiffness (Question 6 of BASDAI); Patient's Global Assessment of Disease Activity (PtGA); tender joint count (TJC68) and swollen joint count (SJC66); resolution of dactylitis; total dactylitis count; EuroQoL-5D-5L (EQ-5D-5L) Questionnaire; 36-Item Short Form Health Survey (SF-36); Physical Activity Assessment, and NSAID score. These indexes are described in detail in the Clinical Endpoint Definitions and Examples.

In one aspect, provided is a method of treating axSpA, including active axSpA, comprising administering a dose of the JAK1 inhibitor to a subject in need thereof in certain amounts and/or at certain intervals as described herein, wherein the subject achieves an Assessment of SpondyloArthritis International Society 40 (ASAS40) response following administration of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks.

In one aspect, the subject achieves an ASAS40 response within 14 weeks of administration of the first dose of the JAK1 inhibitor (including at week 14). In one aspect, the subject achieves an ASAS40 response within 14 weeks of administration of the first dose of the JAK1 inhibitor (including at week 14), and the response is maintained or improved after week 14 by continuing to administer the daily dose. In one aspect, the subject achieves an ASAS40 response within 2 weeks of administration of the first dose of the JAK1 inhibitor (including at week 2). In one aspect, the subject achieves an ASAS40 response within 2 weeks of administration of the first dose of the JAK1 inhibitor (including at week 2), and the response is maintained or improved after week 2 by continuing to administer the daily dose. In one aspect, the subject achieves an ASAS40 response within 52 weeks of administration of the first dose of the JAK1 inhibitor (including at week 52). In one aspect, the subject achieves an ASAS40 response within 52 weeks of administration of the first dose of the JAK1 inhibitor (including at week 52), and the response is maintained or improved after week 52 by continuing to administer the daily dose. In one aspect, the subject achieves an ASAS40 response within 2 weeks, within 4 weeks, within 8 weeks, within 12 weeks, within 14 weeks, within 18 weeks, within 24 weeks, within 32 weeks, within 40 weeks, and/or within 52 weeks of administration of the first dose of the JAK1 inhibitor (including at week 2, week 4, week 8, week 12, week 14, week 18, week 24, week 32, week 40, and/or week 52). In one embodiment, the subject achieves an ASAS40 response within 2 weeks of administration of the first dose (including at week 2) and maintains the ASAS40 response until at least 14 weeks after administration of the first dose (e.g., until at least week 14). In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 2 weeks, for at least 4 weeks, for at least 8 weeks, for at least 12 weeks, for at least 14 weeks, for at least 18 weeks, for at least 24 weeks, for at least 32 weeks, for at least 40 weeks, and/or for at least 52 weeks. In one embodiment, the JAK1 inhibitor is administered orally once a day for at least 14 weeks. In one aspect, the JAK1 inhibitor is administered orally once a day for at least 52 weeks.

In another aspect, provided is a method of treating axSpA, including active axSpA, comprising administering the JAK1 inhibitor to a subject in need thereof in certain amounts and/or at certain intervals as described herein, wherein the subject achieves an ASAS40 response at a certain interval as described herein, and additionally achieves at least one of the results set forth hereinafter for treatment of ankylosing spondylitis (AS) and/or non-radiographic axial spondyloarthritis (nr-axSpA) following administration of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks.

In another aspect, provided is a method of treating axSpA, including active axSpA, in a population of subjects in need thereof, the method comprising administering a dose of the JAK1 inhibitor to the subjects in certain amounts and/or at certain intervals as described herein, wherein a portion of subjects in the treated population achieve an ASAS40 response following administration of the JAK1 inhibitor (e.g., a statistically significant population of the subjects in the treated population, and/or at least 10%, at least 15%, at least 20%, at least 25%, at least 30%, at least 35%, at least 40%, at least 44%, or at least 45% of the subjects in the treated population achieve the response). In one aspect, the subjects in the treated population achieve an ASAS40 response within 14 weeks of administration of the first dose of the JAK1 inhibitor (including at week 14). In one aspect, subjects in the treated population achieve an ASAS40 response within 14 weeks of administration of the first dose of the JAK1 inhibitor (including at week 14), and the response is maintained or improved after week 14 by continuing to administer a daily dose of the JAK1 inhibitor to the subjects. In one aspect, subjects in the treated population achieve an ASAS40 response within 52 weeks of administration of the first dose of the JAK1 inhibitor (including at week 52). In one aspect, subjects in the treated population achieve an ASAS40 response within 52 weeks of administration of the first dose of the JAK1 inhibitor (including at week 52), and the response is maintained or improved after week 52 by continuing to administer a daily dose of the JAK1 inhibitor to the subjects. In one aspect, the subjects in the treated population achieve an ASAS40 response within 2 weeks of administration of the first dose of the JAK1 inhibitor (including at week 2). In one aspect, subjects in the treated population achieve an ASAS40 response within 2 weeks of administration of the first dose of the JAK1 inhibitor (including at week 2), and the response is maintained or improved after week 2 by continuing to administer a daily dose of the JAK1 inhibitor to the subjects. In one aspect, subjects in the treated population achieve at least one of the results set forth hereinafter for treatment of ankylosing spondylitis (AS) and/or non-radiographic axial spondyloarthritis (nr-axSpA) following administration of the JAK1 inhibitor (e.g., a statistically significant population of subjects in the treated population, and/or at least 10%, at least 15%, at least 20%, at least 25%, at least 30%, at least 35%, at least 40%, at least 44%, or at least 45% of the subjects in the treated population achieve at least one of the results). In one aspect, the JAK1 inhibitor is upadacitinib freebase. In one aspect, a dose of the JAK1 inhibitor is administered to the population in an amount sufficient to deliver 15 mg of upadacitinib freebase equivalent. In one aspect, the JAK1 inhibitor is administered to the subjects orally once a day for at least 14 weeks. In one aspect, the JAK1 inhibitor is administered to the subjects orally once a day for at least 52 weeks.

Further provided are methods of reducing the signs and symptoms of axSpA. In one aspect, provided is a method of reducing the signs and symptoms of axSpA, including active axSpA, comprising administering a dose of the JAK1 inhibitor to a subject in need thereof in certain amounts and/or at certain intervals. In one aspect, the JAK1 inhibitor is upadacitinib freebase or a pharmaceutically acceptable salt thereof. In one aspect, the JAK1 inhibitor is administered in an amount sufficient to deliver 15 mg of upadacitinib freebase equivalent. In one aspect, the JAK1 inhibitor is administered once a day for 14 weeks. In one aspect, the JAK1 inhibitor is administered once a day for 52 weeks.

In one aspect, the signs and symptoms of axSpA, including active axSpA, are reduced following administration of the JAK1 inhibitor when the subject achieves, within 14 weeks of administration of the first dose of the JAK1 inhibitor (including at week 14), at least one result selected from the group consisting of: an ASAS40 response; a change (improvement) from baseline in ASDAS (e.g., ASDAS CRP); a change (improvement) from baseline in MRI SPARCC score for spine (MRI-Spine SPARCC); ASAS partial remission (PR); a BASDAI50 response; a change (improvement) from baseline in BASFI; a change (improvement) from baseline in ASQoL; a change (improvement) from baseline in ASAS Health Index (HI); a change (improvement) from baseline in MASES (enthesitis); a change (improvement) from baseline in BASMIlin (mobility); a change (improvement) from baseline in WPAI-Axial SpA; and a change (improvement) from baseline in MRI SPARCC score for SI joints (MRI-SI joints SPARCC); or when the subject achieves, within 52 weeks of administration of the first dose of the JAK1 inhibitor (including at week 52), an ASAS40 response. In one aspect, the subject achieves the response within 14 weeks of administration of the first dose of the JAK1 inhibitor (including at week 14), and the response is maintained or improved after week 14 by continuing to administer a daily dose of the JAK1 inhibitor. In another aspect, the subject achieves the response within 52 weeks of administration of the first dose of the JAK1 inhibitor (including at week 52), and the response is maintained or improved after week 52 by continuing to administer a daily dose of the JAK1 inhibitor. In one aspect, the subject achieves the response within 2 weeks of administration of the first dose of the JAK1 inhibitor (including at week 2), and the response is maintained or improved after week 2 by continuing to administer a daily dose of the JAK1 inhibitor.

For any of the methods of treating axSpA and/or methods for reducing the signs and symptoms of axSpA described herein, the subject and/or subjects in the treated population i) may be biologic disease-modifying anti-rheumatic drug (bDMARD) naïve or ii) may have had an inadequate response or intolerance to a bDMARD (bDMARD-IR) at baseline. In certain embodiments, the subject (or subjects in the treated population) may have had a prior inadequate response to, intolerance to, or contraindication to NSAIDs at baseline.

IX. Methods of Treating Non-Radiographic Axial Spondyloarthritis (nr-axSpA)

Further provided are methods of treating non-radiographic axial spondyloarthritis (nr-axSpA). In one aspect, provided are methods of treating active nr-axSpA, comprising administering a dose of the JAK1 inhibitor to a subject in need thereof in certain amounts and/or at certain intervals. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks. In one aspect, the subject is bDMARD naïve. In one aspect, the subject is bDMARD-IR.

Disease activity/severity for nr-axSpA may be measured using a variety of indexes, including those set forth above for the treatment of axSpA. In one particular aspect, provided is a method of treating nr-axSpA, including active nr-axSpA, comprising administering a dose of the JAK1 inhibitor to a subject in need thereof in certain amounts and/or at certain intervals as described herein, wherein the subject achieves an Assessment of SpondyloArthritis International Society 40 (ASAS40) response following administration of the JAK1 inhibitor. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks. In one aspect, the subject is bDMARD naïve. In one aspect, the subject is bDMARD-IR.

In one aspect, the subject achieves an ASAS40 response within 14 weeks of administration of the first dose of the JAK1 inhibitor (including at week 14). In one aspect, the subject achieves an ASAS40 response within 14 weeks of administration of the first dose of the JAK1 inhibitor (including at week 14), and the response is maintained or improved after week 14 by continuing to administer a daily dose of the JAK1 inhibitor. In one aspect, the subject achieves an ASAS40 response within 52 weeks of administration of the first dose of the JAK1 inhibitor (including at week 52). In one aspect, the subject achieves an ASAS40 response within 52 weeks of administration of the first dose of the JAK1 inhibitor (including at week 52), and the response is maintained or improved after week 52 by continuing to administer a daily dose of the JAK1 inhibitor. In one aspect, the subject achieves an ASAS40 response within 2 weeks of administration of the first dose of the JAK1 inhibitor (including at week 2). In one aspect, the subject achieves an ASAS40 response within 2 weeks of administration of the first dose of the JAK1 inhibitor (including at week 2), and the response is maintained or improved after week 2 by continuing to administer a daily dose of the JAK1 inhibitor. In one aspect, the subject achieves an ASAS40 response within 2 weeks, within 4 weeks, within 8 weeks, within 12 weeks, within 14 weeks, within 18 weeks, within 24 weeks, within 32 weeks, within 40 weeks, within 52 weeks, within 104 weeks, and/or within 152 of administration of the first dose of the JAK1 inhibitor (including at week 2, week 4, week 8, week 12, week 14, week 18, week 24, week 32, week 40, week 52, week 104, and/or week 152). In one embodiment, the subject achieves an ASAS 40 response within 2 weeks of administration of the first dose (including at week 2), and maintains the ASAS40 response until at least 14 weeks after administration of the first dose (e.g., until at least week 14). In one embodiment, the subject achieves an ASAS 40 response within 2 weeks of administration of the first dose (including at week 2), and maintains the ASAS40 response until at least 52 weeks after administration of the first dose (e.g., until at least week 52). In one embodiment, the subject achieves an ASAS 40 response within 2 weeks of administration of the first dose (including at week 2), and maintains the ASAS40 response until at least 104 weeks after administration of the first dose (e.g., until at least week 104). In one embodiment, the subject achieves an ASAS 40 response within 2 weeks of administration of the first dose (including at week 2), and maintains the ASAS40 response until at least 152 weeks after administration of the first dose (e.g., until at least week 152). In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 2 weeks, for at least 4 weeks, for at least 8 weeks, for at least 12 weeks, for at least 14 weeks, for at least 18 weeks, for at least 24 weeks, for at least 32 weeks, for at least 40 weeks, for at least 52 weeks, for at least 104 weeks, and/or for at least 152 weeks. In one embodiment, the JAK1 inhibitor is administered orally once a day for at least 14 weeks. In one aspect, the JAK1 inhibitor is administered orally once a day for at least 52 weeks.

In one aspect, provided is a method of treating nr-axSpA, including active nr-axSpA, in a population of subjects in need thereof, the method comprising administering a dose of the JAK1 inhibitor to the subjects in certain amounts and/or at certain intervals as described herein, wherein a portion of the subjects in the treated population (e.g., a statistically significant population of subjects in the treated population, and/or at least 10%, at least 15%, at least 20%, at least 25%, at least 30%, at least 35%, at least 40%, at least 44%, or at least 45% of the subjects in the treated population) achieve an ASAS40 response following administration of the JAK1 inhibitor. In one aspect, subjects in the treated population achieve an ASAS40 response within 14 weeks of administration of the first dose of the JAK1 inhibitor (including at week 14). In one aspect, subjects in the treated population achieve an ASAS40 response within 14 weeks of administration of the first dose of the JAK1 inhibitor (including at week 14), and the result is maintained or improved after week 14 by continuing to administer a daily dose of the JAK1 inhibitor. In one aspect, subjects in the treated population achieve an ASAS40 response within 52 weeks of administration of the first dose of the JAK1 inhibitor (including at week 52). In one aspect subjects in the treated population achieve an ASAS40 response within 52 weeks of administration of the first dose of the JAK1 inhibitor (including at week 52), and the result is maintained or improved after week 52 by continuing to administer a daily dose of the JAK1 inhibitor. In one aspect, the JAK1 inhibitor is upadacitinib freebase. In one aspect, a dose of the JAK1 inhibitor is administered to the subjects in an amount sufficient to deliver 15 mg of upadacitinib freebase equivalent. In one aspect, the JAK1 inhibitor is administered to the subjects orally once a day for at least 14 weeks. In one aspect, the JAK1 inhibitor is administered to the subjects orally once a day for at least 52 weeks. In one aspect, the subjects in the population are bDMARD naïve. In one aspect, the subjects in the population are bDMARD-IR.

In one aspect of a method of treating nr-axSpA, including active nr-axSpA, the subject (or subjects in the treated population) additionally achieves within 14 weeks of administration of the first dose of the JAK1 inhibitor (including at week 14), at least one result selected from the group consisting of: a change (improvement) from baseline in ASDAS; a change (improvement) from baseline in MRI-SI Joint SPARCC; BASDAI50 response; ASDAS inactive disease (ID); a change (improvement) from baseline in Total Back Pain; a change (improvement) from baseline in Nocturnal Back Pain; ASDAS low disease activity (LDA); ASAS partial remission (PR); a change (improvement) from baseline in BASFI; a change (improvement) from baseline in ASQoL; a change (improvement) from baseline in ASAS Health Index (HI); ASAS20 response; a change (improvement) from baseline in MASES (enthesitis); and a change (improvement) from baseline in BASMIlin (mobility).

Further provided are methods of reducing the signs and symptoms of nr-axSpA. In one aspect, provided is a method of reducing the signs and symptoms of active nr-axSpA, in particular methods comprising administering a dose of the JAK1 inhibitor to a subject in need thereof in certain amounts and/or at certain intervals as described herein. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks. In one aspect, the subject is bDMARD naïve. In one aspect, the subject is bDMARD-IR.

In one aspect of a method of reducing the signs and symptoms of nr-axSpA, including active nr-axSpA, the subject (or subjects in the treated population) achieves within 14 weeks of administration of the first dose of the JAK1 inhibitor (including at week 14), at least one result selected from the group consisting of: an ASAS40 response; a change (improvement) from baseline in ASDAS; a change (improvement) from baseline in MRI-Spine SPARCC; ASAS partial remission (PR); a BASDAI50 response; a change (improvement) from baseline in BASFI; a change (improvement) from baseline in ASQoL; a change (improvement) from baseline in ASAS Health Index (HI); a change (improvement) from baseline in MASES (enthesitis); and a change (improvement) from baseline in BASMIlin (mobility); or the subject achieves within 52 weeks of administration of the first dose of the JAK1 inhibitor (including at week 52) an ASAS40 response. In one aspect, the subject (or subjects in the treated population) achieves the result within 14 weeks of administration of the first dose of the JAK1 inhibitor (including at week 14), and the result is maintained or improved after week 14 by continuing to administer a daily dose of the JAK1 inhibitor. In one aspect, the subject (or subjects in the treated population) achieves the result within 52 weeks of administration of the first dose of the JAK1 inhibitor (including at week 52), and the result is maintained or improved after week 52 by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In one aspect of a method of reducing the signs and symptoms of nr-axSpA, including active nr-axSpA, the subject (or subjects in the treated population) achieves within 14 weeks of administration of the first dose of the JAK1 inhibitor (including at week 14), at least one result selected from the group consisting of: an ASAS40 response; a change (improvement) from baseline in ASDAS; a change (improvement) from baseline in MRI-SI Joint SPARCC; BASDAI50 response; ASDAS inactive disease (ID); a change (improvement) from baseline in Total Back Pain; a change (improvement) from baseline in Nocturnal Back Pain; ASDAS low disease activity (LDA); ASAS partial remission (PR); a change (improvement) from baseline in BASFI; a change (improvement) from baseline in ASQoL; a change (improvement) from baseline in ASAS Health Index (HI); ASAS20 response; a change (improvement) from baseline in MASES (enthesitis); and a change (improvement) from baseline in BASMIlin (mobility); or the subject achieves within 52 weeks of administration of the first dose of the JAK1 inhibitor (including at week 52) an ASAS40 response. In one aspect, the subject (or subjects in the treated population) achieves the result within 14 weeks of administration of the first dose of the JAK1 inhibitor (including at week 14), and the result is maintained or improved after week 14 by continuing to administer a daily dose of the JAK1 inhibitor. In one aspect, the subject (or subjects in the treated population) achieves the result within 52 weeks of administration of the first dose of the JAK1 inhibitor (including at week 52), and the result is maintained or improved after week 52 by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, at least 44%, or at least 45% of the subjects in the treated population, achieve at least one result.

Further provided are methods of improving back pain, inflammation, physical function, and/or quality of life associated with nr-axSpA. In one aspect, provided is a method of improving back pain, inflammation, physical function, and/ or quality of life associated with active nr-axSpA, in particular methods comprising administering a dose of the JAK1 inhibitor to a subject in need thereof in certain amounts and/or at certain intervals as described herein. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered orally once a day for at least 14 weeks. In one aspect, the JAK1 inhibitor is administered orally once a day for at least 52 weeks. In one aspect, the subject is bDMARD naïve. In one aspect, the subject is bDMARD-IR.

Further provided are methods of statistically significant treatment of nr-axSpA. In one aspect, provided is a method of statistically significant treatment of nr-axSpA, including active nr-axSpA, in a subject or a population of subjects, the method comprising administering a dose of the JAK1 inhibitor to a subject in need thereof or to subjects in the population in certain amounts and/or at certain intervals, wherein the treatment results in a statistically significant higher ASAS40 response rate as compared to placebo control within 14 weeks of administration of the first dose of the JAK1 inhibitor (including at week 14). In another aspect, the statistically significant higher ASAS40 response rate has a p value of less than 0.05. In one aspect, the statistically significant higher ASAS40 response rate has a p-value of less than 0.01. In one aspect, the statistically significant higher ASAS40 response rate has a p-value of less than 0.001. In one aspect, the statistically significant higher ASAS40 response rate has a p value of less than 0.0001. In one aspect, the JAK1 inhibitor is upadacitinib freebase. In one aspect, the JAK1 inhibitor is administered in an amount sufficient to deliver 15 mg of upadacitinib freebase equivalent. In one aspect, the JAK1 inhibitor is administered in an amount sufficient to deliver a 15 mg dose of upadacitinib. In one aspect, the JAK1 inhibitor is administered orally once a day for at least 14 weeks. In one aspect, the subject is bDMARD naïve. In one aspect, the subject is bDMARD-IR. In one aspect, the subject is an adult.

In one aspect, the subject (or population of subjects) in need of treatment has active nr-axSpA at baseline. In one aspect, the subject (or subjects in the treated population) fulfills the 2009 ASAS classification criteria for axSpA, but does not meet the radiologic criteria of the 1984 modified New York Criteria for AS at baseline. In one embodiment, the subject (or subjects in the treated population) meets at least one criteria at baseline selected from the group consisting of: (i) a BASDAI score ≥4; (ii) an ASDAS of ≥2.1; (iii) a Patient's Assessment of Total Back Pain (Total Back Pain score) of ≥4 (based on a 0-10 numerical rating scale); and (iv) an objective sign of inflammatory activity selected from the group consisting of: a) an objective sign of active inflammation on MRI of sacroiliac (SI) joints; and b) high-sensitivity C reactive protein (hsCRP)>upper limit of normal (ULN). In one aspect, the subject meets criteria (i), (ii), (iii), and (iv). In one aspect, the subject (or subjects in the treated population) is an adult subject. In another aspect, the subject (or subjects in the treated population) is a juvenile subject.

In one aspect, the subject (or population of subjects) in need of treatment has active nr-axSpA at baseline. In one aspect, the subject (or subjects in the treated population) fulfills the 2009 ASAS classification criteria for axSpA, but does not meet the radiologic criteria of the 1984 modified New York Criteria for AS at baseline. In one embodiment, the subject (or subjects in the treated population) meets the following criteria at screening and baseline: (i) a BASDAI score ≥4; (ii) a Patient's Assessment of Total Back Pain (Total Back Pain score) of ≥4 (based on a 0-10 numerical rating scale); and (iii) an objective sign of inflammatory activity selected from the group consisting of: a) an objective sign of active inflammation on MRI of sacroiliac (SI) joints; and b) high-sensitivity C reactive protein (hsCRP) >upper limit of normal (ULN). In one aspect, the subject meets criteria (i), (ii), and (iii). In one aspect, the subject (or subjects in the treated population) is an adult subject. In another aspect, the subject (or subjects in the treated population) is a juvenile subject.

In one aspect, the subject (or subjects in the treated population) is bDMARD naïve at baseline. Exemplary bDMARDs include, but are not limited to, a biologic tumor necrosis factor inhibitor (e.g., adalimumab, etanercept) and interleukin (IL)-17 inhibitors (e.g., secukinumab, ixekizumab).

In another aspect, the subject (or subjects in the treated population) is bDMARD-IR at baseline. In one aspect, the subject (or subjects in the treated population) has had an inadequate response or intolerance to a bDMARD. Subjects who are bDMARD-IR include those subjects who have had prior exposure to one bDMARD (either 1 tumor necrosis factor (TNF) inhibitor (e.g., adalimumab, etanercept) or 1 interleukin (IL)-17 inhibitor (e.g., secukinumab, ixekizumab)), and have discontinued the bDMARD due to either intolerance or lack of efficacy (e.g., as determined by a physician). In one embodiment, the subject (or subjects in the treated population) has not had prior exposure to a second bDMARD, if the reason for discontinuation was not due to lack of efficacy. In one embodiment, the subject (or subjects in the treated population) has not discontinued both a TNF inhibitor and an IL-17 inhibitor due to lack of efficacy. In certain embodiments, the subject (or subjects in the treated population) has discontinued the bDMARD prior to receiving the first dose of the JAK1 inhibitor for:
- ≥4 weeks for etanercept;
- ≥8 weeks for adalimumab, infliximab, certolizumab, golimumab, abatacept, tocilizumab, and ixekizumab;
- ≥12 weeks for ustekinumab;
- ≥16 weeks for secukinumab;
- ≥1 year for rituximab or ≥6 months if B cells have returned to pre-treatment level or normal reference range (central lab) if pre-treatment levels are not available; or
- ≥12 weeks or at least 5 times the mean terminal elimination half-life, whichever is longer, for other bDMARDs.

In one aspect, the subject (or subjects in the treated population) further has had i) an inadequate response or intolerance to at least two NSAIDs (e.g., over at least a four week period at the maximum recommended or tolerated doses); ii) intolerance to NSAIDs; and/or iii) contraindication for NSAIDs at baseline. Examples of NSAIDs include, but are not limited to, traditional NSAIDs (e.g., ibuprofen) and salicylates (e.g., aspirin).

In certain aspects, the subject (or population of subjects) to be treated is further receiving at least one additional therapy. Additional therapies include, but are not limited to concomitant administration of non-biologic DMARDs, NSAIDs, corticosteroids, and combinations thereof. Suitable additional therapies for use in combination with the methods described herein include:

1) Concomitant administration of non-biologic DMARDs, including methotrexate (MTX), leflunomide, sulfasalazine (SSZ), hydroxychloroquine, chloroquine, or apremilast. In one embodiment, the subject is on a stable dose of MTX (≤25 mg/week), SSZ (≤3 g/day), hydroxychloroquine (≤400 mg/day), chloroquine (≤400 mg/day); leflunomide (≤20 mg/day), or apremilast (≤60 mg/day)), for at least 28 days prior to baseline. In some embodiments, a combination of up to two background non-biologic DMARDs is allowed, except the combination of MTX and leflunomide.

2) Concomitant administration of oral corticosteroids. In one embodiment, the subject is on a stable dose of prednisone (≤10 mg/day), or oral corticosteroid equivalents, for at least 14 days prior to baseline.

3) Concomitant administration of NSAIDs, tramadol, a combination of acetaminophen/paracetamol and codeine or combination of acetaminophen/paracetamol and hydrocodone, and/or non-opioid analgesics. In one embodiment, the subject is on stable dose(s) for at least 14 days prior to baseline.

In one embodiment, the subject (or subjects in the treated population) has not been previously exposed to any JAK inhibitor at baseline.

In one aspect of the methods of treating nr-axSpA described herein, the subject (or subjects in the treated population) alternately or additionally achieves within 14 weeks of administration of the first dose (including at week 14) at least one result selected from the group consisting of: a) a change (improvement) from baseline in ASDAS; b) a change (improvement) from baseline in MRI SPARCC score for SI joints (MRI-SI joints SPARCC); c) ASAS partial remission (PR); d) BASDAI50 response; e) a change (improvement) from baseline in BASFI; f) change (improvement) from baseline in ASQoL; g) a change (improvement) from baseline in ASAS Health Index (HI); h) a change (improvement) from baseline in MASES (enthesitis); and i) a change (improvement) from baseline in BASMIlin (mobility); In one embodiment, the subject achieves the result within 2 weeks of administration of the first dose (including at week 2). In one embodiment, the subject achieves each of the results within 14 weeks of administration of the first dose (including at week 14). In certain embodiments, for any of the aforementioned results achieved, the result (or results) is maintained or improved after week 2 or week 14 by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, at least 44%, or at least 45% of the subjects in the treated population, achieve at least one result.

In one aspect of the methods of treating nr-axSpA described herein, the subject (or subjects in the treated population) alternately or additionally achieves within 14 weeks of administration of the first dose (including at week 14) at least one result selected from the group consisting of: j) ASAS 20 response; and k) a change (improvement) from baseline in MRI SPARCC score for spine (MRI-Spine SPARCC). In one embodiment, each of the results is achieved within 14 weeks of administration of the first dose (including at week 14). In certain embodiments, for any of the aforementioned results achieved, the result (or results) is maintained or improved after week 14 by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

In one aspect of the methods of treating nr-axSpA described herein, the subject (or subjects in the treated population) alternately or additionally achieves at least one result selected from the group consisting of: l) ASAS20 response; m) ASAS40 response; n) ASAS PR; o) ASDAS Inactive Disease; p) ASDAS Low Disease; q) ASDAS Major Improvement; r) ASDAS Clinically Important Improvement; s) discontinuation of opioids among subjects with opioid use at baseline; t) change (improvement) from baseline in ASAS HI; u) change (improvement) from baseline in ASDAS; v) change (improvement) from baseline in ASQoL; w) change (improvement) from baseline in BASDAI and BASDAI Questions, including change (improvement) from baseline in mean of questions 5 and 6 of the BASDAI; x) change (improvement) from baseline in BASFI; y) change (improvement) from baseline in BASMIlin; z) change (improvement) from baseline in high sensitivity C-reactive protein (hsCRP); aa) change (improvement) from baseline in FACIT-F; bb) change (improvement) from baseline in EQ-5D-5L; cc) change (improvement) from baseline in MASES; dd) change (improvement) from baseline in mASSS (with conventional radiograph); ee) change (improvement) from baseline in MRI SPARCC score of SI joints; ff) change (improvement) from baseline in MRI SPARCC score of spine; gg) change (improvement) from baseline in Patient's Assessment of Total Back Pain score (Total Back Pain score); hh) change (improvement) from baseline in Patient's Assessment of Nocturnal Back Pain (Nocturnal Back Pain); ii) change (improvement) from baseline in Patient's Global Assessment of Pain (Pt Pain); jj) change (improvement) from baseline in Physician's Global Assessment of Disease Activity (PGA-Disease Activity); kk) change (improvement) from baseline in Patient's Global Assessment of Disease Activity (PtGA); ll) change (improvement) from baseline in SF-36; mm) change (improvement) from baseline in TJC68 and SJC66; nn) change (improvement) from baseline in (WPAI-Axial SpA); and oo) change (improvement) from baseline in Change of NSAID score. In certain embodiments, for any of the aforementioned results achieved, the result (or results) is maintained or improved after the result (or results) is achieved by continuing to administer a daily dose of the JAK1 inhibitor. In certain embodiments, for any of the aforementioned results achieved, a statistically significant population of subjects in the treated population, and/or at least 10%, at least 15%, at least 20%, at least 25%, at least 30%, at least 35%, at least 40%, or at least 45% of the subjects in the treated population, achieve at least one result.

EXAMPLES

Examples 1-4: Extended Release Tablets

The Freebase Hydrate Form C and Amorphous Freebase solid state forms of Compound 1 were formulated into 24 mg extended release tablets according to the formulations set forth in Table 4.

TABLE 4

Extended Release Tablets (no pH modifier)

| Component | Function | Ex. 1 (ER1) (mg) | Ex. 2 (ER2) (mg) | Ex. 3 (ER3) (mg) | Ex. 4 (mg) |
|---|---|---|---|---|---|
| Freebase Hydrate Form C | Active | 24.0 | 24.0 | 24.0 | — |
| Amorphous Freebase | Active | — | — | — | 24.0 |
| Microcrystalline cellulose (Avicel ® PH 102) | Filler | 351.4 | 303.4 | 303.4 | 303.4 |
| HPMC (Methocel ® K100 Premium LVCRLH) | Release control polymer | 96.0 | 96.0 | — | — |
| HPMC (Methocel ® K4M Premium CR) | Release control polymer | — | 48.0 | 144.0 | 144.0 |
| Colloidal silicon dioxide | Glidant | 3.8 | 3.8 | 3.8 | 3.8 |
| Magnesium stearate impalpable powder | Lubricant | 4.8 | 4.8 | 4.8 | 4.8 |
| Uncoated weight of tablet | | 480.0 | 480.0 | 480.0 | 480.0 |

The formulations were prepared by combining and blending the active, microcrystalline cellulose, hydroxypropyl methyl cellulose (HPMC), and colloidal silicone dioxide. The blend was milled using a Mobil Mill fitted with a 610-micron screen. The magnesium stearate was screened through mesh #30 and was added to the bin and blended.

The lubricated granulation was compressed into 480 mg weight tablets using a rotary tablet press. The tablets may optionally be coated with any suitable film coating.

The effect of solid state form on the dissolution profile of the tablets was evaluated. In particular, the dissolution profile of the Example 3 (containing Freebase Hydrate Form C as active) and Example 4 (containing Amorphous Freebase as active) tablets was evaluated at pH 6.8 (representative of the pH in the lower intestine). The dissolution test was carried out using the following dissolution parameters and conditions:

Apparatus: USP Dissolution Apparatus 2 and fraction collector
Medium: 900 mL of 50 mM sodium phosphate buffer solution, pH 6.8.
Temperature: 37° C.±0.5° C.
RPM: 75 RPM±4%
Filter: 35 μm PE filter, or equivalent, for automatic sampling
Sampling Times: 1, 2, 4, 6, 8, 10, 12, 16, and 20 Hours. Other samples may be taken at other times, as appropriate.
Sample Volume: 1.5 mL obtained automatically, without media replacement.

The medium used for the study was a 0.05 M sodium phosphate buffer solution, pH 6.8±0.05. The medium was prepared using an acid stage medium (0.1 N hydrochloric acid solution) and a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The medium was prepared by mixing 500 mL of the acid stage medium and 400 mL of buffer stage concentrate in an appropriate size container or directly in the dissolution vessel and adjusting the pH with 1 N phosphoric acid or 1 N sodium hydroxide, if the pH was not within 6.8±0.05.

For the dissolution test, one tablet each was added to a dissolution vessel containing 900 mL of the 0.05 M sodium phosphate buffer solution maintained at 37° C. The paddles of the dissolution apparatus were operated at 75 RPM, with 1.5 mL samples from the dissolution vessel automatically obtained at the designated time periods. The sample filtrate was the sample preparation.

For the analysis of the sample, conventional liquid chromatography methods were utilized, wherein the % of the labelled amount of active released (% LA Released) was calculated. The formulation containing Freebase Hydrate Form C (Example 3) as the active showed a slower rate of dissolution than the formulation containing Amorphous Freebase (Example 4) as the active at pH 6.8.

The dissolution profile of formulations comprising Freebase Hydrate Form C as an active was further evaluated at pH 6.8 and in a dual pH system. In particular, the dissolution profile of the Example 1 (ER1), Example 2 (ER2), and Example 3 (ER3) tablets at pH 6.8 was carried out as described above. The dissolution profile of the Examples 1-3 tablets was also carried out in a dual pH system using the following dissolution parameters and conditions:

Apparatus: USP Dissolution Apparatus 2 and fraction collector
Medium: Acid Stage: 500 mL of Acid Stage Medium (0.1 N hydrochloric acid solution)
Buffer Stage: 900 mL of 50 mM sodium phosphate buffer solution, pH 6.8.
Temperature: 37° C.±0.5° C.
RPM: 75 RPM±4%
Filter: 35 μm PE filter, or equivalent, for automatic sampling
Sampling Times: Acid Stage: 1 Hour
Buffer Stage: 2, 4, 6, 8, 10, 12, 16, and 20 Hours.
Other samples may be taken at other times, as appropriate.

Sample Volume: Acid: 1.5 mL obtained automatically, without media replacement.

The acid stage medium is a 0.1 N hydrochloric acid solution. A buffer stage medium for the study was prepared using a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The buffer stage medium of a 0.05 M sodium phosphate buffer solution, pH 6.8±0.05, was prepared by mixing 500 mL of the acid stage medium and 400 mL of buffer stage medium concentrate in an appropriate size container or directly in the dissolution vessel and adjusting the pH of the buffer stage medium concentrate with 1 N phosphoric acid or 1 N sodium hydroxide, if the pH was not within 6.8±0.05.

For the dissolution test, one tablet each was added to a dissolution vessel containing 500 mL of a 0.1 N hydrochloric acid solution maintained at 37° C. The paddles of the dissolution apparatus were operated at 75 RPM for 1 hour, and then a 1.5 mL sample from the dissolution vessel was automatically obtained. After the acid stage sample was obtained, 400 mL of buffer stage medium concentrate was added, maintained at 37° C. The dissolution test was continued, with the paddles remaining at a speed of 75 RPM. The sample filtrate was the sample preparation.

For the analysis of the sample, conventional liquid chromatography methods were utilized, wherein the % relative standard deviation (RSD) of peak areas was calculated for each set of six standard injections.

After the initial release at the low pH (representative of the pH in the stomach), release of the drug is slowed at the higher pH (representative of the pH in the lower intestine). Therefore, in order to achieve the desired bioavailability, a formulation which allowed pH independent release was required.

Examples 5-12: Extended Release Tablets

The Freebase Hydrate Form C solid state form of Compound 1 was formulated into 15 mg, 24 mg, or 30 mg extended release tablets according to the formulations set forth in Table 5 using direct compression.

TABLE 5

Extended Release Tablets (tartaric acid pH modifier)

| Component | Function | Ex. 5 (mg) (ER7) | Ex. 6 (mg) | Ex. 7 (mg) | Ex. 8 (mg) (ER8) | Ex. 9 (mg) (ER4) | Ex. 10 (mg) (ER4, no mannitol) | Ex. 11 (mg) (ER5) | Ex. 12 (mg) (ER6) |
|---|---|---|---|---|---|---|---|---|---|
| Freebase Hydrate Form C | Active | 15.4$^a$ | 15.4$^a$ | 15.4$^a$ | 30.7$^b$ | 24.6$^c$ | 24.6$^c$ | 24.6$^c$ | 24.6$^c$ |
| Microcrystalline cellulose (Avicel ® PH 102) | Filler | 162.4 | 162.4 | 162.4 | 147.1 | 158.0 | 210.6 | 282.6 | 258.6 |
| Mannitol (Pearlitol ® 100 SD) | Filler | 52.6 | 52.4 | — | 52.6 | 52.7 | — | — | — |
| Mannitol (Pearlitol ® 200 SD) | Filler | — | — | 52.4 | — | — | — | — | — |
| Tartaric acid | pH modifier | 144.0 | 144.0 | 144.0 | 144.0 | 144.0 | 144.0 | 96.0 | 96.0 |
| HPMC (Hypromellose 2208) | Release control polymer | 96.0 | — | — | 96.0 | — | — | — | — |

TABLE 5-continued

Extended Release Tablets (tartaric acid pH modifier)

| Component | Function | Ex. 5 (mg) (ER7) | Ex. 6 (mg) | Ex. 7 (mg) | Ex. 8 (mg) (ER8) | Ex. 9 (mg) (ER4) | Ex. 10 (mg) (ER4, no mannitol) | Ex. 11 (mg) (ER5) | Ex. 12 (mg) (ER6) |
|---|---|---|---|---|---|---|---|---|---|
| HPMC (Methocel ® K4M Premium CR) | Release control polymer | — | 96.0 | 96.0 | — | 96.0 | 96.0 | — | — |
| Carbopol ® 71G | Release control polymer | — | — | — | — | — | — | 48.0 | 72.1 |
| Carbopol ® 971P | Release control polymer | — | — | — | — | — | — | 24.0 | 24.0 |
| Colloidal silicon dioxide | Glidant | 2.4 | 2.4 | 2.4 | 2.4 | — | — | — | — |
| Magnesium stearate impalpable powder | Lubricant | 7.2 | 7.2 | 7.2 | 7.2 | 4.8 | 4.8 | 4.8 | 4.8 |
| Uncoated weight of tablet | | 480.0 | 479.8 | 479.8 | 480.0 | 480.1 | 480.0 | 480.0 | 480.1 |
| Opadry ® II Yellow (PVA based) | Film coat | 14.40 | — | — | 14.40 | — | — | — | — |
| Total weight of tablet | | 494.39 | | | 494.43 | — | — | — | — |

[a]Provides 15 mg of Compound 1 freebase equivalent.
[b]Provides 30 mg of Compound 1 freebase equivalent.
[c]Provides 24 mg of Compound 1 freebase equivalent.

The formulations were prepared by first milling the tartaric acid through a Fitz mill Model M5A, fitted with a 1512-0027 screen. The Freebase Hydrate Form C, microcrystalline cellulose, mannitol (when present), milled tartaric acid, release control polymer, and colloidal silicone dioxide (when present) were combined and blended. The blend was milled using a Mobil Mill fitted with a 610- or 1397-micron screen. The magnesium stearate was screened through mesh #30 and was then added to the bin and blended. The lubricated granulation was compressed into about 480 mg weight tablets using a rotary tablet press.

The Example 5 and 8 tablets were coated using a film coater, which sprayed a solution containing the Opadry® II Yellow film coat and purified water until 14.40 mg of coating had been applied to the tablets.

The dissolution profile of the Example 9 (ER4, 24 mg active), Example 10 (ER4, no mannitol, 24 mg active), Example 11 (ER5, 24 mg active), and Example 12 (ER6, 24 mg active) tablets was evaluated at pH 1.2, at pH 6.8, and in a dual pH system. The pH 6.8 study was performed as described above for Examples 3 and 4. For the dual pH study, an acid stage medium of 0.05 M sodium phosphate solution, pH 3.5±0.05, was prepared by dissolving about 41.4 g of sodium phosphate, monobasic, monohydrate in about 4 L of water, measuring the pH and adding phosphoric acid, 85%, dropwise as needed to adjust to the target pH. The mixture was diluted to 6 L with water and mixed. A buffer stage medium for the study was prepared using a buffer stage concentrate (0.05 M sodium phosphate buffer concentrate solution, prepared by dissolving about 41.4 g of sodium phosphate, monobasic, monohydrate and about 14.4 g of sodium hydroxide pellets in about 4 L of water, dilute to 6 L with water and mixing well). The buffer stage medium of a 0.05 M sodium phosphate buffer solution, pH 6.8±0.05, was prepared by mixing 500 mL of the acid stage medium and 400 mL of buffer stage medium concentrate in an appropriate size container or directly in the dissolution vessel and adjusting the pH of the buffer stage medium concentrate with 1 N phosphoric acid or 1 N sodium hydroxide, if the pH was not within 6.8±0.05.

The dissolution test was carried out using the following dissolution parameters and conditions:
  Apparatus: USP Dissolution Apparatus 2 and fraction collector
  Medium: Acid Stage: 500 mL of Acid Stage Medium
    Buffer Stage: 900 mL of 50 mM sodium phosphate buffer solution, pH 6.8
  Temperature: 37° C.±0.5° C.
  RPM: 75 RPM±4%
  Filter: 35 μm PE filter, or equivalent, for automatic sampling
  Sampling Times: Acid Stage: 1 Hour
    Buffer Stage: 2, 4, 6, 8, 10, 12, 16, and 20 Hours.
    Other samples may be taken at other times, as appropriate.
  Sample Volume: Acid and Buffer Stage: 1.5 mL obtained automatically, without media replacement.

For the dissolution test, one tablet each was added to a dissolution vessel containing 500 mL of the acid stage medium, maintained at 37° C. The paddles of the dissolution apparatus were operated at 75 RPM for 1 hour, and then a 1.5 mL sample from the dissolution vessel was automatically obtained. After the acid stage sample was obtained, 400 mL of buffer stage medium concentrate was added, and then the mixture was maintained at 37° C. The dissolution test was continued, with the paddles remaining at a speed of 75 RPM. The sample filtrate was the sample preparation.

For the pH 1.2 study, the dissolution test was carried out using the following dissolution parameters and conditions:
  Apparatus: USP Dissolution Apparatus 2 and fraction collector
  Medium: 500 mL of Acidic Medium, pH 1.2

Temperature: 37° C.±0.5° C.
RPM: 75 RPM±4%
Filter: 35 μm PE filter, or equivalent, for automatic sampling
Sampling Times: 1, 2, 4, 6, 8, 10, 12, 16, and 20 Hours. Other samples may be taken at other times, as appropriate.
Sample Volume: 1.5 mL obtained automatically, without media replacement.

For this study, an acidic medium of 0.05 M sodium phosphate solution, pH 3.5±0.05, was prepared by dissolving about 41.4 g of sodium phosphate, monobasic, monohydrate in about 4 L of water, measuring the pH and adding phosphoric acid, 85%, dropwise as needed to adjust to the target pH of 1.2. The mixture was diluted to 6 L with water and mixed.

For the dissolution test, one tablet each was added to a dissolution vessel containing 500 mL of the acidic medium, maintained at 37° C. The paddles of the dissolution apparatus were operated at 75 RPM, with 1.5 mL samples from the dissolution vessel automatically obtained at the designated time periods. The sample filtrate was the sample preparation.

For the analysis of the sample, conventional liquid chromatography methods were utilized, wherein the % relative standard deviation (RSD) of peak areas was calculated for each set of six standard injections. The results shown that pH independence is achieved in the once daily formulations.

The dissolution profile of the Example 5 (ER7), Example 8 (ER8), and Example 9 (ER4) tablets were evaluated in a dual pH system, as described above. The formulations provide an extended release profile of 80-100% over a period of about 8-10 hours.

The formulations of Examples 5 and 8-12 all exhibited pH independent release of the active ingredient. In contrast, after the initial release at the low pH, release of the active is slowed at the higher pH for the formulations of Examples 1-3. Without wishing to be bound to any particular theory, it is believed that the inclusion of tartaric acid as a pH modifier in the Example 5 and 8-12 formulations contributed to the pH independent release observed for these tablets.

Example 13: Extended Release Tablet

The Freebase Hydrate Form C solid state form of Compound 1 was formulated into a 7.5 mg extended release tablet according to the formulation set forth in Table 6.

TABLE 6

Extended Release Tablets (tartaric acid pH modifier)

| Component | Function | Ex. 34 (mg) (ER9) |
|---|---|---|
| Freebase Hydrate Form C* | Active | 7.678[a] |
| Microcrystalline cellulose (Avicel ® PH 102) | Filler | 170.1 |
| Mannitol (Pearlitol ® 100 SD) | Filler | 52.62 |
| Tartaric acid (crystalline) | pH modifier | 144.0 |
| HPMC (Hypromellose 2208) | Release control polymer | 96.0 |
| Colloidal silicon dioxide | Glidant | 2.4 |
| Magnesium stearate | Lubricant | 7.2 |
| Uncoated weight of tablet | | 479.998 |
| Opadry ® II Yellow | Film coat | 14.40 |
| Purified water | Processing aid | n/a |
| Total weight of tablet | | 494.398 |

[a]Provides 7.5 mg of Compound 1 freebase equivalent.

The formulation was prepared by first milling the tartaric acid through a Fitz mill Model M5A, fitted with a 1512-0027 screen. The Freebase Hydrate Form C, microcrystalline cellulose, mannitol, milled tartaric acid, release control polymer, and colloidal silicone dioxide were combined and blended. The blend was milled using a Mobil Mill fitted with a 610-micron screen. The magnesium stearate was screened through mesh #30 and was then added to the bin and blended. The lubricated granulation was compressed into about 480 mg weight tablets using a rotary tablet press.

The tablets were coated using a film coater, which sprayed a solution containing the Opadry® II Yellow film coat and purified water until 14.4 mg of coating had been applied to the tablets.

Examples 14-19: Extended Release Tablets

The Freebase Hydrate Form C solid state form of Compound 1 was formulated into 15 mg or 30 mg extended release tablets according to the formulations set forth in Table 7. The tablets were prepared using a wet granulation process, and were compressed into tablets having a core weight of about 480 mg.

TABLE 7

Extended Release Tablets (tartaric acid pH modifier)

| Component | Function | Ex. 14 (mg) (ER10) | Ex. 15 (mg) (ER11) | Ex. 16 (mg) (ER12) | Ex. 17 (mg) (ER13) | Ex. 18 (mg) (ER14) | Ex. 19 (mg) (ER15) |
|---|---|---|---|---|---|---|---|
| Tablet Core (Intragranular) | | | | | | | |
| Freebase Hydrate Form C | Active | 30.7[a] | 30.7[a] | 30.7[a] | 15.4[b] | 15.4[b] | 15.4[b] |
| Microcrystalline cellulose (Avicel ® PH 101) | Filler | 79.9 | 79.9 | 79.9 | 40.0 | 40.0 | 40.0 |
| HPMC (Hypromellose 2208) | Release control polymer | 9.5 | 9.5 | 9.5 | 4.8 | 4.8 | 4.8 |

TABLE 7-continued

| | | Extended Release Tablets (tartaric acid pH modifier) | | | | | |
|---|---|---|---|---|---|---|---|
| Component | Function | Ex. 14 (mg) (ER10) | Ex. 15 (mg) (ER11) | Ex. 16 (mg) (ER12) | Ex. 17 (mg) (ER13) | Ex. 18 (mg) (ER14) | Ex. 19 (mg) (ER15) |
| Tablet Core (Extragranular) | | | | | | | |
| Microcrystalline cellulose (Avicel ® PH 102) | Filler | 67.2 | 67.2 | 67.2 | 122.5 | 122.5 | 122.5 |
| Mannitol | Filler | 52.6 | 100.6 | 148.6 | 52.6 | 100.6 | 148.6 |
| Tartaric acid (crystalline) | pH modifier | 144.0 | 96.0 | 48.0 | 144.0 | 96.0 | 48.0 |
| HPMC (Hypromellose 2208) | Release control polymer | 86.5 | 86.5 | 86.5 | 91.2 | 91.2 | 91.2 |
| Colloidal silicon dioxide/silica | Glidant | 2.4 | 2.4 | 2.4 | 2.4 | 2.4 | 2.4 |
| Magnesium stearate | Lubricant | 7.2 | 7.2 | 7.2 | 7.2 | 7.2 | 7.2 |
| Uncoated weight of tablet | | 480.0 | 480.0 | 480.0 | 480.1 | 480.1 | 480.1 |
| Opadry ® II Yellow[c] | Film coat | 14.4 | 14.4 | 14.4 | 14.4 | 14.4 | 14.4 |
| Total weight of tablet | | 494.4 | 494.4 | 494.4 | 494.5 | 494.5 | 494.5 |

[a]Provides 30 mg of Compound 1 freebase equivalent.
[b]Provides 15 mg of Compound 1 freebase equivalent.
[c]Film coat weight is approximate.

The formulation was prepared by first milling the tartaric acid through a Fitz mill Model M5A, fitted with a 1512-0027 screen. The intragranular portion of the hydroxypropylmethyl cellulose release control polymer, the Freebase Hydrate Form C, and intragranular portion of the microcrystalline cellulose filler were added to a granulator, and mixed. Water was sprayed to granulate. The granulated material was then dried and milled using a comill fitted with a 610-micron screen. The milled granulation was then added to the extragranular tablet components other than magnesium stearate, and sieved using a comill fitted with a 1397-micron screen, followed by blending. The magnesium stearate was then added to the bin and blended. The lubricated granulation was compressed into about 480 mg weight tablets using a rotary tablet press.

The tablets were coated using a film coater, which sprayed a solution containing the Opadry® II Yellow film coat and purified water until 14.4 mg of coating had been applied to the tablets.

Example 20: Evaluation of the Effect of Organic Acids on Dissolution Profile of Extended Release Tablets In this example, the effect of various organic acid pH modifiers (e.g., tartaric acid, citric acid, succinic acid, and fumaric acid) on the release rate of Freebase Hydrate Form C from 24 mg once-daily extended release (ER) tablets was evaluated. Freebase Hydrate Form C was formulated into 24 mg extended release tablets according to the formulations set forth in Table 8.

TABLE 8

| | | Extended Release Tablets | | | | | | | |
|---|---|---|---|---|---|---|---|---|---|
| | | Tartaric acid | | Citric acid | | Succinic acid | | Fumaric acid | |
| Component | Function | A | B | C | D | E | F | G | H |
| Freebase Hydrate Form C | Active | 24.6 | 24.6 | 24.6 | 24.6 | 24.6 | 24.6 | 24.6 | 24.6 |
| Microcrystalline cellulose (Avicel ® PH102) | Filler | 306.6 | 306.6 | 306.6 | 306.6 | 306.6 | 306.6 | 306.6 | 306.6 |
| HPMC (Methocel ® K4M) | Release control polymer | 96.0 | — | 96.0 | — | 96.0 | — | 96.0 | — |
| Carbopol ® 71G | Release control polymer | — | 96.0 | — | 96.0 | — | 96.0 | — | 96.0 |
| Organic acid | pH modifier | 48.0 | 48.0 | 48.0 | 48.0 | 48.0 | 48.0 | 48.0 | 48.0 |
| Magnesium stearate | Lubricant | 4.8 | 4.8 | 4.8 | 4.8 | 4.8 | 4.8 | 4.8 | 4.8 |
| Total | | 480.0 | 480.0 | 480.0 | 480.0 | 480.0 | 480.0 | 480.0 | 480.0 |

The formulations were prepared by first milling the organic acid through a Fitz mill Model M5A, fitted with a 1512-0027 screen. The active, microcrystalline cellulose, milled organic acid, and release control polymer, were combined and blended. The blend was milled using a Mobil Mill fitted with a 610-micron screen. The magnesium stearate was screened through mesh #30 and was added to the bin and blended. The lubricated granulation was compressed into 480 mg weight tablets using a rotary tablet press.

The effect of the organic acids on the dissolution profile of the tablets was evaluated at pH 1.2 and pH 6.8. The dissolution tests were carried out using the dissolution parameters and conditions as described above in Examples 3 and 4 and 9-12. For analysis of the sample, conventional liquid chromatography methods were utilized, wherein the % of the labelled amount of active released (% LA Released) was calculated. The results show that organic acids improved dissolution rate at high pH, with tartaric acid showing the best improvement. The formulations comprising the control release polymer Carbopol® with tartaric acid provided near linear release at pH 6.8.

Example 21: Gel pH Measurements for Tablets with Different Amounts of Tartaric Acid To measure the pH of the environment created when Compound 1 reacts with HPMC, the following experiment was performed.

The Freebase Hydrate Form C solid state form of Compound 1 was formulated into 30 mg extended release tablets according to the formulations set forth in Table 9A. The tablets were prepared using a wet granulation process, as described in Examples 14-19.

Dissolution media of 0.01 N HCl (pH 2) and 113 mM sodium phosphate buffer (pH 6.8) was prepared at 37° C. One tablet was added to 500 mL of 0.01 N HCl media and stirred at 75 rpm at 37° C. for one hour in a Vankel VK 7010 dissolution bath. Then 400 mL of sodium phosphate buffer was added. The solution was stirred an additional three hours. The tablet was removed, rinsed with water and dried using laboratory tissues. The gel that formed on the tablet was separated from the dry core for pH measurement. This procedure was repeated three times for each formulation. The pH of the gel formed on the tablets is set forth in Table 9B.

TABLE 9A

Formulations

| Component | Formulation 1 mg/tab | Formulation 2 mg/tab | Formulation 3 mg/tab | Formulation 4 mg/tab | Formulation 5 mg/tab |
|---|---|---|---|---|---|
| Intragranular | | | | | |
| Freebase Hydrate Form C | 30.71 | 30.71 | 30.71 | 30.71 | 30.71 |
| HPMC (Methocel® K4M) | 3.920 | 3.920 | 3.920 | 3.920 | 3.920 |
| Microcrystalline cellulose (Avicel® PH102) | 30.71 | 30.71 | 30.71 | 30.71 | 30.71 |
| Extragranular | | | | | |
| Microcrystalline cellulose (Avicel® PH102) | 116.4 | 164.4 | 188.4 | 212.4 | 260.4 |
| Tartaric Acid (milled) | 144.0 | 96.00 | 72.00 | 48.00 | 0.00 |
| Mannitol (Pearlitol® 100SD) | 52.62 | 52.62 | 52.62 | 52.62 | 52.62 |
| HPMC (Methocel® K4M) | 92.08 | 92.08 | 92.08 | 92.08 | 92.08 |
| Colloidal silicon dioxide | 2.400 | 2.400 | 2.400 | 2.400 | 2.400 |
| Magnesium Stearate | 7.200 | 7.200 | 7.200 | 7.200 | 7.200 |
| Total | 480.04 | 480.04 | 480.04 | 480.04 | 480.04 |

TABLE 9B pH Results

| Formulation | % Tartaric Acid | $1^{st}$ tablet | $2^{nd}$ tablet | $3^{rd}$ tablet | Average |
|---|---|---|---|---|---|
| 1 | 30 | 2.63 | 2.68 | 2.81 | 2.71 |
| 2 | 20 | 3.17 | 3.09 | 3.23 | 3.16 |
| 3 | 15 | 3.42 | 3.94 | 3.65 | 3.67 |
| 4 | 10 | 3.88 | 3.67 | 3.77 | 3.77 |
| 5 | 0 | 6.26 | 6.21 | 6.55 | 6.34 |

Example 22: Evaluation of the In Vivo Pharmacokinetic Profile of 15 mg Extended Release Tablets (Fasting)

The pharmacokinetic profile of the 15 mg once-daily extended release (ER) tablets prepared in Example 5 was evaluated, and compared to that of a 12 mg immediate-release (IR) capsule comprising Tartrate Hydrate as the active.

Healthy human subjects (n=11) were administered a single dose of the 12 mg IR capsule (Regimen A) and the 15 mg ER (once-daily) tablet from Example 5 (Regimen B) under fasting conditions in a randomized, two-period, crossover study design. Subjects were administered Regimen A in the first study period and Regimen B in the second study period, or administered Regimen B in the first study period and Regimen A in the second study period. Serial blood samples were collected from each subject prior to dosing and for 72 hours after dosing in each study period. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 10A.

TABLE 10A

Mean (% CV)[c] Pharmacokinetic Parameters for Compound 1 Following Administration of 15 mg ER Tablet and 12 mg IR Capsule Formulations Under Fasting Conditions

| PK Parameter | Units | Regimen A (IR Capsule, 12 mg) | Regimen B (ER Tablet, 15 mg) |
|---|---|---|---|
| $C_{max}$ | ng/mL | 64.6 (16) | 26.0 (37) |
| $T_{max}$[a] | hours | 1.0 (0.5-1.5) | 3.0 (1.0-4.0) |
| $t_{1/2}$[b] | hours | 9.2 (119) | 12.5 (90) |
| $AUC_t$ | ng · h/mL | 231 (15) | 227 (26) |
| $AUC_{inf}$ | ng · h/mL | 234 (15) | 242 (26) |

[a]Median (minimum, maximum)
[b]Harmonic mean (pseudo-% CV)
[c]Data in parentheses is coefficient of variance of the PK parameter (% CV), unless otherwise indicated.

As can be seen from this data, the 15 mg ER tablet provided a lower $C_{max}$ and comparable AUC to the 12 mg IR capsule under fasting conditions.

The relative bioavailability for a single dose of the once-daily (ER) tablet formulation (Regimen B) relative to the IR capsule formulation (Regimen A) was also determined based on analysis of the natural logarithms of $C_{max}$ and AUC. The results are summarized in Table 10B below.

TABLE 10B

Relative Bioavailability and 90% Confidence Intervals for Bioequivalence Assessment

| | Relative Bioavailability | |
|---|---|---|
| PK Parameter | Point Estimate | 90% Confidence Interval |
| $C_{max}$ | 0.373 | 0.312-0.446 |
| $AUC_t$ | 0.939 | 0.869-1.013 |
| $AUC_{inf}$ | 0.992 | 0.909-1.082 |

For Regimen B versus Regimen A, the point estimates for the ratios of $AUC_t$ and $AUC_{inf}$ were near unity, and the 90% confidence intervals were within the 0.86-1.09 range.

Example 23: Evaluation of the In Vivo Pharmacokinetic Profile of 30 mg Extended Release Tablets (Fasting)

The pharmacokinetic profile of the 30 mg once daily extended release (ER) tablets prepared in Example 8 was evaluated, and compared to that of a 24 mg dose of an immediate release (IR) capsule comprising Tartrate Hydrate as the active.

Healthy human subjects (n=12) were administered a single 24 mg dose (two 12 mg IR capsules) (Regimen C) and the 30 mg ER (once daily) tablet from Example 8 (Regimen D) under fasting conditions in a randomized, two-period, cross-over study design. Half the subjects were administered Regimen C in the first study period and Regimen D in the second study period, while the other half were administered Regimen D in the first study period and Regimen C in the second study period. Serial blood samples were collected from each subject prior to dosing and for 72 hours after dosing in each study period. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 11A.

TABLE 11A

Mean (% CV)[c] Pharmacokinetic Parameters for Compound 1 Following Administration of 30 mg ER Tablet and 24 mg Dose (2 × 12 mg) IR Capsule Formulations Under Fasting Conditions

| PK Parameter | Units | Regimen C (IR Capsules, 24 mg) | Regimen D (ER Tablet, 30 mg) |
|---|---|---|---|
| $C_{max}$ | ng/mL | 176 (37) | 63.7 (33) |
| $T_{max}$[a] | hours | 0.5 (0.5-1.5) | 2.0 (1.5-4.0) |
| $t_{1/2}$[b] | hours | 9.9 (52) | 10.8 (67) |
| $AUC_t$ | ng · h/mL | 520 (25) | 477 (27) |
| $AUC_{inf}$ | ng · h/mL | 524 (25) | 491 (27) |

[a]Median (minimum-maximum)
[b]Harmonic mean (pseudo % CV)
[c]Data in parentheses is the coefficient of variance of the PK parameter (% CV), unless otherwise indicated.

As can be seen from this data, the 30 mg ER tablet provided a lower $C_{max}$ and comparable AUC to the 24 mg dose IR capsule (2×12 mg) under fasting conditions.

The relative bioavailability for a single dose of the once-daily (ER) tablet formulation (Regimen D) relative to the IR capsule formulations (Regimen C) was also determined based on analysis of the natural logarithms of $C_{max}$ and AUC. The results are summarized in Table 11B below.

TABLE 11B

Relative Bioavailability and 90% Confidence Intervals for Bioequivalence Assessment

| | PK Value | | Relative Bioavailability | |
|---|---|---|---|---|
| PK Parameter | Regimen D | Regimen C (reference) | Point Estimate | 90% Confidence Interval |
| $C_{max}$ | 63.7 | 176 | 0.368 | 0.326-0.415 |
| $AUC_t$ | 477 | 520 | 0.912 | 0.828-1.004 |
| $AUC_{inf}$ | 491 | 524 | 0.933 | 0.845-1.029 |

For Regimen D versus Regimen C, the point estimates for the ratios of $AUC_t$ and $AUC_{inf}$ were near unity, and the 90% confidence intervals were within the 0.82-1.03 range.

Example 24: Comparison of the In Vivo Pharmacokinetic Profile of 30 mg Extended Release Tablets Under Fasting Versus Fed Conditions The pharmacokinetic profile of the 30 mg extended release tablets prepared in Example 8 after a high-fat meal was evaluated, and compared to the pharmacokinetic profile of the 30 mg extended release tablets under fasting conditions (see Example 23).

Following completion of the Example 23 study, the healthy human subjects (n=12) were administered single doses of the 30 mg ER (once daily) tablet from Example 8 after a high-fat meal (Regimen E). Serial blood samples were collected from each subject prior to dosing and for 72 hours after dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter, and compared to the pharmacokinetic parameters for the 30 mg tablets administered under fasting conditions (see Example 23, Regimen D). The results are summarized in Table 12A.

TABLE 12A

Mean (% CV)$^c$ Pharmacokinetic Parameters for Compound 1 Following Administration of 30 mg ER Tablet Under Fasting Conditions or After a High-Fat Meal

| PK Parameter | Units | Regimen D (Fasting) | Regimen E (After High-Fat Meal) |
|---|---|---|---|
| $C_{max}$ | ng/mL | 63.7 (33) | 76.8 (39) |
| $T_{max}{}^a$ | hours | 2.0 (1.5-4.0) | 4.0 (1.5-8.0) |
| $t_{1/2}{}^b$ | hours | 10.8 (67) | 11.9 (51) |
| $AUC_t$ | ng·h/mL | 477 (27) | 564 (26) |
| $AUC_{inf}$ | ng·h/mL | 491 (27) | 577 (27) |

$^a$Median (minimum-maximum)

$^b$Harmonic mean (pseudo-CV %)

$^c$Data in parentheses is coefficient of variance of the PK parameter (% CV), unless otherwise indicated.

The relative bioavailability for a single dose of the once-daily (ER) 30 mg tablet formulation after a high-fat meal (Regimen E) relative to the bioavailability of the ER 30 mg tablet under fasting conditions (Regimen D) was also determined based on analysis of the natural logarithms of $C_{max}$ and AUC. The results are summarized in Table 12B below.

TABLE 12B

Relative Bioavailability and 90% Confidence Intervals for Bioequivalence Assessment

| | PK Value | | Relative Bioavailability | |
|---|---|---|---|---|
| PK Parameter | Regimen E (after high-fat meal) | Regimen D (fasting) | Point Estimate | 90% Confidence Interval |
| $C_{max}$ | 76.8 | 63.7 | 1.197 | 1.027-1.395 |
| $AUC_t$ | 564 | 477 | 1.184 | 1.042-1.344 |
| $AUC_{inf}$ | 577 | 491 | 1.171 | 1.035-1.326 |

As can be seen from Tables 13A and 13B, there is no clinically meaningful food effect for the 30 mg ER tablets. Administration following a high-fat meal increased the Compound 1 mean AUC and $C_{max}$ by 17% and 20%, respectively.

Example 25: Observed Steady State Exposures for 15 mg and 30 mg Extended Release Tablets Under Non-Fasting Conditions The steady state pharmacokinetic profile of the 15 mg once daily extended release (ER) tablets (prepared in Example 5) and the 30 mg once daily ER tablets (prepared in Example 8) was evaluated.

Healthy human subjects (n=24) were assigned to one of two regimens. Subjects in Regimen F (n=12) were administered the 15 mg ER tablet from Example 5 once daily for seven days under non-fasting conditions. Subjects in Regimen G (n=12) were administered the 30 mg ER tablet from Example 8 once daily for seven days under non-fasting conditions. On days one and seven, serial blood samples were collected from each subject prior to the daily dosing and up to 24 hours after dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 13A.

TABLE 13A

Mean (% CV)$^c$ Pharmacokinetic Parameters for Compound 1 Following Administration of 15 mg ER Tablet or 30 mg ER Tablet QD for Seven Days (Non-Fasting)

| PK Parameter | Units | Regimen F (15 mg ER Tablet) | | Regimen G (30 mg ER Tablet) | |
|---|---|---|---|---|---|
| | | Day 1 | Day 7 | Day 1 | Day 7 |
| $C_{max}$ | ng/mL | 36.8 (26) | 36.0 (24) | 74.3 (32) | 79.5 (40) |
| $T_{max}{}^a$ | hours | 4.0 (3.0-6.0) | 4.0 (2.0-6.0) | 4.0 (2.0-6.0) | 4.0 (1.5-6.0) |
| $AUC_{24}$ | ng·h/mL | 305 (24) | 317 (21) | 517 (30) | 582 (30) |
| $C_{24}$ | ng/mL | 2.42 (45) | 3.22 (46) | 4.27 (48) | 5.25 (44) |
| $C_{trough}$ | ng/mL | — | 2.96 (35) | — | 5.02 (42) |
| $C_{min,ss}$ | ng/mL | — | 2.80 (41) | — | 4.62 (38) |
| Fluctuation Index | % | 291 (14) | 251 (14) | 345 (14) | 306 (17) |
| $t_{1/2}{}^b$ | hours | — | 9.43 (76) | — | 10.4 (44) |
| $C_{max}$ to $C_{24}$ ratio | | 17 (7.8-44) | 13 (5.6-35) | 17 (9.9-38) | 14 (7.0-30) |
| $C_{max}$/Dose | (ng/mL)/mg | 2.46 (26) | 2.40 (24) | 2.48 (32) | 2.65 (40) |
| $C_{trough}$/Dose | (ng/mL)/mg | 0.16 (45) | 0.21 (46) | 0.14 (48) | 0.18 (44) |
| $AUC_{24}$/Dose | (ng·h/mL)/mg | 20.3 (24) | 21.2 (21) | 17.2 (30) | 19.4 (30) |

TABLE 13A-continued

Mean (% CV)[e] Pharmacokinetic Parameters for Compound 1 Following Administration of 15 mg ER Tablet or 30 mg ER Tablet QD for Seven Days (Non-Fasting)

| PK Parameter | Units | Regimen F (15 mg ER Tablet) | | Regimen G (30 mg ER Tablet) | |
|---|---|---|---|---|---|
| | | Day 1 | Day 7 | Day 1 | Day 7 |
| $R_{AUC}$[c] | | — | 1.02 (0.91-1.40) | — | 1.16 (0.92-1.31) |
| $R_{Cmax}$[d] | | — | 1.00 (0.84-1.26) | — | 1.02 (0.82-1.40) |

[a]Median (minimum-maximum)
[b]Harmonic mean (pseudo-% CV)
[c]$R_{AUC}$ = $AUC_{24}$Day 7/$AUC_{24}$Day 1; median (range)
[d]$R_{Cmax}$ = $C_{max}$Day 7/$C_{max}$Day 1; median (range)
[e]Data in parentheses is the coefficient of variance of the PK parameter (% CV), unless otherwise indicated As can be seen from this data, the observed steady state $C_{max}$ and $AUC_{24}$ following 15 mg QD and 30 mg QD administration are generally consistent with the single dose and food-effect results obtained in previous studies. The bioavailability of the 15 mg and 30 mg ER tablets is 70% to 80% relative to the same dose of IR capsules.

Example 26: Observed Steady State Exposures for 15 mg Extended Release Tablets and 6 mg Immediate Release Capsules Under Fasting Conditions The steady state pharmacokinetic profile of the 15 mg once daily extended release (ER) tablets (prepared in Example 5) under fasting conditions was evaluated, and compared to that of a 6 mg immediate release (IR) twice daily (BID) capsule comprising Tartrate Hydrate as the active.

Healthy human subjects were assigned to one of two regimens under fasting conditions in a randomized, two-period, cross-over study design. Subjects in Regimen K (n=12 at onset; n=11 on Day 7) were administered the 6 mg IR capsule twice daily for seven days under fasting conditions. Subjects in Regimen L (n=12) were administered the 15 mg ER tablet from Example 5 once daily for seven days under fasting conditions. On days one and seven, serial blood samples were collected from each subject prior to the daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen. The results are summarized in Table 14A.

TABLE 14A

Mean (% CV)[e] Pharmacokinetic Parameters for Compound 1 Following Administration of 6 mg BID (IR) Capsules and 15 mg QD (ER) Tablets for Seven Days (Fasting Conditions)

| PK Parameter | Units | Regimen K (6 mg IR Capsules (BID)) | | Regimen L (15 mg ER Tablet (QD)) | |
|---|---|---|---|---|---|
| | | Day 1 | Day 7 | Day 1 | Day 7 |
| $C_{max}$ | ng/mL | 36.5 (25) | 33.9 (26) | 31.7 (40) | 31.9 (35) |
| $T_{max}$[a] | hours | 1.0 (1.0-13) | 1.0 (0.5-14) | 3.0 (1.5-6.0) | 2.5 (1.5-4.0) |
| $AUC_{24}$ | ng · h/mL | 289 (21) | 288 (22) | 249 (29) | 279 (26) |
| $C_{12}$ | ng/mL | 2.0 (30) | 2.8 (24) | — | — |
| $C_{24}$ | ng/mL | 3.2 (36) | 3.6 (23) | 1.9 (42) | 3.1 (37) |
| $C_{min}$ | ng/mL | — | 2.7 (26) | — | 3.1 (37) |
| Fluctuation Index | % | 303 (13) | 259 (13) | 299 (22) | 246 (21) |
| $t_{1/2}$[b] | hours | — | 14.7 (77) | — | 10.3 (76) |
| $C_{max}$ to $C_{24}$ ratio[a] | — | 12 (7.7-19) | 8.8 (7.4-13) | 22 (5.8-43) | 12 (4.2-20) |
| $C_{max}$ to $C_{min}$ ratio[a] | — | — | 13 (8.3-18) | — | 12 (4.2-20) |
| $AUC_{24}$/Dose | (ng · h/mL)/mg | 24.8 (23) | 24.0 (22) | 16.6 (29) | 18.6 (26) |
| $R_{AUC}$[c] | — | — | 1.02 (0.88-1.09) | — | 1.11 (0.87-1.99) |
| $R_{Cmax}$[d] | — | — | 0.97 (0.68-1.17) | — | 1.01 (0.65-3.01) |

[a]Median (minimum-maximum)
[b]Harmonic mean (pseudo-% CV)
[c]$R_{AUC}$ = $AUC_{24}$Day 7/$AUC_{24}$Day 1; median (range)
[d]$R_{Cmax}$ = $C_{max}$Day 7/$C_{max}$Day 1; median (range)
[e]Data in parentheses is the coefficient of variance of the PK parameter (% CV), unless otherwise indicated The relative bioavailability for the once-daily (ER) tablet formulation (Regimen L) relative to the twice daily (IR) capsule formulation (Regimen K) at steady state was also determined based on analysis of the natural logarithms of $C_{max}$, $AUC_{24}$, $C_{min}$, and $C_{24}$. The results are summarized in Table 14B below.

TABLE 14B

Relative Bioavailability Estimates and 90% Confidence Intervals for 15 mg QD Tablets Relative to 6 mg BID Capsules at Steady State under Fasting Conditions

| PK Parameter | Relative Bioavailability | |
|---|---|---|
| | Point Estimate | 90% Confidence Interval |
| $C_{max}$ | 0.909 | 0.736-1.122 |
| $AUC_{24}$ | 0.939 | 0.837-1.053 |
| $C_{min}$ | 1.090 | 0.852-1.395 |

The ratio of steady-state AUC for the 15 mg QD tablets relative to the 6 mg BID capsules was approximately 1, with the 90% confidence intervals within the equivalence boundaries. The ratio of the steady-state $C_{min}$ was approximately 1 for the 15 mg QD tablet relative to the 6 mg BID capsules.

The pre-morning dose trough concentration ($C_{trough}$) for the 6 mg BID capsules and 15 mg QD tablets was determined prior to the morning dose on Days 2-8. At steady state under fasting conditions, the 15 mg QD tablets provided equivalent $AUC_{24}$ and comparable $C_{max}$ and $C_{min}$ relative to the 6 mg BID capsules. The steady state $C_{max}$ was 10% lower for the 15 mg QD tablet compared to the 6 mg BID capsule.

Example 27: Observed Steady State Exposures for 30 mg Extended Release Tablets and 12 mg Immediate Release Capsules Under Fasting Conditions The steady state pharmacokinetic profile of the 30 mg once daily extended release (ER) tablets (prepared in Example 8) under fasting conditions was evaluated, and compared to that of a 12 mg immediate release (IR) twice daily (BID) capsule comprising Tartrate Hydrate as the active.

Healthy human subjects were assigned to one of two regimens under fasting conditions in a randomized, two-period, cross-over study design. Subjects in Regimen M (n=11) were administered the 12 mg IR capsule twice daily for seven days under fasting conditions. Subjects in Regimen N (n=12 at onset; n=11 at Day 7) were administered the 30 mg ER tablet from Example 8 once daily for seven days under fasting conditions. On days one and seven, serial blood samples were collected from each subject prior to the daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

The results are summarized in Table 15A.

TABLE 15A

Mean (% CV)[e] Pharmacokinetic Parameters for Compound 1 Following Administration of 12 mg BID (IR) Capsules and 30 mg QD (ER) Tablets for Seven Days (Fasting Conditions)

| PK Parameter | Units | Regimen M (12 mg IR Capsules (BID)) | | Regimen N (30 mg ER Tablet (QD)) | |
|---|---|---|---|---|---|
| | | Day 1 | Day 7 | Day 1 | Day 7 |
| $C_{max}$ | ng/mL | 80.8 (23) | 73.9 (19) | 65.7 (22) | 68.2 (30) |
| $T_{max}$[a] | hours | 1.0 (0.5-13) | 1.0 (0.5-1.5) | 2.5 (1.5-4.0) | 3.0 (2.0-4.0) |
| $AUC_{24}$ | ng · h/mL | 497 (15) | 534 (18) | 454 (23) | 525 (23) |
| $C_{12}$ | ng/mL | 3.0 (46) | 4.1 (55) | — | — |
| $C_{24}$ | ng/mL | 6.5 (54) | 6.9 (37) | 2.8 (37) | 4.4 (39) |
| $C_{min}$ | ng/mL | — | 3.8 (58) | — | 3.8 (43) |
| Fluctuation Index | % | 388 (15) | 317 (14) | 349 (12) | 291 (17) |
| $t_{1/2}$[b] | hours | — | 7.3 (60) | — | 14.4 (64) |
| $C_{max}$ to $C_{24}$ ratio[a] | — | 15 (5.4-20) | 12 (5.9-16) | 29 (13-38) | 17 (4.1-33) |
| $C_{max}$ to $C_{min}$ ratio[a] | — | — | 19 (8.4-31) | — | 17 (11-37) |
| $AUC_{24}$/Dose | (ng · h/mL)/mg | 21.1 (15) | 22.3 (18) | 15.1 (22) | 17.5 (23) |
| $R_{AUC}$[c] | — | — | 1.08 (0.97-1.18) | — | 1.11 (0.79-1.67) |
| $R_{Cmax}$[d] | — | — | 0.98 (0.65-1.18) | — | 1.03 (0.40-1.82) |

[a]Median (minimum-maximum)
[b]Harmonic mean (pseudo-% CV)
[c]$R_{AUC}$ = $AUC_{24}$Day 7/$AUC_{24}$Day 1; median (range)
[d]$R_{Cmax}$ = $C_{max}$Day 7/$C_{max}$Day 1; median (range)
[e]Data in parentheses is the coefficient of variance of the PK parameter (% CV), unless otherwise indicated The relative bioavailability for a single dose of the once-daily (ER) tablet formulation (Regimen N) relative to the twice daily (IR) capsule formulation (Regimen M) was also determined based on analysis of the natural logarithms of $C_{max}$, $AUC_{24}$, $C_{min}$, and $C_{24}$. The results are summarized in Table 15B below.

TABLE 15B

Relative Bioavailability Estimates and 90% Confidence Intervals for 30 mg QD Tablets Relative to 12 mg BID Capsules at Steady State under Fasting Conditions

| PK Parameter | Relative Bioavailability | |
|---|---|---|
| | Point Estimate | 90% Confidence Interval |
| $C_{max}$ | 0.900 | 0.732-1.107 |
| $AUC_{24}$ | 0.974 | 0.869-1.092 |
| $C_{min}$ | 0.874 | 0.747-1.022 |

The ratio of steady-state AUC for the 30 mg QD tablets relative to the 12 mg BID capsules was approximately 1, with the 90% confidence intervals within the equivalence boundaries. The steady-state $C_{min}$ for the 30 mg QD tablet was approximately 13% lower than for the 12 mg BID capsules. Outliers with high $C_{min}$ in the 12 mg BID dose may have contributed to this difference.

The pre-morning dose trough concentration ($C_{trough}$) for the 12 mg BID capsules and 30 mg QD tablets was determined prior to the morning dose on Days 2-8. The results show that, at steady state under fasting conditions, the 30 mg QD tablets provided equivalent $AUC_{24}$ and comparable $C_{max}$ and $C_{min}$ relative to the 12 mg BID capsules. The steady state $C_{max}$ was 10% lower for the 30 mg QD tablet compared to the 12 mg BID capsules.

Example 28: Comparison of AM vs. PM Pharmacokinetic Profile Following Administration of 6 mg or 12 mg Immediate Release Capsules Under Fasting Conditions The pharmacokinetic profile of the 6 mg immediate release (IR) twice daily (BID) capsules and the 12 mg IR twice daily capsules was determined on Day 7 of Regimen K (Example 26) and Regimen M (Example 27), respectively, after administration of the morning (AM dose) and evening (PM dose). The results are summarized in Table 16.

Example 29: Evaluation of the In Vivo Pharmacokinetic Profile of 30 mg Extended Release Tablets The pharmacokinetic profiles of the 30 mg once-daily extended release (ER) tablets that were prepared in Examples 14 (ER10, 30% tartaric acid), 15 (ER11, 20% tartaric acid), and 16 (ER12, 10% tartaric acid) using wet granulation were evaluated, and compared to that of the 30 mg ER tablet that was prepared in Example 8 (ER8, 30% tartaric acid) using direct compression (no wet granulation). The effect of a high-fat meal on the Example 14, 15, and 16 formulations was also evaluated.

Healthy human subjects (n=36) were administered a single dose of the 30 mg ER (once daily) tablet from Example 8 (ER8), Example 14 (ER10), Example 15 (ER11), and Example 16 (ER12) under fasting conditions or after a high-fat meal (non-fasting), in an open-label, randomized, four-period, incomplete crossover study. Doses in the four periods were separated by at least four days. Dosing regimens were as set forth below in Table 17A.

TABLE 17A

Dosing Regimens

| Regimen | Dose | Formulation | Fasting/Non-Fasting |
|---|---|---|---|
| A | Single 30 mg | Example 31 (ER8) | Fasting |
| B | Single 30 mg | Example 37 (ER10) | Fasting |
| C | Single 30 mg | Example 37 (ER10) | Non-Fasting |
| D | Single 30 mg | Example 38 (ER11) | Fasting |
| E | Single 30 mg | Example 38 (ER11) | Non-Fasting |
| F | Single 30 mg | Example 39 (ER12) | Fasting |
| G | Single 30 mg | Example 39 (ER12) | Non-Fasting |

Serial blood samples were collected from each subject prior to dosing and for 72 hours after dosing in each study period. Upon collection, the samples were promptly placed in an ice bath, and within 1 hour after sample collection they were centrifuged at about 4° C. The resulting plasma samples were placed in clean polypropylene-tubes and stored in a freezer until analysis. The plasma samples were assayed for Compound 1 using appropriate liquid chromatography mass spectrometry procedures. Pharmacokinetic parameters were estimated using non-compartmental methods, and summary statistics were computed for each parameter by regimen.

TABLE 16

Mean (% CV)[b] Pharmacokinetic Parameters for Compound 1 Following Administration of AM and PM Doses of 6 mg and 12 mg Immediate Release Capsules on Day 7 (Fasting Conditions)

| PK Parameter | Units | Regimen K (6 mg IR Capsules) | | Regimen M (12 mg IR Capsules) | |
|---|---|---|---|---|---|
| | | AM Dose | PM Dose[c] | AM Dose | PM Dose[c] |
| $C_{max}$ | ng/mL | 33.6 (28) | 24.4 (22) | 73.9 (19) | 46.0 (26) |
| $T_{max}$[a] | hours | 1 (0.5-1.5) | 2 (1.0-3.0) | 1 (0.5-1.5) | 3 (1.0-4.0) |
| $AUC_{12}$ | ng · h/mL | 152 (26) | 153 (19) | 290 (19) | 244 (19) |
| $C_{12}$ | ng/mL | 2.76 (24) | 3.63 (23) | 4.1 (55) | 6.94 (37) |
| $C_{max}/C_{12}$ | — | 12.3 (23) | 6.9 (22) | 18.0 (30) | 7.4 (39) |

[a]Median (Minimum-Maximum)
[b]Data in parentheses is the coefficient of variance of the PK parameter (% CV), unless otherwise indicated
[c]The PM dose was administered 3 hours after starting dinner and 4 hours before a snack.

Bioavailability Under Fasting Conditions

The results for administration under fasting conditions are summarized in Table 17B.

TABLE 17B

Mean (% CV)[c] Pharmacokinetic Parameters for Compound 1 Following Administration of a Single 30 mg Dose of Various Compound 1 Once-Daily Formulations Prepared Using Wet Granulation Compared to Administration of a Single 30 mg Dose of a Compound 1 Once-Daily Formulation Prepared Via Direct Compression Under Fasting Conditions

| PK Parameter | Units | Regimen A (ER8) (n = 36) | Regimen B (ER10) (n = 24) | Regimen D (ER11) (n = 24) | Regimen F (ER12) (n = 24) |
|---|---|---|---|---|---|
| $C_{max}$ | ng/mL | 57.0 (33) | 55.8 (27) | 61.0 (25) | 58.6 (34) |
| $T_{max}$[a] | hours | 2.5 (1.0-4.0) | 3.0 (1.0-4.0) | 2.0 (1.0-4.0) | 2.0 (1.0-4.0) |
| $AUC_t$ | ng · h/mL | 495 (24) | 473 (24) | 487 (22) | 481 (23) |
| $AUC_{inf}$ | ng · h/mL | 513 (26) | 484 (24) | 499 (22) | 495 (23) |
| $t_{1/2}$[b] | hours | 9.2 (61) | 10.1 (50) | 9.0 (61) | 9.3 (63) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the three once-daily (ER) tablet formulations prepared using wet granulation (Regimens B, D, and F) relative to the ER tablet prepared via direct compression (no wet granulation) (Regimen A) was also determined based on analysis of the natural logarithms of $C_{max}$, $AUC_t$, and $AUC_{inf}$. The results are summarized in Table 17C below.

TABLE 17C

Bioavailability for Three Compound 1 Once-Daily Formulations Prepared Using Wet Granulation (30 mg; ER10, ER11, ER12) Relative to a Formulation Prepared Via Direct Compression (30 mg, ER8) under Fasting Conditions

| | | Relative Bioavailability | |
|---|---|---|---|
| Regimens | PK Parameter | Point Estimate | 90% Confidence Interval |
| Regimen B (ER10) | $C_{max}$ | 1.024 | 0.917-1.143 |
| vs. | $AUC_t$ | 0.990 | 0.933-1.049 |
| Regimen A (ER8) | $AUC_{inf}$ | 0.976 | 0.918-1.037 |
| Regimen D (ER11) | $C_{max}$ | 1.063 | 0.952-1.187 |
| vs. | $AUC_t$ | 0.985 | 0.929-1.044 |
| Regimen A (ER8) | $AUC_{inf}$ | 0.977 | 0.919-1.038 |
| Regimen F (ER12) | $C_{max}$ | 1.034 | 0.926-1.154 |
| vs. | $AUC_t$ | 0.958 | 0.904-1.016 |
| Regimen A (ER8) | $AUC_{inf}$ | 0.958 | 0.901-1.018 |

As can be seen from this data, all three of the 30 mg tablets prepared using wet granulation (ER10, ER11, and ER12) were bioequivalent under fasting conditions to the tablet prepared via direct compression (no wet granulation).

Effect of a High-Fat Meal on Example 37 Formulation (ER10)

The effect of a high-fat meal on the pharmacokinetic parameters of the Example 14 (ER10, 30 mg active, 30% tartaric acid) formulation is summarized in Table 17D.

TABLE 17D

Mean (% CV)[c] Pharmacokinetic Parameters for Compound 1 Following Administration of Single 30 mg Dose of the Once-Daily Tablet Formulation ER10 under Fasting Conditions and After High-Fat Meal

| PK Parameter | Units | Regimen B (ER10, fasting) (n = 24) | Regimen C (ER10, high fat meal) (n = 12) |
|---|---|---|---|
| $C_{max}$ | ng/mL | 55.8 (27) | 76.3 (30) |
| $T_{max}$[a] | hours | 3.0 (1.0-4.0) | 4.0 (1.5-8.0) |

TABLE 17D-continued

Mean (% CV)[c] Pharmacokinetic Parameters for Compound 1 Following Administration of Single 30 mg Dose of the Once-Daily Tablet Formulation ER10 under Fasting Conditions and After High-Fat Meal

| PK Parameter | Units | Regimen B (ER10, fasting) (n = 24) | Regimen C (ER10, high fat meal) (n = 12) |
|---|---|---|---|
| $AUC_t$ | ng · h/mL | 473 (24) | 605 (23) |
| $AUC_{inf}$ | ng · h/mL | 484 (24) | 609 (23) |
| $t_{1/2}$[b] | hours | 10.1 (50) | 9.1 (35) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 14 formulation (ER10) administered after a high-fat meal relative to administration under fasting conditions was also determined based on analysis of the natural logarithms of $C_{max}$, $AUC_t$, and $AUC_{inf}$. The results are summarized in Table 17E below.

TABLE 17E

Bioavailability of Single Dose of the 30 mg Once-Daily Tablet ER10 Administered after High-Fat Meal Relative to under Fasting Conditions

| | | Relative Bioavailability | |
|---|---|---|---|
| | PK Parameter | Point Estimate | 90% Confidence Interval |
| Regimen C (ER10, high-fat meal) | $C_{max}$ | 1.322 | 1.134-1.541 |
| | $AUC_t$ | 1.296 | 1.194-1.405 |
| vs. | $AUC_{inf}$ | 1.278 | 1.174-1.392 |
| Regimen B (ER10, fasting) | | | |

As can be seen from this data, a high-fat meal increased the $C_{max}$ and $AUC_{inf}$ for the ER10 formulation (30 mg active, 30% tartaric acid) by about 32% and 28%, respectively.

Effect of a High-Fat Meal on Example 38 Formulation (ER11)

The effect of a high-fat meal on the pharmacokinetic parameters of the Example 15 (ER11, 30 mg, 20% tartaric acid) formulation is summarized in Table 17F.

TABLE 17F

Mean (% CV)[c] Pharmacokinetic Parameters for Compound 1 Following Administration of Single 30 mg Dose of the Once-Daily Tablet Formulation ER11 under Fasting Conditions and After High-Fat Meal

| PK Parameter | Units | Regimen D (ER11, fasting) (n = 24) | Regimen E (ER11, high fat meal) (n = 12) |
|---|---|---|---|
| $C_{max}$ | ng/mL | 61.0 (25) | 82.2 (33) |
| $T_{max}$[a] | hours | 2.0 (1.0-4.0) | 4.0 (3.0-8.0) |
| $AUC_t$ | ng·h/mL | 487 (22) | 648 (24) |
| $AUC_{inf}$ | ng·h/mL | 499 (22) | 657 (24) |
| $t_{1/2}$[b] | hours | 9.0 (61) | 9.7 (53) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 15 formulation (ER11) administered after a high-fat meal relative to administration under fasting conditions was also determined based on analysis of the natural logarithms of $C_{max}$, $AUC_t$, and $AUC_{inf}$. The results are summarized in Table 17G below.

TABLE 17G

Bioavailability of Single Dose of the 30 mg Once-Daily Tablet ER11 Administered after High-Fat Meal Relative to under Fasting Conditions

| | PK Paramenter | Relative Bioavailability | |
|---|---|---|---|
| | | Point Estimate | 90% Confidence Interval |
| Regimen E (ER11, high-fat meal) vs. Regimen D (ER11, fasting) | $C_{max}$ | 1.343 | 1.153-1.563 |
| | $AUC_t$ | 1.305 | 1.204-1.415 |
| | $AUC_{inf}$ | 1.285 | 1.181-1.398 |

As can be seen from this data, a high-fat meal increased the $C_{max}$ and $AUC_{inf}$ for the ER11 formulation (30 mg active, 20% tartaric acid) by about 34% and 29%, respectively, which was a similar food effect as that observed for the Example 14 (ER10) tablet.

Effect of a High-Fat Meal on Example 16 Formulation (ER12)

The effect of a high-fat meal on the pharmacokinetic parameters of the Example 16 (ER12, 30 mg active, 10% tartaric acid) formulation is summarized in Table 17H.

TABLE 17H

Mean (% CV)[c] Pharmacokinetic Parameters for Compound 1 Following Administration of Single 30 mg Dose of the Once-Daily Tablet Formulation ER12 under Fasting Conditions and After High-Fat Meal

| PK Parameter | Units | Regimen E (ER12, fasting) (n = 24) | Regimen G (ER12, high fat meal) (n = 12) |
|---|---|---|---|
| $C_{max}$ | ng/mL | 58.6 (34) | 84.2 (33) |
| $T_{max}$[a] | hours | 2.0 (1.0-4.0) | 4.0 (4.0-6.0) |
| $AUC_t$ | ng·h/mL | 481 (23) | 615 (24) |
| $AUC_{inf}$ | ng·h/mL | 495 (23) | 622 (23) |
| $t_{1/2}$[b] | hours | 9.3 (63) | 11.7 (91) |

[a]Median (minimum-maximum)
[b]Harmonic mean (pseudo-% CV)
[c]Data in parentheses is coefficient of variance of the PK parameter (% CV), unless otherwise indicated.

The relative bioavailability for a single dose of the Example 16 formulation (ER12) administered after a high-fat meal relative to administration under fasting conditions was also determined based on analysis of the natural logarithms of $C_{max}$, $AUC_t$, and $AUC_{inf}$. The results are summarized in Table 17I below.

TABLE 17I

Bioavailability of Single Dose of the 30 mg Once-Daily Tablet ER12 Administered after High-Fat Meal Relative to under Fasting Conditions

| | PK Paramenter | Relative Bioavailability | |
|---|---|---|---|
| | | Point Estimate | 90% Confidence Interval |
| Regimen G (ER12, high-fat meal) vs. Regimen F (ER12, fasting) | $C_{max}$ | 1.527 | 1.314-1.774 |
| | $AUC_t$ | 1.295 | 1.196-1.402 |
| | $AUC_{inf}$ | 1.272 | 1.171-1.381 |

As can be seen from this data, a high-fat meal increased the $C_{max}$ and $AUC_{inf}$ for the ER12 formulation (30 mg active, 10% tartaric acid) by about 53% and 27%, respectively.

Example 30: Predicted Pharmacokinetic Parameters for 15 mg Extended Release Tablets The mean pharmacokinetic parameters under fasting conditions for the once daily (QD) 15 mg extended release tablets prepared in Examples 17 (ER13), 18 (ER14), and 19 (ER15) using wet granulation were extrapolated from the single dose data obtained in Example 29 for the Examples 14 (ER10), 15 (ER11), and 16 (ER12) formulations, respectively, under fasting conditions. The results are set forth in Table 18A.

TABLE 18A

Predicted Mean Pharmacokinetic Parameters under Fasting Conditions for Compound 1 Following Administration of Single 15 mg Once-Daily Formulations (Extrapolated from Single-Dose Profiles in Example 52 for 30 mg Doses)

| PK Parameters | Units | Single 15 mg Dose (ER 13) | Single 15 mg dose (ER14) | Single 15 mg dose (ER15) |
|---|---|---|---|---|
| $C_{max}$ | ng/mL | 27.9 | 30.5 | 29.3 |
| $T_{max}$[a] | h | 3.0 | 2.0 | 2.0 |
| $AUC_{inf}$ | ng·h/mL | 242 | 250 | 248 |

[a]Median (minimum-maximum)

Example 31: A Phase 2/3 Ankylosing Spondylitis Clinical Study (SELECT-AXIS 1)

Figure 1:
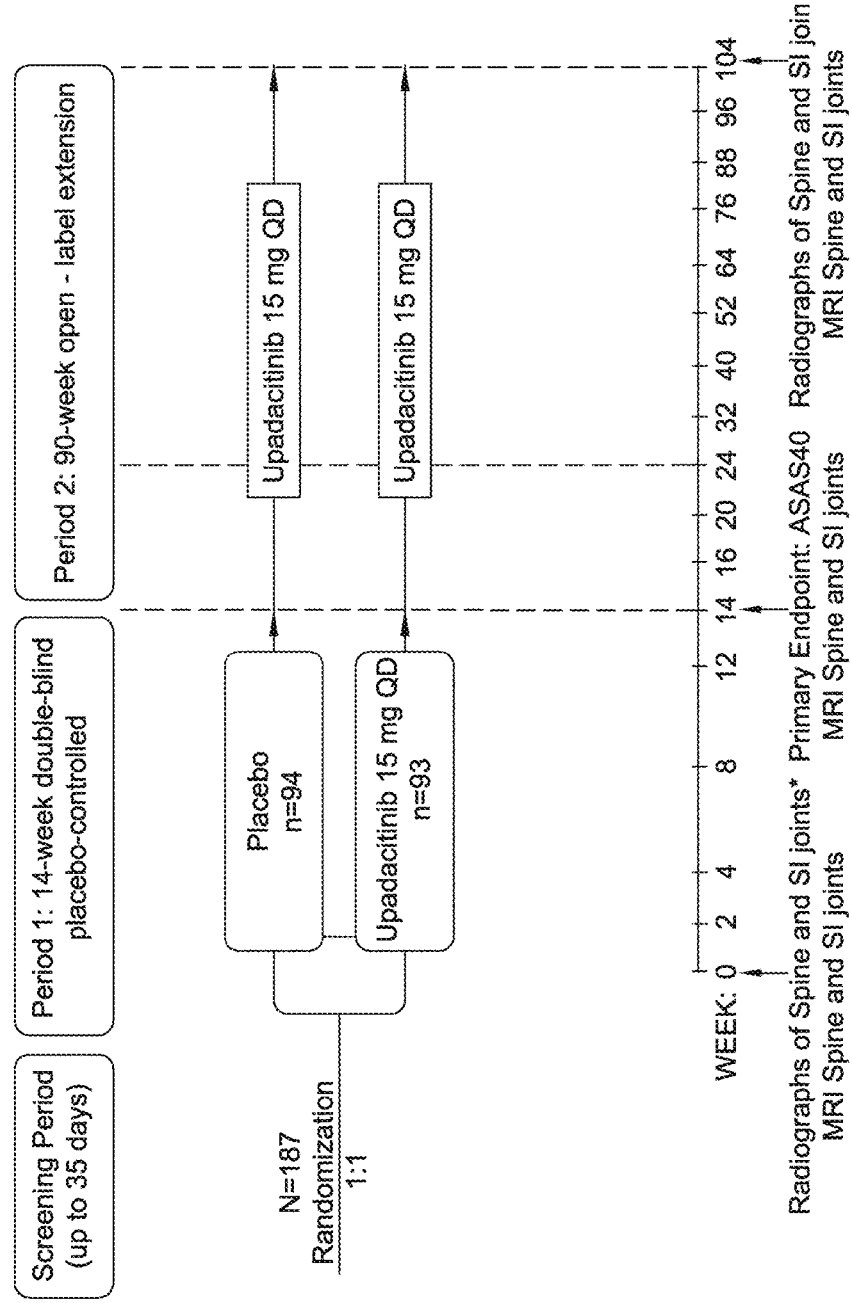
FIG. 1 depicts the Phase 2/3 Ankylosing Spondylitis (SELECT-AXIS 1) clinical study plan. Asterisk (*) indicates radiographs were conducted during the screening period. ASAS40=Assessment of SpondyloArthritis international Society 40% response. MRI=magnetic resonance imaging. QD=once daily. SI=sacroiliac.

SELECT-AXIS 1 is a multicentre, randomised, double-blind, parallel-group, placebo-controlled, Phase 2/3, two-period study of upadacitinib (FIG. 1). 15 mg upadacitinib refers to the 15 mg once-daily (QD) upadacitinib Extended Release (ER) Wet Granulated Tablets drug product as described herein are provided in the following Table 19A. The 15 mg upadactinib ER tablet (or matching placebo) is taken orally once daily, beginning on Day 1 (Baseline), and should be taken at approximately the same time each day, with or without food.

TABLE 19A

Upadacitinib 15 mg Extended Release (ER) Tablets (Wet Granulated)

| Component | Function | Weight |
|---|---|---|
| Tablet Core | | |
| *Intragranular* | | |
| Upadacitinib* | Drug substance | 15.4 |
| Microcrystalline cellulose (≥65% through 75 um screen) (Avicel PH 102) | Filler | 41.2 |
| Hypromellose 2208 | Control release polymer and binder | 4.9 |
| Purified water | Wetting agent | N/A |
| *Extragranular* | | |
| Microcrystalline cellulose (≥65% through 75 um screen) (Avicel PH 102) | Filler | 121.3 |
| Mannitol (Pearlitol 100 SD) | Filler | 100.6 |
| Tartaric acid powder | pH modifier | 96.0 |
| Hypromellose 2208 | Control release polymer | 91.1 |
| Colloidal Silicon Dioxide | Glidant | 2.4 |
| Magnesium Stearate | Lubricant | 7.2 |
| Film Coat | | |
| OPADRY II Yellow (PVA, TiO$_2$, PEG3350, Talc, Iron Oxide Yellow) | Film coat | 14.40 |
| Purified water** | Processing Aid | N/A |

*hemihydrate upadacitinib free base Form C as disclosed in WO2017066775 and WO 2018/165581 is used. 15 mg amount per tablet refers to the amount of anhydrous upadacitinib free base in the tablet;
**removed during processing.

Period 1 is the 14-week randomized, double-blind, parallel-group, placebo-controlled period designed to compare the safety and efficacy of upadacitinib free base 15 mg QD (once daily) versus placebo for the treatment of signs and symptoms of subjects with active AS who have had an inadequate response to at least two NSAIDs over an at least 4-week period in total at maximum recommended or tolerated doses or intolerance to or a contraindication for NSAIDs, and who are biologic Disease Modifying Anti-Rheumatic Drug (bDMARD)-naïve.

Period 2 is an open label long-term extension to evaluate the long-term safety, tolerability, and efficacy of upadacitinib free base 15 mg QD in subjects with AS who have completed Period 1.

X-rays of the pelvis were performed within the 35-day screening period to evaluate the SI joints to confirm the fulfillment of the modified New York Criteria for AS. X-rays of the spine were also performed within the 35-day screening period to assess for total spinal ankylosis; subjects with total spinal ankylosis were not eligible for this study. The x-rays of the spine and pelvis were not required during the Screening Period if the subject had a previous anteroposterior (AP) pelvis x-ray and lateral spine x-rays within 90 days of the Screening Period, provided that the x-rays are confirmed to be adequate for the required evaluations and are deemed acceptable by the central imaging vendor.

Subjects who met eligibility criteria were randomized in a 1:1 ratio to one of two treatment groups:
  Group 1: Upadacitinib free base 15 mg QD, N=85 (Day 1 to Week 14)→Upadacitinib free base 15 mg QD (Week 14 and thereafter)
  Group 2: Placebo, N=85 (Day 1 to Week 14)→Upadacitinib free base 15 mg QD (Week 14 and thereafter)

Starting at Week 16, subjects who did not achieve at least an ASAS 20 response at two consecutive visits had the option to add or modify doses of NSAIDs, acetaminophen/paracetamol, low potency opioid medications (tramadol or combination of acetaminophen and codeine or hydrocodone), and/or modify dose of MTX or SSZ at Week 20 or thereafter.

Starting at Week 24, subjects who still did not achieve at least an ASAS 20 response at two consecutive visits were discontinued from study drug treatment.

Subjects who completed the Week 14 visit (end of Period 1) entered the open-label long-term extension portion of the study, Period 2 (90 weeks). Subjects who were assigned to Upadacitinib in Period 1 continued to receive Upadacitinib free base 15 mg QD in an open-label manner. Subjects who were randomized to placebo at Baseline also received open-label upadacitinib free base 15 mg QD at Week 14.

Main Inclusion Criteria:
1. Male or female ≥18 years of age.
2. Subject with a clinical diagnosis of AS and meeting the modified New York Criteria for AS.
3. Subject must have baseline disease activity as defined by having a Bath Ankylosing Spondylitis Disease Activity Index (BASDAI) score ≥4 and a Patient's Assessment of Total Back Pain score (Total Back Pain score) ≥4 based on a 0-10 Numeric Rating Scale (NRS) at the Screening and Baseline Visits.
4. Subject has had an inadequate response to at least two NSAIDs over an at least 4-week period in total at maximum recommended or tolerated doses, or subject has an intolerance to or contraindication for NSAIDs.
5. If entering the study on concomitant methotrexate (MTX), leflunomide, sulfasalazine (SSZ), and/or hydroxychloroquine, subject must be on a stable dose of MTX (≤25 mg/week) and/or SSZ (≤3 g/day) and/or hydroxychloroquine (≤400 mg/day) or leflunomide (≤20 mg/day) for at least 28 days prior to the Baseline Visit. A combination of up to two background conventional-synthetic disease modifying anti-rheumatic drugs (csDMARDs) is allowed EXCEPT the combination of MTX and leflunomide.
6. If entering the study on concomitant oral corticosteroids, subject must be on a stable dose of prednisone (≤10 mg/day), or oral corticosteroid equivalents, for at least 14 days prior to the Baseline Visit.
7. If entering the study on concomitant NSAIDs, tramadol, combination of acetaminophen and codeine or hydrocodone, and/or non-opioid analgesics, subject must be on stable dose(s) for at least 14 days prior to the Baseline Visit.

Main Exclusion Criteria:
1. Patients with total spinal ankylosis were ineligible.
2. Prior exposure to any Janus kinase (JAK) inhibitor (including but not limited to tofacitinib, baricitinib, and filgotinib).
3. Prior exposure to any biologic therapy with a potential therapeutic impact on spondyloarthritis (SpA).
4. Intra-articular joint injections, spinal/paraspinal injection(s), or parenteral administration of corticosteroids within 28 days prior to the Baseline Visit. Inhaled or topical corticosteroids are allowed.
5. Subject on any other DMARDs (other than those allowed), thalidomide, or apremilast within 28 days or five half-lives (whichever is longer) of the drug prior to the Baseline Visit.
6. Subject on opioid analgesics (except for combination acetaminophen/codeine or acetaminophen/hydrocodone which are allowed) or use of inhaled marijuana within 14 days prior to the Baseline Visit.

7 Subject has a history of inflammatory arthritis of different etiology other than axial SpA (including but not limited to rheumatoid arthritis [RA], psoriatic arthritis [PsA], mixed connective tissue disease, systemic lupus erythematosus, reactive arthritis, scleroderma, polymyositis, dermatomyositis, fibromyalgia), or any arthritis with onset prior to 17 years of age.

Primary Endpoint

The primary efficacy endpoint is ASAS 40 response at Week 14.

Key Secondary Endpoints

The key multiplicity adjusted secondary efficacy endpoints at Week 14 are:
1. Change from Baseline in Ankylosing Spondylitis Disease Activity Score (ASDAS(CRP));
2. Change from Baseline in MRI Spondyloarthritis Research Consortium of Canada (SPARCC) score (Spine);
3. Proportion of subjects with BASDAI 50 response (defined as 50% improvement in the Bath AS Disease Activity Index);
4. Change from Baseline in AS quality of life (ASQoL);
5. Proportion of subjects with ASAS partial remission (PR) (defined as an absolute score of ≤2 units for each of the four domains identified in ASAS 40);
6. Change from Baseline in BASFI;
7. Change from Baseline in $BASMI_{lin}$;
8. Change from Baseline in Maastricht Ankylosing Spondylitis Enthesitis Score (MASES) (i.e., for subjects with baseline enthesitis);
9. Change from Baseline in Work Productivity and Activity Impairment (WPAI) (the overall work impairment due to SpA);
10. Change from Baseline in ASAS HI.

Additional key secondary endpoints are:
11. ASAS 20 response at Week 14.
12. Change from Baseline in MRI SPARCC score (SI joints) at Week 14.

Additional endpoints are the following measurements assessed in subjects treated with upadacitinib versus placebo at scheduled time points other than those specified for the primary and key secondary variables:
1. Proportion of subjects with ASAS 20 response;
2. Proportion of subjects with ASAS 40 response;
3. Proportion of subjects with ASAS PR;
4. Proportion of subjects with ASAS 5/6 (20% improvement from Baseline in five out of the following six domains: BASFI, patient's assessment of total back pain, PtGA, inflammation [mean of Questions 5 and 6 of the BASDAI] lateral lumbar flexion from BASMIlin, and high sensitivity CRP [hsCRP]);
5. Proportion of subjects with Inactive Disease based on ASDAS(CRP) and ASDAS(ESR) (ASDAS score <1.3);
6. Proportion of subjects with Major Improvement based on ASDAS(CRP) and ASDAS(ESR) (a change from Baseline <−2.0);
7. Proportion of subjects with Clinically Important Improvement based on ASDAS(CRP) and ASDAS (ESR) (a change from Baseline ≤−1.1);
8. Proportion of subjects with Resolution of dactylitis (i.e., for subjects with baseline presence of dactylitis);
9. Change from Baseline in ASAS HI;
10. Change from Baseline in ASDAS(CRP) and ASDAS (ESR) respectively;
11. Change from Baseline in AsQoL;
12. Change from Baseline in BASDAI;
13. Change from Baseline in BASFI;
14. Change from Baseline in BASMIlin;
15. Change from Baseline in CRP;
16. Change from Baseline in Total dactylitis count (i.e., for subjects with baseline presence of dactylitis);
17. Change from Baseline in FACIT-F;
18. Change from Baseline in ISI;
19. Change from Baseline in MASES (i.e., for subjects with baseline MASES >0);
20. Change from Baseline in Modified Stoke Ankylosing Spondylitis Spine Score (mSASSS) score with conventional radiograph;
21. Change from Baseline in MRI SPARCC score of SI joints;
22. Change from Baseline in MRI SPARCC score of Spine;
23. Change from Baseline in Patient's Assessment of Total Back Pain NRS score 0-10;
24. Change from Baseline in Patient's Assessment of Nocturnal Back Pain NRS score 0-10;
25. Change from Baseline in Patient's Global Assessment of Pain NRS score 0-10;
26. Change from Baseline in Physician's Global Assessment of Disease Activity NRS score 0-10;
27. Change from Baseline in Inflammation (mean of Questions 5 and 6 of BASDAI NRS scores 0-10);
28. Change from Baseline in Patient's assessment of total back pain (BASDAI Question 2 NRS score 0-10);
29. Change from Baseline in Peripheral pain/swelling (BASDAI Question 3 NRS score 0-10);
30. Change from Baseline in Duration of morning stiffness (BASDAI Question 6 NRS score 0-10);
31. Change from Baseline in Patient's Global Assessment of Disease Activity NRS score 0-10;
32. Change from Baseline in TJC68 and SJC66;
33. Change from Baseline in WPAI (all 4 dimension scores);
34. Change from Baseline in Categories in ISI. See, e.g., Machado et al., *Ann Rheum Dis* (2018) 77: 1539-40; Maksymowych et al., *Arthritis Rheum* (2005) 53: 502-9.

Analysis Windows

For each protocol-specified study visit, a target study day will be identified to represent the corresponding visit along with a window around the target day. Windows will be selected in a non-overlapping fashion so that a collection date does not fall into multiple visit windows. If a subject has two or more actual visits in one visit window, the visit closest to the target day will be used for analysis. If two visits are equidistant from the target day, then the later visit will be used for analysis.

Statistical Analyses

The planned sample size of 170 for this study (with 1:1 randomisation ratio) was determined to provide ≥90% power for detecting a 26% difference in ASAS40 response rate (assuming a placebo ASAS40 response rate of 20%). Power and sample size calculations were performed at a two-sided significance level of 0.05 accounting for a 10% dropout rate. The full analysis set included all randomised patients who received at least one dose of study drug. The safety analysis set included all patients who received at least one dose of study drug. The SPARCC MRI assessment population was pre-specified in the statistical analysis plan (baseline included MRI data ≤3 days after first dose of study drug, and week 14 included MRI data up to first dose of Period 2 study drug; first dose in Period 2 was at week 14). A supplemental post hoc SPARCC MRI analysis was conducted to include all MRI data collected at nominal visits at baseline and week 14. Cumulative probability plots were generated to illustrate MRI SPARCC score changes on a patient level.

Figure 2:
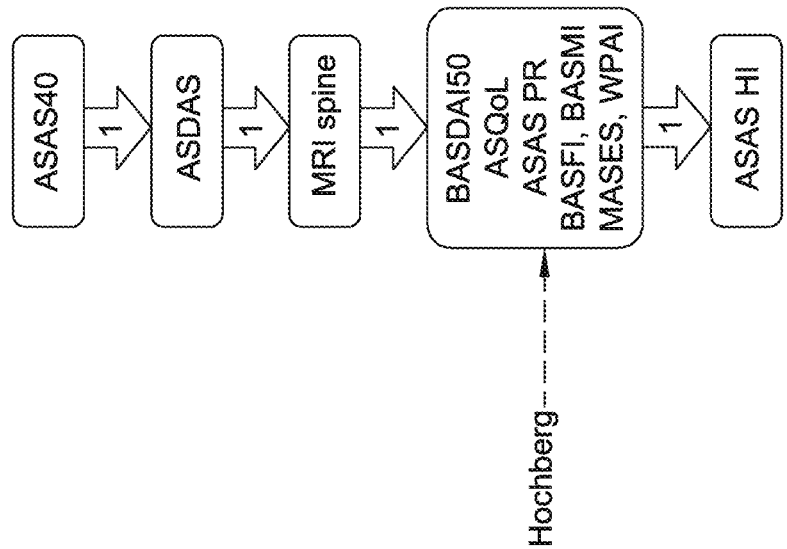
FIG. 2 depicts the multiplicity-controlled analysis used in the Phase 2/3 Ankylosing Spondylitis (SELECT-AXIS 1) clinical trial using the Hochberg Procedure. Asterisk (*) indicates result was statistically significant in multiplicity-controlled analysis, otherwise nominal p values are shown. The multiplicity-controlled endpoints are tested in a sequential manner with initially assigned a=0.05. Statistical significance (p<0.05) can be claimed for a lower ranked endpoint only if the previous endpoint in the sequence meets the requirements of statistical significance. ASAS HI can be evaluated only if the group of endpoints tested by Hochberg procedure are all statistically significant. Within the Hochberg procedure, BASDAI50, BASFI, and ASAS PR achieved the required statistical significance; however, WPAI, MASES, BASMI, and ASQoL did not meet the requirement of statistical significance, so ASAS HI was not tested. Per Hochberg procedure, all endpoints are tested using assigned a according to the magnitude of nominal p value starting from the largest one. If an endpoint is rejected, all endpoints with smaller p values are rejected. If an endpoint fails, then the procedure advances to the next endpoint. ASAS=Assessment of SpondyloArthritis International Society. ASAS40=ASAS 40% response. ASAS HI=ASAS Health Index. ASAS PR=ASAS Partial Remission. ASDAS=Ankylosing Spondylitis Disease Activity Score. ASQoL=Ankylosing Spondylitis Quality of Life. BASDAI50=50% improvement from baseline in Bath Ankylosing Spondylitis Disease Activity Index. BASFI=Bath Ankylosing Spondylitis Functional Index. BASMI=Bath Ankylosing Spondylitis Metrology Index. MASES=Maastricht Ankylosing Spondylitis Enthesitis Score. MRI=magnetic resonance imaging. QD=once daily. SPARCC=Spondyloarthritis Research Consortium of Canada. WPAI=Work Productivity and Activity Impairment.

In the full analysis set, the primary endpoint was compared between the upadacitinib and the placebo group using the Cochran-Mantel-Haenszel test, adjusting for the stratification factor of screening hsCRP level. Non-responder imputation was used for handling missing data. Similar analyses as for the primary endpoint were conducted for secondary efficacy binary endpoints. For continuous secondary efficacy endpoints, comparisons between the upadacitinib and the placebo group were performed using mixed model for repeated measures with treatment group, visit, and treatment-by-visit interaction as fixed effects and the corresponding baseline value and the stratification factor of screening hsCRP level as the covariates. In order to preserve the overall type I error rate at α=0.05 level, a step-down approach was used to test the primary and multiplicity-controlled key secondary endpoints. The testing sequence includes a group of endpoints tested by the Hochberg procedure, including BASDAI50, ASQoL, ASAS PR, BASFI, BASMI, MASES, and WPAI (FIG. 2). See, e.g., Hochberg Y, Tamhane A C. Multiple comparison procedures: John Wiley & Sons, Inc., 1987.

Week 14 Results

Between Oct. 24, 2017, and Sep. 10, 2018, 395 patients were assessed for eligibility, and 187 were enrolled into the study. Of the 395 patients screened, 208 (52.7%) did not meet eligibility criteria and were excluded from the study (main reason for screening failure was not meeting the radiographic criterion of the modified New York criteria for AS). The remaining 187 patients who met eligibility criteria were randomised to placebo (n=94) or upadacitinib (n=93). Overall, 95.2% of patients completed Period 1 through week 14 on study drug (placebo, 89/94 [94.7%]; upadacitinib, 89/93 [95.7%]); one patient in the placebo group discontinued study drug but completed Period 1 visits. The most common primary reason for study drug discontinuation by week 14 were adverse events in the placebo group (n=3 [3.2%]) and adverse events (n=2 [2.2%]) and withdrawal of consent (n=2 [2.2%]) in the upadacitinib group.

Mean age was 45.4 years, mean duration from onset of symptoms was 14.4 years, and mean duration since diagnosis was 6.9 years. Most patients were male (132 [70.6%]), were human leukocyte antigen (HLA) B27 positive (143 [76.5%]) and were receiving concomitant NSAIDs at baseline (150 [80.2%]). Baseline disease characteristics were generally balanced between the two groups. Key demographics and baseline characteristics of the patients are summarized in the below Table 19B.

TABLE 19B

Key demographics and baseline characteristics of patients

| Key Demographic and Baseline Characteristics Mean (SD) or n (%) | PLACEBO N = 94 | Upadacitinib 15 mg qd n = 93 |
|---|---|---|
| Male | 69 (73.4) | 63 (67.7) |
| Age (Yrs) | 44 (12.1) | 47 (12.8) |
| HLA-B27 Positive | 73 (77.7) | 70 (75.3) |
| White | 76 (80.9) | 79 (84.9) |
| Region | | |
| North America | 10 (10.6) | 9 (9.7) |
| South/Central America | 0 | 0 |
| Western Europe | 33 (35.1) | 30 (32.3) |

TABLE 19B-continued

Key demographics and baseline characteristics of patients

| Key Demographic and Baseline Characteristics Mean (SD) or n (%) | PLACEBO N = 94 | Upadacitinib 15 mg qd n = 93 |
|---|---|---|
| Eastern Europe | 34 (36.2) | 36 (38.7) |
| Asia[a] | 14 (14.9) | 12 (12.9) |
| Other[b] | 3 (3.2) | 6 (6.5) |
| Duration of AS Diagnosis (Yrs) | 6.0 (6.79) | 7.8 (10.64) |
| Duration of AS Symptom (Yrs) | 14.0 (9.86) | 14.8 (11.64) |
| NSAID Use at Baseline | 80 (85.1) | 70 (75.3) |
| Prior NSAID Use | 94 (100) | 92 (98.9) |
| csDMARDs Use at Baseline | 17 (18.1) | 13 (14.0) |
| BASDAI | 6.5 (1.56) | 6.3 (1.76) |
| Total back pain (NRS 0-10) | 6.7 (1.78) | 6.8 (1.77) |
| Patient Global Assessment (NRS 0-10) | 6.8 (1.66) | 6.6 (1.81) |
| ASDAS(CRP) | 3.7 (0.74) | 3.5 (0.76) |
| BASFI (Function) | 5.5 (2.17) | 5.4 (2.36) |
| BASMI (Mobility) | 3.5 (1.48) | 3.7 (1.45) |
| Presence of Enthesitis (MASES > 0) | 55 (58.5) | 54 (58.1) |
| MASES Score[c] | 3.7 (2.71) | 3.9 (2.79) |
| MRI Spine SPARCC[d] | 11.9 (14.52) | 10.4 (14.36) |
| MRI Sacroiliac Joint SPARCC[d] | 5.4 (8.55) | 7.9 (10.91) |
| hsCRP at Screening (mg/L) | 11.7 (11.11) | 9.6 (12.57) |
| hsCRP > ULN at Screening | 68 (72.3) | 67 (72.0) |
| AS QoL | 10.3 (4.65) | 10.0 (5.27) |
| WPAI - Overall Work Impairment[e] | 53.3 (24.64) | 54.3 (28.10) |
| ASAS Health Index | 8.2 (3.84) | 8.6 (4.12) |

[a]South Korea and Japan.
[b]New Zealand and Australia.
[c]Summarized for subjects with presence of enthesitis at baseline.
[d]Summarized for subjects whose baseline MRI data up to 3 days post first dose of study drug.
[e]Summarized for subjects employed at baseline.

Figure 3A:
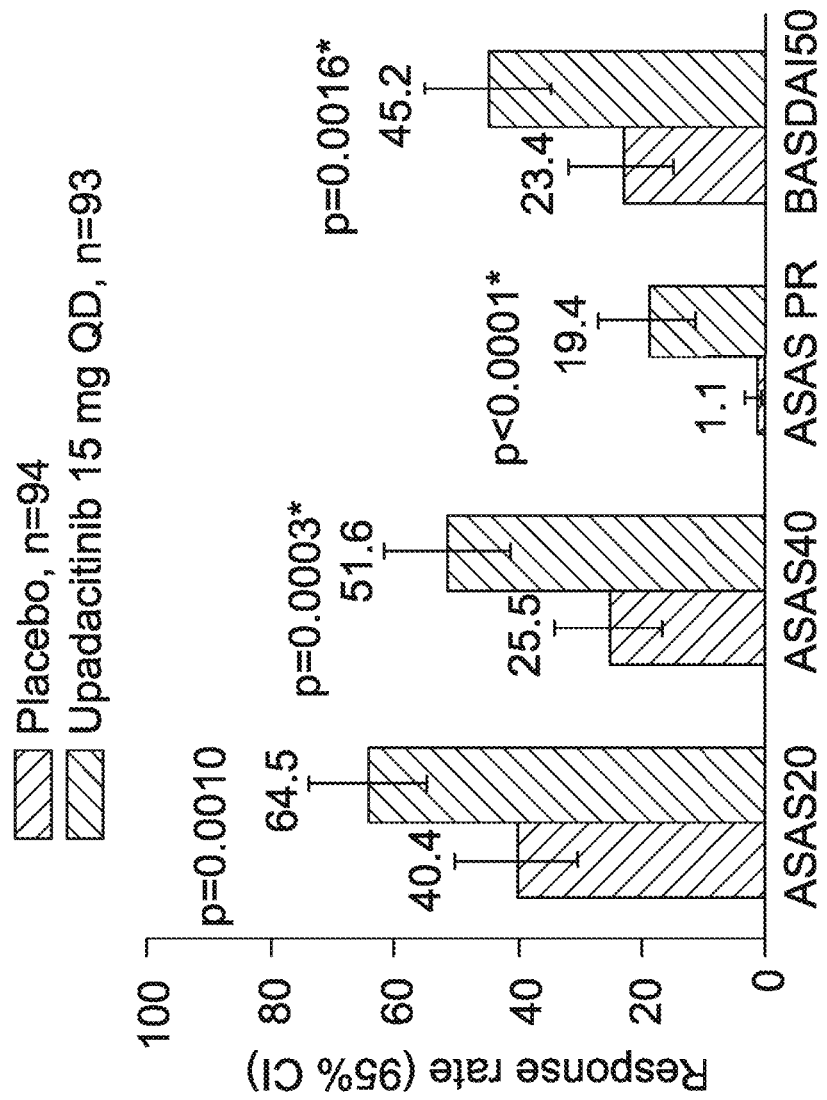

The study met its primary endpoint, with statistically significantly more patients treated with upadacitinib versus placebo achieving ASAS40 response at week 14 (48/93 [51.6%] vs 24/94 [25.5%]; p=0.0003) with a treatment difference (95% CI) of 26.1% (12.6-39.5%) (FIG. 3A). A significant difference for upadacitinib versus placebo in ASAS40 (FIG. 13A) and the mean change for each of its four individual domains (FIGS. 3B-3E) was observed as early as the first post-baseline visit (week 2), and this difference was maintained consistently through week 14, with week 14 achieving a statistically significant difference in the multiplicity-controlled analysis. Accounting for multiplicity adjustment, change from baseline to week 14 in ASDAS (CRP) (FIG. 3C), SPARCC MRI spine (FIG. 3B), and BASFI (FIG. 3C) and proportion of patients who achieved BASDAI50 (FIG. 3A) and ASAS PR (FIG. 3A) were statistically significant for upadacitinib versus placebo. Upadacitinib versus placebo mean (95% CI) change from baseline to week 14 was −1.45 (−1.62 to −1.28) versus −0.54 (−0.71 to −0.37; treatment difference, −0.91 [−1.14 to −0.68; p<0.0001]) for ASDAS (CRP) and −2.29 (−2.73 to −1.85) versus −1.30 (−1.74 to −0.86; treatment difference, −1.00 [−1.60 to −0.39; p=0.0013]) for BASFI. BASDAI50 was achieved by 42/93 (45.2%) patients treated with upadacitinib versus 22/94 (23.4%) patients in the placebo group (treatment difference, 21.8% [8.5-35.0%; p=0.0016]) and ASAS PR was achieved by 18/93 (19.4%) patients in the upadacitinib group versus 1/94 (1.1%) in the placebo group (treatment difference, 18.3% [10.0-26.6%; p<0.0001]).

For the other multiplicity-controlled key efficacy endpoints, statistical significance based on multiplicity adjustment was not met per the Hochberg procedure. Consistent improvement was observed in patients receiving upadacitinib versus placebo with nominal p values <0.05 for MASES (p=0.0488), BASMI (p=0.0296), ASQoL (p=0.0156), and ASAS HI (p=0.0073) at week 14, except for WPAI (FIG. 3C).

Figure 3B:
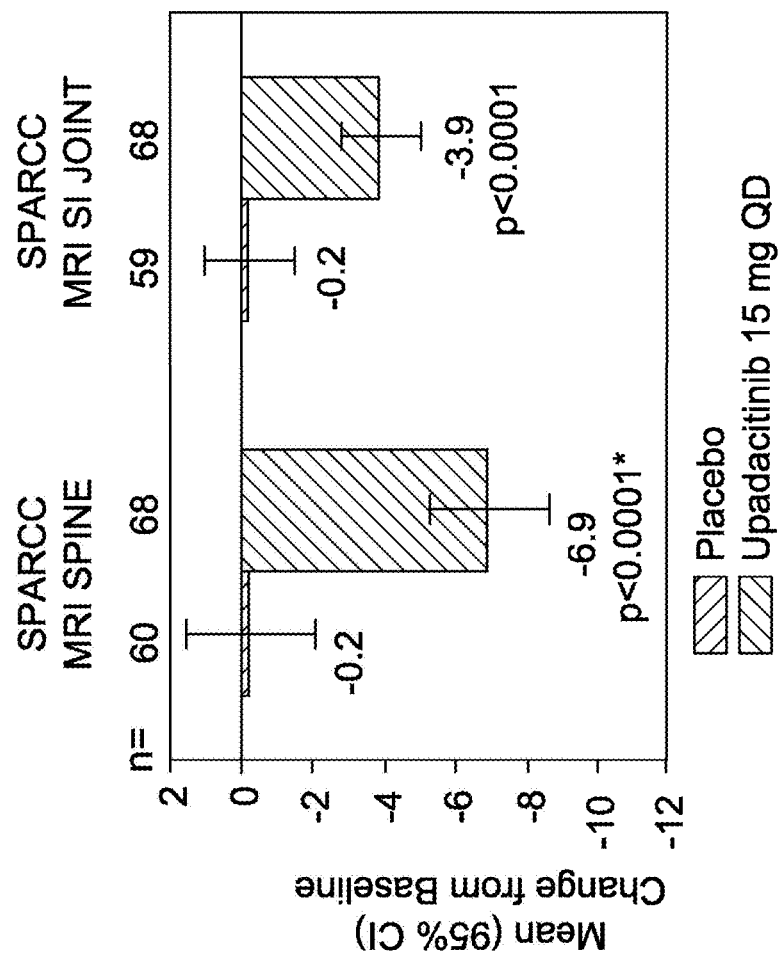
Figure 3C:
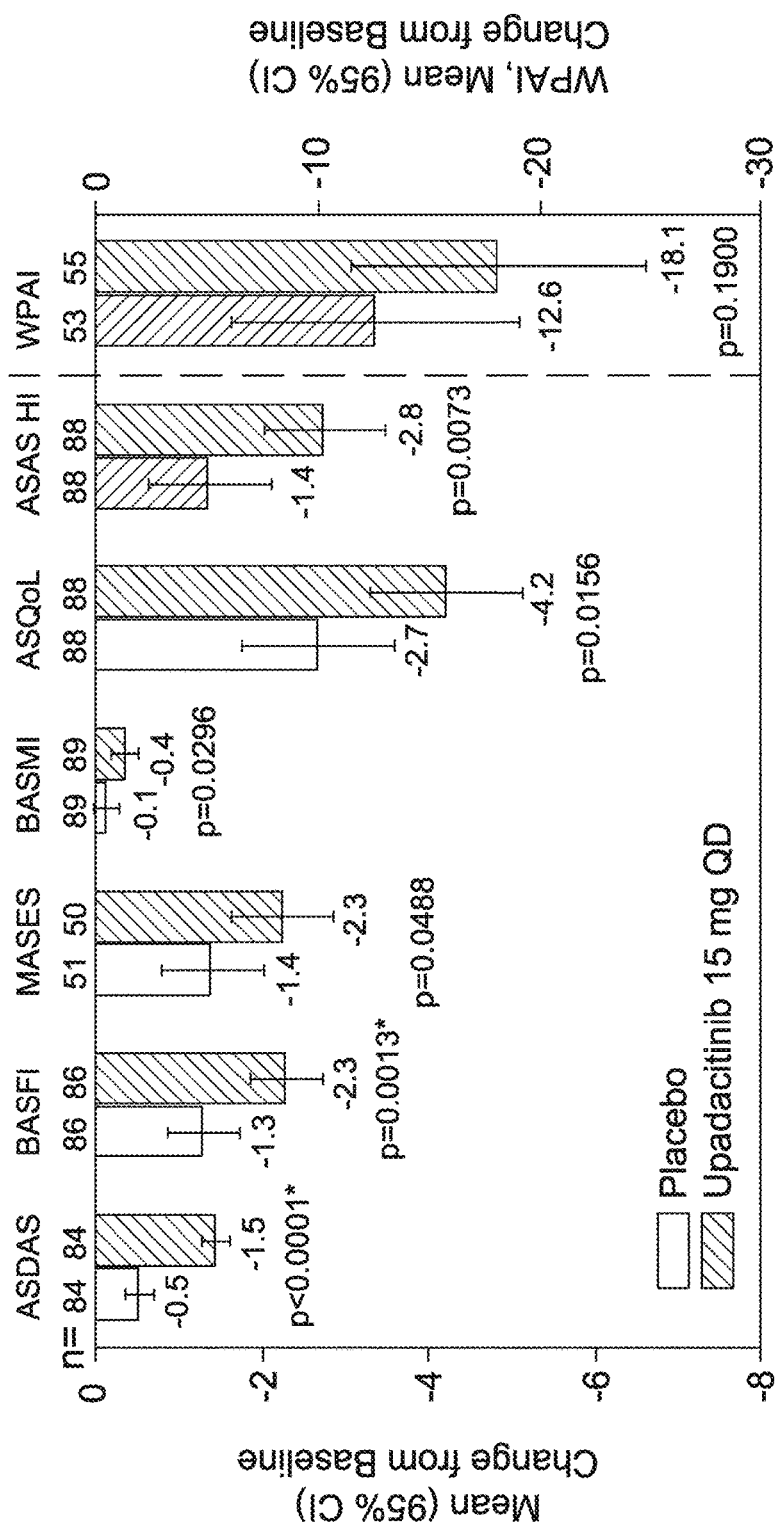

The additional key secondary efficacy endpoints, ASAS20 and SPARCC MRI SI joint score, also improved with upadacitinib versus placebo based on nominal p values (FIGS. 3A and 3B). ASAS20 was achieved by 60/93 (64.5%) patients treated with upadacitinib versus 38/94 (40.4%) of patients in the placebo group at week 14 (treatment difference, 24.1% [10.2-38.0%; p=0.0010]).

Figure 6B:
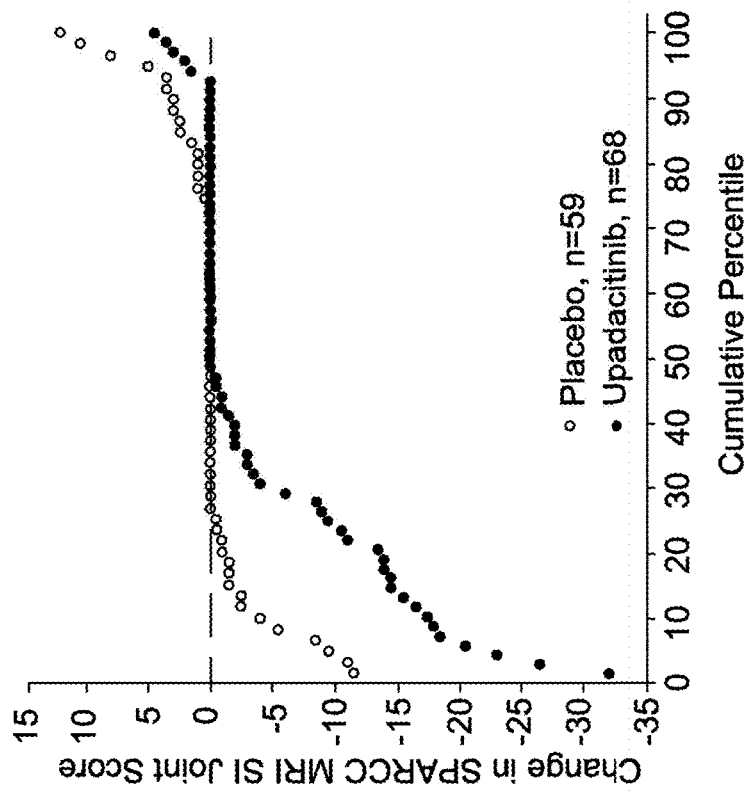
FIGS. 6A-6D depict the cumulative probability plots of change in SPARCC scores as described in FIG. 5 for the Phase 2/3 Ankylosing Spondylitis (SELECT-AXIS 1), demonstrating that the SPARCC MRI spine and SI joint scores improved from baseline to week 14 to a greater extent in patients receiving upadacitinib compared with placebo. Results for the primary MRI analyses (FIGS. 6A-6B) and supplemental MRI analyses (FIGS. 6C-6D) were consistent.
Figure 6A:
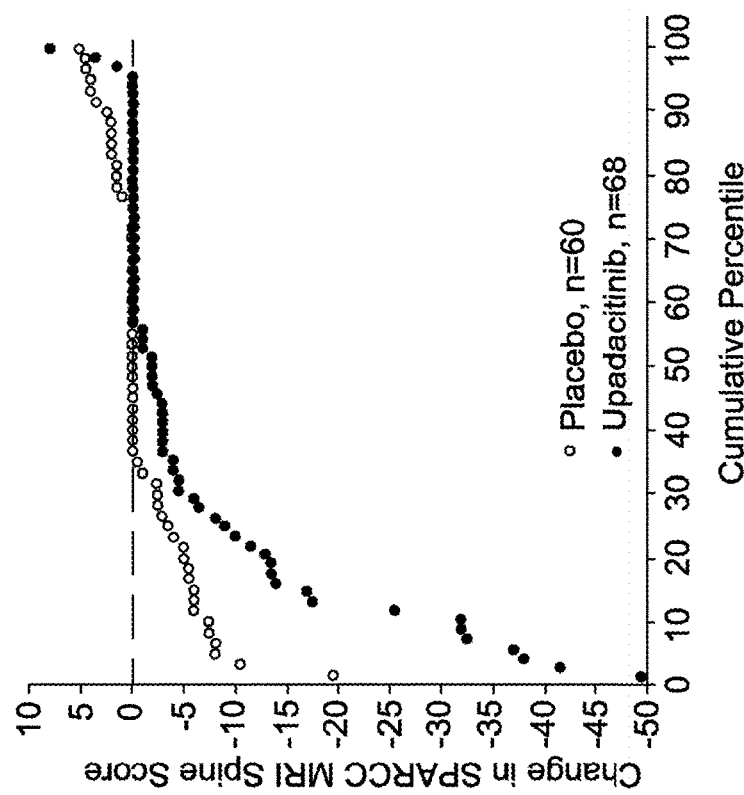
Figure 6D:
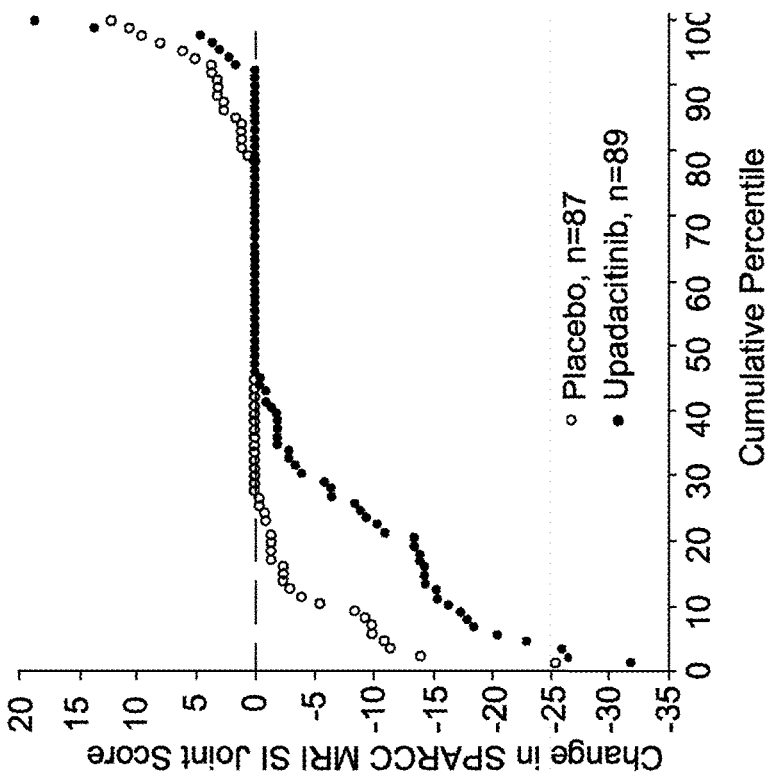
Figure 6C:
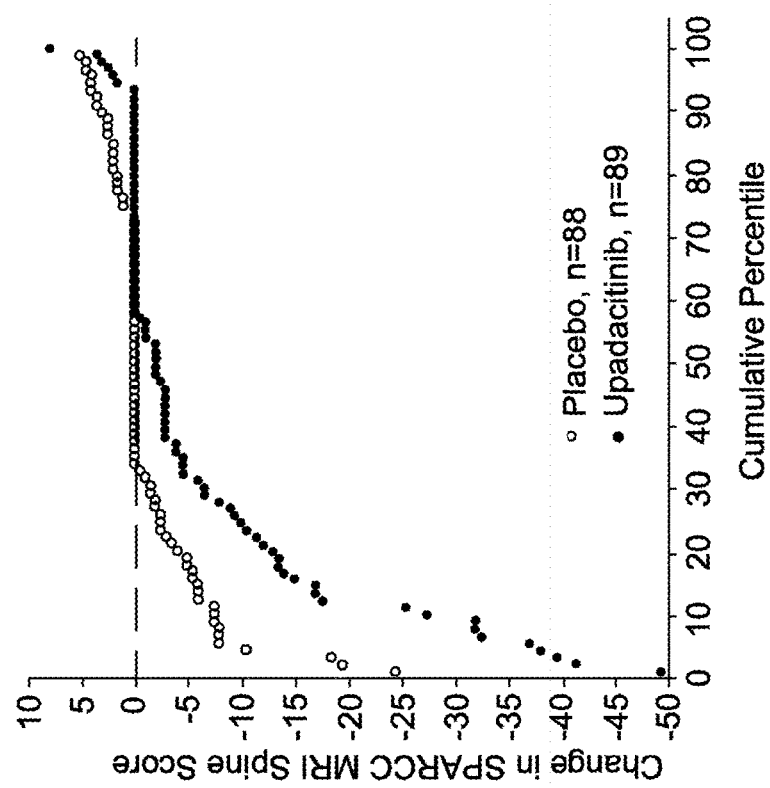

For the SPARCC MRI outcomes, change from baseline to week 14 in SPARCC MRI spine was −6.93 (−8.58 to −5.28) for upadacitinib versus −0.22 (−2.01 to 1.57) for placebo (treatment difference, −6.71 [−9.01 to −4.41; significant in multiplicity-controlled analysis, p<0.0001]) and change from baseline to week 14 in SPARCC MRI SI joint was −3.91 (−5.05 to −2.77) for upadacitinib versus −0.22 (−1.47 to −1.04) for placebo (treatment difference, −3.69 [−5.31 to −2.08; p<0.0001]; FIG. 3B). The supplemental MRI analysis conducted in all patients with available data confirmed the results of the primary SPARCC MRI analysis for both the spine and SI joints (FIG. 5). The cumulative probability plots of change in SPARCC scores demonstrated that SPARCC MRI spine and SI joint scores improved from baseline to week 14 to a greater extent in patients receiving upadacitinib compared with placebo; results for the primary MRI analyses (FIG. 6A-6B) and supplemental MRI analyses (FIG. 6C-6D) were consistent. Table 19C below summarizes the primary and key secondary efficacy endpoints at Week 14. Table 19D below provides additional efficacy measurements at Week 14.

TABLE 19C

Primary and Key Secondary Efficacy Endpoints at Week 14[a]

| | Endpoint | PLACEBO N = 94 | Upadacitinib 15 mg qd N = 93 |
|---|---|---|---|
| Primary | ASAS40 | 25.5% | 51.6% |
| Multiplicity Adjusted Key Secondary | ASDAS(CRP) | −0.54 | −1.45 |
| | MRI Spine SPARCC[b] | −0.22 | −6.93 |
| | BASDAI50 | 23.4% | 45.2% |
| | AS QoL | −2.7 | −4.2 |
| | ASAS Partial Remission | 1.1% | 19.4% |
| | BASFI (Function) | −1.30 | −2.29 |
| | BASMI (Mobility) | −0.1 | −0.4 |
| | MASES (Enthesitis)[c] | −1.4 | −2.3 |
| | WPAI - Overall Work Impairment[d] | −12.6 | −18.1 |
| | ASAS Health Index | −1.4 | −2.8 |
| Other Key Secondary | ASAS20 | 40.4% | 64.5% |
| | MRI SI Joints SPARCC[c] | −0.22 | −3.91 |

[a]Results for binary endpoints are based on NRI analysis. Analyses for all continuous endpoints are for the change from baseline value. Results for continuous endpoints are based on MMRM or ANCOVA analysis.
[b]Summarized for subjects whose baseline MRI data up to 3 days post first dose of study drug and week 14 data up to the first dose of period 2 study drug.
[c]Summarized for subjects with presence of enthesitis at baseline.
[d]Summarized for subjects employed at baseline.

Figure 7A:
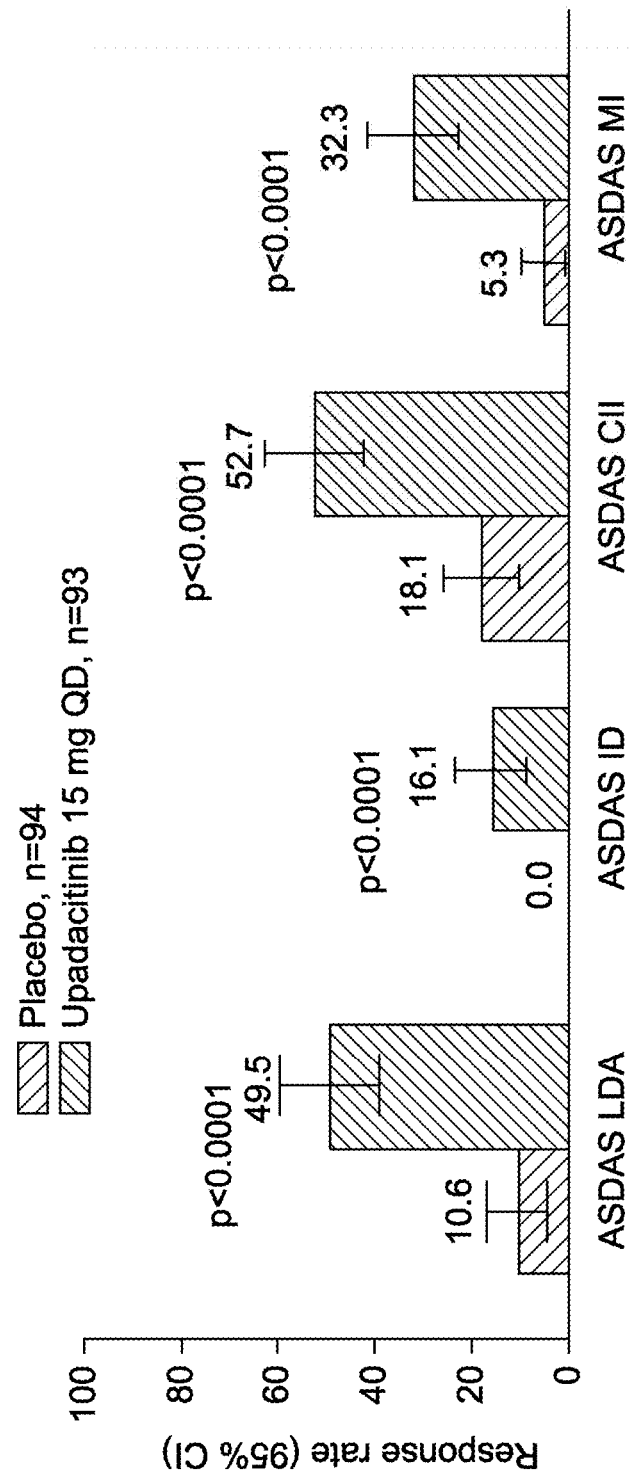
FIGS. 7A-7C depict the percentage of patients achieving ASDAS LDA, ASDAS ID, ASDAS CII, and ASDAS MI at Week 14 (FIG. 7A), Change From Baseline in Mean ASDAS Over Time (FIG. 7B), and ASDAS MI Over Time (FIG. 7C) in the Phase 2/3 Ankylosing Spondylitis (SELECT-AXIS 1) clinical trial. The proportions of patients who achieved ASDAS LDA, ASDAS ID, ASDAS CII, and ASDAS MI were greater (nominal p<0.0001) for upadacitinib freebase versus placebo at Week 14 (FIG. 7A). ASDAS=Ankylosing Spondylitis Disease Activity Score. BL=baseline. CII=Clinically Important Improvement (≥1.1-point decrease from baseline). ID=Inactive Disease (score <1.3). LDA=low disease activity (<2.1). MI=Major Improvement (≥2-point decrease from baseline). MMRM=mixed model for repeated measures. NRI=non-responder imputation. QD=once daily.
Figure 7B:
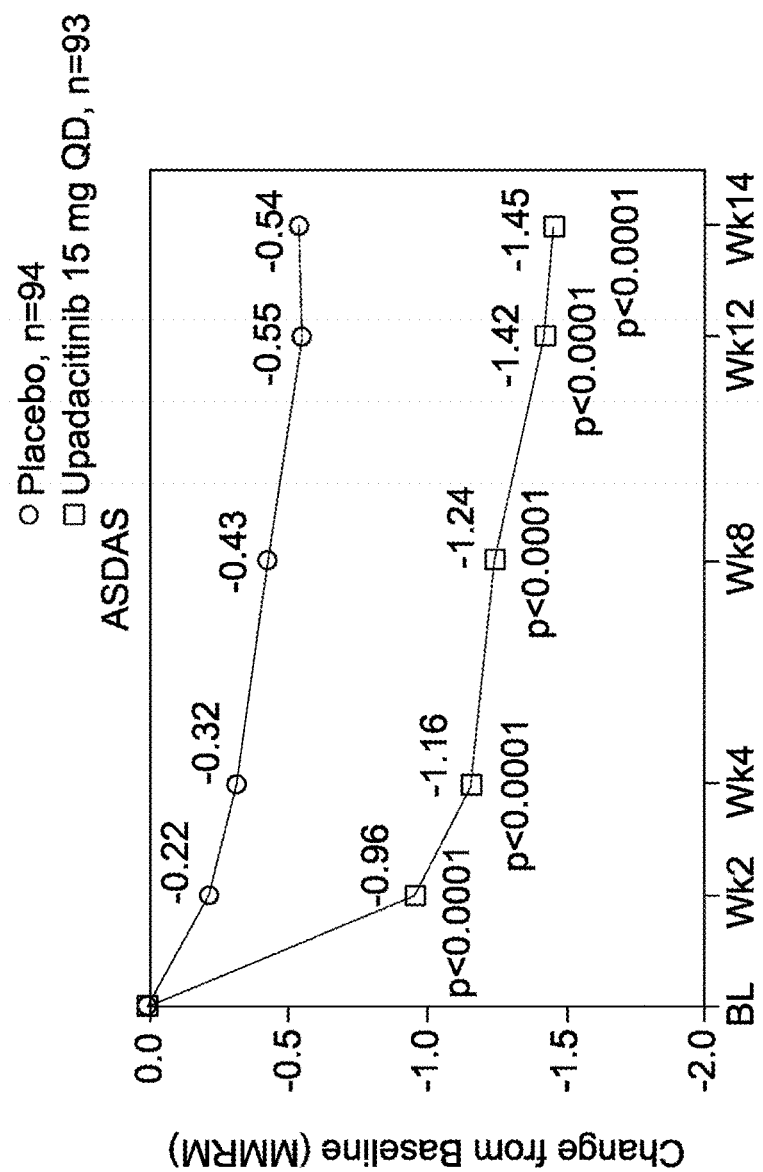
Figure 7C:
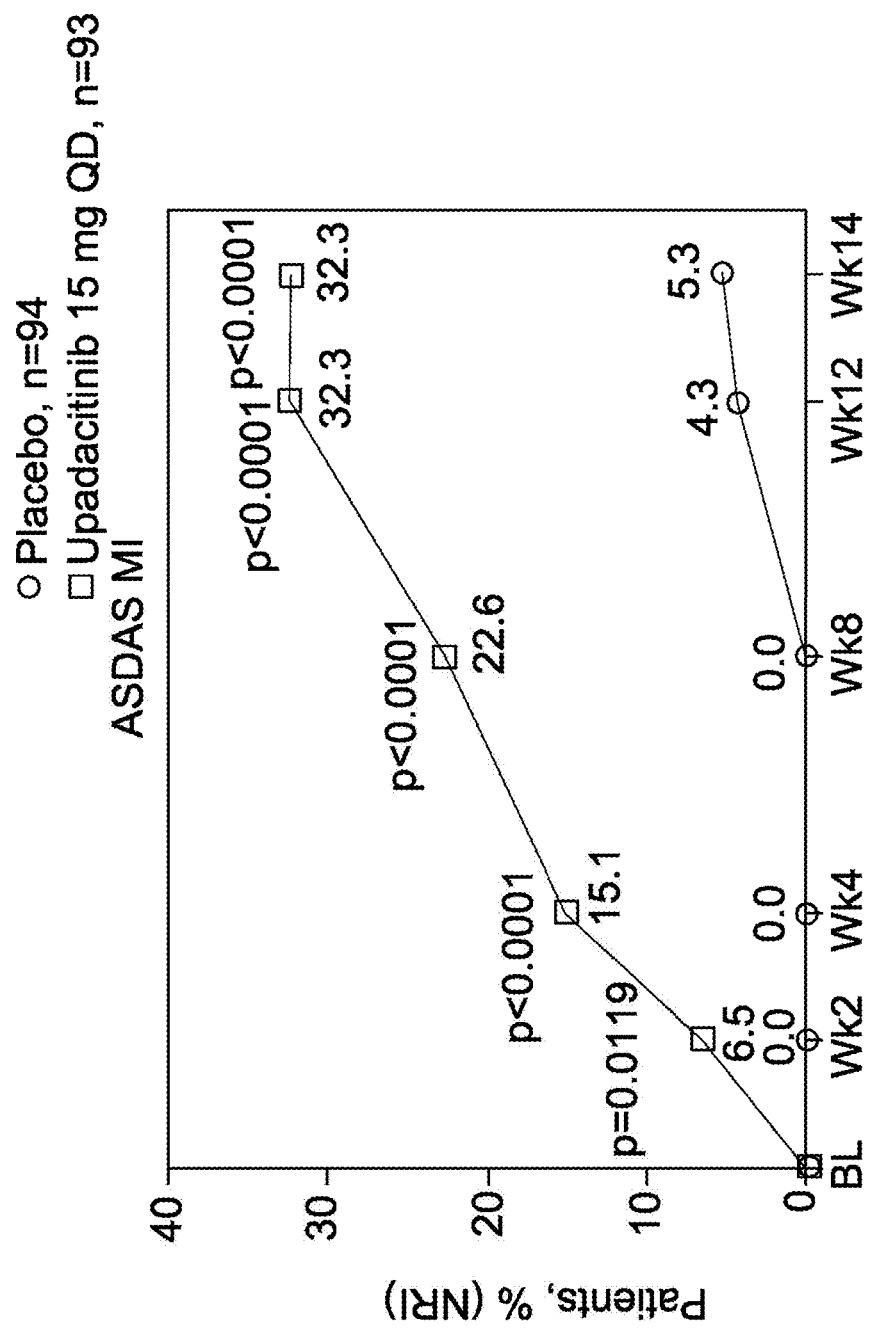
Figure 8B:
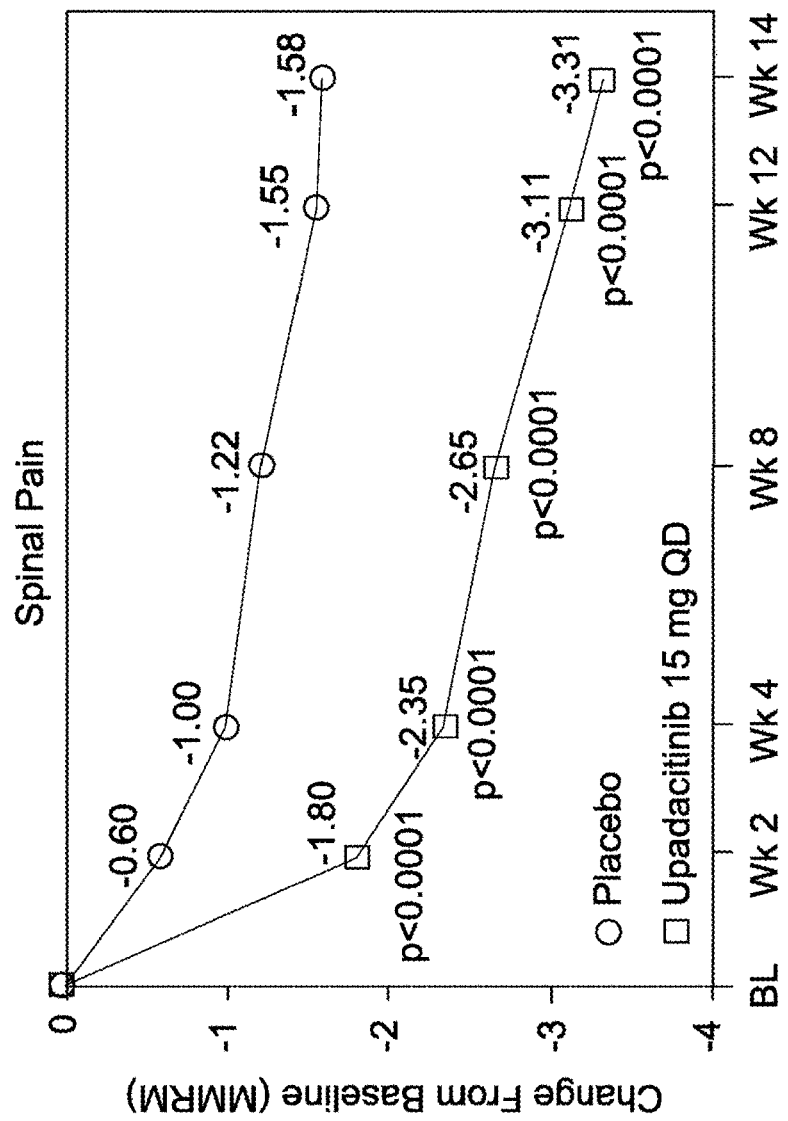
Figure 8C:
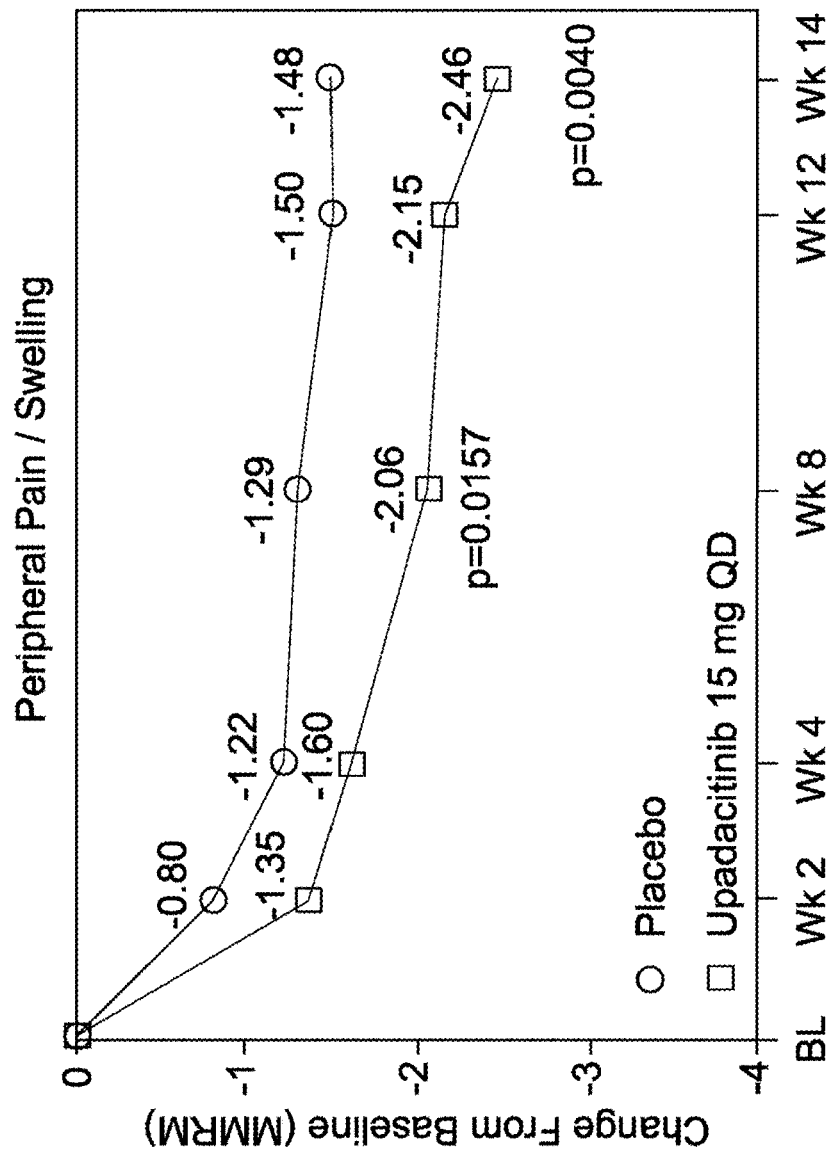

The proportions of patients who achieved ASDAS LDA, ASDAS ID, ASDAS CII, and ASDAS MI were greater (nominal p<0.0001) for upadacitinib versus placebo at week 14 (FIG. 7A). These results are summarized in the below Table 19D. Improvement in the mean ASDAS (FIG. 7B) and the individual ASDAS components (FIGS. 8A-8D) was seen as early as week 2 with continued improvement up to week 14 with upadacitinib.

TABLE 19D

Additional Efficacy Measurements at Week 14

| Endpoint | PLACEBO (N = 94) | Upadacitinib 15 mg qd (N = 93) |
|---|---|---|
| ASDAS ID | 0% | 16.1% |
| ASDAS LDA[a] | 10.6% | 49.5% |
| ASDAS MI | 5.3% | 32.3% |
| ASDAS CII | 18.1% | 52.7% |

[a]post-hoc analysis

Patients treated with the upadacitinib 15 mg QD dose showed greater improvement in back pain as assessed by the Total Back Pain component of ASAS response compared to placebo at Week 14. Improvement in the overall level of neck, back, or hip pain was demonstrated using BASDAI Question 2. Improvements were also demonstrated for peripheral pain and swelling (assessed by BASDAI question 3 on overall pain in joints other than in the neck, back, or hips) and nocturnal back pain. Improvements in total and nocturnal back pain were observed as early as Week 2.

No serious infections, herpes zoster, malignancy, venous thromboembolic events, or deaths were reported in Period 1. The proportion of patients with adverse events was higher in the upadacitinib group 58/93 (62.4%) versus placebo group 52/94 (55.3%). One serious adverse event in each group was reported during Period 1: cardiovascular disorder/circulation dysregulation in the placebo group (patient was not feeling well and was hospitalised but no significant findings were obtained) and worsening of spinal osteoarthritis in the upadacitinib group in a patient with a history of spondylosis and disc protrusion in the cervical spine. The proportion of patients with adverse events leading to discontinuation of study drug (upadacitinib, 2/93 [2.2%]; placebo, 3/94 [3.2%]) and infections (upadacitinib, 19/93 [20.4%]; placebo, 26/94 [27.7%]) was similar for both treatment groups. The most common adverse event in patients in the upadacitinib group was blood creatine phosphokinase (CPK), which increased (8/93 [8.6%] vs 2/94 [2.1%] patients in the placebo group), with four events (vs one with placebo) assessed by the investigator to be possibly related to study drug; all patients were asymptomatic with elevations <4×ULN, except for one patient in the placebo group with muscle pain and an increase to 4.3×ULN. Most of these events were reversible without study drug interruption (6/8 with upadacitinib, 1/2 with placebo). One patient in the upadacitinib group who already had grade 2 neutropenia at baseline experienced a mild adverse event of grade 2 neutropenia.

Seven patients reported hepatic disorder adverse events (upadacitinib, 5/93 [5.4%]; placebo, 2/94 [2.1%]); none resulted in study drug discontinuation, and all were asymptomatic alanine aminotransferase or aspartate aminotransferase increases, with associated elevations <2×ULN in 6/7 and an elevation <3×ULN in the remaining patient. No differences in mean haemoglobin levels were observed throughout the 14-week period in either group.

Increases from baseline to week 14 in low-density lipoprotein cholesterol (0.318 mmol/L) and high-density lipoprotein (HDL) cholesterol (0.263 mmol/L) were observed in the upadacitinib group versus the placebo group (−0.083 and 0.010 mmol/L, respectively); however, no changes in the total cholesterol/HDL ratio were observed (upadacitinib, −0.071 mmol/L; placebo, −0.083 mmol/L).

Week 14 Results Discussion

The SELECT-AXIS 1 is the first clinical trial of upadacitinib in AS and demonstrated consistent efficacy results supported by multiplicity-controlled endpoints. The study met its primary endpoint of ASAS40 response at week 14 (51.6% vs 25.5%) as well as several multiplicity-controlled secondary endpoints reflecting statistically significant improvement in disease activity (ASAS PR, BASDAI50, ASDAS), function (BASFI), and MRI outcomes (SPARCC MRI spine). The other multiplicity-controlled secondary endpoints did not meet significance in the multiplicity testing but demonstrated consistent improvements for ASQoL, BASMI, MASES, and ASAS HI, with upadacitinib versus placebo (nominal p<0.05), with the exception of WPAI.

A rapid onset of response to upadacitinib free base 15 mg QD treatment was observed for ASAS40 and ASDAS composite scores and their individual domains of disease activity (e.g., back pain, PtGA, morning stiffness, function, and serum markers of inflammation [hsCRP]), with responses observed as early as week 2 (first post-baseline visit) and consistently maintained through week 14. The results of upadacitinib on improving the signs and symptoms of AS are further confirmed by a significant reduction of active inflammation on MRI for both the spine and the SI joints.

In addition, outcomes related to clinically relevant treatment goals of remission or low disease activity, such as ASDAS ID or LDA, were also achieved, with 50% of patients reaching ASDAS LDA (difference vs placebo, 39%). See, e.g., Smolen et al., Ann Rheum Dis 2018; 77: 3-17. Of note, the placebo response rates for ASAS20 and ASAS40 in this study were similar to rates observed in recent clinical studies of AS; differences in ASAS40 response with upadacitinib versus placebo were p<0.05 (based on nominal p values) as early as week 2 and maintained throughout 14 weeks. See e.g., van der Heijde et al., Ann Rheum Dis 2017; 76: 1340-47; van der Heijde et al., Lancet 2018; 392: 2378-87; van der Heijde et al., Lancet 2018; 392: 2441-51; Landewe et al., Ann Rheum Dis 2014; 73: 39-47. Interestingly, mean changes from baseline to week 14 in the MRI SPARCC scores for the spine and SI joints in the placebo group were quite small.

The study results are in line with findings from two Phase 2/3 JAK inhibitor studies in patients with active AS. See, e.g., van der Heijde et al., Ann Rheum Dis 2017; 76: 1340-47; van der Heijde et al., Lancet 2018; 392: 2378-87. Together with these findings, the SELECT-AXIS 1 results further support that JAK inhibitors could represent an effective treatment option for AS. Currently, only TNF-α and IL-17 inhibition have been proven to be effective in axSpA; but, these cytokines are not directly blocked by JAK inhibitors including upadacitinib. See, e.g., Furst and Louie, Arthritis Res Ther 2019; 21: 135. However, emerging data from upadacitinib RA studies suggest that selective inhibition of JAK1 may result in the secondary inhibition of additional pathways that do not depend on JAK1 signalling, such as TNF-α and IL-12. See, e.g., Sornasse et al., Ann Rheum Dis 2019; 78: 365-66. Also, other JAK1-associated pathways, including IL-7 and IL-22, have been described in preclinical studies, but further research is needed to evaluate the mechanism of action of JAK inhibitors in axSpA. See, e.g., Veale et al., Rheumatology (Oxford) 2019; 58: 197-205; Gracey et al., Ann Rheum Dis 2016; 75: 2124-32.

The proportion of patients with adverse events was generally similar in the upadacitinib and placebo groups, and no new safety findings were observed compared with previous upadacitinib phase 3 RA studies. See, e.g., Burmester et al., Lancet 2018; 391: 2503-12; Genovese et al., Lancet 2018; 391: 2513-24; Fleischmann R, Pangan A L, Song I, et al. Upadacitinib versus placebo or adalimumab in patients with rheumatoid arthritis and an inadequate response to methotrexate: results of a phase 3, double-blind, randomized controlled trial. Arthritis Rheumatol 2019; doi: 10.1002/art.41032. [Epub ahead of print]; Cohen et al., Ann Rheum Dis (2019) 78. No serious infections, malignancies, anaemia, lymphopenia, herpes zoster, renal dysfunction, adjudicated major adverse cardiovascular events, venous thromboembolic events, or deaths were reported, and haemoglobin levels remained consistent throughout the study.

A higher proportion of patients in the upadacitinib group experienced adverse events of CPK elevation, all of which were asymptomatic and most were mild and reversible without study drug interruption. One patient in the placebo group experienced symptoms (muscle pain) in the setting of elevated CPK and permanently discontinued study drug. In the two previous JAK inhibitor studies, elevations in CPK were also observed. See e.g., van der Heijde et al., Ann Rheum Dis 2017; 76: 1340-47; van der Heijde et al., Lancet 2018; 392: 2378-87. Additional data are needed to better understand the safety profile of upadacitinib in axSpA.

JAK inhibitors, such as upadacitinib, could help address the unmet need in axSpA treatment given that only approximately half of bDMARD-naive patients achieve an ASAS40 response and even less achieve remission with TNF or IL-17 inhibitor treatment. See, e.g., Sieper et al., Ann Rheum Dis 2017; 76: 571-92; Deodhar et al., Arthritis Rheumatol 2019; 71: 599-611; van der Heijde et al., Lancet 2018; 392: 2441-51; Landewe et al., Ann Rheum Dis 2014; 73: 39-47; Lie E et al., Ann Rheum Dis 2011; 70: 157-63; Glintborg et al., Ann Rheum Dis 2013; 72: 1149-55. Furthermore, fewer patients are expected to achieve the treatment goal of sustained remission/LDA, and response rates are even lower in patients with AS who have not responded to bDMARD therapy. See, e.g., Sieper et al., Lancet 2017; 390: 73-84; Sieper et al., Ann Rheum Dis 2017; 76: 571-92; Deodhar et al., Arthritis Rheumatol 2019; 71: 599-611. Furthermore, some patients with axSpA may not be eligible for or might have contraindications common to IL-17 and TNF inhibitor therapy, such as allergic reactions and injection site pain, or specific to TNF inhibitors, such as congestive heart failure and concomitant demyelinating disease. See, e.g., Cortese et al., Mult Scler Relat Disord 2019; 35: 193-95. The use of IL-17 inhibitors is also not recommended for patients with concomitant inflammatory bowel disease. See, e.g., van der Heijde et al., Ann Rheum Dis 2017; 76: 978-91; Fragoulis et al., World J Gastroenterol 2019; 25: 2162-76. Because patients with AS are typically younger and may have more active lifestyles, a treatment option administered orally may be particularly important in this patient population. See e.g., Alten et al., Patient Prefer Adherence 2016; 10: 2217-28. Considering these unmet needs, the findings of the SELECT-AXIS 1 study, which demonstrated that upadacitinib treatment effects are within the range observed with bDMARDs and other JAK inhibitors in AS, support further investigation of upadacitinib for AS. See, e.g., Sieper et al., Ann Rheum Dis 2017; 76: 571-92; Deodhar et al., Arthritis Rheumatol 2019; 71: 599-611; van der Heijde et al., Ann Rheum Dis 2017; 76: 1340-47; van der Heijde et al., Lancet 2018; 392: 2378-87; van der Heijde et al., Lancet 2018; 392: 2441-51; Landewe et al., Ann Rheum Dis 2014; 73: 39-47.

This study is not without limitations. The focus on patients with AS who were bDMARD-naive allowed for a focused evaluation of benefit and risk in a homogeneous population, but the safety and efficacy of upadacitinib in patients with AS who are bDMARD-IR or in patients with non-radiographic axSpA has not yet been evaluated, and further studies are needed in these patient populations. Furthermore, only one dose of upadacitinib was evaluated in this study, and thus there are no data to confirm whether a higher dose could have resulted in greater efficacy. Lastly, only 14-week, short-term data are reported here, but the long-term efficacy and safety of upadacitinib will be collected in the ongoing SELECT-AXIS 1 extension period for up to 2 years.

In conclusion, oral upadacitinib free base 15 mg QD significantly improved disease activity, function, and MRI-detected axial inflammation in patients with active AS after 14 weeks of treatment. The incidence of adverse events was similar with upadacitinib and placebo, and no new safety signals were observed compared with previous studies in RA. Overall, these results support the further investigation of upadacitinib for the treatment of AS/axSpA.

Year 1 Results

The phase 2/3 SELECT-AXIS 1 study included a randomized, placebo-controlled, 14-week period followed by 90-week open-label extension; reported here are data through week 64.

The study enrolled adults (≥18 years) with active AS who had an inadequate response to ≥2 non-steroidal anti-inflammatory drugs therapy (or intolerance to or contraindication for NSAIDs) and were biologic disease-modifying antirheumatic drugs naïve, and who met the modified New York criteria based on independent central reading of radiographs of the sacroiliac joints and who had active disease at baseline defined as Bath Ankylosing Spondylitis Disease Activity Index (BASDAI) score ≥4 and patient's assessment of back pain score ≥4 (numeric rating scale [NRS], 0-10) at screening and baseline visit. Patients receiving a stable dose of concomitant conventional synthetic disease-modifying antirheumatic drugs (DMARDs), oral glucocorticoids, NSAIDs and analgesics were eligible; patients with prior exposure to JAK inhibitors or biologic DMARDs with potential impact on spondyloarthritis were excluded. Of the 187 patients randomized to Period 1, 178 (continuous upadacitinib, n=89; placebo switch, n=89) completed week 14 on study drug and entered the open-label extension; 160 patients (continuous upadacitinib n=78 [83.9%]; placebo switch, n=82 [87.2%]) completed week 64. Lack of efficacy (n=10) and AEs (n=4) were the most common reasons for discontinuation of study drug between weeks 14 and 64. In the continuous upadacitinib and the placebo-to-upadacitinib switch groups, mean duration since AS symptom onset was 14.8 and 14.0 years, mean duration since diagnosis was 7.8 and 6.0 years, mean ASDAS was 3.5 and 3.7, and mean hsCRP levels were 9.6 and 11.4 mg/L, respectively. Concomitant medications included NSAIDs (76% and 86%), conventional synthetic DMARDs (14% and 18%), and glucocorticoids (6% and 13%, respectively).

Efficacy was assessed based on percentage of patients achieving ASAS20 response, ASAS40 response, ASAS partial remission, BASDAI50, and Ankylosing Spondylitis Disease Activity Score (ASDAS) inactive disease (ID; <1.3), low disease activity (LDA; <2.1), major improvement (MI; decrease from baseline ≥2.0), and clinically important improvement (CII; decrease from baseline ≥1.1) through 64 weeks. In addition, change from baseline in ASDAS based on C-reactive protein (ASDAS-CRP), Bath Ankylosing Spondylitis Functional Index (BASFI), and linear Bath Ankylosing Spondylitis Metrology Index (BASMI) through 64 weeks and Maastricht Ankylosing Spondylitis Enthesitis Score (MASES), Work Productivity and Activity Impairment (WPAI; on a scale of 0-100), ASAS Health Index (HI), and AS quality of life (ASQoL) through 52 were assessed.

ASAS20 and ASAS40 responses were defined as ≥20% or ≥40% improvement and an absolute improvement of ≥1 or ≥2 units (on an NRS scale of 0-10), respectively, from baseline in ≥3 of the following 4 domains (with no worsening of ≥20% and ≥1 unit or no worsening at all, respectively, in the remaining domain): Patient Global Assessment of disease activity (PtGA), patient assessment of back pain, BASFI, and inflammation defined as the mean of BASDAI questions 5 and 6 (severity and duration of morning stiffness). ASAS partial remission was defined as an absolute score of ≤2 units for each of the 4 domains identified for ASAS40 response. ASDAS-CRP consists of patient-reported outcomes about back pain (BASDAI item 2), peripheral pain/swelling (BASDAI item 3), duration of morning stiffness (BASDAI item 6), the PtGA, and CRP.

Figure 3D:
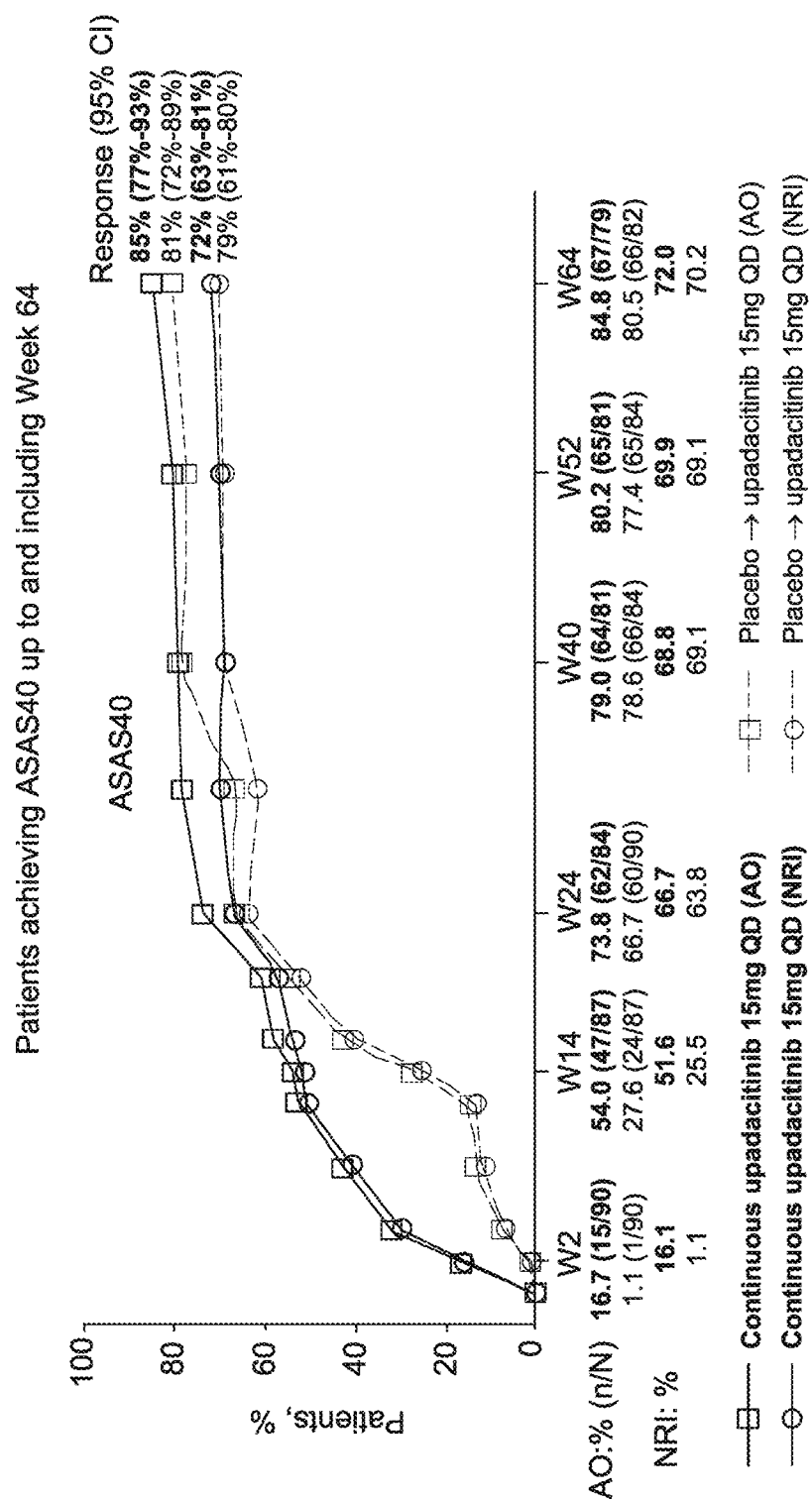
Figure 3E:
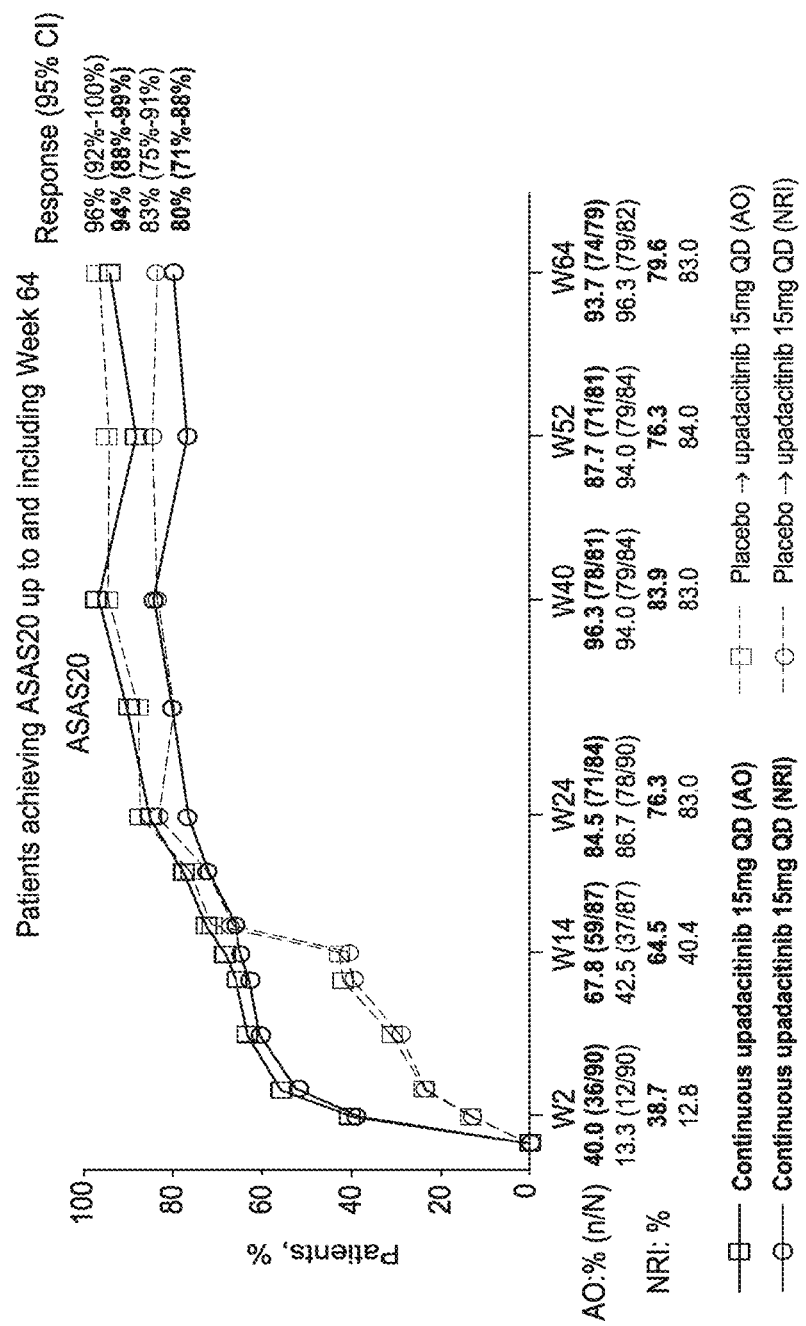
Figure 3F:
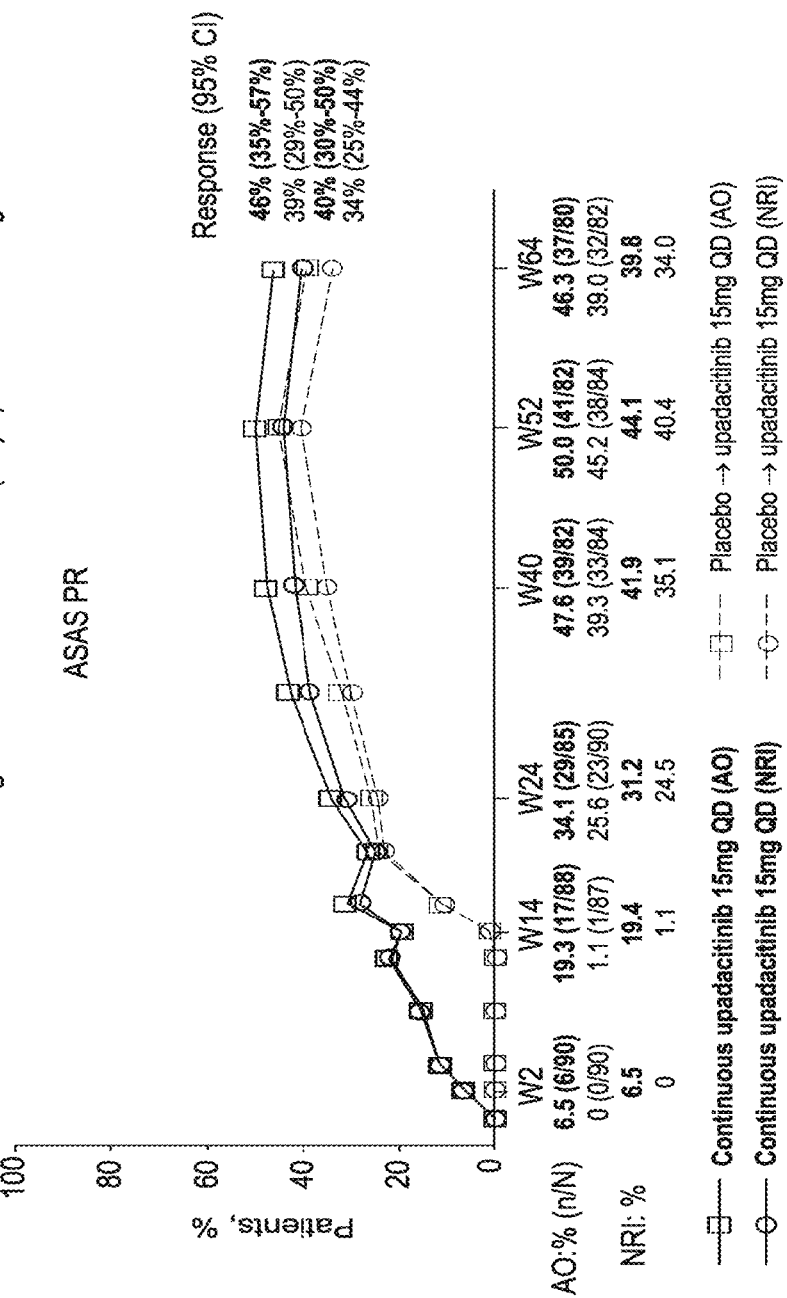
Figure 3G:
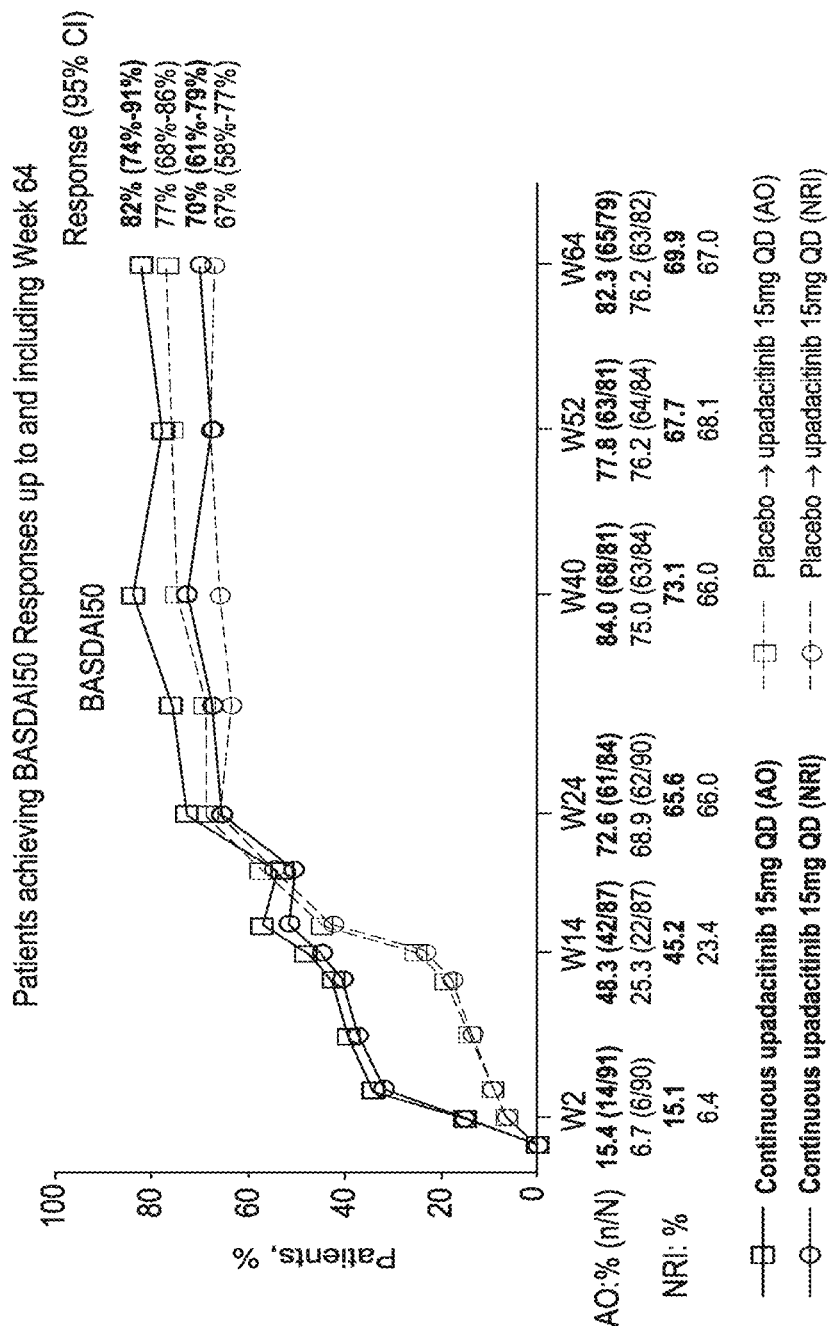
Figure 3H:
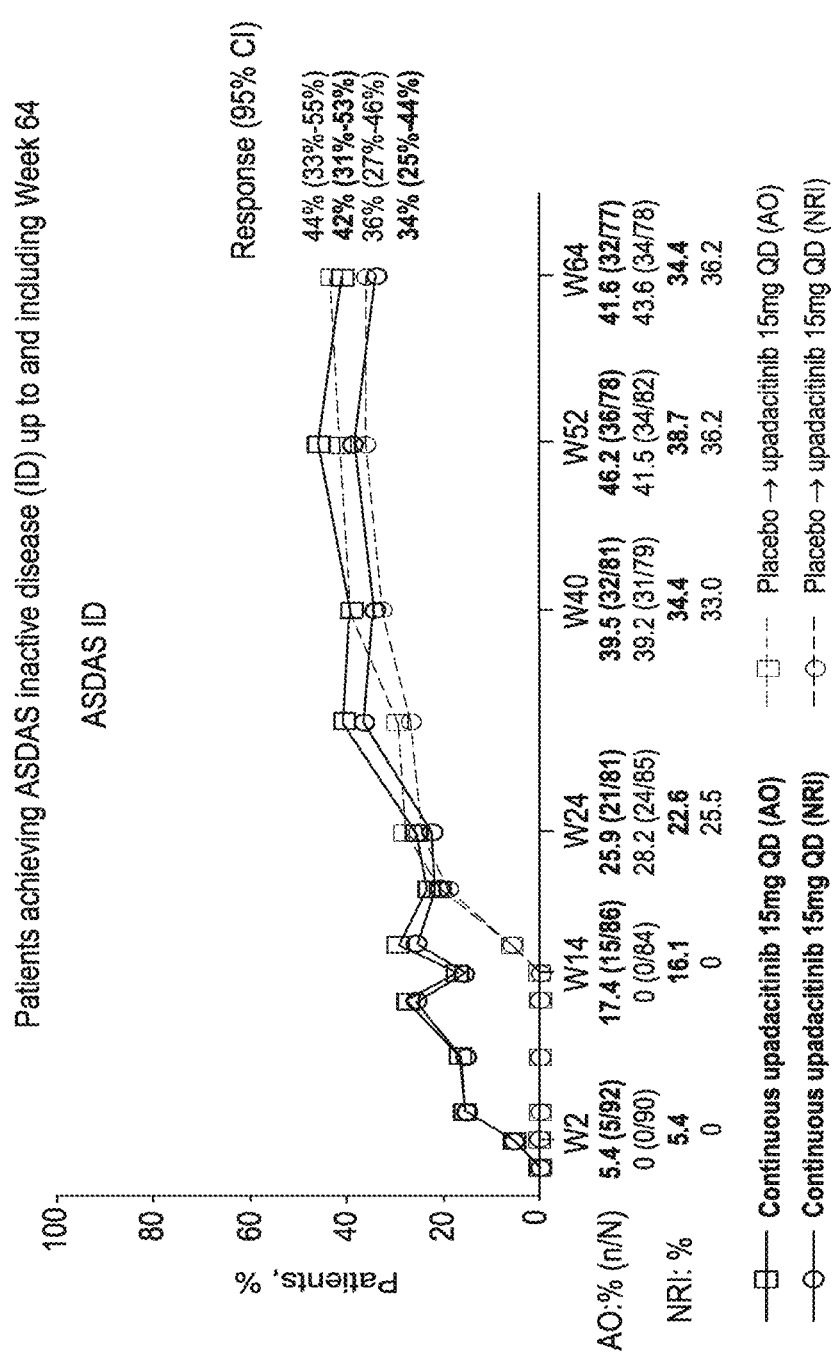
Figure 3I:
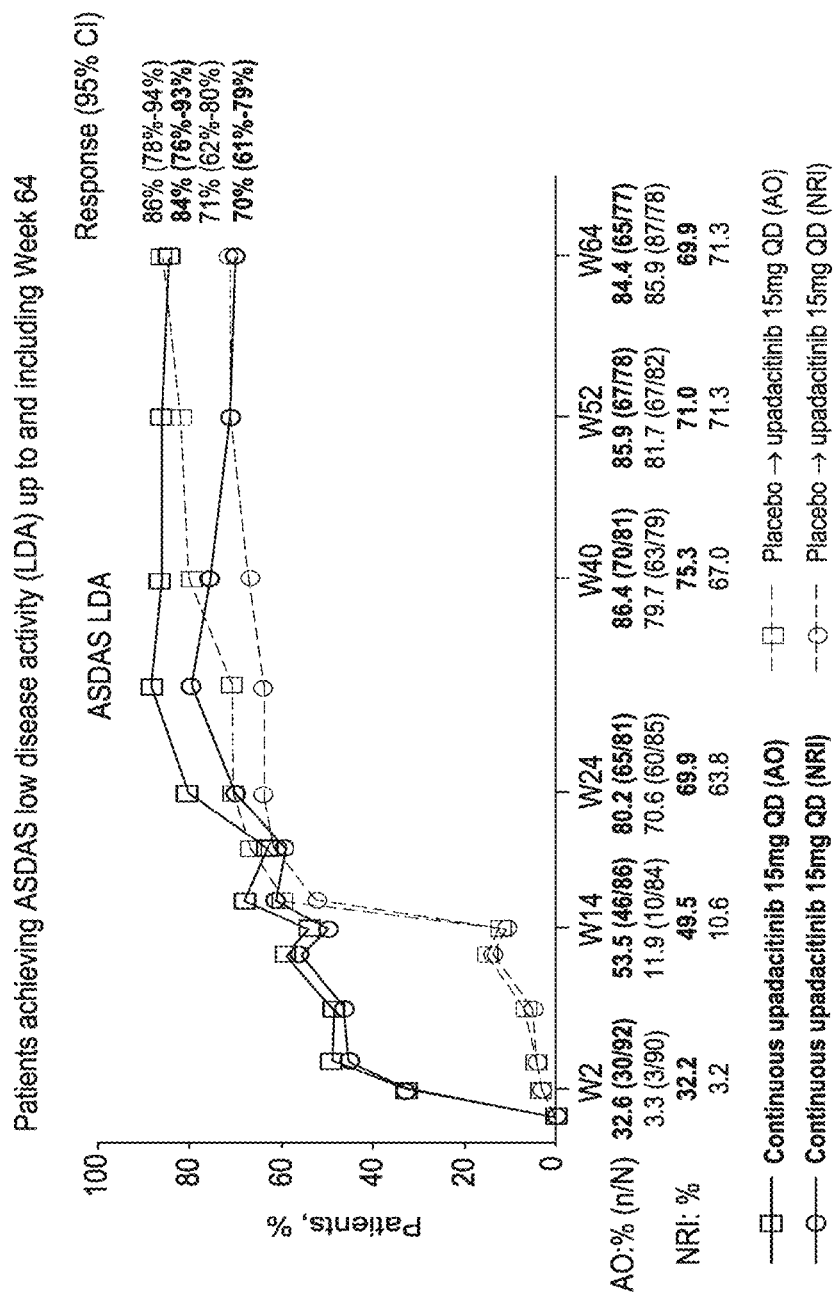
Figure 3K:
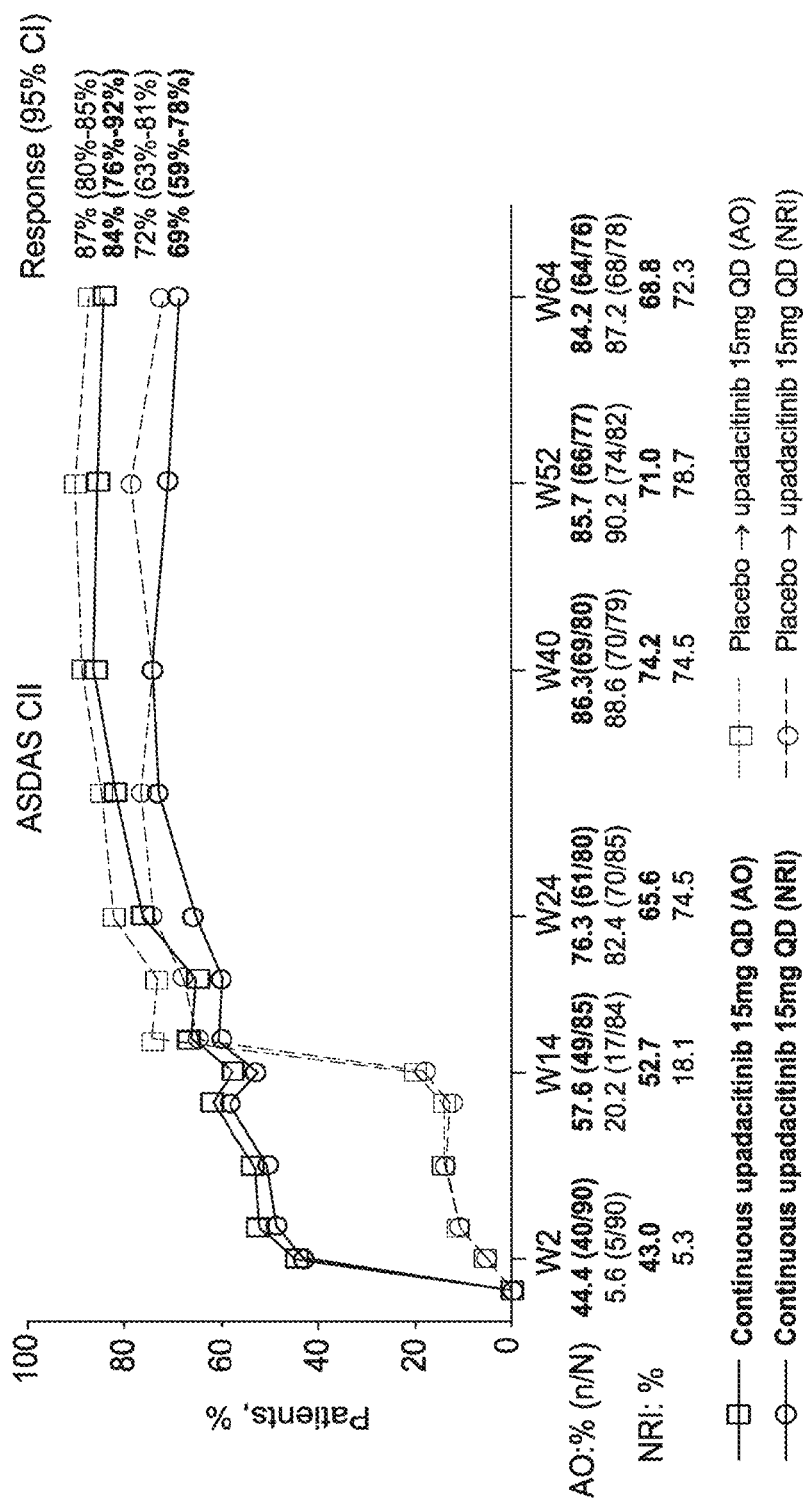

The percentage of patients achieving the primary efficacy endpoint of ASAS40 at week 14 continued to increase throughout the study in the continuous upadacitinib group: 85% (95% CI, 77%-93%) of patients achieved ASAS40 at week 64 in the as-observed analysis and 72% (63%-81%) in the NRI analysis (FIG. 3D). An analogous pattern of improvement was observed in the ASAS20 (94% [88%-99%] as-observed analysis and 80% [71%-88%] NRI analysis) (FIG. 3E), ASAS partial remission (46% [35%-57%] as-observed analysis and 40% [30%-50%] NRI analysis) (FIG. 3F), and BASDAI50 endpoints (82% [74%-91%] as-observed analysis and 70% [61%-79%] NRI analysis) (FIG. 3G). Patients who switched from placebo to upadacitinib at week 14 showed a speed of onset and magnitude of responses comparable with patients who were initially randomized to upadacitinib (responses at week 64 were ASAS40: 81% [72%-89%] as-observed analysis and 70% [61%-80%] NRI analysis; ASAS20: 96% [92%-100%] as-observed analysis and 83% [75%-91%] NRI analysis; ASAS partial remission: 39%[29%-50%] as-observed analysis and 34% [25%-44%] NRI analysis; and BASDAI50: (77% [68%-86%] as-observed analysis and 67% [58%-77%] NRI analysis). Likewise, the percentage of patients achieving ASDAS ID (FIG. 3H), ASDAS LDA (FIG. 3I), ASDAS MI (FIG. 3J), and ASDAS CII (FIG. 3K) continued to improve throughout the study in the continuous upadacitinib group; patients who switched to upadacitinib from placebo at week 14 showed a rapid onset of response for theses endpoints, with responses at week 64 similar to those observed in patients on continuous upadacitinib.

Mean changes from baseline to 1 year in disease activity (ASDAS), physical function (BASFI), patient assessment of pain and disease activity (PtGA), and inflammation (hsCRP) showed consistent improvement or sustained maintenance throughout the study in the continuous upadacitinib group; a similar magnitude of improvement was seen in the placebo-to-upadacitinib switch group after initiation of upadacitinib at week 14. Analogous patterns of improvement were shown in assessments of quality of life (ASQoL and ASAS HI), spinal mobility (BASMI), and enthesitis (MASES) over time, as well as in measurements of back pain, nocturnal back pain, BASDAI Q2 (back pain) and BASDAI Q5/6. Among patients who were employed at baseline, the mean (95% CI) WPAI overall work impairment score continued to improve throughout the study in the continuous upadacitinib group (from −20.5 [−27.1, −14.0] at week 14 to −35.6 [−43.2, −28.0] at week 52; as-observed analysis) and placebo-to-upadacitinib switch group (from −12.3 [−19.8, −4.8] at week 14 to −27.7 [−35.4, −20.0] at week 52).

Figure 3L:
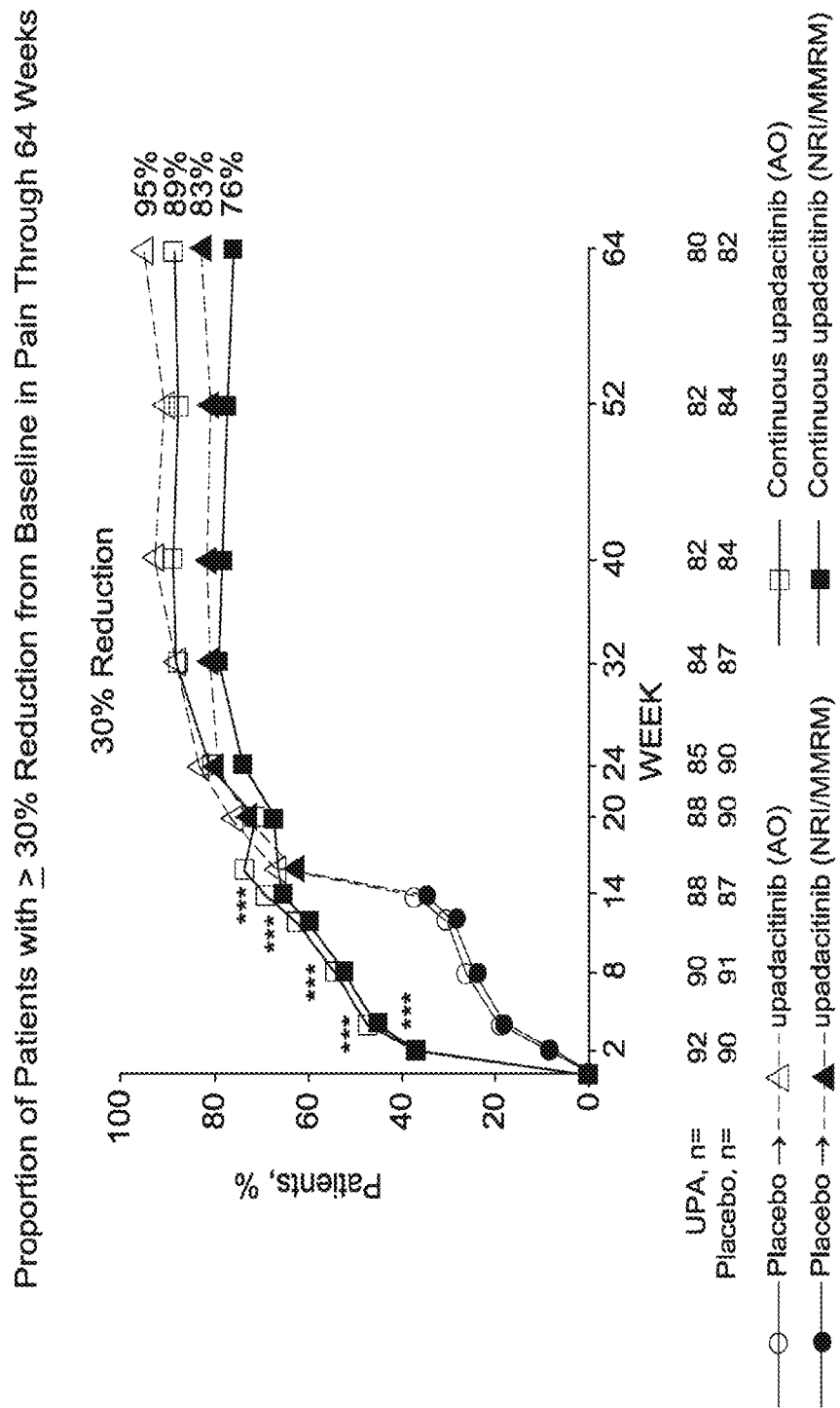
Figure 3M:
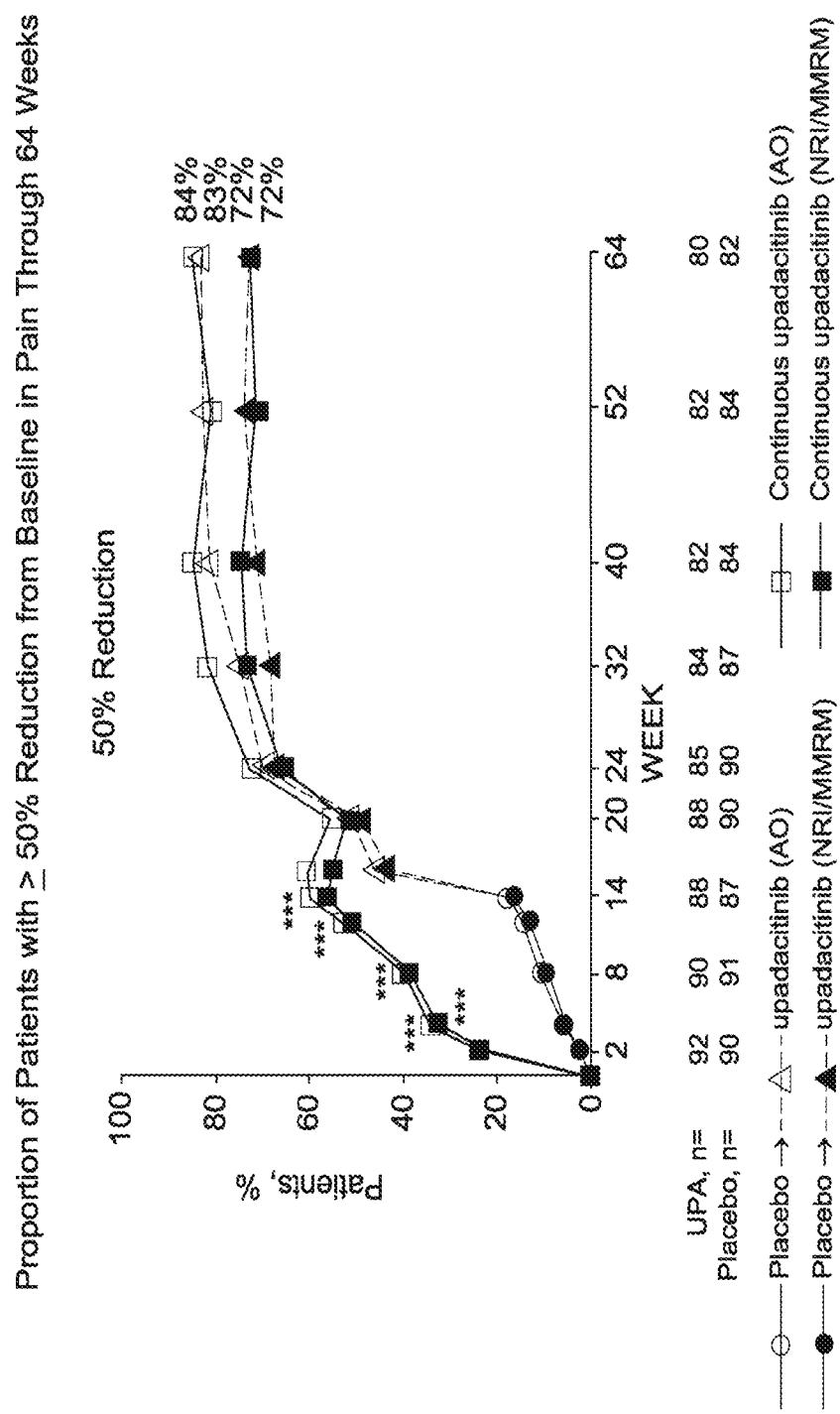
Figure 3N:
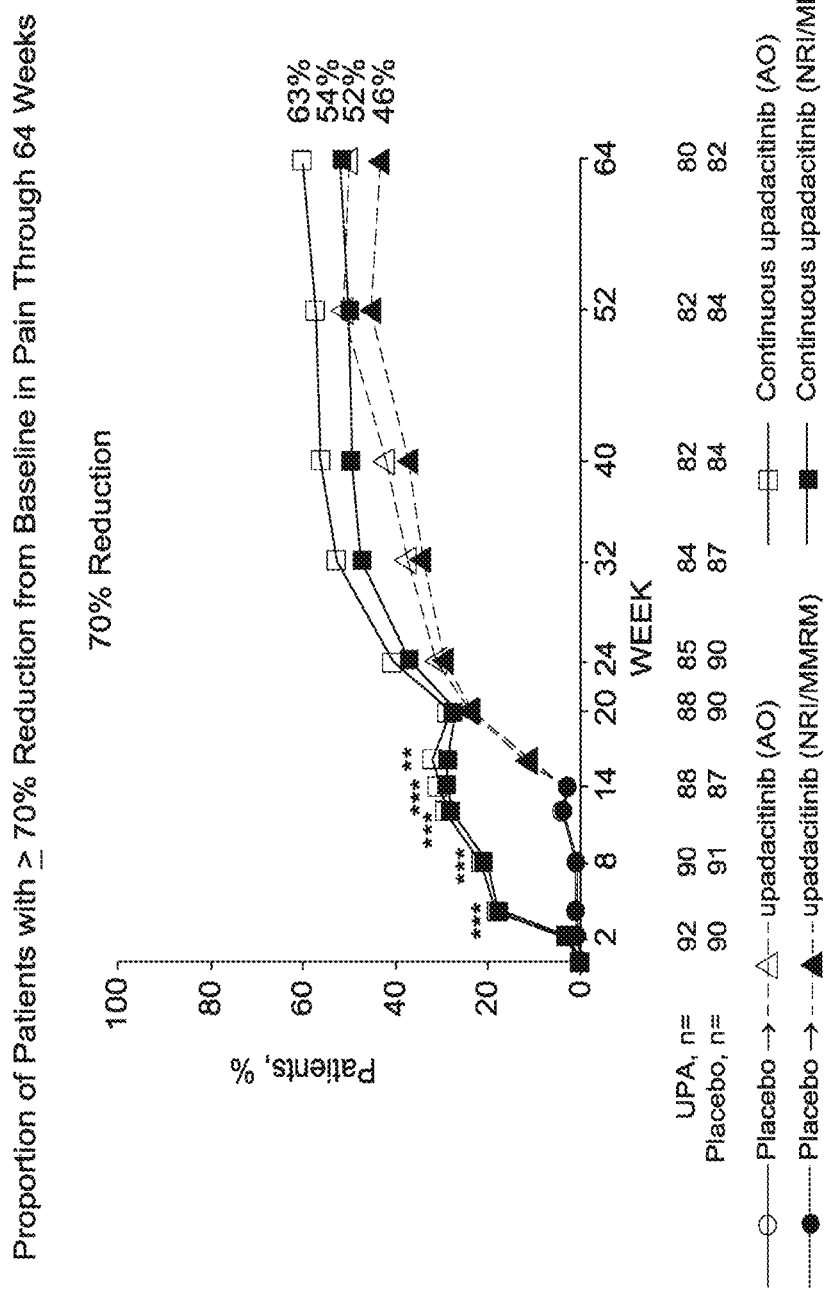
Figure 4B:
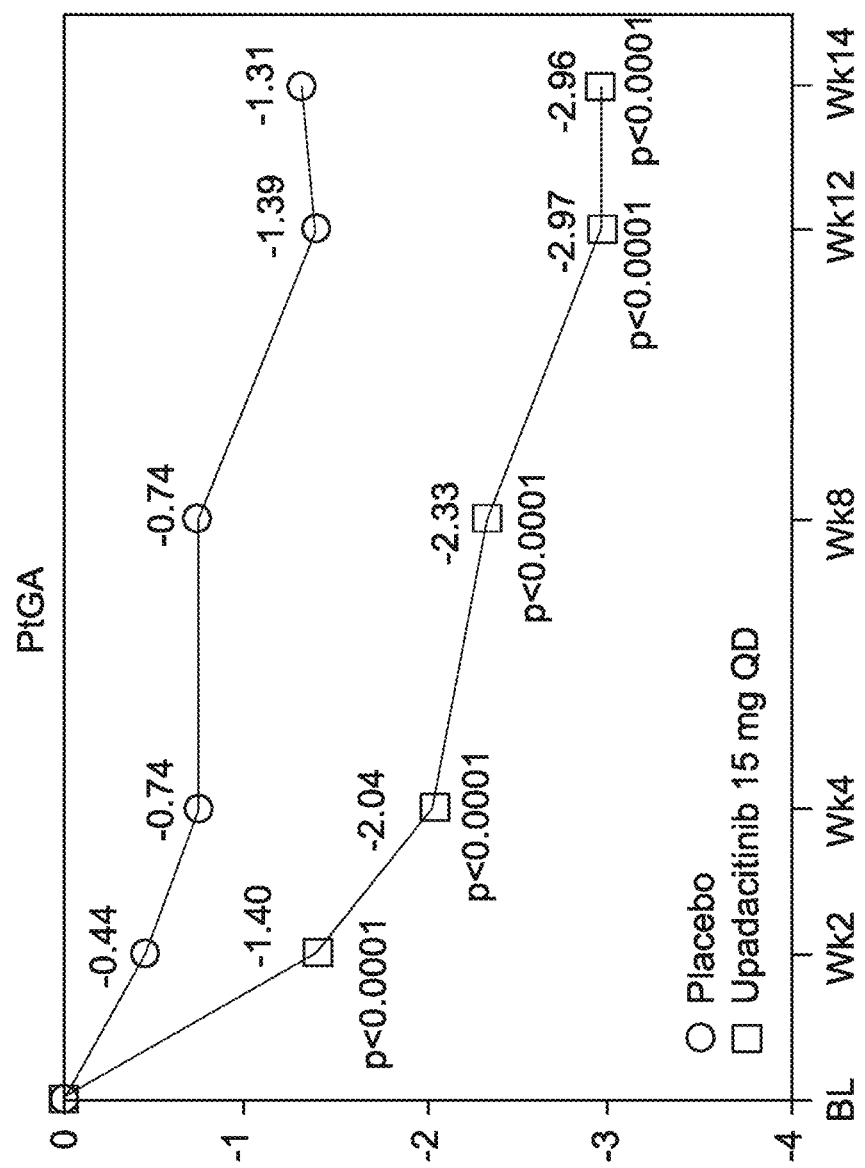
Figure 4D:
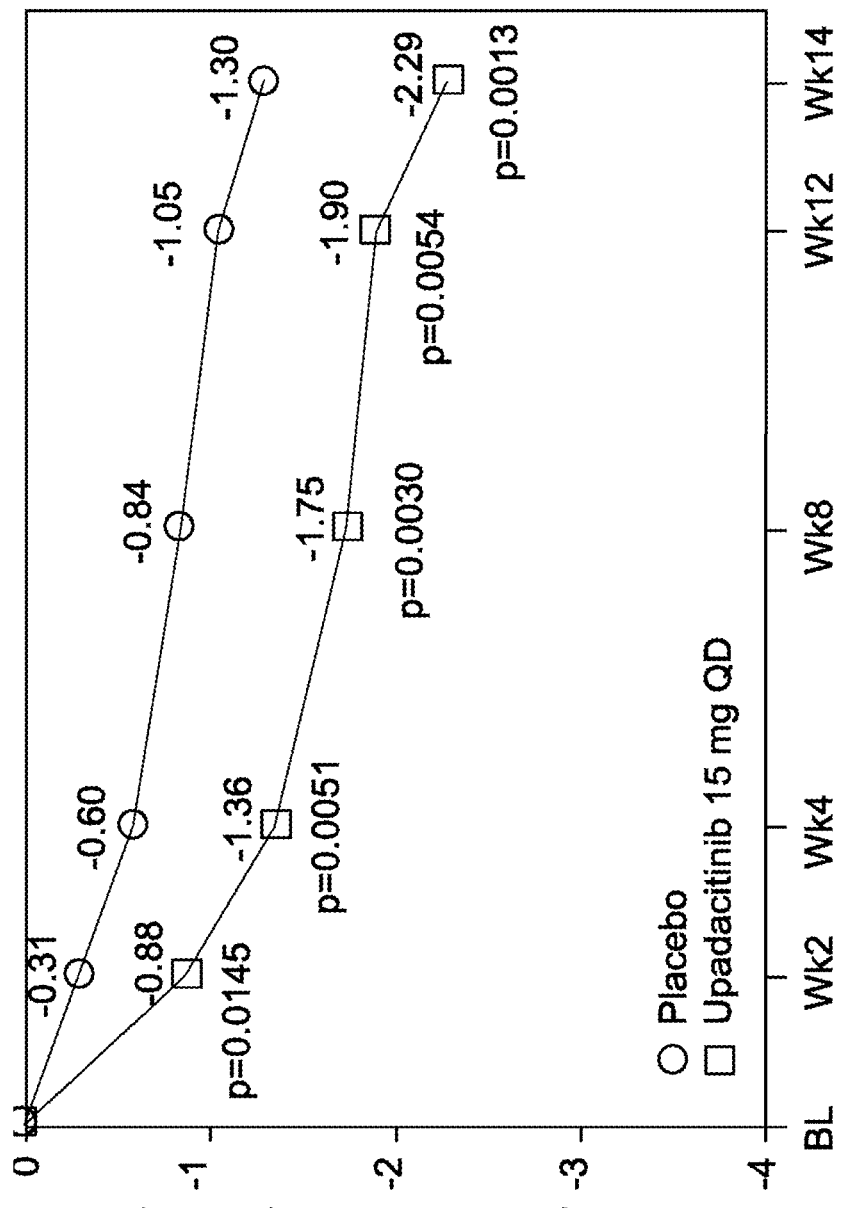
Figure 4E:
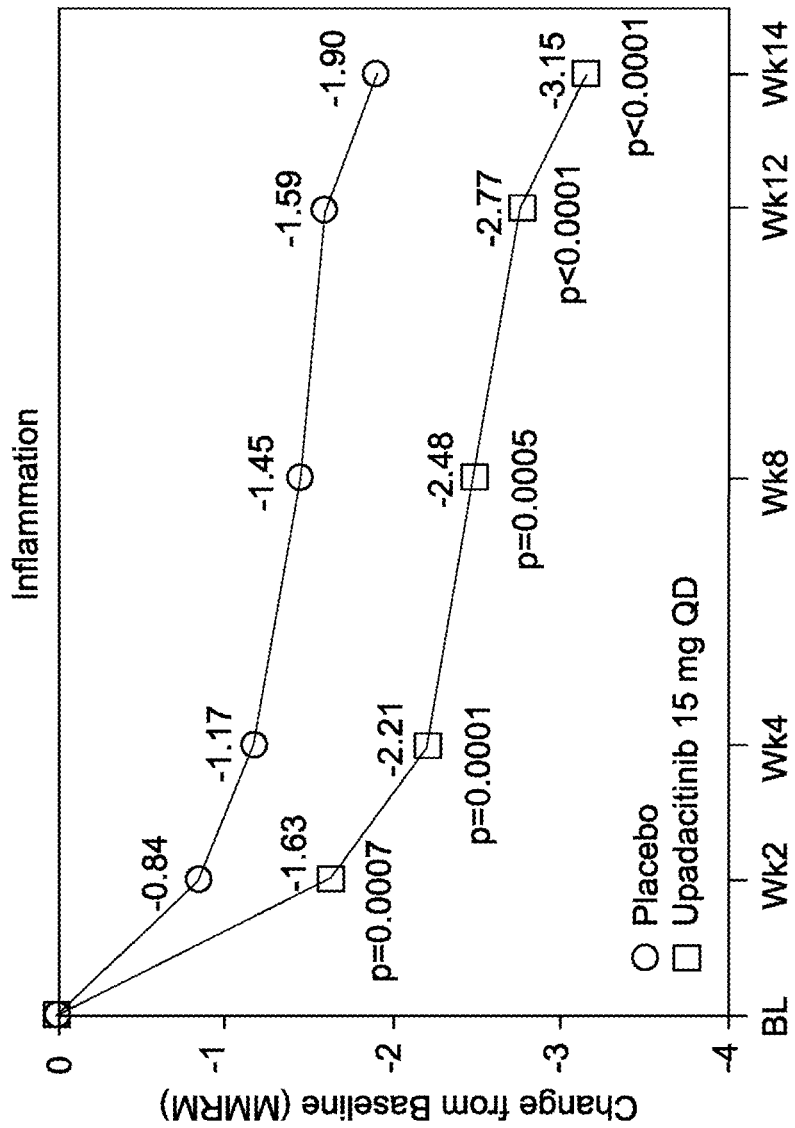

A significantly higher proportion of patients receiving upadacitinib versus placebo achieved ≥30% and ≥50% reduction in Patient's Global Assessment (PGA) of pain and back pain as early as week 2, and ≥70% reduction as early as week 4, and efficacy achieved was sustained thereafter. See, e.g., FIGS. 3L-3N. Patients who switched from placebo to open-label upadacitinib at week 14 generally reached the same level of pain reduction after week 14 as those initially randomized to upadacitinib.

Upadacitinib as a Promising Oral Therapy in AS and nr-AxSpA

SELECT-AXIS 1, the first study to report long-term data with a JAK inhibitor in AS, showed that upadacitinib 15 mg QD therapy led to sustained and consistent efficacy up to and including Week 64 in both NRI and as-observed analyses in patients with active AS who had an inadequate response to NSAIDs. Improvements were seen in disease activity measures (ASDAS, BASDAI, ASAS, and their components), inflammation (hsCRP), physical function (BASFI), quality of life (ASQoL, ASAS HI), and other aspects of disease (BASMI, MASES) with continuous upadacitinib therapy. In patients who switched from placebo to upadacitinib at week 14, a similar speed of onset and magnitude of efficacy response was observed up to and including Week 64 compared with those who received continuous upadacitinib starting at Week 0. Of note, approximately 40%-45% of patients receiving upadacitinib reached remission based on the more difficult to achieve endpoints ASAS partial remission (PR) or ASDAS inactive disease (ID) up to and including Week 64, and >80% were in a state of ASDAS low disease activity (LDA).

The below Table 19E provides placebo corrected data for upadacitinib at Week 14, biologics Ixekizumab and Adalimumab at Week 16, and JAK small molecule inhibitors Tofacitinib and Filgotinib at Week 12 for key primary and secondary endpoints. While this data is not a head to head comparison, the placebo corrected response calculated for upadacitinib for the more difficult to achieve endpoints ASAS PR, ASDAS ID, and ASDAS LDA shows decided promise over the efficacy demonstrated by the other two JAK small molecule inhibitors, with a remarkable efficacy only comparable to that demonstrated with the biologics. Furthermore, this efficacy, once achieved at Week 14, was sustained or improved over time, with long term efficacy in these difficult to achieve endpoints (including ASDAS major improvement (MI) and ASDAS clinically important improvement (CII)), sustained or improved up to and including Week 64. Coupled with the fact that upadacitinib is well tolerated with no new or unexpected safety findings (particularly compared to the other JAK inhibitors), the data suggests upadacitinib will be a promising new safe oral therapy for AS patients, especially for those AS patients who have active disease and inadequate response to NSAIDs.

TABLE 19E

Placebo Corrected Responses (% response/placebo response, p value)

| Endpoint | Upadacitinib 15 mg QD Week 14 (naiive) | Ixekizumab vs. Adalimumab H2H Study | | ADA 40 mg EOW Week 16 (TNF naiive) | Tofacitinib 5 mg BID Week 12 (bDMARD-naiive) | Filgotinib 200 mg QD Week 12 (Mixed) |
|---|---|---|---|---|---|---|
| | | Ixekizumab Q4W Week 16 (TNF naiive) | | | | |
| ASAS20 | 24.1% (64.5%/40.4%, p < 0.001) | 24% (64%/40%, p = 0.0015) | | 19% (59%/40%, p = 0.0075) | 39.6% (80.8%/41.2%, p ≤ 0.001) | 36.2% (75.9%/39.7%, p < 0.0001) |
| ASAS40 | 26.1% (51.6%/25.5%, p < 0.001*) | 30% (48%/18%, p < 0.0001,) | | 18% (36%/18%, p = 0.0053) | 26.6% (46.2%/19.6%, p ≤ 0.01) | 18.9% (37.9%/19%, p = 0.0189) |
| BASDAI50 | 21.8% (45.2%/23.4%, p = 0.002*) | 25% (42%/17%, p = 0.0003) | | 15% (32%/17%, p = 0.0119) | 18.8% (42.3%/23.5%, p ≤ 0.05) | NA |
| ASAS Partial Remisson (PR) | 18.3% (19.4%/1.1%, p < 0.001*) | NA | | NA | 7.4% (19.2%/11.8%, NS) | 8.7% (12.1%/3.4%, p = 0.1028) |
| ASDAS Inactive Disease (ID) | 16.1% (16.1%/0%, p < 0.001) | 14% (16%/2%, p = 0.0074) | | 14% (16%/2%. p = 0.0087) | 5.7% (13.5%/7.8%. NS) | 5% (5%/0%, p = 0.092) |
| ASDAS low disease activity (LDA) | 38.9% (49.5%/10.6%, p < 0.001) | 30% (43%/13%, p < 0.0001) | | 25% (38%/13%, p = 0.0002) | 34.3% (53.9%/19.6%, p ≤ 0.001) | NA |

NS: non-significant; NA: not available; UPA p values are nominal, unless
*significant after multiplicity-adjustment; Ixekizumab bDMARD-naïve AS COAST-V Study. Van der Heijde et al. Lancet 2018; 392: 2441-51; Tofacitinib study: van der Heijde D, et al. ARD 2017; 0: 1-8.; Filgotinib study: van der Heijde et al. Lancet 2018; 392: 2378-87.

Example 32. A Phase 3 Randomized, Placebo-Controlled, Double-Blind Program to Evaluate Efficacy and Safety of Upadacitinib in Adult Subjects with Axial Spondyloarthritis Followed by a Remission-Withdrawal Period (SELECT AXIS 2) (Study 1)

The safety and efficacy data from the Phase 2/3 study (as described in U.S. Pat. App. No. 2021/0228575) show a favorable benefit:risk profile for upadacitinib and support the continued investigation of upadacitinib in adult subjects with active axSpA who had an inadequate response to biologic disease-modifying anti-rheumatic drug therapy (bDMARD-IR) (Study 1; Example 32) and in adult subjects with active nr-axSpA (Study 2; Example 33). The Phase 3 clinical study plan is set forth in FIG. 9.

Adult Subjects with Active Ankylosing Spondylitis (AS) Who had an Inadequate Response to Biologic Disease-Modifying Anti-Rheumatic Drug Therapy (bDMARD-IR) (Study 1)

Study 1 is a Phase 3, randomized, placebo-controlled, double-blind multicenter study to evaluate the safety, tolerability, and efficacy of upadacitinib compared with placebo on reduction of signs and symptoms in adult subjects with active ankylosing spondylitis (AS) who had an inadequate response to biologic disease-modifying anti-rheumatic drug therapy (bDMARD-IR).

Study 1 (main study) is comprised of a 35-day Screening Period; a 14-week randomized, double-blind, parallel-group, placebo-controlled period (the Double-Blind Period) designed to compare the safety and efficacy of upadacitinib freebase 15 mg QD versus placebo for the treatment of signs and symptoms of subjects with active AS who have an inadequate response to bDMARD therapy; and a 90-week open-label, long-term extension period (the Open-Label Extension Period) to evaluate the long-term safety, tolerability, and efficacy of upadacitinib free base 15 mg QD in subjects who have completed the Double-Blind Period up to Week 104 (see FIG. 9).

Subjects in Study 1 who reach Week 104 on study drug (upadacitinib free base 15 mg QD) will be assessed whether they are in remission. Subjects in remission at Week 104 will be eligible for the Remission-Withdrawal Period. Subjects will be followed without study drug treatment and assessed for disease flare through Week 152. Subjects who flare will receive open-label upadacitinib free base 15 mg QD from the time of flare for 24 weeks (re-treatment) or longer.

Subjects were enrolled from 119 sites in 22 countries. Eligible subjects were adult females and males who were at least 18 years of age at Screening with a clinical diagnosis of AS, met the modified New York Criteria for AS, and were without total spinal ankylosis. Eligible study subjects must have had a Bath Ankylosing Spondylitis Disease Activity Index score ≥4 and a Patient's Assessment of Total Back Pain score (Total Back Pain score) ≥4 based on a 0-10 numerical rating scale at the Screening and Baseline Visits.

Subjects were randomized in a 1:1 ratio to one of two treatment groups, stratified by screening hsCRP (≤ULN vs >ULN), the class of prior bDMARD use (1 TNF, 1 IL-17, other) and geographic region:
  Group 1: Upadacitinib free base 15 mg QD (N=211) (Double-Blind Period)→Upadacitinib free base 15 mg QD (Open-Label Period)
  Group 2: Placebo (N=209) (Double-Blind Period)→Upadacitinib free base 15 mg QD (Open-Label Period)

Study 1 Primary Endpoint

The primary endpoint was the proportion of subjects achieving an ASAS40 response at Week 14. Secondary endpoints for Study 1 are described below.

Study 1: bDMARD-IR AS Specific Criteria
 1. Subject must have a clinical diagnosis of AS and subjects must meet the modified New York criteria for AS.
 2. Subject must not have total spinal ankylosis.
 3. Subjects with prior exposure to 1 bDMARD (either 1 tumor necrosis factor [TNF] inhibitor or 1 interleukin [IL]-17 inhibitor) may be enrolled, and the subject must have discontinued the bDMARD due to either intolerance or lack of efficacy. Prior exposure to a $2^{nd}$ bDMARD was allowed for no more than 30% of subjects if the reason for discontinuation was not due to lack of efficacy. Subjects who have had lack of efficacy to both a TNF inhibitor and IL-17 inhibitor were not eligible.

Study 1 Eligibility Criteria:
 1. Subject must be an adult male or female, at least 18 years of age at Screening.
 2. Subject must meet the following scores at Screening and Baseline Visits: BASDAI score ≥4 and Total Back Pain score ≥4 based on a 0-10 NRS.
 3. Subject has had an inadequate response to at least 2 NSAIDs over an at least 4-week period in total at maximum recommended or tolerated doses, or subject has an intolerance to or contraindication for NSAIDs.
 4. The washout period for bDMARDs prior to the first dose of study drug is specified below:
    ≥4 weeks for etanercept;
    ≥8 weeks for adalimumab, infliximab, certolizumab, golimumab, abatacept, tocilizumab, and ixekizumab;
    ≥12 weeks for ustekinumab;
    ≥16 weeks for secukinumab;
    ≥1 year for rituximab OR ≥6 months if B cells have returned to pre-treatment level or normal reference range (central lab) if pre-treatment levels are not available;
    ≥12 weeks or at least 5 times the mean terminal elimination half-life, whichever is longer, for other bDMARDs.
 5. If entering the study on the following concomitant csDMARDs (MTX (≤25 mg/week); or Sulfasalazine (SSZ) 3 g/day); or Hydroxychloroquine (≤400 mg/day); or Chloroquine (≤400 mg/day); or Leflunomide (≤20 mg/day); or Apremilast 60 mg/day)), subject must be on a stable dose as indicated below for at least 28 days prior to the Baseline Visit. A combination of up to 2 background csDMARDs is allowed EXCEPT the combination of methotrexate (MTX) and leflunomide.
 6. If entering the study on concomitant oral corticosteroids, subject must be on a stable dose of prednisone (≤10 mg/day) or oral corticosteroid equivalent for at least 14 days prior to the Baseline Visit.
 7. If entering the study on concomitant NSAIDs, tramadol, combination of acetaminophen/paracetamol and codeine or combination of acetaminophen/paracetamol and hydrocodone, and/or non-opioid analgesics, subject must be on stable dose(s) for at least 14 days prior to the Baseline Visit.
 8. Subject must not have been exposed to any JAK inhibitor.
 9. Subject must not have used the following prohibited concomitant treatments within the specified timeframe prior to Baseline Visit:
    Intra-articular joint injections, spinal/paraspinal injection(s), or parenteral administration of corticosteroids within 28 days prior to the Baseline Visit. Inhaled or topical corticosteroids are allowed;
    Any other csDMARDs (other than those allowed per eligibility criterion), including thalidomide, within 28 days or 5 half-lives (whichever is longer) of the drug prior to the Baseline Visit;
    Opioid analgesics (except for combination of acetaminophen/paracetamol and codeine or combination of acetaminophen/paracetamol and hydrocodone which are allowed) within 14 days prior to the Baseline Visit.
 10. Subject must not have received a live vaccine within 28 days (or longer if required locally) prior to the first dose of study drug or have expected need of live vaccination during study participation including at least 30 days (or longer if required locally) after the last dose of study drug.

11. Subject must have no systemic use of known strong cytochrome P450 3A (CYP3A) inhibitors from Screening through the end of study drug administration or strong CYP3A inducers 30 days prior to study drug administration through the end of study drug administration. Subjects must not use herbal therapies or other traditional medicines with unknown effects on CYP3A from Screening through the end of study drug administration.

12. Subject must not have been treated with any investigational drug of chemical or biologic nature within a minimum of 30 days or 5 half-lives of the drug (whichever is longer) prior to the first dose of study drug or is currently enrolled in another interventional study.

13. Subject must not have a history of an allergic reaction or significant sensitivity to constituents of the study drug (and its excipients) and/or other products in the same class.

Study 1 Secondary Endpoints

The key multiplicity-controlled secondary endpoints at Week 14 are as follows:

TABLE 20A

Key multiplicity-controlled secondary endpoints at Week 14 (Study 1)

1 Change from Baseline in Ankylosing Spondylitis Disease Activity Score (ASDAS) (CRP)
2 Change from Baseline in magnetic resonance imaging (MRI) Spondyloarthritis Research Consortium of Canada (SPARCC) score (spine) (MRI-Spine SPARCC)
3 Proportion of subjects with Bath Ankylosing Spondylitis Disease Activity Index (BASDAI) 50 response
4 Proportion of subjects with ASAS20 response
5 Proportion of subjects with ASDAS (CRP) Inactive Disease (ASDAS score < 1.3)
6 Change from Baseline in Patient's Assessment of Total Back Pain (Total Back Pain score)
7 Change from Baseline in Patient's Assessment of Nocturnal Back Pain (Nocturnal Back Pain)
8 Proportion of subjects with ASDAS (CRP) Low Disease Activity (ASDAS score < 2.1)
9 Change from Baseline in Bath Ankylosing Spondylitis Functional Index (BASFI) (Function)
10 Proportion of subjects with ASAS partial remission (PR) (an absolute score of ≤2 units for each of the 4 domains identified in ASAS40)
11 Change from Baseline in Ankylosing Spondylitis Quality of Life (ASQoL)
12 Change from Baseline in ASAS Health Index (HI)
13 Change from Baseline in Linear Bath Ankylosing Spondylitis Metrology Index ($BASMI_{lin}$) (Mobility)
14 Change from Baseline in Maastricht Ankylosing Spondylitis Enthesitis Score (MASES) (Enthesitis)

Additional key secondary endpoints at Week 14 include: Change from Baseline in MRI SPARCC score (SI joints).

Additional Study 1 Endpoints

Additional endpoints are the following measurements assessed at time points other than those specified for the primary and key secondary variables are as follows:

TABLE 20B

Additional endpoints (Study 1)

1 Proportion of subjects with ASAS20 response
2 Proportion of subjects with ASAS40 response
3 Proportion of subjects with ASAS PR
4 Proportion of subjects with ASDAS Inactive Disease (ASDAS score <1.3)
5 Proportion of subjects with ASDAS Low Disease (ASDAS score <2.1)
6 Proportion of subjects with ASDAS Major Improvement (a change from Baseline of ≤−2.0)
7 Proportion of subjects with ASDAS Clinically Important Improvement (a change from Baseline of ≤−1.1)
8 Proportion of subjects with Discontinuation of opioids among subjects with opioid use at Baseline
9 Change from Baseline in ASAS HI
10 Change from Baseline in ASDAS
11 Change from Baseline in ASQoL
12 Change from Baseline in BASDAI and BASDAI Questions including mean of question 5 and 6 of the BASDAI
13 Change from Baseline in BASFI
14 Change from Baseline in BASMIlin
15 Change from Baseline in High sensitivity C-reactive protein (hsCRP)
16 Change from Baseline in Functional Assessment of Chronic Illness Therapy-Fatigue (FACIT-F)
17 Change from Baseline in EuroQoL-5D-5L (EQ-5D-5L)
18 Change from Baseline in MASES
19 Change from Baseline in Modified Stoke Ankylosing Spondylitis Spine Score (mSASSS) with conventional radiograph
20 Change from Baseline in MRI SPARCC score of SI joints
21 Change from Baseline in MRI SPARCC score of spine
22 Change from Baseline in Patient's Assessment of Total Back Pain (Total Back Pain Score)
23 Change from Baseline in Patient's Assessment of Nocturnal Back Pain (Nocturnal Back Pain)
24 Change from Baseline in Patient's Global Assessment of Pain (Pain)

TABLE 20B-continued

Additional endpoints (Study 1)

25 Change from Baseline in Physician's Global Assessment of Disease Activity (PGA)
26 Change from Baseline in Patient's Global Assessment of Disease Activity (PtGA)
27 Change from Baseline in 36-Item Short Form Health Survey (SF-36)
28 Change from Baseline in Tender joint count (TJC) and swollen joint count (SJC);
29 Change from Baseline in Work Productivity and Activity Impairment (WPAI)
30 Change from Baseline in Change of NSAID score
31 Change from Baseline in Physical Activity Assessment (step count, physical activity, and spinal range of motion tasks) as measured by a wearable device (in countries where the digital health technology device is approved)

A total of 420 subjects were randomized in Study 1 and received double blind study drug treatment, out of which 409 (97.4%) completed study drug through Week 14. The rates of premature discontinuation of study drug were low and similar in the placebo group and the upadacitinib treatment group (Table 20C). The key demographics and baseline characteristics were balanced across the treatment groups and generally consistent with the targeted patient population (Table 20D).

TABLE 20C

Subject Disposition

| Subject Disposition | PLACEBO | UPADACITINIB FREE BASE 15 MG QD |
|---|---|---|
| Randomized | 209 | 211 |
| Full Analysis Set (FAS) | 209 | 211 |
| Per Protocol Analysis Set | 194 | 186 |
| Safety Analysis Set | 209 | 211 |
| Completed Study Drug Through Week 14, n(%)[b] | 203 (97.1) | 206 (97.6) |
| Prematurely Discontinued Study Drug by Week 14[a], n(%)[b] | 6 (2.9) | 5 (2.4) |
| Adverse Events | 3 (1.4) | 0 |
| Withdrew Consent | 1 (0.5) | 0 |
| Lost To Follow-Up | 1 (0.5) | 1 (0.5) |
| Lack of Efficacy | 1 (0.5) | 1 (0.5) |
| COVID-19 Infection | 0 | 0 |
| COVID-19 Logistical Restrictions | 0 | 1 (0.5) |
| Other | 0 | 2 (0.9) |

[a]Primary reasons for premature discontinuation of study drug are summarized.
[b]Percentage is calculated based upon the FAS.

TABLE 20D

Key Demographics and Baseline Characteristics

| Key Demographic and Baseline Characteristics Mean (SD) or n (%) | PLACEBO N = 209 | UPADACITINIB 15 MG QD N = 211 |
|---|---|---|
| Male | 158 (75.6) | 153 (72.5) |
| Age (Yrs) | 42.2 (11.78) | 42.6 (12.39) |
| HLA-B27 Positive | 168 (81.2) | 180 (85.3) |
| White | 169 (80.9) | 168 (79.6) |
| Region | | |
| North America | 25 (12.0) | 25 (11.8) |
| South/Central America | 14 (6.7) | 13 (6.2) |
| Western Europe | 25 (12.0) | 16 (7.6) |
| Eastern Europe | 98 (46.9) | 109 (51.7) |
| Asia[a] | 34 (16.3) | 41 (19.4) |
| Other[b] | 13 (6.2) | 7 (3.3) |
| Duration since AS Diagnosis (Yrs) | 7.5 (7.51) | 7.9 (7.54) |
| Duration of AS Symptom (Yrs) | 12.6 (9.29) | 12.9 (9.08) |
| NSAIDs Use at Baseline | 163 (78.0) | 163 (77.3) |
| Oral Corticosteroids Use at Baseline | 18 (8.6) | 27 (12.8) |
| csDMARDs Use at Baseline | 62 (29.7) | 68 (32.2) |
| Prior bDMARD Use Class | | |
| 1 TNF | 158 (76.0) | 154 (73.0) |
| 1 IL-17 | 24 (11.5) | 29 (13.7) |
| 2 bDMARDs exposure | 26 (12.5) | 28 (13.3) |
| BASDAI (0-10) (disease activity) | 6.8 (1.26) | 6.8 (1.34) |
| Total Back Pain (NRS 0-10) | 7.4 (1.43) | 7.5 (1.48) |
| Nocturnal Back Pain (NRS 0-10) | 7.2 (1.50) | 7.1 (1.77) |
| Patient Global Assessment (NRS 0-10) | 7.2 (1.40) | 7.4 (1.48) |
| ASDAS(CRP) | 3.9 (0.77) | 3.9 (0.79) |
| BASFI (Function) (0-10) | 6.2 (1.87) | 6.3 (2.03) |
| BASMI (Mobility) | 3.9 (1.55) | 3.9 (1.57) |
| Presence of Enthesitis at baseline (MASES > 0) | 162 (77.9) | 148 (70.1) |
| MASES Score[c] (0-13) | 4.2 (3.13) | 4.9 (2.99) |
| MRI Spine SPARCC[d] (0-108) | 8.8 (12.52) | 10.7 (15.43) |
| MRI Sacroiliac Joint SPARCC[d] (0-72) | 5.6 (10.63) | 5.0 (10.80) |
| hsCRP at Screening (mg/L) | 14.5 (17.84) | 15.8 (17.69) |
| hsCRP > ULN (2.87 mg/L) at Screening | 163 (78.0) | 165 (78.2) |
| AS QoL (0-18) | 11.5 (4.44) | 11.6 (4.38) |
| ASAS Health Index (0-17) | 8.9 (3.75) | 9.4 (3.50) |

[a]China, Taiwan, South Korea and Japan.
[b]New Zealand, Australia and Israel.
[c]Summarized for subjects with presence of enthesitis at baseline.
[d]Summarized for subjects with available baseline MRI data up to 3 days post first dose of study drug.

Efficacy

The primary endpoint was the achievement of ASAS40 response at Week 14. The primary analysis, using Non-Responder Imputaion in conjunction with Multiple Imputation (NRI-MI) to handle missing data due to COVID-19, showed a statistically significantly higher response rate (p<0.0001) in the upadacitinib group (44.5%) as compared to placebo (18.2%) (FIG. 10A). Sensitivity and supplementary analyses using NRI, As Observed (AO) data, and analyses on the Per Protocol population showed consistent results.

All ranked secondary endpoints were statistically significant (all p<0.0001, Table 20E; FIGS. 11A-11F). FIG. 10B shows ASAS 40 response rate over time up to Week 14. Upadacitinib showed onset of effect in ASAS40 as early as Week 4.

TABLE 20E

Primary and Ranked Key Secondary Efficacy Endpoints at Week 14[a]

|  | Endpoint | PLACEBO N = 209 | UPADACITINIB 15 MG QD N = 211 | UPA – PBO (95% CI) | P-VALUE[b] |
|---|---|---|---|---|---|
| Primary | ASAS40 | 18.2% | 44.5% | 26.4 (17.9, 34.9) | <0.0001* |
| Ranked Key Secondary | 1 ASDAS(CRP) | −0.49 | −1.52 | −1.02 (−1.20, −0.85) | <0.0001* |
|  | 2 MRI Spine SPARCC[c] | −0.04 | −3.95 | −3.90 (−5.47, −2.33) | <0.0001* |
|  | 3 BASDAI50 | 16.7% | 43.1% | 26.4 (18.0, 34.8) | <0.0001* |
|  | 4 ASAS20 | 38.3% | 65.4% | 27.1 (17.9, 36.3) | <0.0001* |
|  | 5 ASDAS(CRP) Inactive Disease | 1.9% | 12.8% | 10.9 (6.0, 15.8) | <0.0001* |
|  | 6 Total Back Pain | −1.47 | −3.00 | −1.53 (−1.96, −1.11) | <0.0001* |
|  | 7 Nocturnal Back Pain | −1.5 | −3.2 | −1.7 (−2.1, −1.2) | <0.0001* |
|  | 8 ASDAS(CRP) Low Disease Activity | 10.1% | 44.1% | 34.0 (26.2, 41.8) | <0.0001* |
|  | 9 BASFI (Function) | −1.09 | −2.26 | −1.17 (−1.55, −0.80) | <0.0001* |
|  | 10 ASAS Partial Remission | 4.3% | 17.5% | 13.2 (7.4, 19.0) | <0.0001* |
|  | 11 AS QoL | −2.03 | −5.10 | −3.07 (−3.90, −2.24) | <0.0001* |
|  | 12 ASAS Health Index | −1.07 | −2.93 | −1.85 (−2.47, −1.24) | <0.0001* |
|  | 13 BASMI (Mobility) | −0.16 | −0.48 | −0.32 (−0.46, −0.18) | <0.0001* |
|  | 14 MASES (Enthesitis)[d] | −1.1 | −2.6 | −1.5 (−2.0, −0.9) | <0.0001* |

[a]Results for binary endpoints are based on NRI-MI analysis. Analyses for all continuous endpoints are for the change from baseline value. Results for continuous endpoints are based on MMRM, except for MRI and BASMI which use ANCOVA analysis.
[b]Unadjusted p-values are presented.
*Denotes multiplicity-controlled statistical significance at the pre- specified two-sided 0.05 level.
[c]Summarized for subjects with available baseline MRI data up to 3 days post first dose of study drug and available week 14 MRI data up to the first dose of open-label period study drug.
[d]Summarized for subjects with presence of enthesitis at baseline (N = 162 in Placebo, N = 148 in UPA).

Safety

In this Phase 3 AS bDMARD-IR study, the safety profile of upadacitinib freebase was consistent with what is known for upadacitinib, and no new risks were identified.

Adverse Events

The overview of TEAEs and AESIs up to Week 14 are summarized in Table 20F and Table 20G respectively. The rate of overall AEs was similar between the upadacitinib freebase 15 mg and placebo groups. Up to Week 14, there were no events of malignancy, adjudicated GI perforation, adjudicated MACE, or adjudicated VTE reported in subjects receiving upadacitinib freebase. There was one malignancy observed in the placebo group. Serious AEs were reported more frequently with upadacitinib freebase 15 mg, the majority of which were COVID-19 or COVID-19 pneumonia. For AEs leading to discontinuation of study drug, none were reported with upadacitinib 15 mg compared to 3 (1.4%) with placebo. No deaths were reported.

Serious infections and herpes zoster were reported with upadacitinib 15 mg (2.4% and 0.9%, respectively). Four of the 5 serious infections were COVID-19 or COVID-19 pneumonia. Both herpes zoster events were nonserious, did not lead to treatment discontinuation, and involved a single dermatome.

One event of tonsil cancer was reported in a subject receiving placebo. No malignancy was reported with upadacitinib 15 mg.

All hepatic disorders reported in the upadacitinib group were mild or moderate transaminase elevations; none were serious or led to discontinuation of treatment.

AEs of anemia, neutropenia, and lymphopenia were generally mild or moderate, nonserious, and did not lead to treatment discontinuation.

There were no events of opportunistic infection, non-melanoma skin cancer, lymphoma, adjudicated GI perforation, renal dysfunction, active tuberculosis, adjudicated MACE or VTE reported.

More COVID-19 related infections were reported with upadacitinib compared to placebo. None of the infections led to discontinuation of study drug.

Through week 14, the most common adverse events (≥3% of patients) for RINVOQ were COVID-19 and headache. The proportion of patients with adverse events leading to discontinuation, serious adverse events and serious infections were 0 percent/2.8 percent/2.4 percent for RINVOQ and 1.4 percent/0.5 percent/0 percent for placebo, respectively. Serious infections included four events of COVID-19 and one of uveitis with RINVOQ; two patients on RINVOQ developed non-serious, mild or moderate herpes zoster limited to one dermatome. One patient treated with placebo developed a malignancy (tonsil cancer). No adjudicated major adverse cardiovascular events, venous thromboembolic events or deaths were reported in either group through week 14.

TABLE 20F

Overview of Treatment-Emergent Adverse
Events (TEAE) up to Week 14

|  | Placebo (N = 209) n (%) | Upadacitinib 15 mg QD (N = 211) n (%) |
|---|---|---|
| Adverse event (AE) | 77 (36.8) | 86 (40.8) |
| AE with reasonable possibility of being related to study treatment$ | 25 (12.0) | 36 (17.1) |
| Severe AE | 8 (3.8) | 7 (3.3) |
| Serious AE | 1 (0.5) | 6 (2.8) |
| AE leading to withdrawal of study treatment | 3 (1.4) | 0 (0.0) |
| AE leading to death | 0 (0.0) | 0 (0.0) |
| COVID-19 related AE# | 6 (2.9) | 12 (5.7) |
| All deaths | 0 (0.0) | 0 (0.0) |

$As assessed by investigator.
As collected in AE eCRF.

TABLE 20G

Overview of Treatment-Emergent Adverse Events
of Special Interest up to Week 14

|  | Placebo (N = 209) n (%) | Upadacitinib 15 mg QD (N = 211) n (%) |
|---|---|---|
| Infection | 27 (12.9) | 31 (14.7) |
| Serious infection | 0 (0.0) | 5 (2.4) |
| Opportunistic infection excluding tuberculosis and herpes zoster | 0 (0.0) | 0 (0.0) |
| Herpes zoster | 0 (0.0) | 2 (0.9) |
| Active tuberculosis | 0 (0.0) | 0 (0.0) |
| Malignancy | 1 (0.5) | 0 (0.0) |
| Non-melanoma skin cancer (NMSC) | 0 (0.0) | 0 (0.0) |
| Malignancy other than NMSC | 1 (0.5) | 0 (0.0) |
| Lymphoma | 0 (0.0) | 0 (0.0) |
| Hepatic disorder | 2 (1.0) | 6 (2.8) |
| Adjudicated gastrointestinal perforation | 0 (0.0) | 0 (0.0) |
| Anemia | 1 (0.5) | 3 (1.4) |
| Neutropenia | 2 (1.0) | 6 (2.8) |
| Lymphopenia | 2 (1.0) | 1 (0.5) |
| Renal dysfunction | 0 (0.0) | 0 (0.0) |
| Adjudicated MACE* | 0 (0.0) | 0 (0.0) |
| Adjudicated venous thromboembolic events** | 0 (0.0) | 0 (0.0) |

*MACE; Major adverse cardiovascular events, defined as cardiovascular death (includes acute myocardial infarction, sudden cardiac death, heart failure, cardiovascular procedure-related death, death due to cardiovascular hemorrhage, fatal stroke, pulmonary embolism and other cardiovascular causes), non-fatal myocardial infarction and non-fatal stroke.
**VTE include deep vein thrombosis (DVT) and pulmonary embolism (PE) (fatal and non-fatal).

Potentially Clinically Significant Lab Findings

Potentially clinically significant lab and vital sign abnormalities were reported infrequently (Table 20H). There was no Hy's law case in this study up to Week 14.

TABLE 20H

Potentially Clinically Significant Labs
in Double-Blind Period (Week 14)

| Lab Parameter[a] n/N_obs (%) | PLACEBO N = 209 | UPADACITINIB 15 MG QD N = 211 |
|---|---|---|
| Hemoglobin (g/L) | | |
| Grade 3 (<80) | 0/209 | 0/211 |
| Lymphocytes (10^9/L) | | |
| Grade 3 (0.2-<0.5) | 0/209 | 1/211 (0.5) |
| Grade 4 (<0.2) | 0/209 | 0/211 |
| Neutrophils (10^9/L) | | |
| Grade 3 (0.5-<1.0) | 1/209 (0.5) | 4/211 (1.9) |
| Grade 4 (<0.5) | 0/209 | 0/211 |
| ALT (U/L) | | |
| Grade 3 (>5.0-20.0 xULN) | 1/209 (0.5) | 1/211 (0.5) |
| Grade 4 (>20.0 xULN) | 0/209 | 0/211 |
| AST (U/L) | | |
| Grade 3 (>5.0-20.0 xULN) | 2/209 (1.0) | 2/211 (0.9) |
| Grade 4 (>20.0 xULN) | 0/209 | 0/211 |
| Creatinine (umol/L) | | |
| Grade 3 (>3.0-6.0 xULN or >3.0 × Baseline) | 2/209 (1.0) | 0/211 |
| Grade 4 (>6.0 xULN) | 0/209 | 0/211 |

[a]Grading is based CTCAE V4 criteria; Grade must be worse than the baseline grade to be counted Discussion Overall, the results from Study 1 support planned regulatory submissions in the AS indication. In bDMARD-IR population, upadacitinib demonstrated significantly greater improvements in AS signs and symptoms of AS, including back pain and inflammation, as well as improvements in physical function, disease activity, mobility, and quality of life compared to placebo at Week 14.

Additionally, significantly more patients treated with the upadacitinib freebase 15 mg QD achieved ASDAS Low Disease Activity (LDA) compared to those treated with placebo (44 percent versus 10 percent). A statistically significantly greater improvement in Magnetic Resonance Imaging (MRI) Spondyloarthritis Research Consortium of Canada (SPARCC) Score (Spine) as measured by mean change from baseline was reported in the treatment group versus the placebo group (−3.95 versus −0.04). Patients in the treatment group experienced a significantly greater mean decrease from baseline in Patient's Assessment of Total Back Pain at week 14 than those on placebo (−3.00 versus −1.47). Additionally, patients in the treatment group experienced significantly greater improvement in physical function as assessed by mean change from baseline in Bath Ankylosing Spondylitis Functional Index (BASFI) compared to patients on placebo (−2.26 versus −1.09). All ranked secondary endpoints achieved p-values of <0.0001 versus placebo. Additional results are summarized below in Table 20I.

TABLE 20I

SELECT-AXIS 2 (Study 1) Efficacy Results at Week 14*,[1]

|  | RINVOQ 15 mg, once daily (n = 211) | Placebo (n = 209) |
|---|---|---|
| Percent of Patients achieving ASAS40[a] | 45% | 18% |
| Percent of Patients achieving ASDAS Low Disease Activity[b] | 44% | 10% |
| Mean Change from Baseline in Magnetic Resonance Imaging (MRI) SPARCC Score (Spine)[c] | −3.95 | −0.04 |

TABLE 20I-continued

SELECT-AXIS 2 (Study 1) Efficacy Results at Week 14*,1

| | RINVOQ 15 mg, once daily (n = 211) | Placebo (n = 209) |
|---|---|---|
| Mean Change from Baseline in Patient's Assessment of Total Back Pain[d] | −3.00 | −1.47 |
| Mean Change from Baseline in BASFI[e] | −2.26 | −1.09 |

*Primary and ranked secondary endpoints at Week 14. Not all ranked secondary endpoints are shown. All primary and ranked secondary endpoints achieved p-values of <0.0001 versus placebo.
[a]ASAS 40 is defined as a ≥40 percent improvement and an absolute improvement of ≥2 units (on a scale of 0 to 10) from Baseline in at least 3 of the 4 domains (patient's global assessment, back pain, function, and inflammation) with no worsening at all in the remaining domain.
[b]ASDAS Low Disease Activity is defined as ASDAS score <2.1.
[c]SPARCC scores for spine are calculated by adding up the dichotomous outcomes from evaluations of the presence, depth, and intensity of bone marrow edema lesions of the spine.
[d]Back Pain is measured using 0-10 numerical rating scale (NRS) for Total Back Pain (0 = no pain and 10 = severe pain).
[e]BASFI is a validated patient-reported outcome (PRO) instrument for use in the AS patient population. It consists of 10 items measured on a 0 to 10 NRS, which assesses the ability to perform activities known to be problematic to AS patients such as dressing, bending, reaching, turning, and climbing steps. The total scores range from 0 to 10.

The observed treatment effects comparing bDMARD-naïve population to bDMARD-IR (Study 1) are also provided in FIG. 12.

Example 33. A Phase 3 Randomized, Placebo-Controlled, Double-Blind Program to Evaluate Efficacy and Safety of Upadacitinib in Adult Subjects with Axial Spondyloarthritis Followed by a Remission-Withdrawal Period (SELECT AXIS 2) (Study 2)

The Phase 3 clinical study plan is set forth in FIG. 9.

Adult Subjects with Active Non-Radiographic Axial Spondyloarthritis (Nr-axSpA) (Study 2)

Study 2 is a Phase 3, randomized, placebo-controlled, double-blind multicenter study to evaluate the safety, tolerability, and efficacy of upadacitinib compared with placebo on reduction of signs and symptoms in adult subjects with active non-radiographic axial spondyloarthritis (nr-axSpA).

Study 2 (nr-axSpA) is comprised of a 35-day Screening Period; a 52-week randomized, double-blind, parallel-group, placebo-controlled period (the Double-Blind Period) designed to compare the safety and efficacy of upadacitinib freebase 15 mg QD versus placebo for the treatment of signs and symptoms of subjects with active nr-axSpA; and a 52-week open-label, long-term extension period (the Open-Label Extension Period) for evaluating the long-term safety, tolerability, and efficacy of upadacitinib freebase 15 mg QD in subjects who have completed the Double Blind Period up to week 104 (FIG. 9). The study team will be unblinded to perform the Week 14 primary analysis. Sites and subjects will remain blinded to the Double-Blind Period treatment assignments for the duration of the study.

Subjects in Study 2 who reach Week 104 on study drug (upadacitinib free base 15 mg QD) will be assessed whether they are in remission. Subjects in remission at Week 104 will be eligible for the Remission-Withdrawal Period. Subjects will be followed without study drug treatment and assessed for disease flare through Week 152. Subjects who flare will receive open-label upadacitinib 15 mg QD from the time of flare for 24 weeks (re-treatment) or longer.

Subjects in the placebo group will be switched to upadacitinib free base 15 mg QD at Week 52 in the Open-Label Extension Period for Study 2 (nr-axSpA).

Subjects were randomized in a 1:1 ratio to one of two treatment groups, stratified by MRI and screening hsCRP status (MRI+/hsCRP>ULN, MRI+hsCRP≤ULN, and MRI−/hsCRP>ULN), and exposure to bDMARDs (yes vs no):
Group 1: Upadacitinib free base 15 mg QD (N=156) (Double-Blind Period)→Upadacitinib free base 15 mg QD (Open-Label Period)
Group 2: Placebo (N=158) (Double-Blind Period)→Upadacitinib free base 15 mg QD (Open-Label Period)

Subjects were enrolled from 113 sites in 23 countries. Eligible subjects were adult females and males who were at least 18 years of age at Screening with a clinical diagnosis of nr-axSpA fulfilling the 2009 ASAS classification criteria for axSpA but not meeting the radiologic criterion of the modified New York criteria for AS and have objective signs of active inflammation on magnetic resonance imaging of sacroiliac joints or based on high sensitivity C-reactive protein >upper limit of normal (Study 2, nr-axSpA). Eligible study subjects must have had a Bath Ankylosing Spondylitis Disease Activity Index score ≥4 and a Patient's Assessment of Total Back Pain score (Total Back Pain score) ≥4 based on a 0-10 numerical rating scale at the Screening and Baseline Visits. Subject must have had objective signs of active inflammation on MRI of SI joints or hsCRP>ULN at screening.

For Study 2, subjects with prior failure of nonsteroidal anti-inflammatory drugs (NSAIDs) were enrolled, and prior treatment with at most 1 bDMARD (either 1 TNF inhibitor or 1 IL-17 inhibitor) was allowed in a subset of subjects (at least 25%, but not exceeding 35% of total enrolled subjects). Subjects with prior exposure to 1 bDMARD (either 1 tumor necrosis factor [TNF] inhibitor or 1 interleukin [IL]-17 inhibitor) may be enrolled, and the subject must have discontinued the bDMARD due to either intolerance or lack of efficacy. Prior exposure to a 2nd bDMARD was allowed for no more than 30% of subjects if the reason for discontinuation was not due to lack of efficacy. Subjects who have had lack of efficacy to both a TNF inhibitor and IL-17 inhibitor were not eligible.

Study 2 Primary Endpoints

The primary endpoint is the proportion of subjects achieving an ASAS40 response at Week 14.

Secondary endpoints for Study 2 are described below.

Study 2: Nr-axSpA-Specific Criteria
1. Subject must have a clinical diagnosis of nr-axSpA fulfilling the 2009 ASAS classification criteria for axSpA but not meeting the radiologic criterion of the modified New York criteria for AS.
2. Subjects with or without prior exposure to a bDMARD may be enrolled. For the subset of subjects with prior bDMARD exposure (at least 25%, but not exceeding 35% of total enrolled subjects), prior treatment with at most 1 bDMARD (either 1 TNF inhibitor or 1 IL-17 inhibitor) is allowed, and the subject must have discontinued the bDMARD due to either intolerance or lack of efficacy. Subjects who have had lack of efficacy to both a TNF inhibitor and IL-17 inhibitor were not eligible.
3. Subject must have objective signs of active inflammation on MRI of SI joints or hsCRP>ULN at screening.
Study 2 Eligibility Criteria:
1. Subject must be an adult male or female, at least 18 years of age at Screening.
2. Subject must meet the following scores at Screening and Baseline Visits: BASDAI score ≥4 and Total Back Pain score ≥4 based on a 0-10 NRS.
3. Subject has had an inadequate response to at least 2 NSAIDs over an at least 4-week period in total at maximum recommended or tolerated doses, or subject has an intolerance to or contraindication for NSAIDs.

4. The washout period for bDMARDs prior to the first dose of study drug is specified below:

≥4 weeks for etanercept;

≥8 weeks for adalimumab, infliximab, certolizumab, golimumab, abatacept, tocilizumab, and ixekizumab;

≥12 weeks for ustekinumab;

≥16 weeks for secukinumab;

≥1 year for rituximab OR ≥6 months if B cells have returned to pre-treatment level or normal reference range (central lab) if pre-treatment levels are not available;

≥12 weeks or at least 5 times the mean terminal elimination half-life, whichever is longer, for other bDMARDs.

5. If entering the study on the following concomitant csDMARDs (MTX (≤25 mg/week); or Sulfasalazine (SSZ) 3 g/day); or Hydroxychloroquine (≤400 mg/day); or Chloroquine (≤400 mg/day); or Leflunomide 20 mg/day); or Apremilast 60 mg/day)), subject must be on a stable dose as indicated below for at least 28 days prior to the Baseline Visit. A combination of up to 2 background csDMARDs is allowed EXCEPT the combination of methotrexate (MTX) and leflunomide.

6. If entering the study on concomitant oral corticosteroids, subject must be on a stable dose of prednisone (≤10 mg/day) or oral corticosteroid equivalent for at least 14 days prior to the Baseline Visit.

7. If entering the study on concomitant NSAIDs, tramadol, combination of acetaminophen/paracetamol and codeine or combination of acetaminophen/paracetamol and hydrocodone, and/or non-opioid analgesics, subject must be on stable dose(s) for at least 14 days prior to the Baseline Visit.

8. Subject must not have been exposed to any JAK inhibitor.

9. Subject must not have used the following prohibited concomitant treatments within the specified timeframe prior to Baseline Visit:

Intra-articular joint injections, spinal/paraspinal injection(s), or parenteral administration of corticosteroids within 28 days prior to the Baseline Visit. Inhaled or topical corticosteroids are allowed;

Any other csDMARDs (other than those allowed per eligibility criterion), including thalidomide, within 28 days or 5 half-lives (whichever is longer) of the drug prior to the Baseline Visit;

Opioid analgesics (except for combination of acetaminophen/paracetamol and codeine or combination of acetaminophen/paracetamol and hydrocodone which are allowed) within 14 days prior to the Baseline Visit.

10. Subject must not have received a live vaccine within 28 days (or longer if required locally) prior to the first dose of study drug or have expected need of live vaccination during study participation including at least 30 days (or longer if required locally) after the last dose of study drug.

11. Subject must have no systemic use of known strong cytochrome P450 3A (CYP3A) inhibitors from Screening through the end of study drug administration or strong CYP3A inducers 30 days prior to study drug administration through the end of study drug administration. Subjects must not use herbal therapies or other traditional medicines with unknown effects on CYP3A from Screening through the end of study drug administration.

12. Subject must not have been treated with any investigational drug of chemical or biologic nature within a minimum of 30 days or 5 half-lives of the drug (whichever is longer) prior to the first dose of study drug or is currently enrolled in another interventional study.

13. Subject must not have a history of an allergic reaction or significant sensitivity to constituents of the study drug (and its excipients) and/or other products in the same class.

Study 2 Secondary Endpoints

The key multiplicity-controlled secondary endpoints at Week 14 were as follows:

TABLE 21A

Key multiplicity-controlled secondary endpoints at Week 14 (Study 2)

1 Change from Baseline in Ankylosing Spondylitis Disease Activity Score (ASDAS) (CRP)
2 Change from Baseline in magnetic resonance imaging (MRI) Spondyloarthritis Research Consortium of Canada (SPARCC) score (SI joints) (MRI-Joints SPARCC)
3 BASDAI 50 score
4 Proportion of subjects with ASDAS (CRP) Inactive Disease (ASDAS score <1.3)
5 Change from Baseline in Total Back Pain
6 Change from Baseline in Nocturnal Back Pain
7 Proportion of subjects with ASDAS (CRP) Low Disease (ASDAS score <2.1)
8 Proportion of subjects with ASAS partial remission (PR) (an absolute score of ≤2 units for each of the 4 domains identified in ASAS40)
9 Change from Baseline in Bath Ankylosing Spondylitis Functional Index (BASFI) (Function)
10 Change from Baseline in Ankylosing Spondylitis Quality of Life (ASQoL)
11 Change from Baseline in ASAS Health Index (HI)
12 Proportion of subjects with ASAS20 response
13 Change from Baseline in Linear Bath Ankylosing Spondylitis Metrology Index (BASMI$_{lin}$) (Mobility)
14 Change from Baseline in Maastricht Ankylosing Spondylitis Enthesitis Score (MASES) (Enthesitis)

Additional key secondary endpoints at Week 14 include: Change from Baseline in MRI SPARCC score (spine) at Week 14.

Additional Study 2 Endpoints

Additional endpoints are the following measurements assessed at time points other than those specified for the primary and key secondary variables are as follows:

TABLE 21B

Additional Study 2 Endpoints

1. Proportion of subjects with ASAS20 response
2. Proportion of subjects with ASAS40 response
3. Proportion of subjects with ASAS PR
4. Proportion of subjects with ASDAS Inactive Disease (ASDAS score <1.3)
5. Proportion of subjects with ASDAS Low Disease (ASDAS score <2.1)
6. Proportion of subjects with ASDAS Major Improvement (a change from Baseline of ≤−2.0)
7. Proportion of subjects with ASDAS Clinically Important Improvement (a change from Baseline of ≤−1.1)
8. Proportion of subjects with Discontinuation of opioids among subjects with opioid use at Baseline
9. Change from Baseline in ASAS HI
10. Change from Baseline in ASDAS
11. Change from Baseline in ASQoL
12. Change from Baseline in BASDAI and BASDAI Questions including mean of question 5 and 6 of the BASDAI
13. Change from Baseline in BASFI
14. Change from Baseline in $BASMI_{lin}$
15. Change from Baseline in hsCRP
16. Change from Baseline in FACIT-F
17. Change from Baseline in EQ-5D-5L
18. Change from Baseline in MASES
19. Change from Baseline in mSASSS with conventional radiograph
20. Change from Baseline in MRI SPARCC score of SI joints
21. Change from Baseline in MRI SPARCC score of spine
22. Change from Baseline in Total Back Pain
23. Change from Baseline in Nocturnal Back Pain
24. Change from Baseline in Pain
25. Change from Baseline in PGA
26. Change from Baseline in PtGA
27. Change from Baseline in SF-36
28. Change from Baseline in TJC and SJC
29. Change from Baseline in WPAI
30. Change from Baseline in Change of NSAID score A total of 314 subjects were randomized in Study 2 and 313 received double blind study drug treatment, out of which 295 (94.2%) completed study drug through Week 14. One subject randomized to the placebo group did not receive study drug. The rates of premature discontinuation of study drug through Week 14 were 4.5% and 7.1% in the placebo group and the upadacitinib treatment group respectively (Table 21C). The key demographics and baseline characteristics were balanced across the treatment groups and generally consistent with the targeted patient population (Table 21D).

TABLE 21C

Subject Disposition

| Subject Disposition | PLACEBO | UPADACITINIB 15 MG QD |
|---|---|---|
| Randomized | 158 | 156 |
| Full Analysis Set (FAS) | 157[c] | 156 |
| Per Protocol Analysis Set | 133 | 135 |
| Safety Analysis Set | 157 | 156 |
| Completed Study Drug Through Week 14, n(%)[b] | 150 (95.5) | 145 (92.9) |
| Prematurely Discontinued Study Drug by Week 14[a], n(%)[b] | 7 (4.5) | 11 (7.1) |
| Adverse Events | 2 (1.3) | 4 (2.6) |
| Withdrew Consent | 1 (0.6) | 2 (1.3) |
| Lost To Follow-Up | 0 | 0 |
| Lack of Efficacy | 3 (1.9) | 3 (1.9) |
| COVID-19 Infection | 0 | 0 |

TABLE 21C-continued

Subject Disposition

| Subject Disposition | PLACEBO | UPADACITINIB 15 MG QD |
|---|---|---|
| COVID-19 Logistical Restrictions | 0 | 1 (0.6) |
| Other | 1 (0.6) | 1 (0.6) |

[a]Primary reasons for premature discontinuation of study drug are summarized.
[b]Percentage is calculated based upon the FAS.
[c]One subject did not receive study drug (decided not to participate after randomization).

TABLE 21D

Key Demographics and Baseline Characteristics

| Key Demographic and Baseline Characteristics Mean (SD) or n (%) | PLACEBO N = 157 | UPADACITINIB 15 MG QD N = 156 |
|---|---|---|
| Male | 63 (40.1) | 67 (42.9) |
| Age (Yrs) | 42.5 (12.44) | 41.6 (12.00) |
| HLA-B27 Positive | 93 (59.6) | 90 (58.8) |
| White | 127 (80.9) | 134 (85.9) |
| Region | | |
| North America | 19 (12.1) | 26 (16.7) |
| South/Central America | 13 (8.3) | 12 (7.7) |
| Western Europe | 19 (12.1) | 24 (15.4) |
| Eastern Europe | 72 (45.9) | 68 (43.6) |
| Asia[a] | 27 (17.2) | 19 (12.2) |
| Other[b] | 7 (4.5) | 7 (4.5) |
| Duration of nr-axSpA Diagnosis (Yrs) | 4.4 (5.83) | 4.5 (5.54) |
| Duration of nr-axSpA Symptom (Yrs) | 9.2 (8.12) | 9.0 (7.86) |

TABLE 21D-continued

Key Demographics and Baseline Characteristics

| Key Demographic and Baseline Characteristics Mean (SD) or n (%) | PLACEBO N = 157 | UPADACITINIB 15 MG QD N = 156 |
|---|---|---|
| NSAIDs Use at Baseline | 113 (72.0) | 121 (77.6) |
| Oral Corticosteroids Use at Baseline | 17 (10.8) | 18 (11.5) |
| csDMARDs Use at Baseline | 50 (31.8) | 41 (26.3) |
| Prior bDMARD Exposure | 54 (34.4) | 49 (31.4) |
| BASDAI (0-10) | 6.91 (1.215) | 6.82 (1.295) |
| Total Back Pain (NRS 0-10) | 7.3 (1.39) | 7.2 (1.55) |
| Nocturnal Back Pain (NRS 0-10) | 7.0 (1.64) | 6.7 (1.94) |
| Patient Global Assessment of Disease Activity (NRS 0-10) | 7.3 (1.38) | 7.0 (1.62) |
| ASDAS(CRP) | 3.65 (0.644) | 3.61 (0.674) |
| BASFI (Function) (0-10) | 5.99 (2.139) | 5.89 (2.077) |
| BASMI (Mobility) | 3.10 (1.269) | 2.98 (1.418) |
| Presence of Enthesitis (MASES > 0) | 125 (79.6) | 125 (80.1) |
| MASES Score[c](0-13) | 4.7 (3.18) | 4.7 (3.09) |
| MRI Spine SPARCC[d] (0-108) | 1.44 (3.724) | 2.72 (6.881) |
| MRI Sacroiliac Joint SPARCC[d] (0-72) | 3.49 (7.601) | 4.38 (8.737) |
| MRI (SI joints) inflammation positive at screening | 66 (42.0) | 70 (44.9) |
| hsCRP at Screening (mg/L) | 10.52 (13.522) | 13.61 24.794) |
| hsCRP > ULN (2.87 mg/L) at Screening | 126 (80.3) | 123 (78.8) |
| hsCRP > 5 mg/L at Screening | 84 (53.5) | 99 (63.5) |
| MRI (SI joints) inflammation and hsCRP level at Screening | | |
| MRI+/hsCRP > ULN | 35 (22.3) | 38 (24.4) |
| MRI+/hsCRP ≤ ULN | 31 (19.7) | 32 (20.5) |
| MRI-/hsCRP > ULN | 91 (58.0) | 86 (55.1) |
| AS QoL(0-18) | 11.9 (4.53) | 11.9 (4.41) |
| ASAS Health Index (0-17) | 9.52 (3.662) | 9.44 (3.575) |

[a]China, Taiwan, South Korea and Japan.
[b]Australia and Israel.
[c]Summarized for subjects with presence of enthesitis at baseline.
[d]Summarized for subjects with available baseline MRI data up to 3 days post first dose of study drug.

Efficacy

The primary endpoint was the achievement of an ASAS40 response at Week 14. The primary analysis, using Non-Responder Imputation in conjunction with Multiple Imputation (NRI-MI) to handle missing data due to COVID-19, showed a statistically significantly higher response rate (p<0.0001) in the upadacitinib group (44.9%) as compared to placebo (22.5%) (FIG. 13A). Sensitivity and supplementary analyses using NRI, As Observed (AO) data, and analyses on the Per Protocol population showed consistent results.

The first 12 of the 14 ranked endpoints at Week 14 were statistically significant. Details of the primary and ranked secondary endpoints are presented in Table 21E and FIGS. 14A-14F. FIG. 13B shows ASAS40 responses up to Week 14. Upadacitinib showed onset of effect in ASAS40 as early as Week 2.

TABLE 21E

Primary and Ranked Key Secondary Efficacy Endpoints at Week 14[a]

| | Endpoint | PLACEBO N = 157 | UPADACITINIB 15 MG QD N = 156 | UPA − PBO (95% CI) | p-VALUE[b] |
|---|---|---|---|---|---|
| Primary | ASAS40 | 22.5% | 44.9% | 22.2 (12.1, 32.3) | <0.0001* |
| Ranked Key Secondary | 1 ASDAS(CRP) | −0.71 | −1.36 | −0.65 (−0.85, −0.45) | <0.0001* |
| | 2 MRI SI Joints SPARCC[c] | 0.57 | −2.49 | −3.06 (−4.08, −2.04) | <0.0001* |
| | 3 BASDAI50 | 22.1% | 42.3% | 20.1 (10.1, 30.1) | 0.0001* |
| | 4 ASDAS(CRP) Inactive Disease | 5.2% | 14.1% | 8.8 (2.5, 15.2) | 0.0063* |
| | 5 Total Back Pain | −2.00 | −2.91 | −0.92 (−1.42, −0.41) | 0.0004* |
| | 6 Nocturnal Back Pain | −1.84 | −2.96 | −1.12 (−1.68, −0.55) | 0.0001* |
| | 7 ASDAS(CRP) Low Disease Activity | 18.3% | 42.3% | 23.8 (14.2, 33.4) | <0.0001* |
| | 8 ASAS Partial Remission | 7.6% | 18.6% | 10.9 (3.6, 18.3) | 0.0035* |
| | 9 BASFI (Function) | −1.47 | −2.61 | −1.14 (−1.60, −0.68) | <0.0001* |
| | 10 AS QoL | −3.15 | −5.38 | −2.23 (−3.26, −1.21) | <0.0001* |
| | 11 ASAS Health Index | −1.48 | −3.26 | −1.78 (−2.56, −1.00) | <0.0001* |
| | 12 ASAS20 | 43.8% | 66.7% | 22.8 (12.2, 33.4) | <0.0001* |
| | 13 BASMI (Mobility) | −0.19 | −0.29 | −0.10 (−0.25, 0.05) | 0.1781 |
| | 14 MASES (Enthesitis)[d] | −1.6 | −2.3 | −0.7 (−1.3, −0.1) | 0.0193 |

[a]Results for binary endpoints are based on NRI-MI analysis. Analyses for all continuous endpoints are for the change from baseline value. Results for continuous endpoints are based on MMRM, except for MRI and BASMI which use ANCOVA analysis.
[b]Unadjusted raw p-values are presented.
*Denotes multiplicity adjusted statistical significance at the pre-specified two-sided 0.05 level.
[c]Summarized for subjects with available baseline MRI data up to 3 days post first dose of study drug and available week 14 MRI data.
[d]Summarized for subjects with presence of enthesitis at baseline (N = 125 in Placebo, N = 124 in UPA).

Safety

In this Phase 3 nr-axSpA study, the safety profile of upadacitinib was consistent with what is known for upadacitinib and no new risks were identified.

Adverse Events

The overview of TEAEs and AESIs up to Week 14 are summarized in Table 21F and Table 21G respectively. Through week 14, the most common adverse events (≥3% of patients) with upadacitinib were headache, COVID-19, nasopharyngitis, and nausea. The proportion of patients with adverse events leading to discontinuation, serious adverse events and serious infections were 2.6 percent/2.6 percent/1.3 percent for upadacitinib and 1.3 percent/1.3 percent/0.6 percent for placebo, respectively. Serious infections included COVID-19 induced pneumonia and pyelonephritis in two patients on upadacitinib and hemorrhagic fever with renal syndrome in one patient on placebo. Two patients treated with upadacitinib and one treated with placebo developed non-serious, mild or moderate herpes zoster limited to one dermatome. One patient treated with placebo developed a malignancy (basal cell carcinoma). No adjudicated major adverse cardiovascular events, venous thromboembolic events or deaths were reported in either group through week 14. In summary:

- The rate of overall AEs was similar between the upadacitinib 15 mg and placebo groups. Serious AEs were reported more frequently with upadacitinib 15 mg (2.6%) compared to placebo (1.3%). AEs leading to discontinuation of study drug were reported more frequently with upadacitinib 15 mg (2.6%) compared to placebo (1.3%). No deaths were reported.
- Serious infections and herpes zoster were reported with upadacitinib 15 mg (both at a rate of 1.3%). Both herpes zoster events were nonserious, did not lead to treatment discontinuation, and involved a single dermatome.
- One event of basal cell carcinoma was reported in a subject receiving placebo. No malignancy was reported with upadacitinib 15 mg.
- All hepatic disorders reported in the upadacitinib group were mild or moderate transaminase elevations; none were serious or led to discontinuation of treatment.
- AEs of anemia and neutropenia were generally mild or moderate, nonserious, and did not lead to treatment discontinuation. There were no AEs of lymphopenia reported.
- There were no events of opportunistic infection, non-melanoma skin cancer, lymphoma, adjudicated GI perforation, renal dysfunction, active tuberculosis, adjudicated MACE or VTE reported.

TABLE 21F

Overview of Treatment-Emergent Adverse Events (TEAE) up to Week 14

|  | Placebo (N = 157) n (%) | Upadacitinib 15 mg QD (N = 156) n (%) |
|---|---|---|
| Adverse event (AE) | 72 (45.9) | 75 (48.1) |
| AE with reasonable possibility of being related to study treatment$ | 30 (19.1) | 29 (18.6) |
| Severe AE | 3 (1.9) | 8 (5.1) |
| Serious AE | 2 (1.3) | 4 (2.6) |
| AE leading to withdrawal of study treatment | 2 (1.3) | 4 (2.6) |
| AE leading to death | 0 (0.0) | 0 (0.0) |
| COVID-19 related AE# | 10 (6.4) | 8 (5.1) |
| All deaths | 0 (0.0) | 0 (0.0) |

$As assessed by investigator.
As collected in AE eCRF.

TABLE 21G

Overview of Treatment-Emergent Adverse Events of Special Interest up to Week 14

|  | Placebo (N = 157) n (%) | Upadacitinib 15 mg QD (N = 156) n (%) |
|---|---|---|
| Infection | 36 (22.9) | 36 (23.1) |
| Serious infection | 1 (0.6) | 2 (1.3) |
| Opportunistic infection excluding tuberculosis and herpes zoster | 0 (0.0) | 0 (0.0) |
| Herpes zoster | 1 (0.6) | 2 (1.3) |
| Active tuberculosis | 0 (0.0) | 0 (0.0) |
| Malignancy | 1 (0.6) | 0 (0.0) |
| Non-melanoma skin cancer (NMSC) | 1 (0.6) | 0 (0.0) |
| Malignancy other than NMSC | 0 (0.0) | 0 (0.0) |
| Lymphoma | 0 (0.0) | 0 (0.0) |
| Hepatic disorder | 5 (3.2) | 4 (2.6) |
| Adjudicated gastrointestinal perforation | 0 (0.0) | 0 (0.0) |
| Anemia | 0 (0.0) | 1 (0.6) |
| Neutropenia | 0 (0.0) | 5 (3.2) |
| Lymphopenia | 0 (0.0) | 0 (0.0) |
| Renal dysfunction | 0 (0.0) | 0 (0.0) |
| Adjudicated MACE* | 0 (0.0) | 0 (0.0) |
| Adjudicated venous thromboembolic events** | 0 (0.0) | 0 (0.0) |

*MACE; Major adverse cardiovascular events, defined as cardiovascular death (includes acute myocardial infarction, sudden cardiac death, heart failure, cardiovascular procedure-related death, death due to cardiovascular hemorrhage, fatal stroke, pulmonary embolism and other cardiovascular causes), non-fatal myocardial infarction and non-fatal stroke.
**VTE include deep vein thrombosis (DVT) and pulmonary embolism (PE) (fatal and non-fatal).

Potentially Clinically Significant Lab Findings

Potentially clinically significant lab abnormalities were reported infrequently (Table 21H). There was no Hy's law case in this study up to Week 14.

TABLE 21H

Potentially Clinically Significant Labs up to Week 14 in Double-Blind Period

| Lab Parameter$^a$ n/N_obs (%) | PLACEBO N = 157 | UPADACITINIB 15 MG QD N = 156 |
|---|---|---|
| Hemoglobin (g/L) | | |
| Grade 3 (<80) | 0/156 | 0/154 |
| Lymphocytes (×10^9/L) | | |
| Grade 3 (0.2-<0.5) | 1/156 (0.6) | 2/154 (1.3) |
| Grade 4 (<0.2) | 0/156 | 0/154 |
| Neutrophils (×10^9/L) | | |
| Grade 3 (0.5-<1.0) | 1/156 (0.6) | 2/154 (1.3) |
| Grade 4 (<0.5) | 0/156 | 0/154 |
| ALT (U/L) | | |
| Grade 3 (>5.0-20.0 xULN) | 0/156 | 0/154 |
| Grade 4 (>20.0 xULN) | 0/156 | 0/154 |

TABLE 21H-continued

Potentially Clinically Significant Labs
up to Week 14 in Double-Blind Period

| Lab Parameter[a]<br>n/N_obs (%) | PLACEBO<br>N = 157 | UPADACITINIB<br>15 MG QD<br>N = 156 |
|---|---|---|
| AST (U/L) | | |
| Grade 3 (>5.0-20.0 xULN) | 0/156 | 0/154 |
| Grade 4 (>20.0 xULN) | 0/156 | 0/154 |
| Creatinine (umol/L) | | |
| Grade 3 (>3.0-6.0 xULN) | 0/156 | 0/154 |
| Grade 4 (>6.0 xULN) | 0/156 | 0/154 |

[a]Grading is based CTCAE V4 criteria; Grade must be worse than the baseline grade to be counted Potential Impact of the Study Overall, the topline results from Study 2 support planned regulatory submissions for the nr-axSpA indication.

Upadacitinib demonstrated significantly greater improvements (e.g., reductions) in nr-axSpA signs and symptoms, including back pain and inflammation, as well as improvements in physical function, disease acrivity, and quality of life compared with placebo at Week 14. Significantly more patients treated with upadacitinib achieved Ankylosing Spondylitis Disease Activity Score (ASDAS) Low Disease Activity compared to those treated with placebo (42 percent versus 18 percent; p<0.0001). A statistically significantly greater improvement in Magnetic Resonance Imaging (MRI) Spondyloarthritis Research Consortium of Canada (SPARCC) Score (SI Joints) as measured by mean change from baseline was reported in the upadacitinib group versus the placebo group (−2.49 versus 0.57; p<0.0001). Patients on upadacitinib experienced significantly greater decrease from baseline in Patient's Assessment of Total Back Pain at week 14 than those on placebo (−2.91 versus −2.00; p=0.0004). Additionally, patients treated with upadacitinib experienced significantly greater improvement in physical function as assessed by mean change from baseline in Bath Ankylosing Spondylitis Functional Index (BASFI) compared to patients on placebo (−2.61 versus −1.47; p<0.0001). Additional results are summarized in Table 21I below.

TABLE 21I

SELECT-AXIS 2 (Study 2) Efficacy Results at Week 14[*,1]

| | Upadacitinib<br>15 mg,<br>once daily<br>(n = 156) | Placebo<br>(n = 157) |
|---|---|---|
| Percent of Patients achieving ASAS40[a] | 45% | 23% |
| Percent of Patients achieving ASDAS Low Disease Activity[b] | 42% | 18% |
| Mean Change from Baseline in Magnetic Resonance Imaging (MRI) SPARCC Score (SI Joints)[c] | −2.49 | 0.57 |
| Mean Change from Baseline in Patient's Assessment of Total Back Pain[d] | −2.91 | −2.00 |
| Mean Change from Baseline in BASFI[e] | −2.61 | −1.47 |

*Primary and ranked secondary endpoints at Week 14. Not all ranked secondary endpoints are shown. All endpoints shown with the exception of total back pain (p = 0.0004) achieved p-values of <0.0001 versus placebo.
[a]ASAS 40 is defined as a ≥40 percent improvement and an absolute improvement of ≥2 units (on a scale of 0 to 10) from Baseline in at least 3 of the 4 domains (patient's global assessment, back pain, function and inflammation) with no worsening at all in the remaining domain.
[b]ASDAS Low Disease Activity is defined as ASDAS score <2.1.
[c]SPARCC scores for SI-Joints are calculated by adding up the dichotomous outcomes from evaluations of the presence, depth, and intensity of bone marrow edema lesions of the SI-joints.
[d]BackPain is measured using 0-10 numerical rating scale (NRS) for Total Back Pain (0 = no pain and 10 = severe pain).
[e]BASFI is a validated patient-reported outcome (PRO) instrument for use in the axial SpA patient population. It consists of 10 items measured on a 0 to 10 NRS, which assesses the ability to perform activities known to be problematic to axial SpA patients such as dressing, bending, reaching, turning, and climbing steps. The total scores range from 0 to 10.

U.S. Patent Application Publication Nos. 2017/0129902 and 2021/0228575 are incorporated by reference in their entirety and for all purposes.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

The foregoing has been described of certain non-limiting embodiments of the present disclosure. Those of ordinary skill in the art will appreciate that various changes and modifications to this description may be made without departing from the spirit or scope of the present disclosure, as defined in the following claims.

What is claimed is:

1. A method of treating a human patient having active ankylosing spondylitis, comprising orally administering once daily to the patient a solid dosage form comprising (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1) in an amount sufficient to deliver to the patient 15 mg of Compound 1 free base equivalent.

2. The method of claim 1, wherein the patient is an adult patient.

3. The method of claim 1, wherein the patient has had an inadequate response or intolerance to one or more disease-modifying antirheumatic drugs.

4. The method of claim 1, wherein the patient has had an inadequate response or intolerance to one or more non-steroidal anti-inflammatory drugs (NSAIDs).

5. The method of claim 1, wherein the patient has had an inadequate response or intolerance to an anti-TNF biologic agent.

6. A method of treating a human patient having active ankylosing spondylitis, comprising orally administering once daily to the patient a solid dosage form comprising (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (Compound 1) in an amount sufficient to deliver to the patient 15 mg of Compound 1 free base equivalent, wherein the method results in an Assessment of SpondyloArthritis International Society 40 (ASAS40) response at 14 weeks after the first daily administration.

7. The method of claim 6, wherein the patient is an adult patient.

8. The method of claim 6, wherein the patient has had an inadequate response or intolerance to one or more disease-modifying antirheumatic drugs.

9. The method of claim 6, wherein the patient has had an inadequate response or intolerance to one or more non-steroidal anti-inflammatory drugs (NSAIDs).

10. The method of claim 6, wherein the patient has had an inadequate response or intolerance to an anti-TNF biologic agent.

\* \* \* \* \*

UNITED STATES PATENT AND TRADEMARK OFFICE
CERTIFICATE OF CORRECTION

| | | |
|---|---|---|
| PATENT NO. | : 11,524,964 B2 | Page 1 of 1 |
| APPLICATION NO. | : 17/717486 | |
| DATED | : December 13, 2022 | |
| INVENTOR(S) | : Mohamed-Eslam F. Mohamed et al. | |

It is certified that error appears in the above-identified patent and that said Letters Patent is hereby corrected as shown below:

On the Title Page

Item (72), the paragraph entitled Inventors should read as follows:
--Mohamed-Eslam F. Mohamed, Gurnee, IL (US); Ahmed A. Othman, Libertyville, IL (US); Ben Klünder, Ludwigshafen (DE); Aileen L. Pangan, La Grange, IL (US); In-Ho Song, Vernon Hills, IL (US); Heidi S. Camp, Winnetka, IL (US); Robert J. Padley, Highland Park, IL (US); Jeffrey W. Voss, Hudson, MA (US)--

Signed and Sealed this
Twenty-fifth Day of February, 2025

Coke Morgan Stewart
*Acting Director of the United States Patent and Trademark Office*